(12) United States Patent
Wood et al.

(10) Patent No.: US 10,876,127 B2
(45) Date of Patent: Dec. 29, 2020

(54) PRODUCTION OF DIHYDROSTERCULIC ACID AND DERIVATIVES THEREOF

(71) Applicants: Craig Christopher Wood, Dickson (AU); Fatima Naim, Oxley (AU); Surinder Pal Singh, Downer (AU); Shoko Okada, Waramanga (AU)

(72) Inventors: Craig Christopher Wood, Dickson (AU); Fatima Naim, Oxley (AU); Surinder Pal Singh, Downer (AU); Shoko Okada, Waramanga (AU)

(73) Assignee: Commonwealth Scientific and Industrial Research Organisation, Acton (AU)

(*) Notice: Subject to any disclaimer, the term of this patent is extended or adjusted under 35 U.S.C. 154(b) by 0 days.

(21) Appl. No.: 15/096,431

(22) Filed: Apr. 12, 2016

(65) Prior Publication Data
US 2016/0348123 A1    Dec. 1, 2016

Related U.S. Application Data

(63) Continuation of application No. 14/369,540, filed as application No. PCT/AU2012/001593 on Dec. 21, 2012, now Pat. No. 9,347,067.

(60) Provisional application No. 61/580,567, filed on Dec. 27, 2011.

(51) Int. Cl.
*C12N 15/82* (2006.01)
*A23K 10/30* (2016.01)

(52) U.S. Cl.
CPC .......... *C12N 15/8247* (2013.01); *A23K 10/30* (2016.05)

(58) Field of Classification Search
CPC ............................ C12N 15/8247; A23K 10/30
See application file for complete search history.

(56) References Cited

U.S. PATENT DOCUMENTS

| | | | |
|---|---|---|---|
| 5,936,139 A | 8/1999 | Schmid et al. | |
| 7,166,766 B1 | 1/2007 | Duhot et al. | |
| 9,397,067 B2 | 5/2016 | Wood et al. | |
| 2007/0204370 A1* | 8/2007 | Mietkiewska | C12N 9/1029 800/281 |
| 2010/0115669 A1* | 5/2010 | Bao | C07K 14/705 800/298 |
| 2011/0314725 A1* | 12/2011 | Petrie | A23K 50/80 44/388 |

FOREIGN PATENT DOCUMENTS

| | | |
|---|---|---|
| WO | WO 99/18217 | 4/1999 |
| WO | WO 2003/060079 | 7/2003 |
| WO | WO 2004/101757 | 11/2004 |
| WO | WO 2007/141257 A1 | 12/2007 |
| WO | WO 2010/057246 | 5/2010 |

OTHER PUBLICATIONS

Schmid et al (Distribution of Cyclopropenoid Fatty Acids in Malvaceous Plant Parts. Phytochemistry, vol. 27, pp. 2831-2834, 1988).*
Yu et al (Identification of bottlenecks in the accumulation of cyclic fatty acids in camelina seed oil. Plant Biotechnology Journal. 16, pp. 926-938, 2018).*
Yu et al (Characterization and analysis of the cotton cyclopropane fatty acid synthase family and their contribution to cyclopropane fatty acid synthesis. BMC Plant Biol. 11:97, p. 1-10. Published online May 25, 2011).*
Yu et al (Coexpressing *Escherichia coli* Cyclopropane Synthase with Sterculia foetida Lysophosphatidic Acid Acyltransferase Enhances Cyclopropane Fatty Acid Accumulation. Plant Physiol. vol. 164, pp. 455-465, 2014).*
Yu et al (Coexpressing *Escherichia coli* Cyclopropane Synthase with Sterculia foetida Lysophosphatidic Acid Acyltransferase Enhances Cyclopropane Fatty Acid Accumulation. Plant Physiol. vol. 164, pp. 455-465, 2014) (Year: 2014).*
Yu et al (Characterization and analysis of the cotton cyclopropane fatty acid synthase family and their contribution to cyclopropane fatty acid synthesis. BMC Plant Biology, 1-10, 2011) (Year: 2011).*
Andrianov et al (Tobacco as a production platform for biofuel: overexpression of Arabidopsis DGAT and LEC2 genes increases accumulation and shifts the composition of lipids in green biomass. Plant Biotechnology Journal 8, pp. 277-287, 2010) (Year: 2010).*
Pouvreau et al (Duplicate Maize Wrinkled1 Transcription Factors Activate Target Genes Involved in Seed Oil Biosynthesis. Plant Physiology, vol. 156, pp. 674-686, Jun. 2011). (Year: 2011).*
Bao, X. et al. (2002). Carbocyclic fatty acids in plants: Biochemical and molecular genetic characterization of cyclopropane fatty acid synthesis of Sterculia foetida. PNAS, 99 (10), 7172-7177.
International Search Report, dated Feb. 28, 2013 in connection with PCT International Application No. PCT/AU2012/001593, filed Dec. 21, 2012.
Written Opinion of the International Searching Authority, dated Feb. 28, 2013 in connection with PCT International Application No. PCT/AU2012/001593, filed Dec. 21, 2012.
Notification Concerning Transmittal of International Preliminary Report on Patentability (Chapter I of the Patent Cooperation Treaty), including an International Preliminary Report on Patentability and Written Opinion of the International Searching Authority, dated Jul. 10, 2014 by the International Bureau of WIPO in connection with PCT International Application No. PCT/AU2012/001593, filed Dec. 21, 2012.
*Escherichia coli* K12 MG1655 section 151 of 400 of the complete genome, GenBank Accession No. AE000261.1, Blattner et al. (1997).

(Continued)

*Primary Examiner* — Soren Harward
*Assistant Examiner* — Wayne Zhong
(74) *Attorney, Agent, or Firm* — John P. White; Gary J. Gershik

(57) ABSTRACT

The present invention relates to recombinant cells, particularly recombinant plant cells, which are capable of producing dihydrosterculic acid and/or derivatives thereof. The present invention also relates to methods of producing oil comprising dihydrosterculic acid and/or derivatives thereof.

14 Claims, 13 Drawing Sheets

Figure 1:
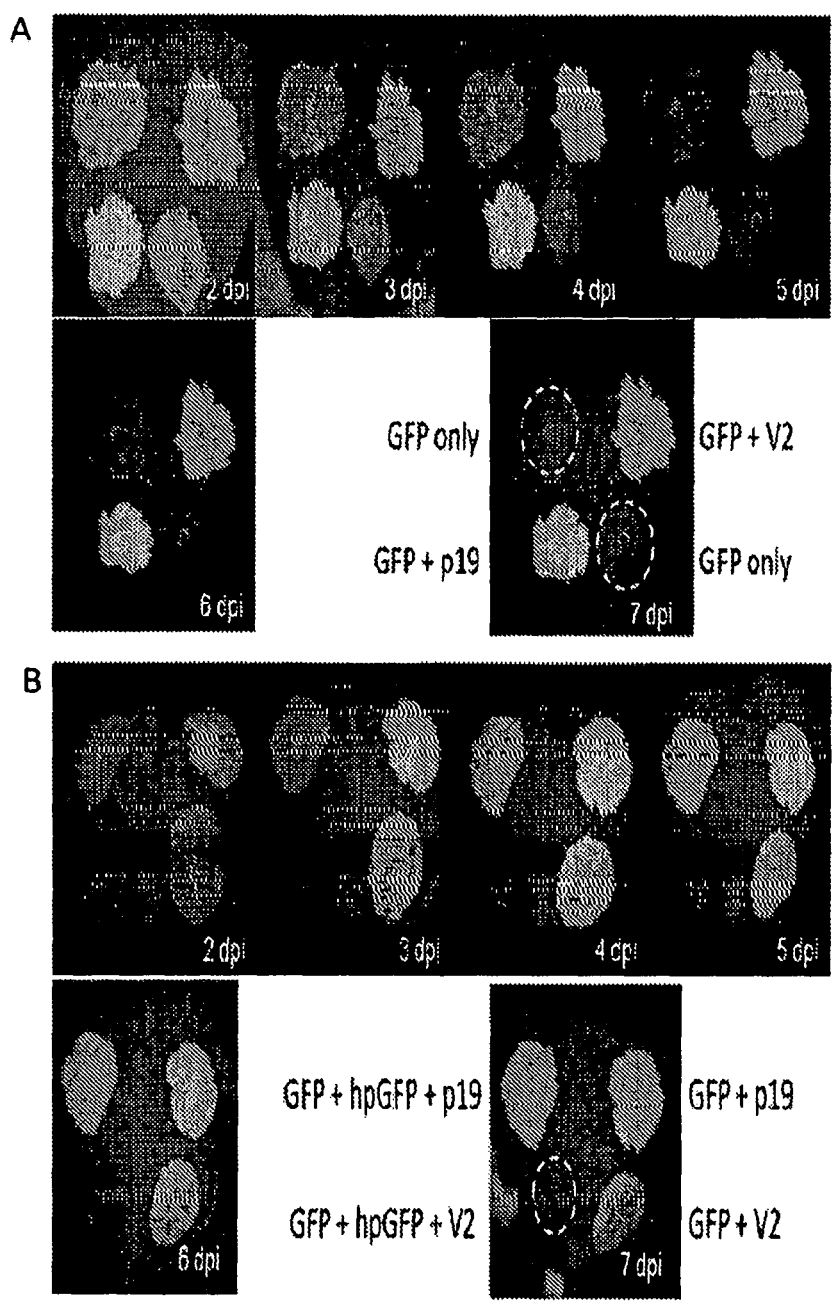

Specification includes a Sequence Listing.

(56) References Cited

OTHER PUBLICATIONS

Bao et al. (2002) "Carbocyclic Fatty Acids in Plants: Biochemical and Molecular Genetic Characterization of Cyclopropane Fatty Acid Synthesis of *Sterculia foetida*." Proc. Natl. Acad. Sci. U.S.A. 99:7172-7177.
Bao et al. (2003) "Characterization of Cyclopropane Fatty-acid Synthase from *Sterculia foetida*." Journal of Biological Chemistry 278:12846-12853.
Fulda et al. (2002) "Two Long-Chain acyl-CoA Synthetases from *Arabidopsis thaliana* Involved in Peroxisomal Fatty Acid β-Oxidation." Plant Journal 32:93-103.
Kinsman (1979) "Isostearic and Other Branched Acids." Journal of the American Oil Chemists Society 56:A823-A827.
Naim et al. (2012) "Advanced Engineering of Lipid Metabolism in *Nicotiana benthamiana* Using a Draft Genome and the V2 Viral Silencing-Suppressor Protein." Plos One 7:e52717.
Stymne and Appelqvist (1978) "The Biosynthesis of Linoleate from Oleoyl-CoA via Oleoyl-Phosphatidylcholine in Microsoomes of Developing Safflower Seeds." European Journal of Biochemistry 90:223-229.
Vanhercke et al. (2013) "Synergistic Effect of WRI1 and DGAT1 Coexpression on Triacylglycerol Biosynthesis in Plants." FEBS Letters:364-369.
Wang et al. (1992) "Cyclopropane Fatty Acid Synthase of *Escherichia coli*: Deduced Amino Acid Sequence, Purification, and Studies of the Enzyme Active Site." Biochemistry 31:11020-11028.
Wood et al. (2009) "A Leaf-Based Assay Using Interchangeable Desgin Principles to Rapidly Assemble Multistep Recombinant Pathways." Plant Biotechnology Journal 7:1-11.
Yu et al. (2011) "Characterization and Analysis of the Cotton Cyclopropane Fatty Acid Synthase Family and Their Contribution to Cyclopropane Fatty Acid Synthesis." BMC Plant Biology 11:97.
Zhang et al. (2004) "New Process for the Production of Branched-Chain Fatty Acids." Journal of Surfactants and Detergents 7:211-215.
Nov. 13, 2014 First Examination Report, issued in connection with corresponding Australian Patent Application No. 2012327162.
Sep. 28, 2015 Supplementary European Search Report issued in connection with corresponding European Patent Application No. 12862139.8.
Aug. 5, 2016 Response to First Examination Report submitted in connection with corresponding Australian Patent Application No. 2012327162.
Aug. 17, 2016 Response to Sep. 28, 2015 Supplementary European Search Report submitted in connection with corresponding European Patent Application No. EP 12862139.8.
Jun. 28, 2017 First Examination Report, issued in connection with corresponding Australian Patent Application No. AU 2016213872.
Jun. 20, 2018 Response to Examiner's first report issued in connection with Australian Patent Application No. 2016213872.
Oct. 22, 2018 First Examination Report issued in connection with Canadian Patent Application No. 2860416.
Apr. 4, 2019 First Examination Report issued in connection with corresponding European Patent Application 12862139.8.
Dec. 13, 2019 Examination Report issued in connection with corresponding Australian Patent Application No. 2018204726.
Jul. 7, 2020 Second Examination Report filed in connection with corresponding European Patent Application No. 12862139.8.
Jan. 20, 2020 Response to First Examination Report filed in connection with corresponding European Patent Application No. 12862139.8.

\* cited by examiner

SEQUENCE LISTING

<160> NUMBER OF SEQ ID NOS: 105

<210> SEQ ID NO 1
<211> LENGTH: 116
<212> TYPE: PRT
<213> ORGANISM: tomato leaf yellow curl virus

<400> SEQUENCE: 1

```
Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Glu Ala Gln Asn Ile Gln Asn
            100                 105                 110

Val Ser Lys Pro
        115
```

<210> SEQ ID NO 2
<211> LENGTH: 172
<212> TYPE: PRT
<213> ORGANISM: tomato bushy stunt virus

<400> SEQUENCE: 2

```
Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170
```

<210> SEQ ID NO 3
<211> LENGTH: 351
<212> TYPE: DNA

<213> ORGANISM: tomato leaf yellow curl virus

<400> SEQUENCE: 3

```
atgtgggatc cacttctaaa tgaatttcct gaatctgttc acggatttcg ttgtatgtta     60
gctattaaat atttgcagtc cgttgaggaa acttacgagc ccaatacatt gggccacgat    120
ttaattaggg atcttatatc tgttgtaagg gcccgtgact atgtcgaagc gaccaggcga    180
tataatcatt tccacgcccg cctcgaaggt tcgccgaagg ctgaacttcg acagcccata    240
cagcagccgt gctgctgtcc ccattgtcca aggcacaaac aagcgacgat catggacgta    300
caggcccatg taccggaagc ccagaatata cagaatgtat cgaagccctg a             351
```

<210> SEQ ID NO 4
<211> LENGTH: 519
<212> TYPE: DNA
<213> ORGANISM: tomato bushy stunt virus

<400> SEQUENCE: 4

```
atggaacgag ctatacaagg aaacgacgct agggaacaag ctaacagtga acgttgggat     60
ggaggatcag gaggtaccac ttctcccttc aaacttcctg acgaaagtcc gagttggact    120
gagtggcggc tacataacga tgagacgaat tcgaatcaag ataatcccct tggtttcaag    180
gaaagctggg gtttcgggaa agttgtattt aagagatatc tcagatacga caggacggaa    240
gcttcactgc acagagtcct tggatcttgg acgggagatt cggttaacta tgcagcatct    300
cgatttttcg gtttcgacca gatcggatgt acctatagta ttcggtttcg aggagttagt    360
atcaccgttt ctggagggtc gcgaactctt cagcatctct gtgagatggc aattcggtct    420
aagcaagaac tgctacagct tgccccaatc gaagtggaaa gtaatgtatc aagaggatgc    480
cctgaaggta ctgagacctt cgaaaaagaa agcgagtaa                           519
```

<210> SEQ ID NO 5
<211> LENGTH: 145
<212> TYPE: PRT
<213> ORGANISM: Sesamum indicum

<400> SEQUENCE: 5

```
Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser
145
```

<210> SEQ ID NO 6
<211> LENGTH: 438
<212> TYPE: DNA
<213> ORGANISM: Sesamum indicum

<400> SEQUENCE: 6

```
atggctgagc attatggtca acaacagcag accagggcgc ctcacctgca gctgcagccg      60
cgcgcccagc gggtagtgaa ggcggccacc gccgtgacag ccggcggctc gcttctcgtc     120
ctctctggcc tcactttagc cggaactgtt attgcgctca ccatcgccac tccgctgctt     180
gtgatcttta gccccgttct ggtgccggcg gtcataacca tttcttgct gggtgcgggt      240
tttctggcat ccggaggctt cggcgtggcg cgctgagtg tgctgtcgtg gatttacaga      300
tatctgacag ggaaacaccc gccgggggcg gatcagctgg aatcggcaaa gacgaagctg     360
gcgagcaagg cgcgagagat gaaggatagg gcagagcagt tctcgcagca gcctgttgcg     420
gggtctcaaa cttcttga                                                   438
```

<210> SEQ ID NO 7
<211> LENGTH: 506
<212> TYPE: PRT
<213> ORGANISM: Arabidopsis thaliana

<400> SEQUENCE: 7

```
Met Thr Ser Val Asn Val Lys Leu Leu Tyr Arg Tyr Val Leu Thr Asn
  1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
```

```
                    245                 250                 255
Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
        275                 280                 285

Arg Arg Ser Lys Tyr Lys Leu Val His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
    370                 375                 380

Val Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Ala Trp Gln Ile Ala Leu Gly Ser Gly Phe Lys Cys Asn Ser Ala Val
    450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
            500                 505

<210> SEQ ID NO 8
<211> LENGTH: 1842
<212> TYPE: DNA
<213> ORGANISM: Arabidopsis thaliana

<400> SEQUENCE: 8
gaattcggta ccccgggttc gaaatcgata agcttggatc tcgatcccgc gaaattaata      60
cgactcacta tagggagacc acaacggttt ccctctgggt aaatttctag ttttttctcct    120 tcatttttctt ggttaggacc cttttctctt tttattttt tgagctttga tctttcttta    180
aactgatcta ttttttaatt gattggttat ggtgtaaata ttacatagct ttaactgata    240
atctgattac tttatttcgt gtgtctatga tgatgatgat agttacagaa ccggcggccg    300
ccgaattcga taaacagagc aatgacgtcc gttaacgtta agctccttta ccgttacgtc    360
ttaaccaact ttttcaacct ctgtttgttc ccgttaacgg cgttcctcgc cggaaaagcc    420
tctcggctta ccataaacga tctccacaac ttcctttcct atctccaaca caaccttata    480
acagtaactt tactctttgc tttcactgtt tcggtttgg ttctctacat cgtaacccga    540
cccaatccgg tttatctcgt tgactactcg tgttaccttc caccaccgca tctcaaagtt    600
agtgtctcta aagtcatgga tatttttctac caaataagaa aagctgatac ttcttcacgg    660
```

```
aacgtggcat gtgatgatcc gtcctcgctc gatttcctga ggaagattca agagcgttca    720
ggtctaggtg atgagacgta cagtcctgag ggactcattc acgtaccacc gcggaagact    780
tttgcagcgt cacgtgaaga gacagagaag gttatcatcg gtgcgctcga aaatctattc    840
gagaacacca aagttaaccc tagagagatt ggtatacttg tggtgaactc aagcatgttt    900
aatccaactc cttcgctatc cgctatggtc gttaatactt tcaagctccg aagcaacatc    960
aaaagcttta atctaggagg aatgggttgt agtgctggtg ttattgccat tgatttggct   1020
aaagacttgt tgcatgttca taaaaacact tatgctcttg tggtgagcac tgagaacatc   1080
acacaaggca tttatgctgg agaaaataga tcaatgatgg ttagcaattg cttgtttcgt   1140
gttggtgggg ccgcgatttt gctctctaac aagtcgggag accggagacg tccaagtac    1200 aagctagttc acacggtccg aacgcatact ggagctgatg acaagtcttt tcgatgtgtg   1260
caacaagaag acgatgagag cggcaaaatc ggagtttgtc tgtcaaagga cataaccaat   1320
gttgcgggga caacttac gaaaaatata gcaacattgg gtccgttgat tcttcctta    1380 agcgaaaagt ttctttttt cgctaccttc gtcgccaaga aacttctaaa ggataaaatc   1440
aagcattact atgttccgga tttcaagctt gctgttgacc atttctgtat tcatgccgga   1500
ggcagagccg tgatcgatga gctagagaag aacttaggac tatcgccgat cgatgtggag   1560
gcatctagat caacgttaca tagatttggg aatacttcat ctagctcaat ttggtatgaa   1620
ttagcataca tagaggcaaa gggaagaatg aagaaaggga ataaagcttg gcagattgct   1680
ttaggatcag ggtttaagtg taatagtgcg gtttgggtgg ctctacgcaa tgtcaaggca   1740
tcggcaaata gtccttggca acattgcatc gatagatatc cggttaaaat tgattctgat   1800
ttgtcaaagt caaagactca tgtccaaaac ggtcggtcct aa                      1842

<210> SEQ ID NO 9
<211> LENGTH: 520
<212> TYPE: PRT
<213> ORGANISM: Arabidopsis thaliana

<400> SEQUENCE: 9

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160
```

Leu Ile Arg Thr Asp Phe Trp Phe Ser Ser Arg Ser Leu Arg Asp Trp
            165                 170                 175

Pro Leu Phe Met Cys Cys Ile Ser Leu Ser Ile Phe Pro Leu Ala Ala
        180                 185                 190

Phe Thr Val Glu Lys Leu Val Leu Gln Lys Tyr Ile Ser Glu Pro Val
    195                 200                 205

Val Ile Phe Leu His Ile Ile Thr Met Thr Glu Val Leu Tyr Pro
210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
            245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
        290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
            325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
            405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
            485                 490                 495

Cys Ile Phe Gly Gln Pro Met Cys Val Leu Leu Tyr Tyr His Asp Leu
        500                 505                 510

Met Asn Arg Lys Gly Ser Met Ser
        515                 520

<210> SEQ ID NO 10
<211> LENGTH: 1563
<212> TYPE: DNA
<213> ORGANISM: Arabidopsis thaliana

<400> SEQUENCE: 10
atggcgattt tggattctgc tggcgttact acggtgacgg agaacggtgg cggagagttc        60

```
gtcgatcttg ataggcttcg tcgacggaaa tcgagatcgg attcttctaa cggacttctt      120
ctctctggtt ccgataataa ttctccttcg gatgatgttg gagctcccgc cgacgttagg      180
gatcggattg attccgttgt taacgatgac gctcagggaa cagccaattt ggccggagat      240
aataacggtg gtggcgataa taacggtggt ggaagaggcg gcggagaagg aagaggaaac      300
gccgatgcta cgtttacgta tcgaccgtcg gttccagctc atcggagggc gagagagagt      360
ccacttagct ccgacgcaat cttcaaacag agccatgccg gattattcaa cctctgtgta      420
gtagttctta ttgctgtaaa cagtagactc atcatcgaaa atcttatgaa gtatggttgg      480
ttgatcagaa cggatttctg gtttagttca agatcgctgc gagattggcc gcttttcatg      540
tgttgtatat cccttcgat ctttcctttg gctgccttta cggttgagaa attggtactt      600
cagaaataca tatcagaacc tgttgtcatc tttcttcata ttattatcac catgacagag      660
gttttgtatc cagtttacgt caccctaagg tgtgattctg cttttttatc aggtgtcact      720
ttgatgctcc tcacttgcat tgtgtggcta aagttggttt cttatgctca tactagctat      780
gacataagat ccctagccaa tgcagctgat aaggccaatc ctgaagtctc ctactacgtt      840
agcttgaaga gcttggcata tttcatggtc gctcccacat tgtgttatca gccaagttat      900
ccacgttctg catgtatacg gaagggttgg gtggctcgtc aatttgcaaa actggtcata      960
ttcaccggat tcatgggatt tataatagaa caatatataa atcctattgt caggaactca     1020
aagcatcctt tgaaaggcga tcttctatat gctattgaaa gagtgttgaa gctttcagtt     1080
ccaaatttat atgtgtggct ctgcatgttc tactgcttct tccacctttg gttaaacata     1140
ttggcagagc ttctctgctt cggggatcgt gaattctaca aagattggtg gaatgcaaaa     1200
agtgtgggag attactggag aatgtggaat atgcctgttc ataaatggat ggttcgacat     1260
atatacttcc cgtgccttgcg cagcaagata ccaaagacac tcgccattat cattgctttc     1320
ctagtctctg cagtctttca tgagctatgc atcgcagttc cttgtcgtct cttcaagcta     1380
tgggcttttc ttgggattat gtttcaggtg ccttttggtct tcatcacaaa ctatctacag     1440
gaaaggtttg gctcaacggt ggggaacatg atcttctggt tcatcttctg catttttcgga     1500
caaccgatgt gtgtgcttct ttattaccac gacctgatga accgaaaagg atcgatgtca     1560
tga                                                                    1563
```

<210> SEQ ID NO 11
<211> LENGTH: 383
<212> TYPE: PRT
<213> ORGANISM: Arabidopsis thaliana

<400> SEQUENCE: 11

```
Met Gly Ala Gly Gly Asn Met Ser Leu Val Thr Ser Lys Thr Gly Glu
1               5                   10                  15

Lys Lys Asn Pro Leu Glu Lys Val Pro Thr Ser Lys Pro Pro Phe Thr
            20                  25                  30

Val Gly Asp Ile Lys Lys Ala Ile Pro Pro His Cys Phe Gln Arg Ser
        35                  40                  45

Leu Val Arg Ser Phe Ser Tyr Val Val Tyr Asp Leu Leu Val Ser
    50                  55                  60

Val Phe Tyr Tyr Ile Ala Thr Thr Tyr Phe His Leu Leu Pro Ser Pro
65                  70                  75                  80

Tyr Cys Tyr Leu Ala Trp Pro Ile Tyr Trp Ile Cys Gln Gly Cys Val
                85                  90                  95

Cys Thr Gly Ile Trp Val Ile Ala His Glu Cys Gly His His Ala Phe
```

| | | | 100 | | | | 105 | | | | 110 | |
|---|---|---|---|---|---|---|---|---|---|---|---|---|
| Ser | Asp | Tyr | Gln | Trp | Val | Asp | Asp | Thr | Val | Gly | Leu | Ile | Leu | His | Ser |
| | | | 115 | | | | 120 | | | | 125 | |
| Ala | Leu | Met | Val | Pro | Tyr | Phe | Ser | Trp | Lys | Tyr | Ser | His | Arg | Arg | His |
| | | | 130 | | | | 135 | | | | 140 | |
| His | Ser | Asn | Thr | Gly | Ser | Leu | Glu | Arg | Asp | Glu | Val | Phe | Val | Pro | Lys |
| 145 | | | | 150 | | | | 155 | | | | 160 |
| Pro | Lys | Ser | Gln | Leu | Gly | Trp | Tyr | Ser | Lys | Tyr | Leu | Asn | Asn | Pro | Pro |
| | | | 165 | | | | 170 | | | | 175 | |
| Gly | Arg | Val | Ile | Ser | Leu | Thr | Ile | Thr | Leu | Thr | Leu | Gly | Trp | Pro | Leu |
| | | | 180 | | | | 185 | | | | 190 | |
| Tyr | Leu | Ala | Phe | Asn | Val | Ser | Gly | Arg | His | Tyr | Asp | Arg | Phe | Ala | Cys |
| | | | 195 | | | | 200 | | | | 205 | |
| His | Tyr | Asp | Pro | Tyr | Gly | Pro | Ile | Tyr | Asn | Asp | Arg | Glu | Arg | Leu | Gln |
| | | | 210 | | | | 215 | | | | 220 | |
| Ile | Phe | Leu | Ser | Asp | Ala | Gly | Val | Ile | Gly | Ala | Gly | Tyr | Leu | Leu | Tyr |
| 225 | | | | 230 | | | | 235 | | | | 240 |
| Arg | Ile | Ala | Leu | Val | Lys | Gly | Leu | Ala | Trp | Leu | Val | Cys | Met | Tyr | Gly |
| | | | 245 | | | | 250 | | | | 255 | |
| Val | Pro | Leu | Leu | Ile | Val | Asn | Gly | Phe | Leu | Val | Leu | Ile | Thr | Tyr | Leu |
| | | | 260 | | | | 265 | | | | 270 | |
| Gln | His | Thr | His | Pro | Ser | Leu | Pro | His | Tyr | Asp | Ser | Ser | Glu | Trp | Asp |
| | | | 275 | | | | 280 | | | | 285 | |
| Trp | Leu | Arg | Gly | Ala | Leu | Ala | Thr | Val | Asp | Arg | Asp | Tyr | Gly | Ile | Leu |
| | | | 290 | | | | 295 | | | | 300 | |
| Asn | Lys | Val | Phe | His | Asn | Ile | Thr | Asp | Thr | His | Val | Val | His | His | Leu |
| 305 | | | | 310 | | | | 315 | | | | 320 |
| Phe | Ser | Thr | Met | Pro | His | Tyr | Asn | Ala | Met | Glu | Ala | Thr | Lys | Ala | Val |
| | | | 325 | | | | 330 | | | | 335 | |
| Lys | Pro | Leu | Leu | Gly | Asp | Tyr | Tyr | Gln | Phe | Asp | Gly | Thr | Pro | Val | Phe |
| | | | 340 | | | | 345 | | | | 350 | |
| Lys | Ala | Met | Trp | Arg | Glu | Ala | Lys | Glu | Cys | Ile | Tyr | Val | Glu | Lys | Asp |
| | | | 355 | | | | 360 | | | | 365 | |
| Glu | Ala | Ser | Gln | Gly | Lys | Gly | Val | Phe | Trp | Tyr | Lys | Asn | Lys | Phe |
| | | | 370 | | | | 375 | | | | 380 | |

<210> SEQ ID NO 12
<211> LENGTH: 661
<212> TYPE: DNA
<213> ORGANISM: Artificial Sequence
<220> FEATURE:
<223> OTHER INFORMATION: Nucleotide sequence encoding dsRNA hairpin targetting N. benthamiana FAD2

<400> SEQUENCE: 12

```
tagaacagat ggtgcacgac gtgagtatcg gtgatgttgt ggaagacctt gtttagaatg      60
ccatagtctc tgtcgacggt tgccaaagct cccttagcc aatcccattc ggatgaatcg     120
tagtgaggca atgacgggtg agtgtgctgc aaataagtga tcaagacgag gaagccgttc     180
acgattagga gtggtacgcc atacatacac acgagccaag ctagcccttt taccaaggca     240
atacgatata gtagataacc agctccaata actccagcat cagaaaggaa gatctgtagc     300
ctctcgcggt cattgtagat tgggccgtaa gggtcatagt gacatgcaaa gcgatcataa     360
tgtcggccag aaacattgaa agccaagtac aaaggccagc caagagtaag ggtgatcgta     420
agtgaaataa cccggcctgg tggattgttc aagtacttgg aataccatcc gagttgtgat     480
```
ttcggcttag gcacaaaaac ctcatcgcgc tcgagtgagc cagtgttgga gtggtggcga    540
cgatgactat atttccaaga gaagtagggc accatcagag cagagtggag gataagcccg    600
acagtgtcat caacccactg gtagtcacta aaggcatggt ggccacattc gtgcgcaata    660
a                                                                   661

<210> SEQ ID NO 13
<211> LENGTH: 26
<212> TYPE: DNA
<213> ORGANISM: Artificial Sequence
<220> FEATURE:
<223> OTHER INFORMATION: forward primer

<400> SEQUENCE: 13
tcattgcgca cgaatgtggc caccat                                         26

<210> SEQ ID NO 14
<211> LENGTH: 22
<212> TYPE: DNA
<213> ORGANISM: Artificial Sequence
<220> FEATURE:
<223> OTHER INFORMATION: reverse primer

<400> SEQUENCE: 14
cgagaacaga tggtgcacga cg                                             22

<210> SEQ ID NO 15
<211> LENGTH: 32
<212> TYPE: DNA
<213> ORGANISM: Artificial Sequence
<220> FEATURE:
<223> OTHER INFORMATION: forward primer

<400> SEQUENCE: 15
aacgcgttcg acgaattaat tccaatccca ca                                  32

<210> SEQ ID NO 16
<211> LENGTH: 26
<212> TYPE: DNA
<213> ORGANISM: Artificial Sequence
<220> FEATURE:
<223> OTHER INFORMATION: reverse primer

<400> SEQUENCE: 16
acgcgtctgc tgagcctcga catgtt                                         26

<210> SEQ ID NO 17
<211> LENGTH: 25
<212> TYPE: DNA
<213> ORGANISM: Artificial Sequence
<220> FEATURE:
<223> OTHER INFORMATION: forward primer

<400> SEQUENCE: 17
tttatgggag ctggtggtaa tatgt                                          25

<210> SEQ ID NO 18
<211> LENGTH: 28
<212> TYPE: DNA
<213> ORGANISM: Artificial Sequence
<220> FEATURE:
<223> OTHER INFORMATION: reverse primer

<400> SEQUENCE: 18

```
ccctcagaat tgttttttgt accagaaa                                         28
```

<210> SEQ ID NO 19
<211> LENGTH: 30
<212> TYPE: DNA
<213> ORGANISM: Artificial Sequence
<220> FEATURE:
<223> OTHER INFORMATION: forward primer

<400> SEQUENCE: 19

```
ttactagtat ggatgctgca catggtatct                                       30
```

<210> SEQ ID NO 20
<211> LENGTH: 36
<212> TYPE: DNA
<213> ORGANISM: Artificial Sequence
<220> FEATURE:
<223> OTHER INFORMATION: reverse primer

<400> SEQUENCE: 20

```
ttactagttc aatcatccat gaaggaatat gcagaa                                36
```

<210> SEQ ID NO 21
<211> LENGTH: 468
<212> TYPE: PRT
<213> ORGANISM: Gossypium hirsutum

<400> SEQUENCE: 21

```
Met Asp Ala Ala His Gly Ile Leu Gly Lys His Ser Val Pro Pro
1               5                   10                  15

Ser Pro Lys Asn Met Ser Pro Ser Leu Pro Lys Asn Met Ser Pro Ser
            20                  25                  30

Phe Met Glu Thr Thr Ala Arg Leu Phe Val Thr Lys Phe Phe Gln Gln
        35                  40                  45

Tyr Ile Ser Met Gly Cys Val Ile Phe Leu Glu Glu Gly Gly Arg Ile
    50                  55                  60

Phe Thr Phe Lys Gly Asn Met Glu Lys Cys Pro Leu Lys Thr Val Leu
65                  70                  75                  80

Lys Val His Asn Pro Gln Phe Tyr Trp Arg Ile Met Lys Glu Ala Asp
                85                  90                  95

Ile Gly Leu Ala Asp Ala Tyr Ile His Gly Asp Phe Ser Phe Leu Asp
            100                 105                 110

Glu Asn Glu Gly Leu Leu Asn Leu Phe Arg Ile Leu Val Ala Asn Lys
        115                 120                 125

Glu Asn Ser Ala Ala Ser Gly Ser Thr Lys Arg Arg Thr Trp Trp Ser
    130                 135                 140

Pro Ala Leu Leu Thr Ala Ser Ile Ser Ser Ala Lys Tyr Phe Val Lys
145                 150                 155                 160

His Leu Leu Arg Gln Asn Thr Ile Thr Gln Ala Arg Arg Asn Ile Ser
                165                 170                 175

Arg His Tyr Asp Leu Ser Asn Glu Leu Phe Ser Leu Tyr Leu Gly Lys
            180                 185                 190

Met Met Gln Tyr Ser Ser Gly Val Phe Arg Thr Gly Glu Glu His Leu
        195                 200                 205

Asp Val Ala Gln Arg Arg Lys Ile Ser Ser Leu Ile Glu Lys Thr Arg
    210                 215                 220

Ile Glu Lys Trp His Glu Val Leu Asp Ile Gly Cys Gly Trp Gly Ser
225                 230                 235                 240
```

```
Leu Ala Ile Glu Thr Val Lys Arg Thr Gly Cys Lys Tyr Thr Gly Ile
                245                 250                 255

Thr Leu Ser Glu Gln Gln Leu Lys Tyr Ala Gln Glu Lys Val Lys Glu
            260                 265                 270

Ala Gly Leu Glu Asp Asn Ile Lys Ile Leu Leu Cys Asp Tyr Arg Gln
        275                 280                 285

Leu Pro Lys Glu His Gln Phe Asp Arg Ile Ile Ser Val Glu Met Val
    290                 295                 300

Glu His Val Gly Glu Tyr Ile Glu Glu Phe Tyr Arg Cys Cys Asp
305                 310                 315                 320

Gln Leu Leu Lys Glu Asp Gly Leu Phe Val Leu Gln Phe Ile Ser Ile
                325                 330                 335

Pro Glu Glu Leu Ser Lys Glu Ile Gln Gln Thr Ala Gly Phe Leu Lys
            340                 345                 350

Glu Tyr Ile Phe Pro Gly Gly Thr Leu Leu Ser Leu Asp Arg Asn Leu
        355                 360                 365

Ser Ala Met Ala Ala Thr Arg Phe Ser Val Glu His Val Glu Asn
370                 375                 380

Ile Gly Met Ser Tyr Tyr His Thr Leu Arg Trp Trp Arg Lys Leu Phe
385                 390                 395                 400

Leu Lys Asn Thr Ser Lys Val Leu Ala Leu Gly Phe Asp Glu Lys Phe
                405                 410                 415

Met Arg Thr Trp Glu Tyr Tyr Phe Asp Tyr Cys Ala Ala Gly Phe Lys
            420                 425                 430

Thr Gly Thr Leu Ile Asp Tyr Gln Val Val Phe Ser Arg Ala Gly Asn
        435                 440                 445

Phe Gly Thr Leu Gly Asp Pro Tyr Lys Gly Phe Pro Ser Ala Tyr Ser
    450                 455                 460

Phe Met Asp Asp
465

<210> SEQ ID NO 22
<211> LENGTH: 460
<212> TYPE: PRT
<213> ORGANISM: Gossypium hirsutum

<400> SEQUENCE: 22

Met Asp Ala Ala His Gly Ile Leu Gly Lys His Ser Ser Val Leu His
1               5                   10                  15

Ser Pro Lys Ser Met Ser Pro Ser Phe Met Glu Thr Thr Ala Arg Leu
            20                  25                  30

Phe Val Thr Lys Phe Phe Gln Gln Tyr Ile Ser Met Gly Cys Val Ile
        35                  40                  45

Phe Leu Glu Glu Gly Gly Arg Ile Phe Thr Phe Lys Gly Asn Met Glu
    50                  55                  60

Lys Cys Pro Leu Lys Thr Val Leu Lys Val His Asn Pro Gln Phe Tyr
65                  70                  75                  80

Trp Arg Ile Met Lys Glu Ala Asp Ile Gly Leu Ala Asp Ala Tyr Ile
                85                  90                  95

His Gly Asp Phe Ser Phe Leu Asp Glu Thr Glu Gly Leu Leu Asn Leu
            100                 105                 110

Phe Arg Ile Leu Val Ala Asn Lys Glu Asn Ser Ala Ala Ser Gly Ser
        115                 120                 125

Asn Lys Arg Arg Thr Trp Trp Ser Pro Ala Leu Leu Thr Ala Ser Ile
    130                 135                 140
```

Ser Ser Ala Lys Tyr Phe Val Lys His Leu Leu Arg Gln Asn Thr Ile
145                 150                 155                 160

Thr Gln Ala Arg Arg Asn Ile Ser Arg His Tyr Asp Leu Ser Asn Glu
            165                 170                 175

Leu Phe Thr Leu Tyr Leu Gly Lys Met Met Gln Tyr Ser Ser Gly Val
        180                 185                 190

Phe Arg Thr Gly Glu Glu His Leu Asp Val Ala Gln Arg Arg Lys Ile
    195                 200                 205

Ser Ser Leu Ile Glu Lys Ala Arg Ile Glu Lys Arg His Glu Val Leu
210                 215                 220

Asp Ile Gly Cys Gly Trp Gly Ser Leu Ala Ile Glu Thr Val Lys Arg
225                 230                 235                 240

Thr Gly Cys Lys Tyr Thr Gly Ile Thr Leu Ser Glu Gln Gln Leu Lys
            245                 250                 255

Tyr Ala Gln Glu Lys Val Lys Glu Ala Gly Leu Gln Asp Asn Ile Lys
        260                 265                 270

Ile Leu Leu Cys Asp Tyr Arg Gln Leu Pro Lys Glu His Gln Phe Asp
    275                 280                 285

Arg Ile Ile Ser Val Glu Met Val Glu His Val Gly Glu Glu Tyr Ile
290                 295                 300

Glu Glu Phe Tyr Arg Cys Cys Asp Gln Leu Leu Lys Glu Asp Gly Leu
305                 310                 315                 320

Phe Val Leu Gln Phe Ile Ser Ile Pro Glu Glu Leu Ser Lys Glu Ile
            325                 330                 335

Gln Gln Thr Ala Gly Phe Leu Lys Glu Tyr Ile Phe Pro Gly Gly Thr
        340                 345                 350

Leu Leu Ser Leu Asp Arg Asn Leu Ser Ala Met Ala Ala Ala Thr Arg
    355                 360                 365

Phe Ser Val Glu His Val Glu Asn Ile Gly Met Ser Tyr Tyr His Thr
370                 375                 380

Leu Arg Trp Trp Arg Lys Leu Phe Leu Glu Asn Thr Ser Lys Val Leu
385                 390                 395                 400

Ala Leu Gly Phe Asp Glu Lys Phe Met Arg Thr Trp Glu Tyr Tyr Phe
            405                 410                 415

Asp Tyr Cys Ala Ala Gly Phe Lys Thr Gly Thr Leu Ile Asp Tyr Gln
        420                 425                 430

Val Val Phe Ser Arg Ala Gly Asn Phe Gly Thr Leu Gly Asp Pro Tyr
    435                 440                 445

Lys Gly Phe Pro Ser Ala Tyr Ser Phe Met Asp Asp
    450                 455                 460

<210> SEQ ID NO 23
<211> LENGTH: 456
<212> TYPE: PRT
<213> ORGANISM: Gossypium hirsutum
<220> FEATURE:
<221> NAME/KEY: misc_feature
<222> LOCATION: (232)..(232)
<223> OTHER INFORMATION: Xaa can be any naturally occurring amino acid

<400> SEQUENCE: 23

Met Ile Ala Ala Asn Gly Leu Leu Gly Lys Ser Cys Asn Ile Leu Ser
1               5                   10                  15

Asn Pro Lys His Met Val Pro Ser Leu Met Glu Thr Gly Ala Arg Leu
            20                  25                  30

Phe Val Thr Arg Phe Leu Ser His Phe Ile Ser Thr Gly Cys Val Ile
            35                  40                  45

Leu Leu Glu Glu Gly Gly Thr Met Phe Thr Phe Glu Gly Thr Ser Asn
 50                  55                  60

Lys Cys Ser Leu Lys Thr Val Ile Lys Val His Ser Pro His Phe Tyr
 65                  70                  75                  80

Trp Lys Val Met Thr Glu Ala Asp Leu Gly Leu Ala Asp Ser Tyr Ile
                 85                  90                  95

Asn Gly Asp Phe Ser Phe Val Asp Lys Lys Asp Gly Leu Leu Asn Leu
            100                 105                 110

Val Met Ile Leu Ile Ala Asn Arg Asp Leu Ile Ser Ser Asn Ser Lys
        115                 120                 125

Leu Ser Lys Lys Arg Gly Trp Trp Thr Pro Leu Leu Phe Thr Ala Gly
130                 135                 140

Leu Thr Ser Ala Lys Tyr Phe Phe Lys His Val Leu Arg Gln Asn Thr
145                 150                 155                 160

Leu Thr Gln Ala Arg Arg Asn Ile Ser Arg His Tyr Asp Leu Ser Asn
                165                 170                 175

Asp Leu Phe Ala Leu Phe Leu Asp Glu Thr Met Thr Tyr Ser Cys Ala
            180                 185                 190

Val Phe Lys Thr Glu Asp Glu Asp Leu Lys Asp Ala Gln His Arg Lys
        195                 200                 205

Ile Ser Leu Leu Ile Glu Lys Ala Arg Ile Asp Ser Lys His Glu Ile
210                 215                 220

Leu Glu Ile Gly Cys Gly Trp Xaa Ser Leu Ala Ile Glu Val Val Lys
225                 230                 235                 240

Arg Thr Gly Cys Lys Tyr Thr Gly Ile Thr Leu Ser Glu Glu Gln Leu
                245                 250                 255

Lys Leu Ala Glu Lys Arg Val Lys Glu Ala Gly Leu Gln Glu Asn Ile
            260                 265                 270

Arg Phe Gln Leu Cys Asp Tyr Arg Gln Leu Pro Ser Thr Tyr Lys Tyr
        275                 280                 285

Asp Arg Ile Ile Ser Cys Glu Met Ile Glu Ala Val Gly His Glu Tyr
290                 295                 300

Met Glu Asp Phe Phe Gly Cys Cys Glu Ser Val Leu Ala Asp Asp Gly
305                 310                 315                 320

Leu Leu Val Leu Gln Phe Ile Ser Ile Pro Glu Glu Arg Tyr Asn Glu
                325                 330                 335

Tyr Arg Arg Ser Ser Asp Phe Ile Lys Glu Tyr Ile Phe Pro Gly Gly
            340                 345                 350

Cys Leu Pro Ser Leu Ala Arg Ile Thr Thr Ala Met Asn Ala Ala Ser
        355                 360                 365

Lys Leu Cys Val Glu His Val Glu Asn Ile Gly Leu His Tyr Tyr Gln
370                 375                 380

Thr Leu Arg Tyr Trp Arg Lys Asn Phe Leu Glu Lys Gln Ser Lys Ile
385                 390                 395                 400

His Ala Leu Gly Phe Asn Asp Lys Phe Ile Arg Thr Trp Glu Tyr Tyr
                405                 410                 415

Phe Asp Tyr Cys Ala Ala Gly Phe Lys Ser Asn Thr Leu Gly Asn Tyr
            420                 425                 430

Gln Val Val Phe Ser Arg Pro Gly Asn Val Val Ala Leu Gly Asn Pro
        435                 440                 445

Tyr Lys Asp Phe Pro Ser Ala Ser

```
           450                 455

<210> SEQ ID NO 24
<211> LENGTH: 447
<212> TYPE: PRT
<213> ORGANISM: Oryza sativa

<400> SEQUENCE: 24

Met Ala Ala Ala Gln Ser Leu Leu Gly Asn Lys Ile Asp Pro Leu Thr
1               5                   10                  15

Asn Pro Lys Gln Met Val Leu Ser Trp Thr Glu Thr Gly Ala Arg Leu
            20                  25                  30

Leu Val Leu Arg Phe Leu Lys Gln Tyr Ile Ser Val Gly Asn Leu Ile
        35                  40                  45

Leu Phe Glu Glu Gly Gly Thr Met Phe Ser Phe Gly Glu Ala Cys Glu
    50                  55                  60

Lys Cys Asn Lys Lys Ser Val Leu Gln Val Gln Asp Pro Leu Phe Tyr
65                  70                  75                  80

Trp Gln Val Ala Thr Glu Ala Asp Leu Gly Leu Ala Asp Ala Tyr Ile
                85                  90                  95

Asn Gly Cys Phe Ser Phe Val Asn Lys Arg Glu Gly Leu Leu Asn Leu
            100                 105                 110

Phe Leu Ile Leu Ile Ala Ser Arg Asp Ala His Arg Ser Ser Cys Arg
        115                 120                 125

Asn Ser Ser Arg Arg Gly Trp Trp Thr Pro Leu Leu Phe Thr Ala Gly
    130                 135                 140

Val Ala Ser Ala Lys Tyr Phe Leu Arg His Ile Ser Arg Lys Asn Ser
145                 150                 155                 160

Val Thr Gln Thr Arg Gln Asn Val Ser Gln His Tyr Asp Leu Ser Asn
                165                 170                 175

Asp Phe Phe Ser Leu Phe Leu Asp Lys Ser Met Thr Tyr Ser Ser Ala
            180                 185                 190

Ile Phe Lys Asp Glu Glu Ser Leu Glu Glu Ala Gln Leu Arg Lys
        195                 200                 205

Ile Asn Leu Leu Ile His Lys Ala Lys Val Gly Gln Asp Asp Glu Val
    210                 215                 220

Leu Glu Ile Gly Ser Gly Trp Gly Ser Leu Ala Met Glu Val Val Lys
225                 230                 235                 240

Gln Thr Gly Cys Lys Tyr Thr Gly Val Thr Gln Ser Val Glu Gln Leu
                245                 250                 255

Lys Tyr Ala Gln Arg Arg Val Lys Glu Ala Gly Leu Glu Asp Arg Ile
            260                 265                 270

Thr Phe Leu Leu Cys Asp Tyr Arg Glu Ile Pro Cys His Lys Tyr Asp
        275                 280                 285

Arg Ile Ile Cys Cys Glu Met Ile Glu Val Gly His Glu Tyr Met
    290                 295                 300

Asp Glu Phe Phe Gly Cys Cys Glu Ser Leu Leu Ala Glu Asn Gly Ile
305                 310                 315                 320

Phe Val Thr Gln Phe Ile Ser Ile Pro Glu Glu Arg Tyr Asp Glu Tyr
                325                 330                 335

Arg Arg Ser Ser Asp Phe Ile Lys Glu Tyr Ile Phe Pro Gly Gly Cys
            340                 345                 350

Leu Pro Ser Leu Thr Arg Ile Ser Ala Met Ser Ala Ala Ser Arg
        355                 360                 365
```

Leu Cys Ile Glu His Val Glu Asn Ile Gly Tyr His Tyr Tyr Thr Thr
370 375 380

Leu Ile Arg Trp Arg Asp Asn Phe Met Ala Asn Lys Asp Lys Ile Leu
385 390 395 400

Ala Leu Gly Phe Asp Glu Lys Phe Ile Arg Thr Trp Glu Tyr Tyr Phe
405 410 415

Ile Tyr Cys Ala Ala Gly Phe Lys Ser Arg Thr Leu Gly Asp Tyr Gln
420 425 430

Ile Val Phe Ser Arg Pro Gly Asn Thr Lys Met Gly Ser Gly Phe
435 440 445

<210> SEQ ID NO 25
<211> LENGTH: 456
<212> TYPE: PRT
<213> ORGANISM: Arabidopsis thaliana

<400> SEQUENCE: 25

Met Ala Ala Arg Gly Leu Leu Gly Lys Glu Thr Ala Leu Leu Asn
1 5 10 15

Asn Pro Arg His Met Val Pro Ser Leu Thr Glu Thr Gly Ala Arg Leu
20 25 30

Phe Val Thr Arg Phe Leu Gly Gln Phe Ile Ser Thr Gly Ser Val Thr
35 40 45

Ile Leu Glu Glu Gly Gly Thr Met Phe Thr Phe Gly Gly Lys Asp Ser
50 55 60

Thr Cys Pro Leu Lys Ser Ile Leu Lys Ile His Ser Pro Gln Phe Tyr
65 70 75 80

Trp Lys Val Met Thr Gln Ala Asp Leu Gly Leu Ala Asp Ala Tyr Ile
85 90 95

Asn Gly Asp Phe Ser Phe Val Asp Lys Glu Ser Gly Leu Leu Asn Leu
100 105 110

Ile Met Ile Leu Ile Ala Asn Arg Asp Thr Lys Ser Asn Leu Thr Lys
115 120 125

Lys Arg Gly Trp Trp Thr Pro Met Phe Leu Thr Ala Gly Leu Ala Ser
130 135 140

Ala Lys Tyr Phe Leu Lys His Val Ser Arg Gln Asn Thr Leu Thr Gln
145 150 155 160

Ala Arg Arg Asn Ile Ser Arg His Tyr Asp Leu Ser Asn Glu Leu Phe
165 170 175

Gly Leu Phe Leu Asp Asp Thr Met Thr Tyr Ser Ser Ala Val Phe Lys
180 185 190

Ser Asp Asp Glu Asp Leu Arg Thr Ala Gln Met Arg Lys Ile Ser Leu
195 200 205

Leu Ile Asp Lys Ala Arg Ile Glu Lys Asp His Glu Val Leu Glu Ile
210 215 220

Gly Cys Gly Trp Gly Thr Leu Ala Ile Glu Val Val Arg Arg Thr Gly
225 230 235 240

Cys Lys Tyr Thr Gly Ile Thr Leu Ser Ile Glu Gln Leu Lys Tyr Ala
245 250 255

Glu Glu Lys Val Lys Glu Ala Gly Leu Gln Asp Arg Ile Thr Phe Glu
260 265 270

Leu Arg Asp Tyr Arg Gln Leu Ser Asp Ala His Lys Tyr Asp Arg Ile
275 280 285

Ile Ser Cys Glu Met Leu Glu Ala Val Gly His Glu Phe Met Glu Met
290 295 300

```
Phe Phe Ser Arg Cys Glu Ala Leu Ala Glu Asp Gly Leu Met Val
305                 310                 315                 320

Leu Gln Phe Ile Ser Thr Pro Glu Glu Arg Tyr Asn Glu Tyr Arg Leu
            325                 330                 335

Ser Ser Asp Phe Ile Lys Glu Tyr Ile Phe Pro Gly Ala Cys Val Pro
            340                 345                 350

Ser Leu Ala Lys Val Thr Ser Ala Met Ser Ser Ser Arg Leu Cys
        355                 360                 365

Ile Glu His Val Glu Asn Ile Gly Ile His Tyr Tyr Gln Thr Leu Arg
        370                 375                 380

Leu Trp Arg Lys Asn Phe Leu Glu Arg Gln Lys Gln Ile Met Ala Leu
385                 390                 395                 400

Gly Phe Asp Asp Lys Phe Val Arg Thr Trp Glu Tyr Tyr Phe Asp Tyr
                405                 410                 415

Cys Ala Ala Gly Phe Lys Thr Arg Thr Leu Gly Asp Tyr Gln Leu Val
            420                 425                 430

Phe Ser Arg Pro Gly Asn Val Ala Ala Phe Ala Asp Ser Tyr Arg Gly
            435                 440                 445

Phe Pro Ser Ala Tyr Cys Val Ser
        450                 455

<210> SEQ ID NO 26
<211> LENGTH: 460
<212> TYPE: PRT
<213> ORGANISM: Sterculia foetida

<400> SEQUENCE: 26

Met Asp Ala Ala His Arg Ile Leu Gly Lys His Phe Ser Val Leu His
1               5                   10                  15

Ser Pro Arg Gln Met Ser Pro Ser Phe Met Glu Thr Ala Arg Leu
            20                  25                  30

Leu Val Thr Lys Phe Phe His Gln Tyr Ile Gln Val Gly Cys Val Ile
        35                  40                  45

Ile Ile Glu Glu Gly Gly Arg Val Tyr Thr Phe Lys Gly Ser Met Glu
    50                  55                  60

Asn Cys Ser Leu Lys Thr Ala Leu Lys Val His Asn Pro Gln Phe Tyr
65              70                  75                  80

Trp Arg Ile Met Lys Glu Ala Asp Ile Gly Leu Ala Asp Ala Tyr Ile
                85                  90                  95

Gln Gly Asp Phe Ser Phe Val Ala Lys Asp Asp Gly Leu Leu Asn Leu
            100                 105                 110

Phe Arg Ile Leu Ile Ala Asn Lys Glu Leu Asn Ser Ala Ser Gly Gln
        115                 120                 125

Asn Lys Arg Arg Thr Trp Leu Ser Pro Ala Leu Phe Thr Ala Gly Ile
    130                 135                 140

Ser Ser Ala Lys Tyr Phe Leu Lys His Tyr Met Arg Gln Asn Thr Val
145                 150                 155                 160

Thr Gln Ala Arg Arg Asn Ile Ser Arg His Tyr Asp Leu Ser Asn Glu
                165                 170                 175

Leu Phe Thr Leu Tyr Leu Gly Glu Met Met Gln Tyr Ser Ser Gly Ile
            180                 185                 190

Phe Lys Thr Gly Glu Glu His Leu Asp Val Ala Gln Arg Arg Lys Ile
        195                 200                 205

Ser Ser Leu Ile Asp Lys Ser Arg Ile Glu Lys Trp His Glu Val Leu
```

```
            210                 215                 220
Asp Ile Gly Cys Gly Trp Gly Ser Leu Ala Met Glu Val Val Lys Arg
225                 230                 235                 240

Thr Gly Cys Lys Tyr Thr Gly Ile Thr Leu Ser Glu Gln Gln Leu Lys
                245                 250                 255

Tyr Ala Glu Glu Lys Val Lys Glu Ala Gly Leu Gln Gly Asn Ile Lys
                    260                 265                 270

Phe Leu Leu Cys Asp Tyr Arg Gln Leu Pro Lys Thr Phe Lys Tyr Asp
                275                 280                 285

Arg Ile Ile Ser Val Glu Met Val Glu His Val Gly Glu Glu Tyr Ile
        290                 295                 300

Glu Glu Phe Phe Arg Cys Cys Asp Ser Leu Leu Ala Glu Asn Gly Leu
305                 310                 315                 320

Phe Val Leu Gln Phe Ile Ser Ile Pro Glu Ile Leu Ser Lys Glu Ile
                        325                 330                 335

Gln Gln Thr Ala Gly Phe Leu Lys Glu Tyr Ile Phe Pro Gly Gly Thr
                340                 345                 350

Leu Leu Ser Leu Asp Arg Thr Leu Ser Ala Met Ala Ala Ala Ser Arg
                355                 360                 365

Phe Ser Val Glu His Val Glu Asn Ile Gly Ile Ser Tyr Tyr His Thr
            370                 375                 380

Leu Arg Trp Trp Arg Lys Asn Phe Leu Ala Asn Glu Ser Lys Val Leu
385                 390                 395                 400

Ala Leu Gly Phe Asp Glu Lys Phe Met Arg Thr Trp Glu Tyr Tyr Phe
                    405                 410                 415

Asp Tyr Cys Ala Ala Gly Phe Lys Thr Gly Thr Leu Ile Asp Tyr Gln
                420                 425                 430

Val Val Phe Ser Arg Ala Gly Asn Phe Ala Ala Leu Gly Asp Pro Tyr
                435                 440                 445

Ile Gly Phe Pro Ser Ala Tyr Ser Tyr Ser Asp Asn
        450                 455                 460

<210> SEQ ID NO 27
<211> LENGTH: 446
<212> TYPE: PRT
<213> ORGANISM: Medicago truncatula

<400> SEQUENCE: 27

Met Asp Ala Ala Tyr Asp Ile Leu Gly Arg Ile Cys Ser Leu Gln Arg
1               5                   10                  15

Asn Leu Lys Tyr Ile Val Pro Ser Trp Thr Glu Val Gly Ala Arg Leu
                20                  25                  30

Phe Val Thr Arg Phe Leu Ser Ala Tyr Ile Thr Thr Gly Cys Leu Met
            35                  40                  45

Leu Leu Glu Asp Gly Gly Thr Ile Phe Thr Phe Glu Gly Ser Lys Lys
50                  55                  60

Lys Cys Ser Leu Lys Ser Val Leu Arg Ile His Asn Pro Gln Phe Tyr
65                  70                  75                  80

Trp Lys Ile Leu Ile Ala Asn Arg Asp Phe Asn Leu Ser Asn Ser Thr
                    85                  90                  95

Leu Lys Asn Arg Gly Trp Trp Thr Pro Val Phe Phe Thr Ala Gly Leu
                100                 105                 110

Ala Ser Ala Lys Phe Phe Ile Lys His Val Ser Arg Lys Asn Thr Val
            115                 120                 125
```

Thr Gln Ala Arg Arg Asn Ile Ser Met His Tyr Asp Leu Ser Asn Asp
130                 135                 140

Leu Phe Ala Cys Phe Leu Asp Glu Lys Met Gln Tyr Ser Cys Gly Val
145                 150                 155                 160

Phe Lys Asp Glu Tyr Glu Asp Leu Lys Asp Ala Gln Lys Arg Lys Ile
                165                 170                 175

Ser Ile Leu Ile Glu Lys Ala Gln Ile Asp Arg Lys His Glu Ile Leu
            180                 185                 190

Asp Ile Gly Cys Gly Trp Gly Phe Ala Ile Glu Val Val Lys Lys
        195                 200                 205

Val Gly Cys Lys Tyr Thr Gly Ile Thr Leu Ser Glu Glu Gln Leu Lys
210                 215                 220

Tyr Ala Glu Asn Lys Val Lys Asp Ala Gly Leu Gln Glu His Ile Thr
225                 230                 235                 240

Phe Leu Leu Cys Glu Tyr Arg Gln Leu Ser Lys Thr Lys Lys Tyr Asp
                245                 250                 255

Arg Ile Val Ser Cys Glu Met Ile Glu Ala Val Gly His Glu Tyr Met
            260                 265                 270

Glu Glu Phe Phe Gly Cys Cys Asp Ser Val Leu Ala Asp Asp Gly Leu
        275                 280                 285

Leu Val Leu Gln Phe Thr Ser Ile Pro Asp Glu Arg Tyr Asp Ala Tyr
290                 295                 300

Arg Arg Ser Ser Glu Phe Ile Lys Glu Tyr Ile Phe Pro Gly Cys Cys
305                 310                 315                 320

Ile Pro Ser Leu Ser Arg Val Thr Leu Ala Met Ala Ala Ala Ser Arg
                325                 330                 335

Leu Trp Tyr Met Leu Tyr Phe Asn Thr Ala Asn Lys Leu Phe Phe Leu
            340                 345                 350

Ser Thr Ile Leu Gln Asn Ile Val Gly Cys Ser Val Glu His Ala Glu
        355                 360                 365

Asn Ile Gly Ile His Tyr Tyr Pro Thr Leu Arg Trp Trp Arg Lys Asn
370                 375                 380

Phe Met Glu Asn His Ser Lys Ile Leu Ala Leu Gly Phe Asp Glu Lys
385                 390                 395                 400

Phe Ile Arg Ile Trp Glu Tyr Tyr Phe Asp Tyr Cys Ala Ala Gly Phe
                405                 410                 415

Lys Ser Arg Thr Leu Gly Asn Tyr Gln Met Val Phe Ser Arg Pro Gly
            420                 425                 430

Asn Lys Thr Ala Phe Ser Asn Leu Asp Lys Lys Met Ala Ser
        435                 440                 445

<210> SEQ ID NO 28
<211> LENGTH: 458
<212> TYPE: PRT
<213> ORGANISM: Zea mays

<400> SEQUENCE: 28

Met Ala Ala Ala Gln Asp Leu Leu Gly Lys Glu Ser Asp Leu Leu Val
1               5                   10                  15

Asn Pro Lys Gln Met Ile Pro Ser Trp Ser Ala Gly Ala Arg Leu
            20                  25                  30

Leu Val Thr Arg Phe Leu Gly Gln Tyr Val Ser Val Gly Asn Leu Val
            35                  40                  45

Leu Leu Glu Glu Gly Gly Thr Met Phe Ser Phe Gly Glu Val Gly Lys
50                  55                  60

-continued

```
Lys Cys His Val Lys Ser Val Leu Arg Val His Asp Pro Met Phe Tyr
 65                  70                  75                  80

Trp Lys Val Ala Thr Glu Ala Asp Leu Gly Leu Ala Asp Ala Tyr Ile
                 85                  90                  95

Asn Gly Tyr Phe Ser Phe Val Asp Lys Arg Glu Gly Leu Leu Asn Leu
            100                 105                 110

Phe Leu Ile Leu Ile Ala Asn Arg Asp Ala Asn Lys Ser Ser Ser Ser
        115                 120                 125

Ala Ala Gly Lys Arg Gly Trp Trp Thr Pro Leu Leu Leu Thr Ala Gly
    130                 135                 140

Val Ala Ser Ala Lys Tyr Phe Leu Arg His Ile Ala Arg Arg Asn Ser
145                 150                 155                 160

Val Ser Gln Thr Arg Gln Asn Ile Ser Gln His Tyr Asp Leu Ser Asn
                165                 170                 175

Glu Phe Phe Ser Leu Phe Leu Asp Pro Ser Met Thr Tyr Ser Cys Ala
            180                 185                 190

Ile Phe Lys Thr Glu Asp Gln Ser Leu Glu Ala Ala Gln Leu Gln Lys
        195                 200                 205

Val Cys Leu Leu Ile Asp Lys Ala Lys Val Glu Arg Asp His His Val
    210                 215                 220

Leu Glu Ile Gly Cys Gly Trp Gly Ser Leu Ala Ile Gln Leu Val Lys
225                 230                 235                 240

Gln Thr Gly Cys Lys Tyr Thr Gly Ile Thr Leu Ser Val Glu Gln Leu
                245                 250                 255

Lys Tyr Ala Gln Arg Lys Val Lys Glu Ala Gly Leu Glu Asp His Ile
            260                 265                 270

Ser Phe Met Leu Cys Asp Tyr Arg Gln Ile Pro Thr Gln Arg Lys Tyr
        275                 280                 285

Asp Arg Ile Ile Ser Cys Glu Met Ile Glu Gly Val Gly His Glu Tyr
    290                 295                 300

Met Asp Asp Phe Phe Gly Cys Cys Glu Ser Leu Leu Ala Gln Asp Gly
305                 310                 315                 320

Ile Phe Val Leu Gln Phe Ile Ser Ile Pro Glu Glu Arg Tyr Glu Glu
                325                 330                 335

Tyr Arg Arg Ser Ser Asp Phe Ile Lys Glu Tyr Ile Phe Pro Gly Gly
            340                 345                 350

Cys Leu Pro Ser Leu Ala Arg Ile Thr Ser Ala Met Ser Ala Ala Ser
        355                 360                 365

Arg Leu Cys Ile Glu His Leu Glu Asn Ile Gly Tyr His Tyr Tyr Pro
    370                 375                 380

Thr Leu Ile Gln Trp Arg Asp Asn Phe Met Ala Asn Lys Asp Ala Ile
385                 390                 395                 400

Leu Ala Leu Gly Phe Asp Glu Lys Phe Ile Arg Ile Trp Glu Tyr Tyr
                405                 410                 415

Phe Ile Tyr Cys Ala Ala Gly Phe Lys Ser Arg Thr Leu Gly Asn Tyr
            420                 425                 430

Gln Ile Val Phe Ser Arg Pro Gly Asn Asp Lys Leu Gly Asp Ser Gly
        435                 440                 445

Ile His Ser Leu Ser Lys Leu Ser Gly Ser
    450                 455

<210> SEQ ID NO 29
<211> LENGTH: 873
```

<212> TYPE: PRT
<213> ORGANISM: Gossypium hirsutum

<400> SEQUENCE: 29

```
Met Glu Val Ala Val Ile Gly Gly Gly Ile Lys Gly Leu Leu Ser Ala
1               5                   10                  15

Tyr Val Leu Val Lys Ala Gly Val Asp Val Val Tyr Glu Lys Glu
            20                  25                  30

Glu Gln Leu Gly Gly His Ala Lys Thr Val Asn Phe Asp Ala Val Asp
            35                  40                  45

Leu Asp Leu Gly Phe Leu Phe Leu Asn Pro Ala Arg Tyr Ala Thr Leu
        50                  55                  60

Leu His Met Phe Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Leu Leu
            100                 105                 110

Asn Pro Phe Asn Trp Gln Ser Leu Arg Glu Ile Ile Lys Phe Gly Asn
            115                 120                 125

Asp Val Glu Ser Tyr Leu Gly Ser Leu Glu Asn Asn Pro Asp Ile Asp
    130                 135                 140

Arg Thr Glu Thr Leu Gly Gln Phe Ile Asn Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Thr Ser Phe Ser Ala Phe Ser Ile Leu Ser
            180                 185                 190

Phe Cys Arg Thr His His Leu Tyr Gln Leu Phe Gly Gln Ser Gln Trp
        195                 200                 205

Leu Thr Ile Lys Gly His Ser His Phe Val Lys Arg Val Arg Glu Val
    210                 215                 220

Leu Glu Thr Lys Gly Cys Gln Phe Lys Leu Gly Cys Glu Val Gln Ser
225                 230                 235                 240

Val Leu Pro Val Asp Asn Gly Thr Ala Met Val Cys Gly Asp Gly Phe
                245                 250                 255

Gln Glu Thr Tyr Asn Gly Cys Ile Met Ala Val Asp Ala Pro Thr Ala
            260                 265                 270

Leu Lys Leu Leu Gly Asn Gln Ala Thr Phe Glu Glu Thr Arg Val Leu
        275                 280                 285

Gly Ala Phe Gln Tyr Ala Thr Ser Asp Ile Phe Leu His Gln Asp Ser
    290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
        355                 360                 365

Ile Pro Ser Val Ala Ala Ser Lys Ala Ser Leu Glu Leu Gly Gln Ile
    370                 375                 380

Gln Gly Lys Arg Gly Ile Trp Phe Cys Gly Tyr Asp Phe Asn Gln Asp
385                 390                 395                 400
```

```
Glu Leu Lys Ala Gly Met Asp Ala Ala His Gly Ile Leu Gly Lys His
            405                 410                 415

Ser Ser Val Pro Pro Ser Pro Lys Asn Met Ser Pro Ser Leu Pro Lys
        420                 425                 430

Asn Met Ser Pro Ser Phe Met Glu Thr Thr Ala Arg Leu Phe Val Thr
            435                 440                 445

Lys Phe Phe Gln Gln Tyr Ile Ser Met Gly Cys Val Ile Phe Leu Glu
    450                 455                 460

Glu Gly Gly Arg Ile Phe Thr Phe Lys Gly Asn Met Glu Lys Cys Pro
465                 470                 475                 480

Leu Lys Thr Val Leu Lys Val His Asn Pro Gln Phe Tyr Trp Arg Ile
                485                 490                 495

Met Lys Glu Ala Asp Ile Gly Leu Ala Asp Ala Tyr Ile His Gly Asp
            500                 505                 510

Phe Ser Phe Leu Asp Glu Asn Glu Gly Leu Leu Asn Leu Phe Arg Ile
    515                 520                 525

Leu Val Ala Asn Lys Glu Asn Ser Ala Ala Ser Gly Ser Thr Lys Arg
    530                 535                 540

Arg Thr Trp Trp Ser Pro Ala Leu Leu Thr Ala Ser Ile Ser Ser Ala
545                 550                 555                 560

Lys Tyr Phe Val Lys His Leu Leu Arg Gln Asn Thr Ile Thr Gln Ala
                565                 570                 575

Arg Arg Asn Ile Ser Arg His Tyr Asp Leu Ser Asn Glu Leu Phe Ser
            580                 585                 590

Leu Tyr Leu Gly Lys Met Met Gln Tyr Ser Ser Gly Val Phe Arg Thr
    595                 600                 605

Gly Glu Glu His Leu Asp Val Ala Gln Arg Arg Lys Ile Ser Ser Leu
610                 615                 620

Ile Glu Lys Thr Arg Ile Glu Lys Trp His Glu Val Leu Asp Ile Gly
625                 630                 635                 640

Cys Gly Trp Gly Ser Leu Ala Ile Glu Thr Val Lys Arg Thr Gly Cys
                645                 650                 655

Lys Tyr Thr Gly Ile Thr Leu Ser Glu Gln Gln Leu Lys Tyr Ala Gln
            660                 665                 670

Glu Lys Val Lys Glu Ala Gly Leu Glu Asp Asn Ile Lys Ile Leu Leu
        675                 680                 685

Cys Asp Tyr Arg Gln Leu Pro Lys Glu His Gln Phe Asp Arg Ile Ile
    690                 695                 700

Ser Val Glu Met Val Glu His Val Gly Glu Glu Tyr Ile Glu Glu Phe
705                 710                 715                 720

Tyr Arg Cys Cys Asp Gln Leu Leu Lys Glu Asp Gly Leu Phe Val Leu
                725                 730                 735

Gln Phe Ile Ser Ile Pro Glu Glu Leu Ser Lys Glu Ile Gln Gln Thr
            740                 745                 750

Ala Gly Phe Leu Lys Glu Tyr Ile Phe Pro Gly Gly Thr Leu Leu Ser
        755                 760                 765

Leu Asp Arg Asn Leu Ser Ala Met Ala Ala Thr Arg Phe Ser Val
    770                 775                 780

Glu His Val Glu Asn Ile Gly Met Ser Tyr Tyr His Thr Leu Arg Trp
785                 790                 795                 800

Trp Arg Lys Leu Phe Leu Lys Asn Thr Ser Lys Val Leu Ala Leu Gly
                805                 810                 815
```

Phe Asp Glu Lys Phe Met Arg Thr Trp Glu Tyr Tyr Phe Asp Tyr Cys
                820                 825                 830

Ala Ala Gly Phe Lys Thr Gly Thr Leu Ile Asp Tyr Gln Val Val Phe
            835                 840                 845

Ser Arg Ala Gly Asn Phe Gly Thr Leu Gly Asp Pro Tyr Lys Gly Phe
850                 855                 860

Pro Ser Ala Tyr Ser Phe Met Asp Asp
865                 870

<210> SEQ ID NO 30
<211> LENGTH: 865
<212> TYPE: PRT
<213> ORGANISM: Gossypium hirsutum

<400> SEQUENCE: 30

Met Glu Val Ala Val Ile Gly Gly Ile Lys Gly Leu Val Ser Ala
1               5                   10                  15

Tyr Val Leu Val Lys Ala Gly Val Asp Val Val Tyr Glu Lys Glu
                20                  25                  30

Glu Gln Leu Gly Gly His Ala Lys Thr Val Asn Phe Asp Ala Val Asp
            35                  40                  45

Leu Asp Leu Gly Phe Leu Phe Leu Asn Pro Ala Arg Tyr Ala Thr Leu
50                  55                  60

Leu Asp Ile Ile Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Leu Leu
                100                 105                 110

Asn Pro Phe Asn Trp Gln Asn Leu Arg Glu Ile Ile Arg Phe Ser Asn
            115                 120                 125

Asp Val Glu Ser Tyr Leu Gly Ser Leu Glu Asn Asn Pro Asp Ile Asp
130                 135                 140

Arg Thr Glu Thr Leu Gly Gln Phe Ile Lys Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Met Ser Phe Ser Ala Phe Ser Ile Leu Ser
            180                 185                 190

Phe Cys Arg Thr His His Leu Tyr Gln Gln Phe Gly Gln Pro Gln Trp
            195                 200                 205

Leu Thr Ile Lys Gly His Ser His Phe Val Lys Arg Val Arg Glu Val
210                 215                 220

Leu Glu Thr Lys Gly Cys Gln Phe Lys Leu Gly Cys Glu Val Gln Ser
225                 230                 235                 240

Val Leu Pro Ala Asp Asn Gly Thr Thr Met Val Cys Gly Asp Gly Phe
                245                 250                 255

Gln Glu Thr Tyr Asn Gly Cys Ile Met Ala Val Asp Ala Pro Thr Ala
            260                 265                 270

Leu Lys Leu Leu Gly Asn Gln Ala Thr Phe Glu Glu Thr Arg Val Leu
            275                 280                 285

Gly Ala Phe Gln Tyr Ala Thr Ser Asp Ile Phe Leu His Arg Asp Ser
        290                 295                 300

Thr Leu Met Pro Gln Asn Lys Ser Ala Trp Ser Ala Leu Asn Phe Leu
305                 310                 315                 320

-continued

```
Asn Ser Ser Lys Asn Ala Phe Leu Thr Tyr Trp Leu Asn Ala Leu
            325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
            355                 360                 365

Ile Pro Ser Val Ala Ala Ser Lys Ala Ser Leu Glu Leu Gly Gln Ile
        370                 375                 380

Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
                405                 410                 415

Ser Ser Val Leu His Ser Pro Lys Ser Met Ser Pro Ser Phe Met Glu
            420                 425                 430

Thr Thr Ala Arg Leu Phe Val Thr Lys Phe Phe Gln Gln Tyr Ile Ser
            435                 440                 445

Met Gly Cys Val Ile Phe Leu Glu Glu Gly Gly Arg Ile Phe Thr Phe
        450                 455                 460

Lys Gly Asn Met Glu Lys Cys Pro Leu Lys Thr Val Leu Lys Val His
465                 470                 475                 480

Asn Pro Gln Phe Tyr Trp Arg Ile Met Lys Glu Ala Asp Ile Gly Leu
                485                 490                 495

Ala Asp Ala Tyr Ile His Gly Asp Phe Ser Phe Leu Asp Glu Thr Glu
            500                 505                 510

Gly Leu Leu Asn Leu Phe Arg Ile Leu Val Ala Asn Lys Glu Asn Ser
            515                 520                 525

Ala Ala Ser Gly Ser Asn Lys Arg Arg Thr Trp Trp Ser Pro Ala Leu
        530                 535                 540

Leu Thr Ala Ser Ile Ser Ser Ala Lys Tyr Phe Val Lys His Leu Leu
545                 550                 555                 560

Arg Gln Asn Thr Ile Thr Gln Ala Arg Arg Asn Ile Ser Arg His Tyr
                565                 570                 575

Asp Leu Ser Asn Glu Leu Phe Thr Leu Tyr Leu Gly Lys Met Met Gln
            580                 585                 590

Tyr Ser Ser Gly Val Phe Arg Thr Gly Glu Glu His Leu Asp Val Ala
        595                 600                 605

Gln Arg Arg Lys Ile Ser Ser Leu Ile Glu Lys Ala Arg Ile Glu Lys
610                 615                 620

Arg His Glu Val Leu Asp Ile Gly Cys Gly Trp Gly Ser Leu Ala Ile
625                 630                 635                 640

Glu Thr Val Lys Arg Thr Gly Cys Lys Tyr Thr Gly Ile Thr Leu Ser
                645                 650                 655

Glu Gln Gln Leu Lys Tyr Ala Gln Glu Lys Val Lys Glu Ala Gly Leu
            660                 665                 670

Gln Asp Asn Ile Lys Ile Leu Leu Cys Asp Tyr Arg Gln Leu Pro Lys
        675                 680                 685

Glu His Gln Phe Asp Arg Ile Ile Ser Val Glu Met Val Glu His Val
        690                 695                 700

Gly Glu Glu Tyr Ile Glu Glu Phe Tyr Arg Cys Cys Asp Gln Leu Leu
705                 710                 715                 720

Lys Glu Asp Gly Leu Phe Val Leu Gln Phe Ile Ser Ile Pro Glu Glu
                725                 730                 735
```

```
Leu Ser Lys Glu Ile Gln Gln Thr Ala Gly Phe Leu Lys Glu Tyr Ile
                740                 745                 750

Phe Pro Gly Gly Thr Leu Leu Ser Leu Asp Arg Asn Leu Ser Ala Met
            755                 760                 765

Ala Ala Ala Thr Arg Phe Ser Val Glu His Val Glu Asn Ile Gly Met
        770                 775                 780

Ser Tyr Tyr His Thr Leu Arg Trp Trp Arg Lys Leu Phe Leu Glu Asn
785                 790                 795                 800

Thr Ser Lys Val Leu Ala Leu Gly Phe Asp Glu Lys Phe Met Arg Thr
                805                 810                 815

Trp Glu Tyr Tyr Phe Asp Tyr Cys Ala Ala Gly Phe Lys Thr Gly Thr
            820                 825                 830

Leu Ile Asp Tyr Gln Val Val Phe Ser Arg Ala Gly Asn Phe Gly Thr
        835                 840                 845

Leu Gly Asp Pro Tyr Lys Gly Phe Pro Ser Ala Tyr Ser Phe Met Asp
    850                 855                 860

Asp
865

<210> SEQ ID NO 31
<211> LENGTH: 865
<212> TYPE: PRT
<213> ORGANISM: Gossypium hirsutum
<220> FEATURE:
<221> NAME/KEY: misc_feature
<222> LOCATION: (641)..(641)
<223> OTHER INFORMATION: Xaa can be any naturally occurring amino acid

<400> SEQUENCE: 31

Met Lys Ile Ala Val Ile Gly Gly Ile Ser Gly Val Val Ser Ala
1               5                   10                  15

Tyr Thr Leu Ala Lys Ala Gly Ala Asn Val Val Leu Tyr Glu Lys Glu
                20                  25                  30

Glu Tyr Leu Gly Gly His Ser Lys Thr Val His Phe Asp Gly Val Asp
            35                  40                  45

Leu Asp Leu Gly Phe Met Val Phe Asn Arg Val Thr Tyr Pro Asn Met
    50                  55                  60

Met Glu Leu Phe Glu Ser Leu Gly Ile Asp Met Glu Pro Phe Asp Met
65                  70                  75                  80

Ser Leu Ser Val Ser Leu Asn Glu Gly Lys Gly Cys Glu Trp Gly Ser
                85                  90                  95

Arg Asn Gly Leu Ser Ala Leu Phe Ala Gln Lys Ser Asn Leu Phe Asn
            100                 105                 110

Pro Tyr Phe Trp Gln Met Leu Arg Glu Ile Leu Lys Phe Lys Asn Asp
        115                 120                 125

Val Ile Ser Tyr Leu Glu Leu Leu Glu Asn Asn Pro Asp Ile Asp Arg
    130                 135                 140

Asn Glu Thr Leu Gly Gln Phe Ile Lys Ser Lys Gly Tyr Ser Asp Leu
145                 150                 155                 160

Phe Gln Lys Ala Tyr Leu Val Pro Val Cys Gly Ser Ile Trp Ser Cys
                165                 170                 175

Pro Thr Glu Arg Val Met Asp Phe Ser Ala Phe Ser Ile Leu Ser Phe
            180                 185                 190

Cys Arg Asn His His Leu Leu Gln Ile Phe Gly Arg Pro Gln Trp Met
        195                 200                 205

Thr Val Arg Trp Arg Ser His Arg Tyr Val Asn Lys Val Arg Glu Glu
```

```
            210                 215                 220
Leu Glu Ser Thr Gly Cys Gln Ile Arg Thr Gly Cys Glu Val His Ser
225                 230                 235                 240

Val Leu Ser Asp Ala Glu Gly Cys Thr Val Leu Cys Gly Asp Asp Ser
                245                 250                 255

His Glu Leu Tyr Gln Gly Cys Ile Met Ala Val His Ala Pro Tyr Ala
                260                 265                 270

Leu Arg Leu Leu Gly Asn Gln Ala Thr Tyr Asp Glu Ser Thr Val Leu
                275                 280                 285

Gly Ala Phe Gln Tyr Val Tyr Ser Asp Ile Tyr Leu His Arg Asp Lys
            290                 295                 300

Asn Leu Met Pro Lys Asn Pro Ala Ala Trp Ser Ala Trp Asn Phe Leu
305                 310                 315                 320

Gly Ser Thr Asp Lys Asn Val Ser Leu Thr Tyr Trp Leu Asn Val Leu
                325                 330                 335

Gln Asn Leu Gly Glu Thr Ser Leu Pro Phe Leu Val Thr Leu Asn Pro
                340                 345                 350

Asp Tyr Thr Pro Lys His Thr Leu Leu Lys Trp Arg Thr Gly His Pro
                355                 360                 365

Val Pro Ser Val Ala Ala Thr Lys Ala Ser Leu Glu Leu Asp Arg Ile
                370                 375                 380

Gln Gly Lys Arg Gly Ile Trp Phe Cys Gly Ala Tyr Leu Gly Tyr Gly
385                 390                 395                 400

Phe His Glu Asp Gly Leu Lys Ala Gly Met Ile Ala Ala Asn Gly Leu
                405                 410                 415

Leu Gly Lys Ser Cys Asn Ile Leu Ser Asn Pro Lys His Met Val Pro
                420                 425                 430

Ser Leu Met Glu Thr Gly Ala Arg Leu Phe Val Thr Arg Phe Leu Ser
                435                 440                 445

His Phe Ile Ser Thr Gly Cys Val Ile Leu Leu Glu Glu Gly Gly Thr
                450                 455                 460

Met Phe Thr Phe Glu Gly Thr Ser Asn Lys Cys Ser Leu Lys Thr Val
465                 470                 475                 480

Ile Lys Val His Ser Pro His Phe Tyr Trp Lys Val Met Thr Glu Ala
                485                 490                 495

Asp Leu Gly Leu Ala Asp Ser Tyr Ile Asn Gly Asp Phe Ser Phe Val
                500                 505                 510

Asp Lys Lys Asp Gly Leu Leu Asn Leu Val Met Ile Leu Ile Ala Asn
                515                 520                 525

Arg Asp Leu Ile Ser Ser Asn Ser Lys Leu Ser Lys Lys Arg Gly Trp
                530                 535                 540

Trp Thr Pro Leu Leu Phe Thr Ala Gly Leu Thr Ser Ala Lys Tyr Phe
545                 550                 555                 560

Phe Lys His Val Leu Arg Gln Asn Thr Leu Thr Gln Ala Arg Arg Asn
                565                 570                 575

Ile Ser Arg His Tyr Asp Leu Ser Asn Asp Leu Phe Ala Leu Phe Leu
                580                 585                 590

Asp Glu Thr Met Thr Tyr Ser Cys Ala Val Phe Lys Thr Glu Asp Glu
                595                 600                 605

Asp Leu Lys Asp Ala Gln His Arg Lys Ile Ser Leu Leu Ile Glu Lys
                610                 615                 620

Ala Arg Ile Asp Ser Lys His Glu Ile Leu Glu Ile Gly Cys Gly Trp
625                 630                 635                 640
```

Xaa Ser Leu Ala Ile Glu Val Val Lys Arg Thr Gly Cys Lys Tyr Thr
            645                 650                 655

Gly Ile Thr Leu Ser Glu Gln Leu Lys Leu Ala Glu Lys Arg Val
        660                 665                 670

Lys Glu Ala Gly Leu Gln Glu Asn Ile Arg Phe Gln Leu Cys Asp Tyr
            675                 680                 685

Arg Gln Leu Pro Ser Thr Tyr Lys Tyr Asp Arg Ile Ile Ser Cys Glu
690                 695                 700

Met Ile Glu Ala Val Gly His Glu Tyr Met Glu Asp Phe Phe Gly Cys
705                 710                 715                 720

Cys Glu Ser Val Leu Ala Asp Asp Gly Leu Leu Val Leu Gln Phe Ile
                725                 730                 735

Ser Ile Pro Glu Glu Arg Tyr Asn Glu Tyr Arg Arg Ser Ser Asp Phe
            740                 745                 750

Ile Lys Glu Tyr Ile Phe Pro Gly Gly Cys Leu Pro Ser Leu Ala Arg
        755                 760                 765

Ile Thr Thr Ala Met Asn Ala Ala Ser Lys Leu Cys Val Glu His Val
770                 775                 780

Glu Asn Ile Gly Leu His Tyr Tyr Gln Thr Leu Arg Tyr Trp Arg Lys
785                 790                 795                 800

Asn Phe Leu Glu Lys Gln Ser Lys Ile His Ala Leu Gly Phe Asn Asp
                805                 810                 815

Lys Phe Ile Arg Thr Trp Glu Tyr Tyr Phe Asp Tyr Cys Ala Ala Gly
            820                 825                 830

Phe Lys Ser Asn Thr Leu Gly Asn Tyr Gln Val Val Phe Ser Arg Pro
        835                 840                 845

Gly Asn Val Val Ala Leu Gly Asn Pro Tyr Lys Asp Phe Pro Ser Ala
850                 855                 860

Ser
865

<210> SEQ ID NO 32
<211> LENGTH: 837
<212> TYPE: PRT
<213> ORGANISM: Oryza sativa

<400> SEQUENCE: 32

Met Gly Pro Ala Ala Pro Ser Ala Gly Ala Ser Gly Glu Arg Gly Ala
1               5                   10                  15

Thr Leu Arg Arg Gly Gly Ser Pro Val Ala Val Arg Arg Ala Leu
            20                  25                  30

Thr Ala Pro Pro Ser Cys Val Thr Ser Pro Asn Met Met Gln Trp Phe
        35                  40                  45

Ala Asp Leu Gly Ala Asn Met Glu Arg Ser Asp Met Ser Phe Ser Val
    50                  55                  60

Arg Thr Gln Leu Asp Ala Cys Gly Glu Cys Trp Ala Ser Ser Asn
65                  70                  75                  80

Gly Ile Ser Gly Leu Leu Ala Lys Arg Ser Asn Ala Leu Ser Pro Ser
                85                  90                  95

Phe Trp Arg Met Ile Ser Glu Thr Leu Lys Phe Lys Arg Asp Ala Leu
            100                 105                 110

Arg Tyr Leu Glu Asp Cys Glu Asn Asn Leu Asp Leu Glu Gln Ser Glu
        115                 120                 125

Thr Leu Gly Gln Phe Val Gln Ser His Gly Tyr Cys Gln Phe Phe Gln

```
                130             135             140
Glu Ala Tyr Leu Phe Pro Ile Cys Gly Trp Met Trp Ser Cys Pro Ser
145                 150                 155                 160

Gln Arg Val Leu Gly Phe Ser Ala Ser Ser Val Leu Ser Phe Phe Arg
                165                 170                 175

Lys His Asn Leu Leu Gln Leu Phe Ser Arg Thr Gln Pro Leu Ile Val
                180                 185                 190

Asn Gly Arg Ser Gln Ser Tyr Phe Asn Lys Val Arg Glu Asp Leu Glu
                195                 200                 205

Ser Arg Ser Cys Arg Ile Lys Thr Asn Cys His Val Lys Ser Ile Ser
        210                 215                 220

Ser Phe Asp Arg Gly Tyr Arg Val Leu Glu Val Asp Gly Ser Glu Glu
225                 230                 235                 240

Met Tyr Asp Arg Ile Ile Val Gly Ile His Ala Leu Asp Ala Leu Lys
                245                 250                 255

Leu Leu Gly Ala Glu Ala Thr His Glu Glu Ser Arg Ile Leu Gly Ala
                260                 265                 270

Phe Gln Tyr Val Ser Ser Asn Leu Tyr Leu His Cys Asp Glu Ser Phe
                275                 280                 285

Met Leu Cys Asn Ser Ser Thr Trp Ser Ala Cys Asn Ile Thr Arg Thr
        290                 295                 300

Arg Ser Gly Ser Val Cys Val Thr Tyr Trp Leu Asn Leu Leu Gln Asn
305                 310                 315                 320

Ile Glu Ser Thr Asn His Phe Leu Val Thr Leu Asn Pro Ser Tyr Val
                325                 330                 335

Pro Asp His Val Leu Leu Lys Trp Asn Thr Asn His Phe Val Pro Thr
                340                 345                 350

Val Ala Ala Ser Lys Ala Ser Leu Glu Leu Asp Gln Ile Gln Gly Lys
                355                 360                 365

Arg Gly Ile Trp Phe Cys Gly Ala Tyr Gln Gly Ser Gly Phe His Glu
        370                 375                 380

Asp Gly Phe Gln Ala Gly Lys Ala Ala Ala Gln Ser Leu Leu Gly Asn
385                 390                 395                 400

Lys Ile Asp Pro Leu Thr Asn Pro Lys Gln Met Val Leu Ser Trp Thr
                405                 410                 415

Glu Thr Gly Ala Arg Leu Leu Val Leu Arg Phe Leu Lys Gln Tyr Ile
                420                 425                 430

Ser Val Gly Asn Leu Ile Leu Phe Glu Glu Gly Gly Thr Met Phe Ser
        435                 440                 445

Phe Gly Glu Ala Cys Glu Lys Cys Asn Lys Lys Ser Val Leu Gln Val
450                 455                 460

Gln Asp Pro Leu Phe Tyr Trp Gln Val Ala Thr Glu Ala Asp Leu Gly
465                 470                 475                 480

Leu Ala Asp Ala Tyr Ile Asn Gly Cys Phe Ser Phe Val Asn Lys Arg
                485                 490                 495

Glu Gly Leu Leu Asn Leu Phe Leu Ile Leu Ile Ala Ser Arg Asp Ala
                500                 505                 510

His Arg Ser Ser Cys Arg Asn Ser Ser Arg Arg Gly Trp Trp Thr Pro
        515                 520                 525

Leu Leu Phe Thr Ala Gly Val Ala Ser Ala Lys Tyr Phe Leu Arg His
                530                 535                 540

Ile Ser Arg Lys Asn Ser Val Thr Gln Thr Arg Gln Asn Val Ser Gln
545                 550                 555                 560
```

```
His Tyr Asp Leu Ser Asn Asp Phe Phe Ser Leu Phe Leu Asp Lys Ser
            565                 570                 575

Met Thr Tyr Ser Ser Ala Ile Phe Lys Asp Glu Glu Glu Ser Leu Glu
            580                 585                 590

Glu Ala Gln Leu Arg Lys Ile Asn Leu Leu Ile His Lys Ala Lys Val
            595                 600                 605

Gly Gln Asp Asp Glu Val Leu Glu Ile Gly Ser Gly Trp Gly Ser Leu
            610                 615                 620

Ala Met Glu Val Val Lys Gln Thr Gly Cys Lys Tyr Thr Gly Val Thr
625                 630                 635                 640

Gln Ser Val Glu Gln Leu Lys Tyr Ala Gln Arg Val Lys Glu Ala
            645                 650                 655

Gly Leu Glu Asp Arg Ile Thr Phe Leu Leu Cys Asp Tyr Arg Glu Ile
            660                 665                 670

Pro Cys His Lys Tyr Asp Arg Ile Ile Cys Cys Glu Met Ile Glu Glu
            675                 680                 685

Val Gly His Glu Tyr Met Asp Glu Phe Phe Gly Cys Cys Glu Ser Leu
            690                 695                 700

Leu Ala Glu Asn Gly Ile Phe Val Thr Gln Phe Ile Ser Ile Pro Glu
705                 710                 715                 720

Glu Arg Tyr Asp Glu Tyr Arg Arg Ser Ser Asp Phe Ile Lys Glu Tyr
            725                 730                 735

Ile Phe Pro Gly Gly Cys Leu Pro Ser Leu Thr Arg Ile Thr Ser Ala
            740                 745                 750

Met Ser Ala Ala Ser Arg Leu Cys Ile Glu His Val Glu Asn Ile Gly
            755                 760                 765

Tyr His Tyr Tyr Thr Thr Leu Ile Arg Trp Arg Asp Asn Phe Met Ala
            770                 775                 780

Asn Lys Asp Lys Ile Leu Ala Leu Gly Phe Asp Glu Lys Phe Ile Arg
785                 790                 795                 800

Thr Trp Glu Tyr Tyr Phe Ile Tyr Cys Ala Ala Gly Phe Lys Ser Arg
            805                 810                 815

Thr Leu Gly Asp Tyr Gln Ile Val Phe Ser Arg Pro Gly Asn Thr Lys
            820                 825                 830

Met Gly Ser Gly Phe
        835

<210> SEQ ID NO 33
<211> LENGTH: 867
<212> TYPE: PRT
<213> ORGANISM: Arabidopsis thaliana

<400> SEQUENCE: 33

Met Lys Val Ala Val Ile Gly Ser Gly Ile Ser Gly Leu Gly Ser Ala
1               5                   10                  15

Tyr Val Leu Ala Asn Gln Gly Val Lys Glu Val Leu Tyr Glu Lys
            20                  25                  30

Glu Glu Ser Leu Gly Gly His Ala Lys Thr Val Arg Phe Asp Gly Val
            35                  40                  45

Asp Leu Asp Leu Gly Phe Met Val Phe Asn Arg Val Thr Tyr Pro Asn
        50                  55                  60

Met Ile Glu Phe Phe Glu Asn Leu Gly Val Glu Met Glu Val Ser Asp
65                  70                  75                  80

Met Ser Phe Ala Val Ser Leu Asp Asn Gly Lys Gly Cys Glu Trp Gly
```

```
                        85                  90                  95
Ser Arg Asn Gly Val Ser Gly Leu Phe Ala Gln Lys Lys Asn Val Leu
                100                 105                 110

Asn Pro Tyr Phe Trp Gln Met Ile Arg Glu Ile Val Arg Phe Lys Glu
                115                 120                 125

Asp Val Leu Asn Tyr Ile Glu Lys Leu Glu Gly Asn Pro Asp Ile Asp
                130                 135                 140

Arg Lys Glu Thr Leu Gly Glu Phe Leu Asn Thr Arg Gly Tyr Ser Glu
145                 150                 155                 160

Leu Phe Gln Gln Ala Tyr Leu Val Pro Ile Cys Gly Ser Ile Trp Ser
                165                 170                 175

Cys Pro Ser Asp Gly Val Leu Ser Phe Ser Ala Tyr Ser Val Leu Ser
                180                 185                 190

Phe Cys Cys Asn His His Leu Leu Gln Ile Phe Gly Arg Pro Gln Trp
                195                 200                 205

Leu Thr Val Ala Gly Arg Ser Gln Thr Tyr Val Ala Lys Val Arg Ala
                210                 215                 220

Glu Leu Glu Arg Leu Gly Cys Lys Ile Arg Thr Ser Cys Asp Val Lys
225                 230                 235                 240

Ser Val Ser Thr Ser Glu Asn Gly Cys Val Thr Val Thr Ser Gly Asp
                245                 250                 255

Gly Ser Glu Glu Val Phe Asp Arg Cys Ile Leu Ala Met His Ala Pro
                260                 265                 270

Asp Ala Leu Arg Leu Leu Gly Glu Glu Val Thr Phe Asp Glu Ser Arg
                275                 280                 285

Val Leu Gly Ala Phe Gln Tyr Val Tyr Ser Asp Ile Tyr Leu His His
                290                 295                 300

Asp Ile Asp Leu Met Pro Arg Asn Lys Ala Ala Trp Ser Ala Trp Asn
305                 310                 315                 320

Phe Leu Gly Ser Thr Glu Lys Lys Val Cys Val Thr Tyr Trp Leu Asn
                325                 330                 335

Ile Leu Gln Asn Leu Gly Glu Asn Ser Glu Pro Phe Phe Val Thr Leu
                340                 345                 350

Asn Pro Asp Glu Thr Pro Lys Lys Ala Leu Leu Lys Trp Thr Thr Gly
                355                 360                 365

His Pro Val Pro Ser Val Ala Ala Ser Ile Ala Ser Gln Glu Leu His
                370                 375                 380

Gln Ile Gln Gly Lys Arg Asn Ile Trp Phe Cys Gly Ala Tyr Gln Gly
385                 390                 395                 400

Tyr Gly Phe His Glu Asp Gly Leu Lys Ala Gly Met Ala Ala Ala Arg
                405                 410                 415

Gly Leu Leu Gly Lys Glu Thr Ala Leu Leu Asn Asn Pro Arg His Met
                420                 425                 430

Val Pro Ser Leu Thr Glu Thr Gly Ala Arg Leu Phe Val Thr Arg Phe
                435                 440                 445

Leu Gly Gln Phe Ile Ser Thr Gly Ser Val Thr Ile Leu Glu Glu Gly
                450                 455                 460

Gly Thr Met Phe Thr Phe Gly Gly Lys Asp Ser Thr Cys Pro Leu Lys
465                 470                 475                 480

Ser Ile Leu Lys Ile His Ser Pro Gln Phe Tyr Trp Lys Val Met Thr
                485                 490                 495

Gln Ala Asp Leu Gly Leu Ala Asp Ala Tyr Ile Asn Gly Asp Phe Ser
                500                 505                 510
```

Phe Val Asp Lys Glu Ser Gly Leu Leu Asn Leu Ile Met Ile Leu Ile
        515                 520                 525

Ala Asn Arg Asp Thr Lys Ser Asn Leu Thr Lys Lys Arg Gly Trp Trp
    530                 535                 540

Thr Pro Met Phe Leu Thr Ala Gly Leu Ala Ser Ala Lys Tyr Phe Leu
545                 550                 555                 560

Lys His Val Ser Arg Gln Asn Thr Leu Thr Gln Ala Arg Arg Asn Ile
                565                 570                 575

Ser Arg His Tyr Asp Leu Ser Asn Glu Leu Phe Gly Leu Phe Leu Asp
            580                 585                 590

Asp Thr Met Thr Tyr Ser Ser Ala Val Phe Lys Ser Asp Asp Glu Asp
        595                 600                 605

Leu Arg Thr Ala Gln Met Arg Lys Ile Ser Leu Leu Ile Asp Lys Ala
    610                 615                 620

Arg Ile Glu Lys Asp His Glu Val Leu Glu Ile Gly Cys Gly Trp Gly
625                 630                 635                 640

Thr Leu Ala Ile Glu Val Val Arg Arg Thr Gly Cys Lys Tyr Thr Gly
                645                 650                 655

Ile Thr Leu Ser Ile Glu Gln Leu Lys Tyr Ala Glu Glu Lys Val Lys
            660                 665                 670

Glu Ala Gly Leu Gln Asp Arg Ile Thr Phe Glu Leu Arg Asp Tyr Arg
        675                 680                 685

Gln Leu Ser Asp Ala His Lys Tyr Asp Arg Ile Ser Cys Glu Met
    690                 695                 700

Leu Glu Ala Val Gly His Glu Phe Met Glu Met Phe Ser Arg Cys
705                 710                 715                 720

Glu Ala Ala Leu Ala Glu Asp Gly Leu Met Val Leu Gln Phe Ile Ser
                725                 730                 735

Thr Pro Glu Glu Arg Tyr Asn Glu Tyr Arg Leu Ser Ser Asp Phe Ile
            740                 745                 750

Lys Glu Tyr Ile Phe Pro Gly Ala Cys Val Pro Ser Leu Ala Lys Val
        755                 760                 765

Thr Ser Ala Met Ser Ser Ser Arg Leu Cys Ile Glu His Val Glu
770                 775                 780

Asn Ile Gly Ile His Tyr Tyr Gln Thr Leu Arg Leu Trp Arg Lys Asn
                785                 790                 795                 800

Phe Leu Glu Arg Gln Lys Gln Ile Met Ala Leu Gly Phe Asp Lys
            805                 810                 815

Phe Val Arg Thr Trp Glu Tyr Tyr Phe Asp Tyr Cys Ala Ala Gly Phe
        820                 825                 830

Lys Thr Arg Thr Leu Gly Asp Tyr Gln Leu Val Phe Ser Arg Pro Gly
    835                 840                 845

Asn Val Ala Ala Phe Ala Asp Ser Tyr Arg Gly Phe Pro Ser Ala Tyr
850                 855                 860

Cys Val Ser
865

<210> SEQ ID NO 34
<211> LENGTH: 864
<212> TYPE: PRT
<213> ORGANISM: Stercula foetida

<400> SEQUENCE: 34

Met Gly Val Ala Val Ile Gly Gly Gly Ile Gln Gly Leu Val Ser Ala

-continued

```
1               5                   10                  15
Tyr Val Leu Ala Lys Ala Gly Val Asn Val Val Tyr Glu Lys Glu
                20                  25                  30

Glu Gln Val Gly Gly His Ala Lys Thr Val Ser Phe Asp Ala Val Asp
                35                  40                  45

Leu Asp Leu Gly Leu Leu Phe Leu Asn Pro Ala Arg Tyr Pro Thr Met
 50                  55                  60

Leu Glu Leu Phe Asp Ser Leu Glu Val Asp Val Glu Ala Thr Asp Val
 65                  70                  75                  80

Ser Phe Ser Val Ser His Asp Lys Gly Asn Gly Tyr Glu Trp Cys Ser
                85                  90                  95

Gln Tyr Gly Phe Ser Asn Phe Leu Ala His Lys Lys Met Leu Asn
                100                 105                 110

Pro Tyr Asn Trp Gln Asp Leu Arg Glu Thr Ile Lys Phe Gly Asn Asp
                115                 120                 125

Val Asn Ser Tyr Leu Glu Ser Leu Glu Lys Asn Pro Asp Ile Asp Arg
    130                 135                 140

Asn Glu Thr Leu Gly His Phe Val Gly Ser Lys Gly Tyr Ser Glu Asn
145                 150                 155                 160

Phe Leu Asn Thr Tyr Leu Ala Pro Ile Cys Gly Ser Met Trp Ser Cys
                165                 170                 175

Ser Lys Glu Glu Val Met Ser Phe Ser Ala Tyr Ser Ile Leu Ser Phe
                180                 185                 190

Cys Arg Thr Tyr His Leu Tyr Gln Leu Phe Gly Asn Pro Gln Trp Leu
                195                 200                 205

Thr Ile Lys Arg His Ser Tyr Leu Val Lys Lys Val Arg Asp Ile Leu
    210                 215                 220

Glu Ser Arg Gly Cys Gln Phe Lys Leu Gly Cys Glu Val Leu Ser Val
225                 230                 235                 240

Leu Pro Ala Asp Asp Gly Ser Ser Ile Val Phe Gly Asp Gly Phe Gln
                245                 250                 255

Glu Thr Tyr Asn Gly Cys Ile Met Ala Val Asn Ala Pro Thr Ala Leu
                260                 265                 270

Lys Ile Leu Gly Asn Gln Ala Thr Phe Glu Glu Met Arg Val Leu Gly
    275                 280                 285

Ala Phe Gln Tyr Ala Ser Ser Asp Ile Tyr Leu His Arg Asp Ser Asn
                290                 295                 300

Leu Met Pro Thr Asn Arg Ser Gly Trp Ser Ala Leu Asn Phe Leu Arg
305                 310                 315                 320

Ser Arg Glu Asn Lys Ala Ser Leu Thr Tyr Trp Leu Asn Val Leu Gln
                325                 330                 335

Asn Val Gly Lys Thr Ser Gln Pro Phe Phe Val Thr Leu Asn Pro Asp
                340                 345                 350

Arg Ile Pro Asp Lys Ile Leu Leu Lys Trp Ser Thr Gly Arg Pro Ile
                355                 360                 365

Pro Ser Val Ala Ala Ser Lys Ala Ser Leu Glu Leu Asp Gln Ile Gln
    370                 375                 380

Gly Lys Arg Gly Ile Trp Phe Cys Gly Tyr Asp Phe His Glu Asp Glu
385                 390                 395                 400

Leu Lys Ala Gly Met Asp Ala Ala His Arg Ile Leu Gly Lys His Phe
                405                 410                 415

Ser Val Leu His Ser Pro Arg Gln Met Ser Pro Ser Phe Met Glu Thr
                420                 425                 430
```

```
Thr Ala Arg Leu Leu Val Thr Lys Phe Phe His Gln Tyr Ile Gln Val
        435                 440                 445
Gly Cys Val Ile Ile Ile Glu Glu Gly Arg Val Tyr Thr Phe Lys
    450                 455                 460
Gly Ser Met Glu Asn Cys Ser Leu Lys Thr Ala Leu Lys Val His Asn
465                 470                 475                 480
Pro Gln Phe Tyr Trp Arg Ile Met Lys Glu Ala Asp Ile Gly Leu Ala
            485                 490                 495
Asp Ala Tyr Ile Gln Gly Asp Phe Ser Phe Val Asp Lys Asp Asp Gly
                500                 505                 510
Leu Leu Asn Leu Phe Arg Ile Leu Ile Ala Asn Lys Glu Leu Asn Ser
            515                 520                 525
Ala Ser Gly Gln Asn Lys Arg Arg Thr Trp Leu Ser Pro Ala Leu Phe
    530                 535                 540
Thr Ala Gly Ile Ser Ser Ala Lys Tyr Phe Leu Lys His Tyr Met Arg
545                 550                 555                 560
Gln Asn Thr Val Thr Gln Ala Arg Arg Asn Ile Ser Arg His Tyr Asp
                565                 570                 575
Leu Ser Asn Glu Leu Phe Thr Leu Tyr Leu Gly Glu Met Met Gln Tyr
            580                 585                 590
Ser Ser Gly Ile Phe Lys Thr Gly Glu Glu His Leu Asp Val Ala Gln
    595                 600                 605
Arg Arg Lys Ile Ser Ser Leu Ile Asp Lys Ser Arg Ile Glu Lys Trp
    610                 615                 620
His Glu Val Leu Asp Ile Gly Cys Gly Trp Gly Ser Leu Ala Met Glu
625                 630                 635                 640
Val Val Lys Arg Thr Gly Cys Lys Tyr Thr Gly Ile Thr Leu Ser Glu
                645                 650                 655
Gln Gln Leu Lys Tyr Ala Glu Glu Lys Val Lys Glu Ala Gly Leu Gln
            660                 665                 670
Gly Asn Ile Lys Phe Leu Leu Cys Asp Tyr Arg Gln Leu Pro Lys Thr
    675                 680                 685
Phe Lys Tyr Asp Arg Ile Ile Ser Val Glu Met Val Glu His Val Gly
    690                 695                 700
Glu Glu Tyr Ile Glu Glu Phe Phe Arg Cys Cys Asp Ser Leu Leu Ala
705                 710                 715                 720
Glu Asn Gly Leu Phe Val Leu Gln Phe Ile Ser Ile Pro Glu Ile Leu
                725                 730                 735
Ser Lys Glu Ile Gln Gln Thr Ala Gly Phe Leu Lys Glu Tyr Ile Phe
            740                 745                 750
Pro Gly Gly Thr Leu Leu Ser Leu Asp Arg Thr Leu Ser Ala Met Ala
    755                 760                 765
Ala Ala Ser Arg Phe Ser Val Glu His Val Glu Asn Ile Gly Ile Ser
    770                 775                 780
Tyr Tyr His Thr Leu Arg Trp Trp Arg Lys Asn Phe Leu Ala Asn Glu
785                 790                 795                 800
Ser Lys Val Leu Ala Leu Gly Phe Asp Glu Lys Phe Met Arg Thr Trp
                805                 810                 815
Glu Tyr Tyr Phe Asp Tyr Cys Ala Ala Gly Phe Lys Thr Gly Thr Leu
            820                 825                 830
Ile Asp Tyr Gln Val Val Phe Ser Arg Ala Gly Asn Phe Ala Ala Leu
    835                 840                 845
```

```
Gly Asp Pro Tyr Ile Gly Phe Pro Ser Ala Tyr Ser Tyr Asp Asn
    850                 855                 860

<210> SEQ ID NO 35
<211> LENGTH: 797
<212> TYPE: PRT
<213> ORGANISM: Medicago truncatula

<400> SEQUENCE: 35

Met Leu Val Val Thr Leu Leu Arg Met Gln Gln Ile Lys Leu Leu Ile
1               5                   10                  15

Thr Lys Gln Val Asn Tyr Pro Asn Ile Met Glu Leu Phe Asp Ser Leu
            20                  25                  30

Glu Val Asp Lys Lys Leu Ser Tyr Leu Ser Thr Ser Val Ser Leu Asp
        35                  40                  45

Asn Gly Lys Gly Tyr Glu Trp Gly Thr Gln Asn Gly Leu Ser Ser Leu
    50                  55                  60

Phe Ala Gln Lys Lys Asn Val Ile Asn Pro Tyr Phe Trp Lys Met Ile
65                  70                  75                  80

Lys Glu Val Ser Lys Phe Lys Glu Asp Val Leu Ser Tyr Leu Asp Ile
                85                  90                  95

Val Glu Thr Asn Gln Asp Ile Glu His Asn Glu Thr Met Glu His Phe
            100                 105                 110

Ile Lys Ser Arg Gly Tyr Ser Glu Leu Phe Gln Lys Ala Tyr Leu Ile
        115                 120                 125

Pro Leu Cys Cys Ser Ile Trp Pro Trp Pro Cys Ser Ser Pro Glu Gly
    130                 135                 140

Val Met Ser Phe Ser Ser Phe Ser Val Leu Thr Phe Leu Ser Asn His
145                 150                 155                 160

His Leu Leu Gln Leu Ile Tyr Ser Pro Gln Cys Lys Ile Val Arg Trp
                165                 170                 175

Asn Ser Gln Asn Phe Ile Lys Lys Val Lys Glu Lys Leu Ala Ser Glu
            180                 185                 190

Asn Cys Gln Ile Lys Val Asn Cys Glu Val His Leu Val Ser Thr Ser
        195                 200                 205

Asp Lys Gly Cys Val Val Leu Cys Lys Asp Gly Ser Glu Glu Met Tyr
    210                 215                 220

Asp Ser Cys Ile Ile Ala Val His Ala Pro Asp Val Leu Lys Ile Leu
225                 230                 235                 240

Gly Asp Glu Ala Thr Ser Asp Glu Cys Arg Ile Leu Gly Ala Phe Gln
                245                 250                 255

Tyr Val Tyr Cys Asp Thr Phe Leu Leu Asn Asp Ser Val Cys Val Thr
            260                 265                 270

Tyr Trp Ile Asp Ile Leu Gln Asn Val Glu Glu Thr Ser Gly Pro Ser
        275                 280                 285

Phe Ile Thr Val Asn Pro Asn Gln Thr Pro Gln Asn Thr Leu Phe Lys
    290                 295                 300

Trp Ser Thr Gly His Leu Val Pro Thr Val Ala Ala Ser Lys Ala Ser
305                 310                 315                 320

His Glu Leu Asn His Ile Gln Gly Lys Arg Lys Ile Trp Phe Ser Gly
                325                 330                 335

Val Tyr Gln Gly Tyr Ala Tyr His Gly Asp Glu Leu Lys Ala Gly Met
            340                 345                 350

Asp Ala Ala Tyr Asp Ile Leu Gly Arg Ile Cys Ser Leu Gln Arg Asn
        355                 360                 365
```

```
Leu Lys Tyr Ile Val Pro Ser Trp Thr Glu Val Gly Ala Arg Leu Phe
    370             375                 380

Val Thr Arg Phe Leu Ser Ala Tyr Ile Thr Thr Gly Cys Leu Met Leu
385                 390                 395                 400

Leu Glu Asp Gly Gly Thr Ile Phe Thr Phe Glu Gly Ser Lys Lys Lys
                405                 410                 415

Cys Ser Leu Lys Ser Val Leu Arg Ile His Asn Pro Gln Phe Tyr Trp
            420                 425                 430

Lys Ile Leu Ile Ala Asn Arg Asp Phe Asn Leu Ser Asn Ser Thr Leu
            435                 440                 445

Lys Asn Arg Gly Trp Trp Thr Pro Val Phe Phe Thr Ala Gly Leu Ala
    450                 455                 460

Ser Ala Lys Phe Phe Ile Lys His Val Ser Arg Lys Asn Thr Val Thr
465                 470                 475                 480

Gln Ala Arg Arg Asn Ile Ser Met His Tyr Asp Leu Ser Asn Asp Leu
                485                 490                 495

Phe Ala Cys Phe Leu Asp Glu Lys Met Gln Tyr Ser Cys Gly Val Phe
            500                 505                 510

Lys Asp Glu Tyr Glu Asp Leu Lys Asp Ala Gln Lys Arg Lys Ile Ser
            515                 520                 525

Ile Leu Ile Glu Lys Ala Gln Ile Asp Arg Lys His Glu Ile Leu Asp
    530                 535                 540

Ile Gly Cys Gly Trp Gly Gly Phe Ala Ile Glu Val Val Lys Lys Val
545                 550                 555                 560

Gly Cys Lys Tyr Thr Gly Ile Thr Leu Ser Glu Glu Gln Leu Lys Tyr
                565                 570                 575

Ala Glu Asn Lys Val Lys Asp Ala Gly Leu Gln Glu His Ile Thr Phe
            580                 585                 590

Leu Leu Cys Glu Tyr Arg Gln Leu Ser Lys Thr Lys Lys Tyr Asp Arg
            595                 600                 605

Ile Val Ser Cys Glu Met Ile Glu Ala Val Gly His Glu Tyr Met Glu
    610                 615                 620

Glu Phe Phe Gly Cys Cys Asp Ser Val Leu Ala Asp Asp Gly Leu Leu
625                 630                 635                 640

Val Leu Gln Phe Thr Ser Ile Pro Asp Glu Arg Tyr Asp Ala Tyr Arg
                645                 650                 655

Arg Ser Ser Glu Phe Ile Lys Glu Tyr Ile Phe Pro Gly Cys Cys Ile
            660                 665                 670

Pro Ser Leu Ser Arg Val Thr Leu Ala Met Ala Ala Ala Ser Arg Leu
            675                 680                 685

Trp Tyr Met Leu Tyr Phe Asn Thr Ala Asn Lys Leu Phe Phe Leu Ser
    690                 695                 700

Thr Ile Leu Gln Asn Ile Val Gly Cys Ser Val Glu His Ala Glu Asn
705                 710                 715                 720

Ile Gly Ile His Tyr Tyr Pro Thr Leu Arg Trp Trp Arg Lys Asn Phe
                725                 730                 735

Met Glu Asn His Ser Lys Ile Leu Ala Leu Gly Phe Asp Glu Lys Phe
            740                 745                 750

Ile Arg Ile Trp Glu Tyr Tyr Phe Asp Tyr Cys Ala Ala Gly Phe Lys
            755                 760                 765

Ser Arg Thr Leu Gly Asn Tyr Gln Met Val Phe Ser Arg Pro Gly Asn
    770                 775                 780
```

```
Lys Thr Ala Phe Ser Asn Leu Asp Lys Lys Met Ala Ser
785                 790                 795
```

```
<210> SEQ ID NO 36
<211> LENGTH: 877
<212> TYPE: PRT
<213> ORGANISM: Zea mays

<400> SEQUENCE: 36
```

```
Met Arg Val Ala Val Gly Ala Gly Val Ser Gly Leu Ala Ala Ala
1               5                   10                  15

His Glu Leu Ala Arg Ser Gly Gly Ser Arg Val Thr Val Tyr Glu Lys
            20                  25                  30

Glu Asp Tyr Leu Gly Gly His Ala Arg Thr Val Ala Val Glu Asp Ala
        35                  40                  45

Asp Ala Ala Ser Thr Val Gln Leu Asp Leu Gly Phe Met Val Phe Asn
    50                  55                  60

Arg Val Thr Tyr Pro Asn Met Leu Glu Trp Phe Glu Gly Leu Gly Val
65                  70                  75                  80

Glu Met Glu Ile Ser Asp Met Ser Phe Ser Val Ser Thr Glu Leu Gly
                85                  90                  95

Ala Ser Gly Ser Arg Cys Glu Trp Gly Ser Arg Asn Gly Ile Ser Gly
            100                 105                 110

Leu Leu Ala Gln Lys Ser Asn Ala Leu Ser Pro Ser Phe Trp Arg Met
        115                 120                 125

Ile Arg Glu Ile Leu Lys Phe Lys Asn Asp Ala Leu Arg Tyr Leu Glu
130                 135                 140

Asp His Glu Asn Asn Pro Asp Met Asp Arg Asn Glu Thr Leu Gly Gln
145                 150                 155                 160

Phe Ile Arg Ser His Gly Tyr Ser Gln Phe Gln Glu Ala Tyr Leu
                165                 170                 175

Thr Pro Ile Cys Ala Cys Ile Trp Ser Cys Pro Ser Gln Gly Val Leu
            180                 185                 190

Gly Phe Ser Ala Phe Phe Val Leu Ser Phe Cys Arg Asn His His Leu
        195                 200                 205

Leu Gln Leu Phe Gly Arg Pro Gln Trp Leu Thr Val Lys Gly Arg Ser
    210                 215                 220

His Ser Tyr Val His Lys Val Arg Glu Glu Leu Glu Ser Met Gly Cys
225                 230                 235                 240

Gln Ile Lys Thr Ser Cys Glu Ile Lys Ser Val Ser Ser Ser Glu Gly
                245                 250                 255

Gly Phe Arg Val Thr Val Phe Asp Gly Ser Glu Glu Thr Tyr Asp Arg
            260                 265                 270

Ile Ile Phe Gly Val His Ala Pro Asp Ala Leu Lys Ile Leu Gly Ala
        275                 280                 285

Glu Ala Thr His Glu Glu Leu Arg Ile Leu Gly Ala Phe Gln Tyr Val
    290                 295                 300

Tyr Ser Asp Ile Tyr Leu His Ser Asp Lys Ser Leu Met Pro Arg Ser
305                 310                 315                 320

Leu Ser Ala Trp Ser Ser Trp Asn Phe Leu Gly Thr Thr Ser Lys Gly
                325                 330                 335

Val Cys Val Thr Tyr Trp Leu Asn Leu Leu Gln Asn Ile Glu Ser Thr
            340                 345                 350

Ser Arg Pro Phe Leu Val Thr Leu Asn Pro Pro His Val Pro Asp His
        355                 360                 365
```

```
Val Phe Leu Lys Trp Tyr Thr Ser His Pro Val Pro Ser Val Ala Ala
            370                 375                 380

Ala Lys Ala Ser Leu Glu Leu His His Ile Gln Gly Asn Arg Gly Ile
385                 390                 395                 400

Trp Phe Cys Gly Ala Tyr Gln Gly Tyr Gly Phe His Glu Asp Gly Leu
                405                 410                 415

Lys Ala Gly Lys Ala Ala Gln Asp Leu Leu Gly Lys Glu Ser Asp
                420                 425                 430

Leu Leu Val Asn Pro Lys Gln Met Ile Pro Ser Trp Ser Glu Ala Gly
            435                 440                 445

Ala Arg Leu Leu Val Thr Arg Phe Leu Gly Gln Tyr Val Ser Val Gly
450                 455                 460

Asn Leu Val Leu Leu Glu Glu Gly Gly Thr Met Phe Ser Phe Gly Glu
465                 470                 475                 480

Val Gly Lys Lys Cys His Val Lys Ser Val Leu Arg Val His Asp Pro
                485                 490                 495

Met Phe Tyr Trp Lys Val Ala Thr Glu Ala Asp Leu Gly Leu Ala Asp
                500                 505                 510

Ala Tyr Ile Asn Gly Tyr Phe Ser Phe Val Asp Lys Arg Glu Gly Leu
            515                 520                 525

Leu Asn Leu Phe Leu Ile Leu Ile Ala Asn Arg Asp Ala Asn Lys Ser
            530                 535                 540

Ser Ser Ser Ala Ala Gly Lys Arg Gly Trp Trp Thr Pro Leu Leu Leu
545                 550                 555                 560

Thr Ala Gly Val Ala Ser Ala Lys Tyr Phe Leu Arg His Ile Ala Arg
                565                 570                 575

Arg Asn Ser Val Ser Gln Thr Arg Gln Asn Ile Ser Gln His Tyr Asp
            580                 585                 590

Leu Ser Asn Glu Phe Phe Ser Leu Phe Leu Asp Pro Ser Met Thr Tyr
            595                 600                 605

Ser Cys Ala Ile Phe Lys Thr Glu Asp Gln Ser Leu Glu Ala Ala Gln
            610                 615                 620

Leu Gln Lys Val Cys Leu Leu Ile Asp Lys Ala Lys Val Glu Arg Asp
625                 630                 635                 640

His His Val Leu Glu Ile Gly Cys Gly Trp Gly Ser Leu Ala Ile Gln
                645                 650                 655

Leu Val Lys Gln Thr Gly Cys Lys Tyr Thr Gly Ile Thr Leu Ser Val
                660                 665                 670

Glu Gln Leu Lys Tyr Ala Gln Arg Lys Val Lys Glu Ala Gly Leu Glu
            675                 680                 685

Asp His Ile Ser Phe Met Leu Cys Asp Tyr Arg Gln Ile Pro Thr Gln
690                 695                 700

Arg Lys Tyr Asp Arg Ile Ile Ser Cys Glu Met Ile Glu Gly Val Gly
705                 710                 715                 720

His Glu Tyr Met Asp Asp Phe Phe Gly Cys Cys Glu Ser Leu Leu Ala
                725                 730                 735

Gln Asp Gly Ile Phe Val Leu Gln Phe Ile Ser Ile Pro Glu Glu Arg
            740                 745                 750

Tyr Glu Glu Tyr Arg Arg Ser Ser Asp Phe Ile Lys Glu Tyr Ile Phe
            755                 760                 765

Pro Gly Gly Cys Leu Pro Ser Leu Ala Arg Ile Thr Ser Ala Met Ser
            770                 775                 780
```

```
Ala Ala Ser Arg Leu Cys Ile Glu His Leu Glu Asn Ile Gly Tyr His
785                 790                 795                 800

Tyr Tyr Pro Thr Leu Ile Gln Trp Arg Asp Asn Phe Met Ala Asn Lys
            805                 810                 815

Asp Ala Ile Leu Ala Leu Gly Phe Asp Glu Lys Phe Ile Arg Ile Trp
        820                 825                 830

Glu Tyr Tyr Phe Ile Tyr Cys Ala Ala Gly Phe Lys Ser Arg Thr Leu
        835                 840                 845

Gly Asn Tyr Gln Ile Val Phe Ser Arg Pro Gly Asn Asp Lys Leu Gly
    850                 855                 860

Asp Ser Gly Ile His Ser Leu Ser Lys Leu Ser Gly Ser
865                 870                 875

<210> SEQ ID NO 37
<211> LENGTH: 1407
<212> TYPE: DNA
<213> ORGANISM: Gossypium hirsutum

<400> SEQUENCE: 37
atggatgctg cacatggtat cttgggaaag cattcttctg ttccgcccag tccaaagaat      60
atgtcaccct ctttaccaaa gaatatgtca ccctctttca tggaaacaac ggcacgcctc     120
tttgttacca aattctttca acaatatata tctatgggct gcgtaatttt tttagaggaa     180
ggaggcagaa ttttcacttt caaggaaac atggaaaagt gtcctcttaa aacagttctg     240
aaagtgcata atcctcagtt ttactggagg atcatgaaag aagctgatat aggccttgca     300
gacgcatata tccatggaga ttttctcttt cttgatgaaa atgaaggcct tcttaatctt     360
ttccggattc ttgttgccaa taagagaac tcagctgcct cagggtcgac taaaagaagg     420
acttggtggt cgcctgctct gttaacagct agtatatcat ctgccaagta ttttgtgaag     480
catctcttaa gacaaaatac tattacacaa gctcgtagga cattttctcg tcattatgat     540
ctgagtaatg aacttttctc tctatacttg ggcaaaatga tgcaatactc ttctggagtc     600
tttaggacag gagaagaaca tttggacgtt gcacagcgaa gaaaaatcag ttctctaatt     660
gagaaaacaa ggatagagaa atggcatgaa gttctagaca ttgggtgcgg ttggggaagc     720
ttagctattg aaactgtgaa agaacagga tgcaaatata ctggcatcac tctatcagaa     780
cagcaactga aatatgctca agaaaaagtg aaggaagctg gactcgagga taacatcaaa     840
atacttctct gtgactatcg ccagttacct aaggaacacc aatttgacag aatcatatct     900
gtagagatgg tagaacatgt tggtgaagaa tatattgagg aatttttacag atgctgtgat     960 caattactga agaagatgg acttttcgtt cttcagttca tatctatccc agaggagctt    1020
tccaaagaaa tccagcaaac agctggtttt cttaaggaat atatattccc tggtggaacc    1080
ctgctttctt tggataggaa tttatcagcc atggctgctg caacaagatt cagtgtggag    1140
catgtggaaa acataggaat gagttattac cacacactga tggtggag aaaactttc      1200 ctgaaaaaca caagcaaagt tctggctttg gggttcgacg agaagttcat gcggacatgg    1260
gaatactatt tcgattactg tgctgctggt tttaagacag aacccttat agattaccag    1320 gttgtattt ctcgagccgg taatttcggt acacttggag atccatacaa aggtttccct    1380
tctgcatatt ccttcatgga tgattga                                       1407

<210> SEQ ID NO 38
<211> LENGTH: 1383
<212> TYPE: DNA
<213> ORGANISM: Gossypium hirsutum
```

<400> SEQUENCE: 38

```
atggatgctg cacatggtat cttgggaaag cattcttctg ttctgcatag tccaaagagt      60
atgtcaccct ctttcatgga aacaacggca cgcctctttg ttactaaatt ctttcaacaa     120
tatatatcta tgggctgtgt aattttctta gaggaaggag gcagaatttt cacttttcaaa    180
ggaaacatgg aaaagtgtcc tcttaaaaca gttctgaaag tacataatcc tcagttttac    240
tggaggatca tgaaagaagc tgatataggc cttgcagatg catatatcca tggagatttt    300
tcttttcttg atgaaactga aggccttctt aatcttttcc ggattcttgt tgccaataaa    360
gagaactcag ctgcctcagg gtcgaataaa agaaggactt ggtggtcacc tgctctgtta    420
acagctagta tatcatctgc aaagtatttt gtgaagcatc tcttgagaca aaatactatt    480
acacaagctc gtaggaacat ttctcgtcat tatgatctga gtaatgaact tttcactcta    540
tacttgggca aaatgatgca atactcttct ggagtcttta ggacgggaga gaacatttg    600
gacgttgcac agcgtagaaa aatcagttct ctaattgaga aagcaaggat agagaaacgg    660
cacgaagttc tcgacattgg gtgcggttgg ggaagcttag ctattgaaac tgtgaaaaga    720
acaggatgca aatatactgg catcactcta tcagaacagc aactgaaata tgctcaagaa    780
aaagtgaagg aagctggact ccaggataac atcaaaatac ttctctgtga ctatcgccag    840
ttacctaagg aacaccaatt tgacagaatc atatctgtag atggtagaa acatgttggt    900
gaagaatata ttgaggagtt ttacagatgc tgtgaccaat tactgaaaga gatgggctt    960
tttgttcttc agttcatatc tatcccagaa gagctttcca agaaatcca gcaaacagca   1020
ggttttctaa aggaatatat attccctgga ggaaccctgc tttctttgga taggaattta   1080
tcagccatgg ctgctgcaac aagattcagt gtggagcatg tggaaaatat aggaatgagt   1140
tattaccaca cactgagatg gtggagaaaa cttttcctgg aaaacacaag caaagttcta   1200
gctctggggt tcgacgagaa gttcatgagg acatgggaat actatttcga ttactgcgct   1260
gccggtttta agacaggaac tcttatagat taccaggttg tattttcaag ggccggaaat   1320
ttcggtacac tcggagatcc atacaaaggt ttcccttctg catattcctt catggatgat   1380
tga                                                                 1383
```

<210> SEQ ID NO 39
<211> LENGTH: 1371
<212> TYPE: DNA
<213> ORGANISM: Gossypium hirsutum

<400> SEQUENCE: 39

```
atgattgctg caaacggtct gctgggaaaa agttgtaata ttctgagcaa tccaaagcat      60
atggtgccct ctctgatgga aacagggggca cgtcttttg ttactagatt cctcagtcat    120
tttatatcaa ccggctgtgt gattttattg gaagaaggtg gcactatgtt tacctttgaa    180
ggaactagca ataagtgttc tctaaaaact gtaattaaag ttcacagtcc acattttat    240
tggaaggtta tgacagaggc agatttaggc cttgcagatt catatatcaa tggggatttt    300
tcttttgttg ataaaaaga cggtctgctg aaccttgtaa tgattcttat tgccaacaga    360
gatttgattt cttccaactc aaaacttagt aagaaagggg ttggtggac accattgttg    420
tttacagctg gtctaacatc agcaaagtat ttcttcaagc atgtcttaag acaaaatact    480
cttacacaag ctcgtaggaa catttctcgc cattacgacy tgagtaatga cctttttgca    540
ctcttcttgg atgagacaat gacatactct tgtgcagtat ttaagacaga agatgaggat    600
```

```
ttgaaagatg cacaacacag aaagatctct cttttgattg aaaaagcaag aattgatagc      660
aagcatgaaa ttcttgagat tggatgtggt tgggkaagct tagctattga ggttgtcaaa      720
cgaactggat gcaaatatac cggcattact ttatccgaag agcaactcaa acttgcagaa      780
aaaagagtga aggaagctgg acttcaggaa aatataagat ttcaactctg tgactatcga      840
caactaccta gcacctacaa gtatgacaga attatatcgt gtgagatgat agaagctgtt      900
ggccatgaat acatggagga cttcttcggt tgctgtgaat cagtgttagc agatgatgga      960
cttcttgttt tacagttcat atcaatacca gaggaacggt acaatgaata caggcgaagc     1020
tcggatttca tcaaggaata catcttccct ggtggatgct taccttctct ggctaggata     1080
acaacagcca tgaatgctgc gtccaaactc tgtgtggagc atgtgaaaaa catcggactt     1140
cattactacc aaacgcttag atattggaga aagaatttct tggagaaaca gagcaaaatc     1200
catgccttgg gattcaatga caagttcatc cggacatggg aatactatttt tgattattgt     1260 gctgctggtt tcaagtccaa tactcttggt aattaccagg ttgtattttc tcggcctgga     1320
aatgtagttg cacttggcaa cccatacaaa gacttcccct cagcttctta a              1371
```

<210> SEQ ID NO 40
<211> LENGTH: 1344
<212> TYPE: DNA
<213> ORGANISM: Oryza sativa

<400> SEQUENCE: 40

```
atggcagcag ctcaaagttt gcttgggaac aagattgatc ccctgacgaa cccaaagcag       60
atggtcctgt catggacaga gactggggca cgtcttctgg tgttaagatt tctcaaacag      120
tacatctctg ttggcaactt gatcttgttt gaagaaggtg cactatgtt cagttttggt       180 gaagcttgtg aaaaatgcaa taaaaaatct gttctgcaag ttcaggaccc actatttat       240 tggcaggttg caacagaagc agaccttggt ttagcagatg cctacataaa tggctgcttc      300
tcttttgtca ataagagaga aggccttctg aatcttttcc ttatcctcat tgccagtaga      360
gatgcacaca ggagttcttg caggaattct agtcgaaggg gttggtggac accttgctt      420 tttactgccg gcgttgcatc tgctaaatat tttctgcgtc acatctcaag gaagaactct      480
gtaacacaaa ctcgtcaaaa tgtctctcag cactatgatt tgagtaatga tttcttctcg      540 cttttttctgg ataagtcaat gacctactca tctgccattt tcaaggatga ggaagaaagc     600
ttagaagagg ctcagctgcg taaaataaac cttctaatcc ataaggctaa agtgggacag     660
gatgatgaag ttcttgagat tggtagtggt tggggcagtt tggctatgga agtggtgaag     720
caaactggct gcaaatatac aggagttaca cagtctgtgg agcaacttaa atatgcccaa     780
agaagggtga agaagctgg cttagaggac cgaataactt ttctgctgtg tgactaccgt      840
gaaataccat gtcacaaata tgacaggatc atatgctgtg agatgattga agaagttggt     900
catgaataca tggatgaatt cttttggctgc tgtgagtccc ttttggctga aaatggcata     960
tttgtcaccc agtttatctc aattccggag gaacggtatg atgagtaccg gagaagctca    1020
gactttatta agaatacat attccctggt ggatgccttc cttctctgac tcggataaca    1080
tctgccatgt ctgctgcatc aaggctctgc attgagcacg ttgagaatat tgggtaccat    1140
tattatacaa ctctgatacg ctggagggac aacttcatgg ccaataaaga taaaattttg    1200 gccctggggct ttgatgagaa gttcattcgt acatgggagt actatttcat atactgcgca   1260
gccggtttta aatccaggac acttggagac taccagattg tattctctcg tcctgggaac    1320
accaagatgg gatctggctt ctaa                                            1344
```

<210> SEQ ID NO 41
<211> LENGTH: 1371
<212> TYPE: DNA
<213> ORGANISM: Arabidopsis thaliana

<400> SEQUENCE: 41

| | | | | | |
|---|---|---|---|---|---|
| atggcggctg | cacgaggttt | gttagggaaa | gaaacagctc | ttctgaacaa | tccgcgacat | 60 |
| atggtcccct | ccttgacaga | aacaggagct | cggcttttcg | ttactagatt | cttgggacaa | 120 |
| tttatatcaa | ccggttctgt | aacaatacta | gaagaaggag | aacaatgtt | cacattcgga | 180 |
| gggaaggatt | ctacttgtcc | tctgaaatct | atcctcaaga | ttcacagtcc | tcaattttac | 240 |
| tggaaggtta | tgacacaagc | ggatttagga | cttgcagatg | cttatatcaa | tggagatttt | 300 |
| tctttcgttg | ataaagaatc | aggactttta | aatctgatta | tgattctcat | gctaacaga | 360 |
| gatacaaaat | caaatcttac | taagaaaagg | ggatggtgga | caccgatgtt | tttaactgcg | 420 |
| ggtttagcat | ctgcaaagta | ttttctaaag | catgtctcta | gcagaacac | tctaacacaa | 480 |
| gctcgtagaa | acatttctcg | tcactatgac | cttagcaacg | agcttttcgg | tttgttcttg | 540 |
| gatgatacca | tgacttactc | ctcggcagta | ttcaagtcgg | atgatgagga | tctgagaact | 600 |
| gcacagatga | aaaaatatc | tcttctgatt | gataaggcga | aatagagaa | ggaccatgag | 660 |
| gttttagaga | taggatgtgg | atggggaact | ttggccatag | aagttgtgag | aagaactgga | 720 |
| tgcaaataca | ccggcattac | gctatctatt | gagcagctta | aatatgctga | agaaaagtg | 780 |
| aaagaagctg | gacttcagga | ccggattact | ttgagctcc | gcgattatcg | ccaactatct | 840 |
| gatgctcaca | aatatgacag | aattatatct | tgcgagatgc | tagaagcggt | cggacatgag | 900 |
| tttatggaga | tgttttcag | tcgatgtgaa | gccgcacttg | ctgaagacgg | cctaatggtc | 960 |
| ttgcagttca | tatcgacacc | cgaagagcgt | tacaatgagt | acagactaag | ttcagatttc | 1020 |
| attaaagaat | acatattccc | tggtgcatgc | gttccttctt | tagccaaagt | cacttcagcc | 1080 |
| atgtcctctt | cttctaggct | atgcattgaa | catgttgaga | cattgggat | tcattactac | 1140 |
| caaacattga | gattgtggag | gaagaacttc | ttggagagac | agaaacaaat | catggctctt | 1200 |
| ggatttgatg | ataaattcgt | aaggacatgg | gaatattatt | ttgattattg | cgcagctgga | 1260 |
| ttcaagactc | gtactcttgg | agactaccag | ttggtgttct | cgcgtccagg | aacgtagct | 1320 |
| gcatttgcgg | attcataccg | aggatttcct | tctgcttatt | gtgtctcttg | a | 1371 |

<210> SEQ ID NO 42
<211> LENGTH: 1383
<212> TYPE: DNA
<213> ORGANISM: Sterculia foetida

<400> SEQUENCE: 42

| | | | | | |
|---|---|---|---|---|---|
| atggatgctg | cacatcgtat | cttgggaaag | catttttctg | ttctgcacag | tccaaggcaa | 60 |
| atgtcaccct | ctttcatgga | aacaacggca | cgtcttcttg | ttactaaatt | ctttcaccaa | 120 |
| tatatacaag | tgggctgcgt | aataatcata | gaggaaggtg | gcagagttta | cactttcaaa | 180 |
| ggaagcatgg | aaaattgttc | tcttaaaaca | gctctgaaag | tgcataatcc | tcagttttac | 240 |
| tggaggatta | tgaaagaagc | tgatataggc | cttgctgatg | catatatcca | aggagatttt | 300 |
| tcttttgttg | acaaggatga | tggtcttctt | aatctttcc | ggatacttat | tgccaataaa | 360 |
| gagttgaact | ctgcctcagg | acagaacaaa | agaaggactt | ggctgtcacc | tgcactgttc | 420 |
| acagctggta | tatcatctgc | aaagtatttc | ttgaagcatt | acatgaggca | aaatactgtt | 480 |

| | |
|---|---|
| acacaggctc gcaggaacat ttctcgtcat tatgacctga gtaatgaact tttcactcta | 540 |
| tacttaggtg aaatgatgca atactcttct ggaattttta agacgggaga agaacatttg | 600 |
| gacgttgcac agcgcagaaa atcagttcc ttaattgata aatcaagaat agagaagtgg | 660 |
| catgaagttc ttgacattgg atgtggttgg ggaagcttag ctatggaagt tgtcaaaaga | 720 |
| acaggatgta aatacactgg catcacactt tcagagcagc aactgaaata tgcagaagaa | 780 |
| aaagtgaagg aagctggact tcagggaaac atcaaatttc ttctctgtga ctatcgccag | 840 |
| ttacccaaga cattcaaata tgacagaatc atatctgttg agatggttga acatgttggt | 900 |
| gaagaatata ttgaggagtt tttcagatgc tgtgactcat tattggcaga gaatgggctt | 960 |
| ttcgttcttc agttcatatc aattccagag atactttcca aagaaatcca gcaaacagct | 1020 |
| ggttttctaa aggaatatat cttccctggt ggaaccctgc tttctctgga taggactttg | 1080 |
| tcagccatgg ctgctgcatc aagatttagt gtggagcatg tggaaaatat aggaattagt | 1140 |
| tattatcaca cactgagatg gtggaggaaa aatttcttgg caaatgaaag caaagttctg | 1200 |
| gctttggggt tcgatgagaa gttcatgcgg acatgggagt attattttga ttactgcgca | 1260 |
| gctggtttta agacagggac acttatagat taccaggttg tattctcacg ggctggcaat | 1320 |
| ttcgctgcac ttggcgatcc atacataggt ttcccttcag catattccta ctcggataat | 1380 |
| tga | 1383 |

<210> SEQ ID NO 43
<211> LENGTH: 1377
<212> TYPE: DNA
<213> ORGANISM: Zea mays

<400> SEQUENCE: 43

| | |
|---|---|
| atggctgcag ctcaagattt gcttggtaag gagagtgacc ttttggtgaa cccaaaacag | 60 |
| atgatcccat cgtggtctga ggctggggcg cgtcttctgg taacaagatt tcttggtcaa | 120 |
| tatgtgtctg tcggcaactt ggtcttgctt gaagaaggag gcactatgtt cagttttggt | 180 |
| gaagtaggca aaaatgcca tgtgaaatct gtcctgcgag tacatgaccc catgttttac | 240 |
| tggaaggttg caactgaagc agaccttggc ttggcagatg cctacattaa cggttatttc | 300 |
| tcatttgtag acaagagaga aggtcttcta aatctttcc tgattctcat tgcgaacagg | 360 |
| gacgcaaaca agagtagtag cagcgctgct ggtaaaaggg gttggtggac acccctgcta | 420 |
| tgacagctg gggttgcctc cgctaaatac ttcctgcgtc acatagcaag gaggaattct | 480 |
| gtctcacaaa cacgtcaaaa catctctcaa cactatgatc tgagtaatga attcttctct | 540 |
| cttttcctgg atccatcgat gacttactct tgtgccatct tcaagacgga ggatcaaagc | 600 |
| ttagaggcag cccagctaca gaaagtttgc ctcctaatcg ataaggctaa agtggagcga | 660 |
| gatcaccatg ttcttgagat tggctgtggt tggggcagct tagcaatcca attggtgaag | 720 |
| caaactggtt gcaaatacac tgggatcaca ttatcagtgg agcaattgaa atatgcacag | 780 |
| agaaaggtga agaagctgg attagaggac acataagct tcatgttgtg tgattaccgt | 840 |
| caaataccaa ctcagcgcaa atacgacagg atcatctctt gcgagatgat cgaaggtgtt | 900 |
| gggcacgaat acatggacga tttcttcggc tgctgcgagt ccctttttggc tcaagacggc | 960 |
| atatttgtcc tgcagttcat ctcaatccca gaagaacggt atgaggaata caggcgcagc | 1020 |
| tcagacttca tcaaggaata catcttccct ggggggttgcc tgccttcgtt agcccggatc | 1080 |
| acgtctgcca tgtctgcagc atcaaggctc tgcatcgagc accttgagaa tattgggtac | 1140 |
| cattactacc caacgctgat acagtggagg gacaacttca tggccaataa ggatgcaatt | 1200 |

```
ttggccctgg gcttcgatga gaaattcatc cgtatatggg aatactactt catatactgc    1260
gccgctggtt tcaagtcacg gacacttggg aactaccaga ttgtgttttc tcgccctggc    1320
aacgacaaat taggtgacag cggtatacac tccttaagca agctttctgg cagctaa       1377

<210> SEQ ID NO 44
<211> LENGTH: 2622
<212> TYPE: DNA
<213> ORGANISM: Gossypium hirsutum

<400> SEQUENCE: 44
atggaagtgg ccgtgatcgg aggtgggata aaagggttgc tttcggccta cgtactggtc      60
aaagccggcg tggacgtggt ggtttacgag aaagaagaac aattaggcgg ccatgcaaag     120
actgttaact tcgacgccgt tgatttagac cttggcttct tgtttctcaa tccagcaaga     180
tatgcaacac tattgcatat gttcgacagc cttggtgttg atgtagaaac atccgatgtt     240
tcattctcta taagccatga caaaggcaac aatggctatg aatggtgcag ccaatatgga     300
ttttccaatt actttgctca aaagaagaaa ctgttgaacc ctttcaattg caaagcctc      360 agagagatca tcaaattcgg caatgatgtc gaaagttacc ttggatcact tgagaacaac     420
ccagacattg atcgtactga gaccttggga cagtttataa actcaaaggg ctactctgaa     480
aattttcaaa acacttatct ggctcctata tgtggttcaa tgtggtcaag ctccaaggaa     540
gatgttacga gcttttcagc ttttttccatc ctttcatttt gccgtactca tcatttgtac     600
cagctatttg ggcagtcaca gtggttgact atcaaagggc actcacattt tgttaaaagg     660
gttagggaag tgctggagac taaaggttgt caatttaaac tcggttgtga agtacaatct     720
gttttgcccg ttgataatgg taccgccatg gtctgtggag atggtttcca agaaacttac     780
aatggatgca taatggctgt tgatgctccc actgccctaa aattattagg aaaccaagca     840
acatttgaag aaacaagagt actgggtgct ttccaatatg ctaccagtga tattttcctt     900
caccaggaca gtactttaat gccacaaaac aaatcagctt ggagtgcatt gaattttctc     960
aatagtagca aaaataatgc attcttaaca tactggctca atgcactaca gaatattggg    1020
aaaacaagtg agccattttt tgtgactgtc aatccagacc atacccgaa gaatacctta     1080 cttaagtggt caaccggcca tgcaattccc tctgttgctg catcaaaagc ttcacttgag    1140
cttggtcaga ttcagggaaa gagaggaatc tggttctgtg ctatgacttt caatcaggat    1200
gaactaaagg ctggtatgga tgctgcacat ggtatcttgg gaaagcattc ttctgttccg    1260
cccagtccaa agaatatgtc accctctttta ccaaagaata tgtcaccctc tttcatggaa    1320
acaacggcac gcctctttgt taccaaattc tttcaacaat atatatctat gggctgcgta    1380
atttttttag aggaaggagg cagaattttc actttcaaag gaaacatgga aaagtgtcct    1440
cttaaaacag ttctgaaagt gcataatcct cagtttttact ggaggatcat gaaagaagct    1500
gatataggcc ttgcagacgc atatatccat ggagattttt cttttcttga tgaaaatgaa    1560
ggccttctta atcttttccg gattcttgtt gccaataaag agaactcagc tgcctcaggg    1620
tcgactaaaa gaaggacttg gtggtcgcct gctctgttaa cagctagtat atcatctgcc    1680
aagtattttg tgaagcatct cttaagacaa atactatta cacaagctcg taggaacatt    1740
tctcgtcatt atgatctgag taatgaactt ttctctctat acttgggcaa aatgatgcaa    1800
tactcttctg gagtctttag gacaggagaa gaacatttgg acgttgcaca gcgaagaaaa    1860
atcagttctc taattgagaa aacaaggata gagaaatggc atgaagttct agacattggg    1920
```

| | |
|---|---|
| tgcggttggg gaagcttagc tattgaaact gtgaaaagaa caggatgcaa atatactggc | 1980 |
| atcactctat cagaacagca actgaaatat gctcaagaaa aagtgaagga agctggactc | 2040 |
| gaggataaca tcaaaatact tctctgtgac tatcgccagt tacctaagga acaccaattt | 2100 |
| gacagaatca tatctgtaga gatggtagaa catgttggtg aagaatatat tgaggaattt | 2160 |
| tacagatgct gtgatcaatt actgaaagaa gatggacttt tcgttcttca gttcatatct | 2220 |
| atcccagagg agcttttccaa agaaatccag caaacagctg ttttcttaa ggaatatata | 2280 |
| ttccctggtg gaaccctgct ttctttggat aggaatttat cagccatggc tgctgcaaca | 2340 |
| agattcagtg tggagcatgt ggaaaacata ggaatgagtt attaccacac actgagatgg | 2400 |
| tggagaaaac ttttcctgaa aaacacaagc aaagttctgg ctttggggtt cgacgagaag | 2460 |
| ttcatgcgga catggaata ctatttcgat tactgtgctg ctggttttaa gacaggaacc | 2520 |
| cttatagatt accaggttgt attttctcga gccggtaatt tcggtacact tggagatcca | 2580 |
| tacaaaggtt tcccttctgc atattccttc atggatgatt ga | 2622 |

<210> SEQ ID NO 45
<211> LENGTH: 2598
<212> TYPE: DNA
<213> ORGANISM: Gossypium hirsutum

<400> SEQUENCE: 45

| | |
|---|---|
| atggaagtgg cggtgatcgg aggtgggata aagggttgg tttcggccta cgtactggtc | 60 |
| aaagccggcg tggacgtggt ggtttacgag aaagaagagc aattaggcgg ccatgcgaag | 120 |
| actgttaact tcgacgccgt tgacttagac cttggcttct tgtttcttaa tcctgcaaga | 180 |
| tatgcaacac tgttggatat aatcgacagc cttggtgttg atgtagaaac atccgatgtt | 240 |
| tcattctcta taagccatga caaaggcaac aatggctatg aatggtgcag tcaatatgga | 300 |
| ttttccaatt actttgcaca aagaagaaa ctgttgaacc cttccaattg caaaaccctt | 360 |
| agagagatca tcagattcag caacgatgtc gaaagttacc ttggatcact tgagaacaac | 420 |
| ccagacattg atcgtactga gaccttggga cagtttataa aatcaaaggg ctactctgaa | 480 |
| aattttcaaa acacttacct ggctcctata tgtggttcaa tgtggtcaag ctccaaggaa | 540 |
| gatgttatga gcttttcagc attttccatc ctttcatttt gccgtactca tcatttgtac | 600 |
| cagcaatttg ggcagccaca gtggttgact atcaaagggc actcacattt tgttaaaagg | 660 |
| gttagggaag tgctggagac taaaggttgt caatttaaac tcggttgtga agtacaatct | 720 |
| gttttgcctg ctgataatgg taccaccatg gtctgtggag atggtttcca agaaacttac | 780 |
| aatggatgca taatggctgt tgatgctccc actgccctaa aattattagg aaaccaagca | 840 |
| acatttgaag aaacaagagt actgggtgct ttccaatatg ctaccagtga tattttccctt | 900 |
| caccgggaca gtacttttaat gccacaaaac aaatcagctt ggagtgcatt gaattttctc | 960 |
| aatagtagca aaaataatgc attcttaaca tactggctca atgcactaca gaatattggg | 1020 |
| aaaacaagtg agccattttt tgtgactgtc aatccagacc tacccccgaa gaataccttg | 1080 |
| cttaagtggt cgactggcca tgcaattccc tctgttgctg catcaaaagc ttcacttgag | 1140 |
| cttggtcaga ttcaggggaa gagaggaatc tggttctgtg gctatgactt caatcaggat | 1200 |
| gaactaaagg ctggtatgga tgctgcacat ggtatcttgg gaaagcattc ttctgttctg | 1260 |
| catagtccaa agagtatgtc accctctttc atggaaacaa cggcacgcct ctttgttact | 1320 |
| aaattctttc aacaatatat atctatgggc tgtgtaattt tcttagagga aggaggcaga | 1380 |
| attttcactt tcaaaggaaa catggaaaag tgtcctctta aaacagttct gaaagtacat | 1440 |

```
aatcctcagt tttactggag gatcatgaaa gaagctgata taggccttgc agatgcatat    1500
atccatggag atttttcttt tcttgatgaa actgaaggcc ttcttaatct tttccggatt    1560
cttgttgcca ataaagagaa ctcagctgcc tcagggtcga ataaaagaag gacttggtgg    1620
tcacctgctc tgttaacagc tagtatatca tctgcaaagt attttgtgaa gcatctcttg    1680
agacaaaata ctattacaca agctcgtagg aacatttctc gtcattatga tctgagtaat    1740 gaactttca ctctatactt gggcaaaatg atgcaatact cttctggagt ctttaggacg    1800
ggagaagaac atttggacgt tgcacagcgt agaaaaatca gttctctaat tgagaaagca    1860
aggatagaga acggcacga agttctcgac attgggtgcg gttggggaag cttagctatt    1920
gaaactgtga aaagaacagg atgcaaatat actggcatca ctctatcaga acagcaactg    1980
aaatatgctc aagaaaaagt gaaggaagct ggactccagg ataacatcaa aatacttctc    2040
tgtgactatc gccagttacc taaggaacac caatttgaca gaatcatatc tgtagagatg    2100
gtagaacatt ttggtgaaga atatattgag gagttttaca gatgctgtga ccaattactg    2160
aaagaagatg ggcttttgt tcttcagttc atatctatcc cagaagagct ttccaaagaa    2220
atccagcaaa cagcaggttt tctaaaggaa tatatattcc ctggaggaac cctgctttct    2280
ttggatagga atttatcagc catggctgct gcaacaagat tcagtgtgga gcatgtggaa    2340
aatataggaa tgagttatta ccacacactg agatggtgga gaaaacttt cctgaaaaac    2400 acaagcaaag ttctagctct ggggttcgac gagaagttca tgaggacatg ggaatactat    2460
ttcgattact gcgctgccgg ttttaagaca ggaactctta tagattacca ggttgtattt    2520
tcaagggccg gaaatttcgg tacactcgga gatccataca aaggtttccc ttctgcatat    2580
tccttcatgg atgattga                                                  2598

<210> SEQ ID NO 46
<211> LENGTH: 2598
<212> TYPE: DNA
<213> ORGANISM: Gossypium hirsutum

<400> SEQUENCE: 46
atgaaaatag cagtgatagg aggagggata agtggggtgg tatcagccta tactttagcc      60
aaagccggtg caaatgtagt gctttacgag aaagaagagt atttgggagg ccattccaag     120
accgttcact cgatggtgt tgatttagac cttggtttca tggtttttaa tcgcgttaca     180
tatccaaata tgatggagtt gtttgagagc cttgggattg atatggaacc atttgatatg     240
tcactctcag tgagccttaa tgaaggcaaa ggctgtgaat ggggcagccg taatggcctt     300
tcggccttgt tgcccaaaaa atccaacctc ttcaatcctt acttttggca atgcttaga     360 gaaattctca aattcaagaa tgatgttatt agttatcttg aattgctcga aaacaacccg     420
gatattgacc gtaatgaaac attgggacag ttcataaaat caagggggtta ctctgattta     480 tttcagaagg cttatctggt gcctgtatgt ggttcaatat ggtcatgccc tacagaaaga     540
gttatggatt tttcagcttt ctctattctt tcatttgcc gcaatcatca tctacttcag     600
atctttggac gaccacagtg gatgaccgtt cgatggcgtt cacatcgtta cgtcaataag     660
gttagagaag agctggagag tacaggttgt caaataagaa ctggttgcga ggtgcattct     720
gttttgagtg atgctgaagg ttgcactgta ttatgtggag atgactctca cgagttatat     780
caagggtgca taatggctgt tcatgcacca tatgctttga gattgttagg gaatcaagca     840
acatatgatg aatcaacagt gcttggcgct ttccaatatg tctatagtga tatttatctt     900
```

```
catcgtgaca aaaatttaat gcccaaaaac ccagcagcat ggagtgcatg gaattttctt        960
ggaagtacag acaagaatgt atctttgaca tactggctta atgtgcttca gaatctagga       1020
gaaacaagcc tacccttttt ggtcactctc aatccagatt atacaccaaa acacaccttg       1080
cttaagtgga gaacaggcca tccagtacca tctgttgctg caacaaaagc ttctcttgag       1140
cttgatcgga ttcaagggaa gagaggaatt tggttttgtg gagcatacct gggctatggc       1200
ttccatgaag atggattaaa ggctgggatg attgctgcaa acggtctgct gggaaaaagt       1260
tgtaatattc tgagcaatcc aaagcatatg gtgccctctc tgatggaaac aggggcacgt       1320 cttttttgtta ctagattcct cagtcatttt atatcaaccg ctgtgtgat tttattggaa       1380 gaaggtggca ctatgtttac ctttgaagga actagcaata agtgttctct aaaaactgta       1440
attaaagttc acagtccaca ttttttattgg aaggttatga cagaggcaga tttaggcctt       1500
gcagattcat atatcaatgg ggatttttct tttgttgata aaaagacgg tctgctgaac        1560 cttgtaatga ttcttattgc caacagagat ttgatttctt ccaactcaaa acttagtaag       1620 aaaagggggtt ggtggacacc attgttgttt acagctggtc taacatcagc aaagtatttc      1680
ttcaagcatg tcttaagaca aaatactctt acacaagctc gtaggaacat ttctcgccat       1740
tacgacytga gtaatgacct ttttgcactc ttccttggatg acaatgac atactcttgt        1800 gcagtattta agacagaaga tgaggattttg aaagatgcac aacacagaaa gatctctctt      1860
ttgattgaaa aagcaagaat tgatagcaag catgaaattc ttgagattgg atgtggttgg      1920
gkaagcttag ctattgaggt tgtcaaacga actggatgca aatataccgg cattacttta      1980
tccgaagagc aactcaaact tgcagaaaaa agagtgaagg aagctggact tcaggaaaat      2040
ataagatttc aactctgtga ctatcgacaa ctacctagca cctacaagta tgacagaatt      2100
atatcgtgtg agatgataga agctgttggc catgaataca tggaggactt cttcggttgc      2160
tgtgaatcag tgttagcaga tgatggactt cttgttttac agttcatatc aataccagag      2220
gaacggtaca atgaatacag gcgaagctcg gatttcatca aggaatacat cttccctggt      2280
ggatgcttac cttctctggc taggataaca acagccatga atgctgcgtc caaactctgt      2340
gtggagcatg tggaaaacat cggacttcat tactaccaaa cgcttagata ttggagaaag      2400
aatttcttgg agaaacagag caaaatccat gccttgggat tcaatgacaa gttcatccgg      2460
acatgggaat actattttga ttattgtgct gctggtttca agtccaatac tcttggtaat      2520
taccaggttg tattttctcg gcctggaaat gtagttgcac ttggcaaccc atacaaagac      2580
ttcccctcag cttcttaa                                                     2598

<210> SEQ ID NO 47
<211> LENGTH: 2514
<212> TYPE: DNA
<213> ORGANISM: Oryza sativa

<400> SEQUENCE: 47
atggggccgg cggcgccttc tgcaggtgca tcgggtgaaa ggggagcgac gctgcgccgc         60
ggcggcggat ccccagttgc cgtccggcga gcgttgacgg cgccgcccag ctgcgtaaca        120
tccccaaaca tgatgcaatg gtttgcagat cttggggcca atatggagag atcagacatg        180
tccttctctg taagaacaca attggatgct tgtggtgaat gtgaatgggc cagcagcaat        240
ggcatctcag gcctcttggc aaagaggagt aatgcgctca gccccagctt tggcgcatg         300 atcagtgaga cactcaagtt caagagggat gctctcaggt acttggagga ttgtgaaaac        360
aaccttgatc tggaacagag cgagactttg ggcaattcg ttcagtccca tggatattgt         420
```

```
cagttcttcc aagaagctta tcttttcca atctgtggtt ggatgtggtc atgtccatca    480
caaagagttt tgggcttctc tgcttcctct gtgctgtcgt tttttcgtaa gcataatctc    540
cttcagttgt ttagtcgcac ccagccgctc attgtcaatg gtcgctctca gtcctatttc    600
aacaaggtaa gagaagatct ggaaagcagg agctgtcgaa taaaaactaa ctgccatgtg    660
aaatccattt caagttttga cagaggttac agagtcttag aggttgatgg ttcagaggag    720
atgtatgaca gaatcatagt tggtatccat gcacttgatg ctctaaaatt actaggagca    780
gaagcaacac atgaagaatc aagaattctt ggtgcttttc agtatgtctc tagtaatcta    840
tatcttcact gcgatgaaag ttttatgcta tgtaattcat ccacatggag tgcctgcaac    900
ataaccagaa caagaagcgg ctctgtctgt gtcacatact ggttgaatct gcttcagaac    960
attgaatcta caaatcattt tctcgtgaca ttgaaccoct cttatgttcc tgatcatgtg   1020
ttgcttaagt ggaatacaaa tcattttgtt ccgactgtgg ctgcttcaaa ggcttctctt   1080
gagcttgatc agatccaggg caagagaggt atatggttct gcggggcata tcaaggatct   1140
ggcttccatg aagatggatt ccaggctggc aaagcagcag ctcaaagttt gcttgggaac   1200
aagattgatc ccctgacgaa cccaaagcag atggtcctgt catggacaga gactggggca   1260
cgtcttctgg tgttaagatt tctcaaacag tacatctctg ttggcaactt gatcttgttt   1320
gaagaaggtg gcactatgtt cagttttggt gaagcttgtg aaaaatgcaa taaaaaatct   1380
gttctgcaag ttcaggaccc actattttat tggcaggttg caacagaagc agaccttggt   1440
ttagcagatg cctacataaa tggctgcttc tcttttgtca ataagagaga aggccttctg   1500
aatcttttcc ttatcctcat tgccagtaga gatgcacaca ggagttcttg caggaattct   1560
agtcgaaggg gttggtggac acccttgctt tttactgccg gcgttgcatc tgctaaatat   1620
tttctgcgtc acatctcaag gaagaactct gtaacacaaa ctcgtcaaaa tgtctctcag   1680
cactatgatt tgagtaatga tttcttctcg ctttttctgg ataagtcaat gacctactca   1740
tctgccattt tcaaggatga ggaagaaagc ttagaagagg ctcagctgcg taaaataaac   1800
cttctaatcc ataaggctaa agtgggacag gatgatgaag ttcttgagat tggtagtggt   1860
tggggcagtt tggctatgga agtggtgaag caaactggct gcaaatatac aggagttaca   1920
cagtctgtgg agcaacttaa atatgcccaa agaagggtga agaagctgg cttagaggac   1980 cgaataactt ttctgctgtg tgactaccgt gaaataccat gtcacaaata tgacaggatc   2040
atatgctgtg agatgattga agaagttggt catgaataca tggatgaatt ctttggctgc   2100
tgtgagtccc ttttggctga aaatggcata tttgtcaccc agtttatctc aattccggag   2160
gaacggtatg atgagtaccg gagaagctca gactttatta agaatacat attccctggt   2220 ggatgccttc cttctctgac tcggataaca tctgccatgt ctgctgcatc aaggctctgc   2280
attgagcacg ttgagaatat tgggtaccat tattatacaa ctctgatacg ctggagggac   2340
aacttcatgg ccaataaaga taaaattttg gccctgggct tgatgagaa gttcattcgt   2400 acatgggagt actatttcat atactgcgca gccggtttta aatccaggac acttggagac   2460
taccagattg tattctctcg tcctgggaac accaagatgg gatctggctt ctaa         2514
```

<210> SEQ ID NO 48
<211> LENGTH: 2604
<212> TYPE: DNA
<213> ORGANISM: Arabidopsis thaliana

<400> SEQUENCE: 48

```
atgaaagtgg cagttatagg aagtggtata agtggattag gaagtgctta cgtacttgcg    60
aatcaaggag ttaaagaagt tgtgttgtac gagaaagaag agtcattagg aggccatgcc   120
aagacggtgc gtttcgatgg cgttgacttg gatcttggtt tcatggtctt taatcgtgtt   180
acatatccaa acatgataga gttcttcgag aaccttggag tagagatgga ggtttcagac   240
atgtctttcg cagtgagcct tgacaatggc aaaggttgtg aatggggaag ccgcaacggt   300
gtctcgggct tatttgctca aaagaagaac gttttaaatc cgtatttctg gcaaatgatc   360
agagaaattg ttagatttaa agaagacgtc ttaaattaca ttgagaagct tgagggtaac   420
cccgatatcg atcgaaagga aaccttagga gaatttctca atacacgtgg atactctgag   480
ttgtttcagc aagcttactt agtaccgata tgcggttcga tatggtcatg cccatcagat   540
ggtgtcttaa gcttctctgc ttactctgtt ctttcgtttt gttgcaacca ccaccttctt   600
cagatctttg ggaggccaca gtggctaact gttgcaggac gttctcagac ttacgtcgca   660
aaggttaggg cagaattgga gagactagga tgcaagatca gaacaagctg cgacgtaaaa   720
tctgtttcga catccgaaaa tggttgtgta actgttacaa gtggagatgg gtctgaagaa   780
gtattcgata ggtgcatatt ggctatgcac gccccagatg ctctgagatt gcttggtgaa   840
gaagttacat ttgacgaatc tagggttctt ggtgctttcc aatacgttta cagcgatata   900
tatctccatc atgacattga tttgatgcca cggaacaaag cagcgtggag tgcgtggaat   960
ttcttgggaa gtacggaaaa gaaagtatgt gtaacatact ggctcaatat acttcagaac  1020
cttggcgaga acagtgaacc attctttgta acacttaacc cagacgagac cccaaagaaa  1080
gcattgctca aatggaccac tggtcaccct gtaccatcag ttgcagcttc gatagcttca  1140
caagagcttc accagattca aggcaaacgt aacatatggt tctgtggtgc atatcagggc  1200
tatggtttcc atgaagacgg gctaaaggcc ggtatggcgg ctgcacgagg tttgttaggg  1260
aaagaaacag ctcttctgaa caatccgcga catatggtcc cttccttgac agaaacagga  1320
gctcggcttt tcgttactag attcttggga caatttatat caaccggttc tgtaacaata  1380
ctagaagaag gaggaacaat gttcacattc ggagggaagg attctacttg tcctctgaaa  1440
tctatcctca agattcacag tcctcaattt tactggaagg ttatgacaca agcggattta  1500
ggacttgcag atgcttatat caatggagat tttctcttcg ttgataaaga atcaggactt  1560
ttaaatctga ttatgattct cattgctaac agagatacaa aatcaaatct tactaagaaa  1620
aggggatggt ggacaccgat gttttaact gcgggtttag catctgcaaa gtattttcta  1680
aagcatgtct ctaggcagaa cactctaaca caagctcgta gaaacatttc tcgtcactat  1740
gaccttagca acgagctttt cggtttgttc ttggatgata ccatgactta ctcctcggca  1800
gtattcaagt cggatgatga ggatctgaga actgcacaga tgagaaaaat atctcttctg  1860
attgataagg cgagaataga gaaggaccat gaggttttag agataggatg tggatgggga  1920
actttggcca tagaagttgt gagaagaact ggatgcaaat acaccggcat tacgctatct  1980
attgagcagc ttaaatatgc tgaagaaaaa gtgaagaag ctggacttca ggaccggatt  2040
acttttgagc tccgcgatta tcgccaacta tctgatgctc acaaatatga cagaattata  2100
tcttgcgaga tgctagaagc ggtcggacat gagtttatgg agatgttttt cagtcgatgt  2160
gaagccgcac ttgctgaaga cggcctaatg gtcttgcagt tcatatcgac acccgaagag  2220
cgttacaatg agtacagact aagttcagat ttcattaaag aatacatatt ccctggtgca  2280
tgcgttcctt ctttagccaa agtcacttca gccatgtcct cttcttctag gctatgcatt  2340
gaacatgttg agaacattgg gattcattac taccaaacat tgagattgtg gaggaagaac  2400
```

```
ttcttggaga gacagaaaca aatcatggct cttggatttg atgataaatt cgtaaggaca    2460
tgggaatatt attttgatta ttgcgcagct ggattcaaga ctcgtactct tggagactac    2520
cagttggtgt tctcgcgtcc agggaacgta gctgcatttg cggattcata ccgaggattt    2580
ccttctgctt attgtgtctc ttga                                           2604

<210> SEQ ID NO 49
<211> LENGTH: 2595
<212> TYPE: DNA
<213> ORGANISM: sterculia foetida

<400> SEQUENCE: 49
atgggagtgg ctgtgatcgg tggtgggatc caagggctgg tttcggccta cgttcttgcc      60
aaagccggcg tcaacgtcgt tgtttacgag aaagaggagc aagtaggtgg ccatgccaag     120
actgttagct ttgacgccgt cgatttggac cttggcctct tgtttctcaa ccctgcaagg     180
tatccaacaa tgttggagct gtttgatagc cttgaagttg atgtggaggc aactgatgtt     240
tcattctctg taagccatga caaaggcaat ggctatgaat ggtgcagcca gtacggtttt     300
tcgaactttt tagcacacaa gaagaaaatg ttgaatcctt acaattggca agacctcaga     360
gaaactatca agttcggaaa tgatgtcaat agttatcttg aatcgcttga aagaatcct      420 gacattgatc gtaatgaaac cttggggcat tttgtagggt caagggtta ctctgaaaat      480 tttctgaaca cttacctggc tccaatatgt ggttcaatgt ggtcctgctc aaggaagaa      540 gttatgagct tttcagccta ctccattctt tcgttttgtc gcacttatca tctgtaccag     600
ctatttggga atccacagtg gctgactatt aaaaggcact catatttagt taaaaaggtc     660
agagatattc tggaaagcag aggttgtcag tttaaacttg gttgtgaagt gctttctgtt     720
ttgcctgctg atgatggtag ctccatagtc tttggagatg gtttccaaga aacgtacaat     780
ggatgcataa tggctgttaa tgctcccaca gccctaaaaa tattaggaaa ccaagcaaca     840
tttgaagaaa tgagagttct gggtgcattc caatatgctt ccagtgatat ttaccttcac     900
cgtgacagca atttaatgcc cacaaacaga tcaggttgga gtgcactgaa ttttctcaga     960
agtagagaaa ataaagcaag cttaacatac tggctcaatg tgctacagaa tgttgggaaa    1020
acaagtcagc cctttttttgt gactctcaat ccagaccgta tcccagacaa aatcttgctt    1080
aagtggtcga ctgacgtcc aattccctct gttgctgcat caaaagcttc acttgagcta    1140
gatcagattc aggggaagag aggaatctgg ttctgtggct atgacttcca tgaggatgaa    1200
ttaaaggctg gtatggatgc tgcacatcgt atcttgggaa agcattttc tgttctgcac    1260 agtccaaggc aaatgtcacc ctctttcatg gaaacaacgg cacgtcttct tgttactaaa    1320
ttctttcacc aatatataca gtgggctgc gtaataatca tagaggaagg tggcagagtt    1380
tacactttca aaggaagcat ggaaaattgt tctcttaaaa cagctctgaa agtgcataat    1440
cctcagtttt actggaggat tatgaaagaa gctgatatag ccttgctga tgcatatatc    1500 caaggagatt tttcttttgt tgacaaggat gatggtcttc ttaatctttt ccggatactt    1560
attgccaata aagagttgaa ctctgcctca ggacagaaca aaagaaggac ttggctgtca    1620
cctgcactgt tcacagctgg tatatcatct gcaaagtatt tcttgaagca ttacatgagg    1680
caaaatactg ttacacaggc tcgcaggaac atttctcgtc attatgacct gagtaatgaa    1740
cttttcactc tatacttagg tgaaatgatg caatactctt ctggaatttt taagacggga    1800
gaagaacatt tggacgttgc acagcgcaga aaaatcagtt ccttaattga taaatcaaga    1860
```

| | |
|---|---:|
| atagagaagt ggcatgaagt tcttgacatt ggatgtggtt ggggaagctt agctatggaa | 1920 |
| gttgtcaaaa gaacaggatg taaatacact ggcatcacac tttcagagca gcaactgaaa | 1980 |
| tatgcagaag aaaaagtgaa ggaagctgga cttcagggaa acatcaaatt tcttctctgt | 2040 |
| gactatcgcc agttacccaa gacattcaaa tatgacagaa tcatatctgt tgagatggtt | 2100 |
| gaacatgttg gtgaagaata tattgaggag tttttcagat gctgtgactc attattggca | 2160 |
| gagaatgggc ttttcgttct tcagttcata tcaattccag agatactttc caaagaaatc | 2220 |
| cagcaaacag ctggttttct aaaggaatat atcttccctg gtggaaccct gctttctctg | 2280 |
| gataggactt tgtcagccat ggctgctgca tcaagattta gtgtggagca gtggaaaat | 2340 |
| ataggaatta gttattatca cacactgaga tggtggagga aaaatttctt ggcaaatgaa | 2400 |
| agcaaagttc tggctttggg gttcgatgag aagttcatgc ggacatggga gtattatttt | 2460 |
| gattactgcg cagctggttt taagacaggg acacttatag attaccaggt tgtattctca | 2520 |
| cgggctggca atttcgctgc acttggcgat ccatacatag gtttcccttc agcatattcc | 2580 |
| tactcggata attga | 2595 |

<210> SEQ ID NO 50
<211> LENGTH: 2634
<212> TYPE: DNA
<213> ORGANISM: Zea mays

<400> SEQUENCE: 50

| | |
|---|---:|
| atgagagtgg cggtggtagg cgccggcgtg agcgggctgg cggcggcgca cgagctggcg | 60 |
| aggagcggcg gctcccgggt gaccgtgtac gagaaggagg actacctcgg tgggcacgcc | 120 |
| aggaccgtgg ccgtcgagga cgccgacgcc gccagcaccg tgcagctcga cctcggcttc | 180 |
| atggtcttca accgggtaac atacccaaac atgctggagt ggtttgaagg gctcggtgta | 240 |
| gagatggaga tatccgacat gtccttctca gtgagcacgg aattgggggc cagcggcagc | 300 |
| agatgcgagt ggggcagccg caatggcatc tcaggactct ggcacagaa aagcaatgca | 360 |
| ctcagcccta gtttctggcg catgattcgg gagatactca agttcaagaa cgatgctctc | 420 |
| aggtacttgg aggaccatga aaacaaccct gatatggacc ggaatgagac tctcgggcaa | 480 |
| ttcattcggt ctcatggata ttcacagttc ttccaagagg cttaccttac cccgatctgt | 540 |
| gcgtgtatat ggtcatgccc atcgcaagga gtgttgggat tctctgcttt ctttgtgctc | 600 |
| tctttctgcc gtaaccatca tcttcttcag ttgttcggtc gccccagtg gctcaccgtg | 660 |
| aagggtcgtt cgcactccta tgtacacaag gtaagggagg agttggaaag tatgggttgc | 720 |
| caaattaaaa ccagctgtga atcaaatct gtttcaagtt ctgagggagg tttcagggtt | 780 |
| acagtgtttg atggttcaga ggagacgtat gacagaatca tatttggtgt ccatgcacct | 840 |
| gatgctctaa agattctagg agctgaagca acacatgaag aattgaggat cctaggagct | 900 |
| tttcagtacg tctacagtga tatataccctc cactccgata aaagtttgat gccacggagt | 960 |
| ttgtctgctt ggagttcctg gaacttcctg gggacgacaa gcaaggggggt ttgtgtaacc | 1020 |
| tactggctaa atctgcttca gaacatagaa tctacaagca gaccttttct ggtgacgctg | 1080 |
| aatcctcctc atgtcccaga ccacgtcttt cttaaatggt acactagcca ccctgtccca | 1140 |
| tctgtggctg ccgcaaaggc ttctcttgag cttcatcaca ttcaaggaaa cagaggaatt | 1200 |
| tggttttgtg gggcatacca aggttatggt ttccatgaag atggactcaa ggctgggaaa | 1260 |
| gctgcagctc aagatttgct tggtaaggag agtgacctt tggtgaaccc aaaacagatg | 1320 |
| atcccatcgt ggtctgaggc tggggcgcgt cttctggtaa caagatttct tggtcaatat | 1380 |

```
gtgtctgtcg gcaacttggt cttgcttgaa gaaggaggca ctatgttcag ttttggtgaa      1440
gtaggcaaaa aatgccatgt gaaatctgtc ctgcgagtac atgacccat gttttactgg       1500 aaggttgcaa ctgaagcaga ccttggcttg gcagatgcct acattaacgg ttatttctca      1560
tttgtagaca agagagaagg tcttctaaat cttttcctga ttctcattgc gaacagggac      1620
gcaaacaaga gtagtagcag cgctgctggt aaaaggggtt ggtggacacc cctgctattg      1680
acagctgggg ttgcctccgc taaatacttc ctgcgtcaca tagcaaggag gaattctgtc      1740
tcacaaacac gtcaaaacat ctctcaacac tatgatctga gtaatgaatt cttctctctt      1800
ttcctggatc catcgatgac ttactcttgt gccatcttca agacggagga tcaaagctta      1860
gaggcagccc agctacagaa agtttgcctc ctaatcgata aggctaaagt ggagcgagat      1920
caccatgttc ttgagattgg ctgtggttgg ggcagcttag caatccaatt ggtgaagcaa      1980
actggttgca aatacactgg gatcacatta tcagtggagc aattgaaata tgcacagaga      2040
aaggtgaaag aagctggatt agaggaccac ataagcttca tgttgtgtga ttaccgtcaa      2100
ataccaactc agcgcaaata cgacaggatc atctcttgcg agatgatcga aggtgttggg      2160
cacgaataca tggacgattt cttcggctgc tgcgagtccc ttttggctca agacggcata      2220
tttgtcctgc agttcatctc aatcccagaa gaacggtatg aggaatacag cgcagctca      2280 gacttcatca aggaatacat cttccctggg ggttgcctgc cttcgttagc ccggatcacg      2340
tctgccatgt ctgcagcatc aaggctctgc atcgagcacc ttgagaatat tgggtaccat      2400
tactacccaa cgctgataca gtggagggac aacttcatgg ccaataagga tgcaattttg      2460
gccctgggct tcgatgagaa attcatccgt atatgggaat actacttcat atactgcgcc      2520 gctggttttca gtcacggac acttgggaac taccagattg tgttttctcg ccctggcaac      2580
gacaaattag gtgacagcgg tatacactcc ttaagcaagc tttctggcag ctaa             2634
```

<210> SEQ ID NO 51
<211> LENGTH: 519
<212> TYPE: PRT
<213> ORGANISM: Aspergillus fumigatus

<400> SEQUENCE: 51

```
Met Thr Lys Ile His Pro Glu Ser Pro Glu Asp Phe Glu Tyr Ile Glu
1               5                   10                  15

Thr Pro Pro Ala Ser Cys Thr Thr Pro Ala Asp Asp Cys Gly Val Arg
            20                  25                  30

Thr Thr Ser Tyr Pro Ala Ile Lys Asn Ala Pro Val Pro Ala Asp Ala
        35                  40                  45

Ala Gly Ser Asp Ser Phe Ser Asn Ile Leu Leu Phe Ser Leu Leu Leu
    50                  55                  60

Phe Val Pro Trp Tyr Leu Ala Arg Gln Val Gly Gly Phe Tyr Thr
65                  70                  75                  80

Thr Ile Phe Phe Ala Ile Phe Thr Val Pro Ile Leu Met Val Phe
                85                  90                  95

Trp Ser Val Ala Ser Ser Ile Ser Pro Arg Lys Asn Glu Lys Ala Lys
            100                 105                 110

Tyr Ala Gly Arg Pro Val Glu His Tyr Leu His Phe His Asn Glu His
        115                 120                 125

Asp Arg Ala Thr Tyr Arg Gly Lys Ser Lys Ile Pro Met Glu Val Phe
    130                 135                 140

Tyr Glu Lys Tyr Phe Asn Gly Glu Val Asp Phe Lys Gly Asp Ala Leu
```

```
            145                 150                 155                 160
    Glu Ala Leu Glu Phe Arg His Asp Trp Ala Asn Phe Arg Phe Thr Met
                    165                 170                 175

Gly Leu Tyr Lys His Phe Leu Phe Gly Phe Ile Pro Glu Leu Leu Val
                    180                 185                 190

His Ser Arg Ser Gln Asp Glu Gln Val Arg Asp His Tyr Asp Arg
                    195                 200                 205

Gly Asp Asp Phe Tyr Ala Trp Phe Leu Gly Pro Arg Met Ile Tyr Thr
                210                 215                 220

Ser Gly Ile Ile Ser Asp Ile Asn Lys Glu Thr Leu Glu Leu
    225                 230                 235                 240

Gln Asp Asn Lys Leu Ala Val Val Cys Glu Lys Ile Asn Val Lys Pro
                    245                 250                 255

Gly Asp Thr Ile Leu Asp Leu Gly Cys Gly Trp Gly Thr Leu Ala Lys
                    260                 265                 270

Phe Ala Ser Val His Tyr Gly Ala His Val Thr Gly Ile Thr Leu Gly
                    275                 280                 285

Arg Asn Gln Thr Ala Trp Gly Asn Lys Gly Leu Arg Ser Ala Gly Ile
                290                 295                 300

Pro Glu Ser Gln Ser Arg Ile Leu Cys Leu Asp Tyr Arg Asp Ala Pro
    305                 310                 315                 320

Arg Val Glu Gly Gly Tyr Lys Lys Ile Thr Cys Leu Glu Met Ala Glu
                    325                 330                 335

His Val Gly Val Arg His Phe Gly Ser Phe Leu Ser Gln Val Tyr Glu
                    340                 345                 350

Met Leu Asp Asp Asp Gly Val Phe Phe Leu Gln Ile Ala Gly Leu Arg
                355                 360                 365

Lys Ser Trp Gln Tyr Glu Asp Leu Ile Trp Gly Leu Phe Met Asn Lys
                370                 375                 380

Tyr Ile Phe Pro Gly Ala Asp Ala Ser Thr Pro Leu Gly Phe Val Val
    385                 390                 395                 400

Asp Lys Leu Glu Gly Ala Gly Phe Glu Ile Lys Gly Val Asp Thr Ile
                    405                 410                 415

Gly Val His Tyr Ser Ala Thr Leu Trp Arg Trp Tyr Arg Asn Trp Met
                    420                 425                 430

Gly Asn Arg Glu Lys Val Glu Ala Lys Tyr Gly Lys Arg Trp Phe Arg
                435                 440                 445

Ile Trp Glu Tyr Phe Leu Ala Tyr Ser Thr Ile Ile Ser Arg Gln Gly
    450                 455                 460

Ser Ala Thr Cys Trp Gln Leu Thr Met Val Lys Asn Ile Asn Ser Thr
    465                 470                 475                 480

His Arg Ile Glu Gly Ile Gly Ser Gln Tyr Gly Leu Lys Gly Ala Arg
                    485                 490                 495

Gln Ala Ala Ile Asp Asn Val Gly His Gly Val Leu Pro Lys Ala His
                    500                 505                 510

Val Pro Thr Val Asn Lys Glu
            515

<210> SEQ ID NO 52
<211> LENGTH: 380
<212> TYPE: PRT
<213> ORGANISM: Escherichia coli

<400> SEQUENCE: 52
```

```
Met Ser Ser Ser Cys Ile Glu Glu Val Ser Val Pro Asp Asp Asn Trp
1               5                   10                  15

Tyr Arg Ile Ala Asn Glu Leu Leu Ser Arg Ala Gly Ile Ala Ile Asn
            20                  25                  30

Gly Ser Ala Pro Ala Asp Ile Arg Val Lys Asn Pro Asp Phe Phe Lys
        35                  40                  45

Arg Val Leu Gln Glu Gly Ser Leu Gly Leu Gly Glu Ser Tyr Met Asp
    50                  55                  60

Gly Trp Trp Glu Cys Asp Arg Leu Asp Met Phe Ser Lys Val Leu
65                  70                  75                  80

Arg Ala Gly Leu Glu Asn Gln Leu Pro His His Phe Lys Asp Thr Leu
                85                  90                  95

Arg Ile Ala Gly Ala Arg Leu Phe Asn Leu Gln Ser Lys Lys Arg Ala
            100                 105                 110

Trp Ile Val Gly Lys Glu His Tyr Asp Leu Gly Asn Asp Leu Phe Ser
            115                 120                 125

Arg Met Leu Asp Pro Phe Met Gln Tyr Ser Cys Ala Tyr Trp Lys Asp
    130                 135                 140

Ala Asp Asn Leu Glu Ser Ala Gln Gln Ala Lys Leu Lys Met Ile Cys
145                 150                 155                 160

Glu Lys Leu Gln Leu Lys Pro Gly Met Arg Val Leu Asp Ile Gly Cys
                165                 170                 175

Gly Trp Gly Gly Leu Ala His Tyr Met Ala Ser Asn Tyr Asp Val Ser
            180                 185                 190

Val Val Gly Val Thr Ile Ser Ala Glu Gln Gln Lys Met Ala Gln Glu
    195                 200                 205

Arg Cys Glu Gly Leu Asp Val Thr Ile Leu Leu Gln Asp Tyr Arg Asp
    210                 215                 220

Leu Asn Asp Gln Phe Asp Arg Ile Val Ser Val Gly Met Phe Glu His
225                 230                 235                 240

Val Gly Pro Lys Asn Tyr Asp Thr Tyr Phe Ala Val Val Asp Arg Asn
                245                 250                 255

Leu Lys Pro Glu Gly Ile Phe Leu Leu His Thr Ile Gly Ser Lys Lys
            260                 265                 270

Thr Asp Leu Asn Val Asp Pro Trp Ile Asn Lys Tyr Ile Phe Pro Asn
    275                 280                 285

Gly Cys Leu Pro Ser Val Arg Gln Ile Ala Gln Ser Ser Glu Pro His
290                 295                 300

Phe Val Met Glu Asp Trp His Asn Phe Gly Ala Asp Tyr Asp Thr Thr
305                 310                 315                 320

Leu Met Ala Trp Tyr Glu Arg Phe Leu Ala Ala Trp Pro Glu Ile Ala
                325                 330                 335

Asp Asn Tyr Ser Glu Arg Phe Lys Arg Met Phe Thr Tyr Tyr Leu Asn
            340                 345                 350

Ala Cys Ala Gly Ala Phe Arg Ala Arg Asp Ile Gln Leu Trp Gln Val
    355                 360                 365

Val Phe Ser Arg Gly Val Glu Asn Gly Leu Arg Val
    370                 375                 380

<210> SEQ ID NO 53
<211> LENGTH: 382
<212> TYPE: PRT
<213> ORGANISM: Salmonella enterica

<400> SEQUENCE: 53
```

```
Met Ser Ser Ser Cys Ile Glu Val Ser Val Pro Asp Asp Asn Trp
1               5                   10                  15

Tyr Arg Ile Ala Asn Glu Leu Phe Ser Arg Ala Asp Ile Thr Ile Asn
            20                  25                  30

Gly Ser Ala Pro Ser Asp Ile Arg Val Lys Asn Pro Asp Phe Phe Lys
        35                  40                  45

Arg Val Leu Gln Glu Gly Ser Leu Gly Leu Gly Glu Ser Tyr Met Asp
    50                  55                  60

Gly Trp Trp Glu Cys Glu Arg Leu Asp Ile Phe Phe Ser Lys Val Leu
65                  70                  75                  80

Arg Ala Gly Leu Glu Asn Gln Leu Pro His His Val Lys Asp Thr Leu
                85                  90                  95

Arg Ile Leu Gly Ala Arg Leu Ile Asn Leu Gln Ser Lys Lys Arg Ala
            100                 105                 110

Trp Ile Val Gly Lys Glu His Tyr Asp Leu Gly Asn Asp Leu Phe Ser
        115                 120                 125

Arg Met Leu Asp Pro Tyr Met Gln Tyr Ser Cys Ala Tyr Trp Lys Asp
    130                 135                 140

Ala Asp Thr Leu Glu Ala Ala Gln Gln Ala Lys Leu Lys Leu Ile Cys
145                 150                 155                 160

Glu Lys Leu Gln Leu Gln Pro Gly Met Arg Val Leu Asp Ile Gly Cys
                165                 170                 175

Gly Trp Gly Gly Leu Ser Gln Tyr Met Ala Thr His Tyr Gly Val Ser
            180                 185                 190

Val Val Gly Val Thr Ile Ser Ala Glu Gln Gln Lys Met Ala Gln Thr
        195                 200                 205

Arg Cys Glu Gly Leu Asp Val Ser Ile Leu Leu Glu Asp Tyr Arg Asp
    210                 215                 220

Leu Asn Asp Gln Phe Asp Arg Ile Val Ser Val Gly Met Phe Glu His
225                 230                 235                 240

Val Gly Pro Lys Asn Tyr Asn Thr Tyr Phe Glu Val Val Asp Arg Asn
                245                 250                 255

Leu Lys Pro Asp Gly Leu Phe Leu Leu His Thr Ile Gly Ser Lys Lys
            260                 265                 270

Thr Asp His Asn Val Asp Pro Trp Ile Asn Lys Tyr Ile Phe Pro Asn
    275                 280                 285

Gly Cys Leu Pro Ser Val Arg Gln Ile Ala Glu Ala Ser Glu Ser His
290                 295                 300

Phe Val Met Glu Asp Trp His Asn Phe Gly Ala Asp Tyr Asp Thr Thr
305                 310                 315                 320

Leu Met Ala Trp His Glu Arg Phe Ile Asn Ala Trp Pro Glu Ile Ala
                325                 330                 335

Gly Asn Tyr Asn Glu Arg Phe Lys Arg Met Phe Ser Tyr Tyr Leu Asn
            340                 345                 350

Ala Cys Ala Gly Ala Phe Arg Ala Arg Asp Ile Gln Leu Trp Gln Val
        355                 360                 365

Val Phe Thr Arg Gly Val Glu Asn Gly Leu Arg Val Pro Arg
    370                 375                 380

<210> SEQ ID NO 54
<211> LENGTH: 488
<212> TYPE: PRT
<213> ORGANISM: Leishmania infantum
```

```
<400> SEQUENCE: 54

Met Glu Asn Arg Pro His Glu Asp Ser Glu Ser Lys Glu Ala Ala Ala
1               5                   10                  15

Ala Ala Leu Leu Ser Arg Glu Ser Tyr Glu Ser Val Gln Arg Leu Ser
            20                  25                  30

Lys Cys Pro Ser Asp Leu Pro Ser Glu Asn Arg Tyr Glu Val Ile
        35                  40                  45

Ala Ala Ala Met Lys Gly Asp Asp His Gly Met Gly Gly Ser Thr Ser
    50                  55                  60

Arg Val Val Asn Tyr Gly Gly Pro His Gly Asn Gly Ser Leu Phe Ser
65                  70                  75                  80

Met Ser Lys Ala Glu Tyr Ala Lys Leu Glu Lys Arg Glu Ala Lys Tyr
                85                  90                  95

Leu Arg Ile Ala Gln Lys Ile Leu Ser Ala Cys Gly Ile Thr Ile Gly
                100                 105                 110

Gly Asp Lys Pro Tyr Asp Met Val Val His Asn Pro Met Leu Phe Arg
            115                 120                 125

Arg Val Ile Arg Lys Gly Ser Leu Gly Leu Gly Glu Ala Tyr Met Glu
130                 135                 140

Gly Trp Trp Asp Thr Arg Asp Phe Tyr Ala Leu Asp Asp Phe Phe Lys
145                 150                 155                 160

Arg Ile Leu Gln Ser Gly Ile Glu Tyr Tyr Phe Pro Asn Asn Ala Lys
                165                 170                 175

Asp Met Leu Asn Ile Ile Arg Ala Lys Val His Asn Pro Gln Thr Lys
            180                 185                 190

Ser Lys Ser Arg Arg Val Gly Met Gln His Tyr Asp Ile Gly Asn Glu
        195                 200                 205

Phe Phe Arg Asn Met Leu Gly Pro Arg Met Gln Tyr Ser Cys Ala Tyr
210                 215                 220

Trp Glu Lys His Val Gly Ser Ala Glu Asp His Met Ile Lys Pro Val
225                 230                 235                 240

Glu Thr Leu Asp Glu Ala Gln Glu Leu Lys Leu His Met Ile Gly Glu
                245                 250                 255

Lys Leu Arg Leu Arg Pro Gly Met Glu Val Leu Asp Cys Gly Cys Gly
            260                 265                 270

Trp Gly Ala Leu Ala Ala Phe Leu Ser Glu Lys Tyr Ser Val Lys Val
        275                 280                 285

Thr Gly Ile Thr Ile Ser Glu Glu Gln Arg Glu Gly Ala Ala Arg Leu
290                 295                 300

Val Lys Asp Asp Pro Asn Val Thr Ile Leu Asn Arg Asp Tyr Arg Asp
305                 310                 315                 320

Ala Thr Phe Asp Arg Lys Phe Asp Arg Ile Val Ser Val Gly Met Phe
                325                 330                 335

Glu His Val Gly Pro Lys Asn Tyr Lys Thr Phe Phe Lys His Met Arg
            340                 345                 350

Arg Leu Leu Arg Asp Asp Asp Pro Glu Ala Val Leu Leu Leu His Thr
        355                 360                 365

Ile Gly Ser Lys Thr Thr Met Ser Ser Ala Asp Gln Trp Tyr Leu Lys
370                 375                 380

Tyr Ile Phe Pro Gly Gly Cys Leu Pro Ser Ile Ser Ser Ile Gly Lys
385                 390                 395                 400

Gly Ile Glu Ala Tyr Phe Val Met Glu Asp Leu His Asn Phe Gly Phe
                405                 410                 415
```

```
Phe Tyr Gly Leu Thr Leu Leu Ala Trp Arg Ser Asn Phe Leu Val His
            420                 425                 430

Trp Asn Lys Ser Ala Glu Ser Thr Lys Pro Gly Ala Asp Ala Phe Phe
            435                 440                 445

Arg Met Phe Tyr Tyr Leu Ser Ser Ser Ala Gly Ala Phe Glu Ala
450                 455                 460

Arg Asp Leu Gln Leu Trp Gln Val Val Leu Ser Pro Lys Gly Thr Pro
465                 470                 475                 480

Gly Tyr Val Ser Val Tyr Arg Pro
                485

<210> SEQ ID NO 55
<211> LENGTH: 379
<212> TYPE: PRT
<213> ORGANISM: Synechococcus sp

<400> SEQUENCE: 55

Met Glu Lys Ser Leu Ser Ile Trp His Arg Leu Ala Arg Arg Tyr Gly
1               5                   10                  15

Leu Arg Leu Leu Ser Ala Ala Asp Ile Ala Val Asn Gly Ser Arg Pro
            20                  25                  30

Trp Asp Leu Gln Ile His Asp Glu Arg Leu Tyr Leu Arg Cys Leu Leu
        35                  40                  45

Tyr Gly Ser Leu Gly Phe Gly Glu Ala Tyr Met Glu Gly Trp Trp Asp
    50                  55                  60

Cys Glu Ala Ile Asp Glu Leu Val Tyr Arg Leu Leu Thr Ser Gln Ala
65                  70                  75                  80

Ala Glu Gln Val Gly Trp Pro Val Arg Leu Leu Leu Ala Leu Asp Ser
                85                  90                  95

Arg Leu Val Asn Arg Gln Arg Gly Lys Gly Ala Phe Val Val Gly Gln
            100                 105                 110

Arg His Tyr Asp Leu Gly Asn Asp Leu Tyr Glu Ala Met Leu Asp Arg
        115                 120                 125

Arg Leu Ile Tyr Ser Cys Ala Tyr Trp Asp Gly Gly Ala Gln Thr Leu
    130                 135                 140

Asp Glu Ala Gln Glu Ala Lys Leu Asp Leu Ile Ala Arg Lys Leu Asp
145                 150                 155                 160

Leu Gln Pro Gly Met Arg Val Leu Asp Ile Gly Cys Gly Trp Gly Gly
                165                 170                 175

Thr Ala Gln Tyr Leu Ala Glu Arg Tyr Gly Val Gln Val Val Gly Ile
            180                 185                 190

Thr Val Ser Gln Glu Gln Ala Lys Leu Ala Ser Glu Arg Cys Gln Gly
        195                 200                 205

Leu Pro Val Glu Ile Arg Leu Glu Asp Tyr Arg Gln Thr Gln Gly Lys
    210                 215                 220

Phe Asp Arg Ile Ile Ser Val Gly Met Phe Glu His Val Gly Tyr Arg
225                 230                 235                 240

Asn Tyr Arg Thr Phe Met Gln Val Ala Arg Arg Leu Leu Asn Asp Asn
                245                 250                 255

Gly Leu Phe Leu Leu His Thr Ile Gly Ser Asn Val Ala Tyr Gln Gly
            260                 265                 270

Arg Asp Pro Trp Ile Glu Arg Tyr Ile Phe Pro Asn Ser Met Leu Pro
        275                 280                 285

Ser Pro Arg Leu Ile Thr Ala Ala Phe Glu Gly Leu Phe Val Leu Glu
```

```
            290                 295                 300
Asp Trp His Asn Phe Gly Ile Asn Tyr Val Ala Thr Leu Lys Ala Trp
305                 310                 315                 320

His Ala Asn Phe Glu Arg Ala Trp Pro Gln Leu Ala Arg Arg Tyr Asp
                325                 330                 335

Glu Arg Phe Arg Arg Met Trp Arg Leu Tyr Leu Leu Met Ser Ala Gly
            340                 345                 350

Ser Phe Lys Ala Arg Ala Ser Gln Leu Trp Gln Leu Val Leu Ser Pro
            355                 360                 365

Arg Gly Val Glu Gly Gly Tyr Arg Ser Val Arg
            370                 375

<210> SEQ ID NO 56
<211> LENGTH: 485
<212> TYPE: PRT
<213> ORGANISM: Neurospora crassa

<400> SEQUENCE: 56

Met Asp His Phe Ala Arg Val Leu Glu Phe Gly Glu Ile His Pro Leu
1               5                   10                  15

Gln His Leu Ala Asn Ile His Gln Gly Leu Thr Glu Ile Phe Tyr Leu
            20                  25                  30

Gly Thr Ala His Leu Arg Tyr Lys Leu Gly Ser Leu Thr Trp Gly Pro
        35                  40                  45

Ala Ile Gln Phe Ala Lys Asp Met Ala Gln Thr Thr Phe Ala Ser Leu
    50                  55                  60

Lys Val Gly Thr Phe Leu Val Asp Gln Val Ser Asp Glu Val Phe
65                  70                  75                  80

Val His Gly Glu Ser Phe Gly Thr Gly Pro Asp Glu Leu Gly Asn Leu
                85                  90                  95

Val Leu Cys Leu Arg Arg Pro Ser Glu Ser Glu Asp Glu Arg Lys Ala
            100                 105                 110

Thr Asp Leu Pro Gly Ala Glu Leu Val Val Lys Asp Asp Ala Phe Trp
        115                 120                 125

Leu Arg Leu Leu Leu Phe Thr Asp Met Gly Phe Ala Glu Ser Tyr Met
    130                 135                 140

Leu Gly Glu Phe Glu Cys Asp Asp Leu Thr Ser Phe Phe Gln Leu Phe
145                 150                 155                 160

Ile Leu Asn Arg Glu Gln Leu Asn Asn Gly Thr Thr Leu Phe Ser Gly
                165                 170                 175

Leu Phe Ser His Val Ala Gly Leu Ala Arg Leu Ala Asn Thr Met Asp
            180                 185                 190

Asn Ala Arg Leu Asn Ile Val Arg His Tyr Asp Ile Ser Asn Gly Met
        195                 200                 205

Phe Ala Ala Phe Leu Ser Pro Asp Met Met Tyr Ser Cys Pro Ile Trp
    210                 215                 220

Asn His Thr Thr Asn Ser Arg Thr Lys Gln Glu Glu Ser Leu Glu Ser
225                 230                 235                 240

Ala Gln Met Arg Lys Ile Asn Tyr Phe Ile Glu Ala Ala Lys Ile Lys
                245                 250                 255

Arg Thr Asp His Val Leu Glu Phe Gly Thr Gly Trp Gly Thr Met Ala
            260                 265                 270

Ile Glu Ala Val Arg Gln Thr Gly Cys Arg Val Thr Thr Ile Thr Leu
        275                 280                 285
```

```
Ser Gln Glu Gln Lys Thr Phe Ala Glu Arg Arg Ile Trp Ala Ala Gly
    290                 295                 300

Phe Ser Asp Lys Ile Ala Val His Leu Leu Asp Tyr Arg Met Leu Pro
305                 310                 315                 320

Asp Pro Glu Val Pro Tyr Asp Lys Ile Ile Ser Cys Glu Met Ile Glu
                325                 330                 335

Ala Val Gly Glu Lys Phe Leu Ala Thr Phe Ser Arg Val Asp Arg
                340                 345                 350

Leu Leu Lys Lys Asp Gly Gly Ile Ala Val Phe His Phe Ile Asn His
            355                 360                 365

Tyr Ile Phe Pro Gly Gly Tyr Leu Pro Ser Val Thr Gln Leu Ile Asn
370                 375                 380

His Ile Thr Thr Glu Ser Asn Gly Thr Leu Ile Val Glu Lys Ile Lys
385                 390                 395                 400

Asn Ile Gly Pro His Tyr Val Lys Ala Leu Arg Leu Trp Arg Glu Ala
                405                 410                 415

Phe Met Asn Arg Phe Asp Ser Val Ile Val Pro Ala Leu Met Val Glu
                420                 425                 430

His Pro Ser Leu Thr Glu Thr Asp Val Glu Val Phe Lys Arg Lys Trp
            435                 440                 445

Glu Tyr Tyr Phe Ser Tyr Ser Glu Ala Gly Phe Leu Thr Lys Thr Leu
450                 455                 460

Gly Asp Val Ile Ile Thr Val Gly Arg Glu Gly Ala Leu Glu Leu Met
465                 470                 475                 480

Glu Gly Ile Pro Leu
            485

<210> SEQ ID NO 57
<211> LENGTH: 474
<212> TYPE: PRT
<213> ORGANISM: Magnaporthe grisea

<400> SEQUENCE: 57

Met Ala Tyr Ile Pro Ala Ala Ile Thr Gly Pro Val Ala Arg Gly Thr
1               5                   10                  15

Glu Val Leu Arg Glu Ser Leu Gly Ser Leu Thr Trp Gly Pro Ala Met
                20                  25                  30

Ala Leu Ala Arg Pro Ala Val Glu Ala Val Phe Ser Gln Ile Glu Ile
            35                  40                  45

Gly Thr Leu Leu Leu Val Asp Glu Pro Gly Gly Arg Arg Ile Val Tyr
    50                  55                  60

Gly Gln Lys Leu Pro Asp Arg Ser Asn Gly Thr Lys Leu Asp Glu Glu
65                  70                  75                  80

Pro Leu Pro Thr Arg Pro Ser Gly Val Arg Lys Ala Thr Thr Ile Pro
                85                  90                  95

Arg Val Glu Leu Val Val Lys Arg Asp Ala Phe Trp Met Arg Leu Phe
            100                 105                 110

Leu Phe Ala Asp Met Gly Leu Ala Glu Ala Tyr Met Leu Gly Asp Val
        115                 120                 125

Glu Cys Ala Asp Leu Thr Ser Phe Phe Gln Leu Phe Ile Val Asn Arg
    130                 135                 140

Asp Gln Met Gly Asn Gly Thr Thr Arg Phe Ser Ala Ile Ser Gly Ala
145                 150                 155                 160

Ile Thr Ser Leu Ala Arg Thr Thr Asn Thr Leu Ser Asn Ser Leu Leu
                165                 170                 175
```

-continued

```
Asn Ile Ser Ala His Tyr Asp Ile Ser Asn Glu Met Phe Ala Ala Phe
                180                 185                 190

Leu Ser Pro Asp Met Thr Tyr Ser Cys Pro Val Trp Lys Ser Val Thr
            195                 200                 205

Asp Gly Ser Asp Glu Gln Glu Glu Ser Leu Glu Ala Ala Gln Leu Thr
        210                 215                 220

Lys Leu Arg Arg Phe Ile Thr Gly Ala Arg Ile Lys Ser Thr Asp His
225                 230                 235                 240

Val Leu Glu Ile Gly Thr Gly Trp Gly Ser Phe Ala Ile Glu Ala Val
                245                 250                 255

Lys Ala Thr Gly Cys Arg Val Thr Ser Leu Thr Leu Ser Lys Glu Gln
            260                 265                 270

Lys Ala Leu Ala Glu Ala Arg Ile Ala Asp Ala Gly Leu Ser Asp Arg
        275                 280                 285

Ile Glu Val Leu Leu Lys Asp Tyr Arg Ala Leu Glu Ala Pro Glu Gly
    290                 295                 300

Arg Pro Phe Asp Lys Ile Val Ser Ile Glu Met Leu Glu Ala Val Gly
305                 310                 315                 320

Gln Glu Phe Leu Ser Thr Tyr Phe Ala Cys Ile Asp Arg Leu Leu Lys
                325                 330                 335

Lys Asp Gly Gly Ile Ala Met Phe Gln Cys Ile Thr Met Pro Glu Gly
            340                 345                 350

Arg His Glu Ala Tyr Ser Lys Ser Glu Asp Phe Ile Asn His Tyr Ile
        355                 360                 365

Phe Pro Gly Gly Tyr Leu Pro Ser Ile Thr Gln Leu Leu Asn His Ile
    370                 375                 380

Ser Lys Glu Ser Gln Gly Thr Leu Ile Val Glu Gly Val Glu Asn Ile
385                 390                 395                 400

Gly Gly His Tyr Ser Lys Thr Leu Arg Leu Trp Lys Glu Ala Phe Leu
                405                 410                 415

Glu Asn Phe Asp Ser Lys Ile Lys Pro Ala Leu Lys Thr Glu His Ala
            420                 425                 430

Gly Met Thr Asp Glu Ala Ile Ala Val Phe Lys Asn Lys Trp Glu Val
        435                 440                 445

Arg Glu Ser Pro Pro Lys Phe Pro Phe Arg Tyr Pro Asp Glu Arg Thr
    450                 455                 460

Gln Pro Arg Ser Val Ser Ala Ser Leu Asn
465                 470
```

<210> SEQ ID NO 58
<211> LENGTH: 469
<212> TYPE: PRT
<213> ORGANISM: Coprinopsis cinerea

<400> SEQUENCE: 58

```
Met Pro Ala His His Pro Ser Ser Ser Ala Pro Cys Val Ser Phe
1               5                   10                  15

Pro Ser Ser Ser Lys Ala Leu Gln Ser Ser Leu Leu Ser Ala Leu
            20                  25                  30

Ser Pro Arg Ser Trp Thr Ile Ser Phe Ala Arg Asn Ser Ile Leu Ala
        35                  40                  45

Val Leu Glu Asp Ala Ile Thr Val Gly Arg Leu Thr Ile Ser Asp Ser
    50                  55                  60

Glu Gly Asp His Gln Tyr Gly Glu Arg Gln Pro Gly Cys Asn Asp Val
```

```
                65                  70                  75                  80
        Arg Leu Arg Ile Val Asn Asp Asn Phe Trp Met Arg Ile Leu Leu Ser
                            85                  90                  95
        Gly Asp Val Gly Phe Ser Glu Ala Tyr Met Ile Gly Asp Cys Glu Val
                        100                 105                 110
        Gln Thr Gly Leu Lys Gly Ala Met Asp Leu Trp Leu Asp Asn Gln Ser
                        115                 120                 125
        Gly Met Glu Met Thr Leu Ser Ser Thr Val Ala Arg Ile Ser Ser Ala
                    130                 135                 140
        Met Thr Ala Leu Tyr Asn Ser Phe Leu Gly Gln Thr Lys Ser Gln Ala
        145                 150                 155                 160
        Arg Leu Asn Ala Ile Ala Ser Tyr Asp Gln Ser Asn Glu Leu Phe Lys
                        165                 170                 175
        Ala Phe Leu Ser Lys Glu Met Met Tyr Ser Cys Ala Leu Trp Gly Glu
                        180                 185                 190
        Asn Glu Gly Gly Val Arg Gly Asp Leu Glu Leu Gly Pro Thr Pro Gly
                    195                 200                 205
        Asp Leu Glu Ala Ala Gln Leu Arg Lys Leu His His Val Leu Arg Ala
                210                 215                 220
        Ala Arg Val Lys Pro Gly Asp Arg Ile Leu Glu Phe Gly Ser Gly Trp
        225                 230                 235                 240
        Gly Gly Leu Ala Ile Glu Ala Ala Arg Thr Phe Gly Cys Glu Val Asp
                        245                 250                 255
        Thr Leu Thr Leu Ser Ile Glu Gln Lys Thr Leu Ala Glu Glu Arg Ile
                        260                 265                 270
        Ala Glu Ala Gly Leu Glu Gly Val Ile Arg Val His Leu Met Asp Tyr
                    275                 280                 285
        Arg Glu Ile Pro Ala Glu Trp Glu His Ala Phe Asp Ala Phe Ile Ser
                290                 295                 300
        Ile Glu Met Ile Glu His Val Gly Pro Lys Tyr Tyr Asn Thr Tyr Phe
        305                 310                 315                 320
        Lys Leu Val Asp Phe Ala Leu Lys Pro Gln Lys Ala Ala Val Ile
                        325                 330                 335
        Thr Ser Ser Thr Phe Pro Glu Ser Arg Tyr Ser Ser Tyr Gln Ala Glu
                        340                 345                 350
        Asp Phe Met Arg Lys Tyr Met Trp Pro Asn Ser Ser Leu Pro Ser Ala
                    355                 360                 365
        Thr Ala Leu Ile Thr Ala Ala His Thr Ala Ser Gln Gly Arg Phe Thr
                370                 375                 380
        Leu Gln Gly Val Glu Asn His Ala Ala His Tyr Pro Arg Thr Leu Arg
        385                 390                 395                 400
        Glu Trp Gly Arg Arg Leu Glu Arg Asn Leu Thr Gln Glu Leu Val Ala
                        405                 410                 415
        Arg Asp Tyr Pro Ser Leu Lys Asp Asn Ala Asp Tyr Glu Ser Phe Lys
                        420                 425                 430
        Arg Lys Trp Gln Tyr Leu Phe Ala Tyr Ala Gly Ala Gly Phe Ser Lys
                    435                 440                 445
        Gly Tyr Ile Thr Cys His Met Leu Thr Phe Ile Arg Glu Asn Asp Ile
                450                 455                 460
        Pro Glu Arg Cys Asp
        465

<210> SEQ ID NO 59
```

```
<211> LENGTH: 1560
<212> TYPE: DNA
<213> ORGANISM: Aspergillus fumigatus

<400> SEQUENCE: 59
atgacgaaaa ttcaccccga gtccctgag gacttcgagt acattgaaac acctcctgct      60
tcttgcacta cccccgcaga cgattgcggt gtgcggacga catcgtaccc ggctatcaaa     120
aatgctcccg tccccgcaga cgctgcaggc agtgatagtt ctccaacat cctgcttttc     180 tctctactgc tgtttgttcc gtggtacttg gcccgccagg tcggtggtgg tttctacacc     240
actatcttct tgcaatctt taccaccgtc cccatcctga tggtcttctg gtccgtggct     300
tcttccattt ctccccgcaa gaatgagaag gccaagtatg ctggtcgccc cgtcgagcac     360
taccttcact tccacaacga gcatgatcgt gccacctacc gcggcaagag caagattccg     420
atggaggtct tctacgaaaa gtacttcaat ggagaggttg atttcaaagg cgacgctctt     480
gaagctctgg agttcagaca cgactgggcc aacttccgct tcaccatggg cctctacaag     540
cacttcctct tcggcttcat tcctgaattg ctggtccact cccgttctca agacgaggaa     600
caggtgcgcg accactatga ccgtggcgac gacttctacg cttggttctt gggccctcgg     660
atgatctaca cctctggcat cattagtgat atcaacaagg aagagacttt ggaagaactt     720
caggacaaca agctagctgt tgtctgtgag aagatcaatg ttaagcccgg tgacactatt     780
ctcgacctgg gttgtggctg gggtactctc gccaaatttg cctcagtcca ctatggcgca     840
cacgtcaccg gtatcacgct cggccgtaac caaactgcct ggggtaacaa gggtctccgc     900
agcgccggta tccccgaatc tcagagccgt attctttgct tggactaccg tgatgctccc     960
cgcgtcgagg gcggttacaa gaagatcact tgtcttgaga tggcagagca cgtcggtgta    1020
cgccacttcg gttccttcct gtctcaggtc tatgaaatgc tagacgatga tggtgtgttc    1080
ttcctccaga tcgcgggtct ccgtaagtcc tggcagtatg aggatctcat ctgggtctg    1140 ttcatgaaca agtacatctt ccccggagct gatgccagca ctcctcttgg attcgtcgtt    1200
gataaattgg agggcgctgg ttttgaaatc aagggcgttg acactattgg tgtccactac    1260
tctgctactc tttggcgctg gtaccgcaac tggatgggta accgcagaa ggtcgaggcc    1320 aagtacggca agagatggtt tagaatctgg gagtacttcc tggcctactc aaccatcatc    1380
tcccgccagg gaagcgctac ctgctggcag ctcaccatgg tcaagaacat caactccacc    1440
caccgtattg agggtattgg ctcccagtac ggcctcaagg gtgcccgcca ggccgccatc    1500
gacaacgtgg ccacggcgt tcttccaaag gcccatgtcc cgaccgttaa caaggagtaa    1560

<210> SEQ ID NO 60
<211> LENGTH: 1140
<212> TYPE: DNA
<213> ORGANISM: Artificial Sequence
<220> FEATURE:
<223> OTHER INFORMATION: Codon optimized E. Coli CPFAS open reading
      frame for plant expression

<400> SEQUENCE: 60
atgtcatcct cctgcatcga agaagtttct gttccagacg ataactggta cagaattgcc      60
aacgaattat tgtccagagc tggtattgct attaacggtt ctgctccagc tgatattaga     120
gttaagaacc cagacttctt caagagagta ttgcaagaag gttctttggg tttgggtgaa     180
tcttatatgg atggttggtg ggaatgcgat agattggata tgttcttctc aaaggttttg     240
agagccggtt tggaaaatca attgccacat catttcaagg acaccttgag aattgctggt     300
```

| | |
|---|---:|
| gctagattat tcaacttgca atctaagaag agagcctgga tcgttggtaa agaacattac | 360 |
| gatttgggta acgacttgtt ctccagaatg ttggatccat tcatgcaata ctcttgtgct | 420 |
| tactggaagg atgctgataa tttggaatct gctcaacaag ccaagttgaa gatgatttgc | 480 |
| gaaaagttgc aattgaagcc aggtatgaga gttttggata ttggttgtgg ttggggtggt | 540 |
| ttggctcatt atatggcttc taactacgat gtttccgttg ttggtgttac catttctgct | 600 |
| gaacaacaaa agatggctca agaaagatgc gaaggtttgg atgttaccat cttgttgcaa | 660 |
| gattacagag acttgaacga ccaattcgat agaatcgttt ccgttggtat gttcgaacat | 720 |
| gttggtccaa agaactacga tacttacttc gctgttgtcg acagaaattt gaagccagaa | 780 |
| ggtattttct tgttgcatac catcggttcc aaaaagaccg atttgaatgt agatccttgg | 840 |
| atcaacaagt acatctttcc aaatggttgc ttgccatccg ttagacaaat tgctcaatct | 900 |
| tctgaaccac acttcgttat ggaagattgg cataatttcg gtgctgatta cgatacaact | 960 |
| ttgatggctt ggtacgaaag attttttggct gcttggccag aaattgctga taattactcc | 1020 |
| gaaagattca agagaatgtt cacctactac ttgaatgctt gtgctggtgc ttttagagcc | 1080 |
| agagatattc aattgtggca agttgttttc tccagaggtg ttgaaaacgg tttgagagtt | 1140 |

<210> SEQ ID NO 61
<211> LENGTH: 1149
<212> TYPE: DNA
<213> ORGANISM: Salmonella enterica

<400> SEQUENCE: 61

| | |
|---|---:|
| atgagttcat cgtgtataga agaagtcagc gtaccggatg ataactggta ccgaatcgcc | 60 |
| aacgaattgt ttagtcgtgc ggatattaca attaatggtt ccgccccgtc tgacattcgt | 120 |
| gttaagaatc ccgatttttt taaacgcgtc ctccaggaag gatcgttggg gttaggtgag | 180 |
| agttacatgg atggctggtg ggaatgcgag cgtctggata ttttcttcag caaagtctta | 240 |
| cgtgccggtc ttgaaaatca actcccccac catgtcaaag atacgctccg tatcctcggc | 300 |
| gcgcgtctga ttaatctaca aagtaaaaaa cgcgcctgga ttgtcggcaa ggaacattac | 360 |
| gatcttggta tgaccttttt tcccgtatg ctcgatccct atatgcaata ttcttgcgcc | 420 |
| tactggaaag atgccgatac gctggaagcg gcacagcaag ccaagctgaa attaatttgc | 480 |
| gaaaagctac agctacaacc ggggatgcgt gtgctggata tcggctgcgg ctggggcggc | 540 |
| ctgtcgcaat atatggcgac ccattatggc gttagcgtgg tgggcgtaac gatctccgct | 600 |
| gaacaacaaa aaatggcgca gacgcgttgc gaaggtctgg atgtctccat tctcctggaa | 660 |
| gattatcgcg accttaacga tcagtttgac cgaatcgtct ccgtcggcat gttcgaacat | 720 |
| gtcgggccaa aaaactacaa cacctatttt gaagttgttg acaggaattt aaaaccggat | 780 |
| ggtcttttcc tgctccatac tattggttct aaaaaaaccg atcataatgt cgatccgtgg | 840 |
| atcaataagt atattttccc caacggttgc ttgccgtctg ttcgtcaaat cgccgaggcc | 900 |
| agcgaatcac actttgtaat ggaagactgg cataactttg cgccgactat tgacacgact | 960 |
| ctgatggcgt ggcatgagcg ctttatcaat gcctggccag agattgcggg caattataac | 1020 |
| gagcgcttta aacgtatgtt cagctattat ctcaacgcct cgcgggtgc gtttcgcgcg | 1080 |
| cgtgatatcc agctttggca ggtggtattt acgcgcggcg ttgaaaacgg tctgcgcgtt | 1140 |
| cctcgctaa | 1149 |

<210> SEQ ID NO 62
<211> LENGTH: 1467

```
<212> TYPE: DNA
<213> ORGANISM: Leishmania infantum

<400> SEQUENCE: 62
atggaaaacc ggccacacga ggactccgaa tcgaaggaag cggcagcggc ggcgctcttg    60
tcgcgtgaat cgtacgaatc cgtgcagagg ctgtcgaagt gccccagcga cttacccagc   120
agcgagaacc gctacgaggt catcgccgcc gccatgaagg gtgacgacca cggcatgggc   180
ggcagcacga gccgcgtagt caactacggt ggcccgcacg gcaacggaag cctgttcagc   240
atgagcaagg cggagtacgc gaagctggag aagagggagg ccaagtactt gcgcatcgcc   300
cagaagatcc tgagtgcttg tggcattacc attggcggcg ataagccata cgacatggtc   360
gtgcacaacc cgatgctgtt ccgccgcgtt atccgcaagg gcagtcttgg cctcggtgag   420
gcctacatgg agggttggtg ggacacccgc gacttctatg ccctggacga cttcttcaag   480
cgcattctgc agagtgggat cgagtactac tttccaaata cgccaaaga catgctcaac   540
atcatccgcg ccaaggtgca aacccgcaa accaagtcga agagtcgcag ggtgggtatg   600
cagcactacg acatcggcaa cgagttcttt cgaaacatgc tggggccgcg catgcaatac   660
agctgcgcgt attgggagaa gcacgtcggc tccgccgaag accacatgat taagccggtg   720
gagacgctgg acgaggcgca ggagctaaag ctgcacatga ttggcgagaa gctgcgcctg   780
cgtccaggga tggaggtgct tgattgcggc tgtgggtggg gcgctctggc ggcgtttctg   840
agcgagaagt acagcgtgaa ggtgacaggc atcacgatct ccgaggagca gcgcgagggt   900
gccgcgcgtt tggtgaagga cgacccgaac gtgactatcc tcaaccgcga ctaccgcgac   960
gccaccttcg accgcaagtt tgaccgcatc gtgagcgtcg gcatgttcga gcacgttggc  1020
cccaagaact acaagacctt tttcaagcac atgcgccgtc tactgcgcga cgacgacccg  1080
gaagcggttc tgttgctgca caccatcggc agcaagacga ccatgagcag cgccgatcag  1140
tggtacctca gtacattttt ccaggcggc tgtctgccga gcatttcgag tattggcaag  1200
ggcatcgagg cgtattttgt catggaggac ctgcataact tcggcttctt ctatggcttg  1260
acgctgcttg cctggcgctc gaactttctc gttcactgga acaagtcggc cgagagcacg  1320
aagcccggcg cggatgcgtt ttttcgcatg ttctactact acctgagcag cagcgctggc  1380
gccttcgagg cacgtgacct tcagctgtgg caagtggtcc tgagcccgaa ggggacacct  1440
gggtacgtca gcgtgtaccg gccgtaa                                      1467

<210> SEQ ID NO 63
<211> LENGTH: 172
<212> TYPE: PRT
<213> ORGANISM: Cymbidium ringspot virus

<400> SEQUENCE: 63

Met Glu Arg Ala Ile Gln Gly Ser Asp Val Arg Glu Gln Ala Asp Ser
1               5                   10                  15

Glu Cys Trp Asp Gly Gly Gly Gly Thr Thr Ser Pro Phe Lys Leu
            20                  25                  30

Pro Asp Glu Ser Pro Ser Leu His Glu Trp Arg Leu His His Ser Glu
        35                  40                  45

Glu Ser Glu Asn Lys Asp Asn Pro Leu Gly Phe Lys Glu Ser Trp Ser
    50                  55                  60

Phe Gly Lys Val Val Phe Lys Arg Tyr Leu Arg Tyr Asp Gly Ala Glu
65                  70                  75                  80

Thr Ser Leu His Arg Ala Leu Gly Ser Trp Glu Arg Asp Ser Val Asn
```

```
                85                  90                  95
Asp Ala Ala Ser Arg Phe Leu Gly Leu Ser Gln Ile Gly Cys Thr Tyr
                100                 105                 110

Ser Ile Arg Phe Arg Gly Thr Arg Leu Thr Leu Ser Gly Gly Ser Gly
                115                 120                 125

Thr Leu Gln Arg Leu Ile Glu Met Ala Ile Arg Thr Lys Arg Thr Met
                130                 135                 140

Leu Gln Pro Thr Pro Ser Glu Arg Glu Gly Asn Val Ser Arg Arg Arg
145                 150                 155                 160

Pro Glu Gly Thr Glu Ala Phe Lys Glu Ser Glu
                165                 170

<210> SEQ ID NO 64
<211> LENGTH: 172
<212> TYPE: PRT
<213> ORGANISM: Pelargonium necrotic spot virus

<400> SEQUENCE: 64

Met Glu Arg Ala Val Gln Gly Gly Asp Ala Arg Glu Gln Ala Asn Ser
1               5                   10                  15

Glu Arg Trp Asp Gly Gly Cys Gly Gly Thr Ile Thr Pro Phe Lys Leu
                20                  25                  30

Ser Asp Glu Ser Pro Ser Leu His Glu Trp Arg Leu His His Ser Glu
                35                  40                  45

Glu Gly Glu Asp Gln Asp His Pro Leu Gly Phe Lys Glu Ser Trp Ser
            50                  55                  60

Phe Gly Lys Val Val Phe Lys Arg Tyr Leu Arg Tyr Gly Gly Thr Glu
65                  70                  75                  80

Thr Ser Leu His Arg Ala Leu Gly Ser Trp Glu Arg Asn Thr Val Asn
                85                  90                  95

Asn Ala Ala Ser Arg Phe Leu Gly Phe Gly Gln Ile Gly Cys Thr Tyr
                100                 105                 110

Ser Ile Arg Phe Arg Gly Ser Cys Leu Thr Ile Ser Gly Gly Ser Arg
                115                 120                 125

Thr Leu Gln Arg Leu Ile Glu Met Ala Ile Arg Thr Lys Cys Thr Val
                130                 135                 140

Leu Gln Leu Thr Pro Ser Glu Val Glu Gly Asn Val Ser Gly Gly Ser
145                 150                 155                 160

Pro Glu Gly Ile Glu Ala Phe Glu Lys Glu Ser Glu
                165                 170

<210> SEQ ID NO 65
<211> LENGTH: 172
<212> TYPE: PRT
<213> ORGANISM: Havel river tombusvirus

<400> SEQUENCE: 65

Met Glu Gly Ala Ile Gln Gly Ser Asp Ala Arg Glu Gln Ala Asn Ser
1               5                   10                  15

Glu Arg Trp Asp Gly Gly Cys Gly Gly Thr Ile Thr Pro Phe Lys Leu
                20                  25                  30

Pro Asp Glu Ser Pro Gly Leu His Glu Trp Arg Leu His Asn Ser Glu
                35                  40                  45

Glu Ser Glu Asp Lys Asp His Pro Leu Gly Phe Lys Glu Ser Trp Gly
            50                  55                  60

Phe Gly Lys Val Val Phe Lys Arg Tyr Leu Arg Tyr Asp Gly Thr Glu
```

```
                  65                  70                  75                  80
Ala Ser Leu His Arg Ala Leu Gly Ser Trp Glu Arg Gly Ser Val Asn
                        85                  90                  95

Asp Ala Ala Ser Arg Phe Leu Gly Leu Gly Gln Val Gly Cys Thr Tyr
                        100                 105                 110

Ser Ile Arg Phe Arg Gly Ser Cys Leu Thr Leu Ser Gly Gly Ser Arg
                        115                 120                 125

Thr Leu Gln Arg Leu Ile Glu Met Ala Ile Arg Thr Lys Arg Thr Met
130                 135                 140

Leu Gln Leu Thr Pro Ser Glu Val Gly Asn Val Ser Arg Gly Arg
145                 150                 155                 160

Pro Glu Gly Ala Lys Ala Phe Glu Lys Glu Ser Glu
                        165                 170

<210> SEQ ID NO 66
<211> LENGTH: 173
<212> TYPE: PRT
<213> ORGANISM: Cucumber necrosis virus

<400> SEQUENCE: 66

Met Glu Arg Ala Ile Gln Gly Ser Asp Ala Arg Glu Gln Ala Tyr Ser
1               5                   10                  15

Glu Arg Trp Asp Gly Gly Cys Gly Gly Thr Ile Thr Pro Phe Lys Leu
                20                  25                  30

Pro Asp Glu Ser Pro Ser Leu His Glu Trp Arg Leu His Asn Ser Glu
            35                  40                  45

Glu Ser Glu Asp Lys Asp His Pro Leu Gly Phe Lys Glu Ser Trp Ser
        50                  55                  60

Phe Gly Lys Val Val Phe Lys Arg Tyr Leu Arg Tyr Asp Gly Thr Glu
65                  70                  75                  80

Thr Ser Leu His Arg Ala Leu Gly Ser Trp Glu Arg Ser Thr Val Asn
                        85                  90                  95

Asp Ala Ala Ser Arg Phe Leu Gly Phe Gly Gln Ile Gly Cys Thr Tyr
                        100                 105                 110

Ser Ile Arg Phe Arg Gly Ser Cys Leu Thr Leu Ser Gly Gly Ser Arg
                        115                 120                 125

Thr Leu Gln Arg Leu Ile Glu Met Ala Ile Arg Thr Lys Tyr Thr Met
130                 135                 140

Leu Gln Leu Thr Pro Ser Glu Val Gly Asp Val Ser Arg Gly Cys
145                 150                 155                 160

Pro Glu Gly Ser Glu Ala Phe Lys Thr Lys Glu Ser Glu
                        165                 170

<210> SEQ ID NO 67
<211> LENGTH: 172
<212> TYPE: PRT
<213> ORGANISM: Grapevine Algerian latent virus

<400> SEQUENCE: 67

Met Glu Arg Thr Ile Gln Gly Ser Asp Val Arg Glu Gln Ala Asn Ser
1               5                   10                  15

Glu Arg Trp Asp Gly Gly Cys Gly Ser Thr Ile Thr Pro Phe Lys Leu
                20                  25                  30

Pro Asp Glu Ser Pro Ser Leu Tyr Glu Trp Arg Leu His Asn Ser Glu
            35                  40                  45

Glu Ser Glu Asp Lys Asp His Pro Leu Gly Phe Lys Glu Ser Trp Cys
```

```
            50                  55                  60
Phe Gly Lys Val Val Phe Lys Arg Tyr Leu Arg Tyr Asp Gly Thr Glu
 65                  70                  75                  80

Ala Ser Leu His Arg Ala Leu Gly Ser Trp Glu Arg Ser Ser Val Asn
                 85                  90                  95

Asp Ala Ala Ser Arg Phe Leu Gly Leu Gly Gln Ile Gly Cys Thr Tyr
                100                 105                 110

Ser Ile Arg Phe Arg Gly Ser Cys Leu Thr Leu Ser Gly Gly Ser Arg
            115                 120                 125

Thr Leu Gln Arg Leu Ile Glu Met Ala Ile Arg Thr Lys Cys Thr Met
        130                 135                 140

Leu Gln Leu Ala Pro Cys Glu Val Glu Ser Asp Val Ser Arg Arg Cys
145                 150                 155                 160

Pro Glu Gly Thr Glu Ala Phe Glu Lys Glu Ser Glu
                165                 170

<210> SEQ ID NO 68
<211> LENGTH: 172
<212> TYPE: PRT
<213> ORGANISM: Pear latent virus

<400> SEQUENCE: 68

Met Glu Arg Ala Ile Gln Gly Ser Asp Ala Arg Glu Gln Ala Tyr Ser
 1               5                  10                  15

Glu Arg Trp Asp Gly Gly Cys Gly Gly Thr Ile Thr Pro Phe Lys Leu
                20                  25                  30

Pro Asp Glu Ser Pro Ser Leu Ile Glu Trp Arg Leu His Asn Ser Glu
            35                  40                  45

Glu Ser Glu Asp Lys Asp Asn Pro Leu Gly Phe Lys Glu Ser Trp Ser
        50                  55                  60

Phe Gly Lys Val Val Phe Lys Arg Tyr Leu Arg Tyr Asp Gly Thr Glu
 65                  70                  75                  80

Ala Ser Leu His Arg Ala Leu Gly Ser Trp Glu Arg Asp Thr Val Asn
                 85                  90                  95

Asn Ala Ala Ser Arg Phe Leu Gly Phe Gly Gln Ile Gly Cys Thr Tyr
                100                 105                 110

Cys Ile Arg Phe Arg Gly Ser Cys Leu Thr Ile Ser Gly Gly Ser Arg
            115                 120                 125

Thr Leu Gln Arg Leu Ile Glu Met Ala Ile Arg Thr Lys Arg Thr Met
        130                 135                 140

Leu Gln Leu Thr Pro Cys Glu Val Glu Gly Asn Val Ser Arg Gly Ser
145                 150                 155                 160

Pro Glu Gly Thr Glu Ala Phe Lys Glu Glu Ser Glu
                165                 170

<210> SEQ ID NO 69
<211> LENGTH: 172
<212> TYPE: PRT
<213> ORGANISM: Lisianthus necrotic virus

<400> SEQUENCE: 69

Met Glu Arg Ala Ile Gln Gly Ser Asp Ala Arg Glu Gln Ala Tyr Ser
 1               5                  10                  15

Glu Arg Trp Asp Gly Gly Cys Gly Gly Thr Ile Thr Pro Phe Lys Leu
                20                  25                  30

Pro Asp Glu Ser Pro Ser Leu Ile Glu Trp Arg Leu His Asn Ser Glu
```

```
                35                  40                  45
Glu Ser Glu Asp Lys Asp Asn Pro Leu Gly Phe Lys Glu Ser Trp Ser
 50                  55                  60

Phe Gly Lys Val Val Phe Lys Arg Tyr Leu Arg Tyr Asp Gly Thr Glu
 65                  70                  75                  80

Ala Ser Leu His Arg Ala Leu Gly Ser Trp Glu Arg Asp Thr Val Asn
                 85                  90                  95

Asp Ala Ala Ser Arg Phe Leu Gly Phe Gly Gln Ile Gly Cys Thr Tyr
                100                 105                 110

Cys Ile Arg Phe Arg Gly Ser Cys Leu Thr Ile Ser Gly Gly Ser Arg
                115                 120                 125

Thr Leu Gln Arg Leu Ile Glu Met Ala Ile Arg Thr Lys Arg Thr Met
                130                 135                 140

Leu Gln Leu Ala Pro Cys Glu Val Glu Gly Asn Val Ser Arg Gly Ser
145                 150                 155                 160

Pro Glu Gly Thr Glu Ala Phe Lys Glu Glu Ser Glu
                165                 170

<210> SEQ ID NO 70
<211> LENGTH: 172
<212> TYPE: PRT
<213> ORGANISM: Lettuce necrotic stunt virus

<400> SEQUENCE: 70

Met Glu Arg Ala Ile Gln Gly Asn Asp Ala Arg Glu Gln Ala Asn Ser
 1               5                  10                  15

Glu Arg Trp Asn Gly Gly Ser Gly Ser Ala Ser Pro Phe Lys Phe
                 20                  25                  30

Pro Asp Glu Ser Pro Ser Trp Thr Glu Trp Arg Leu His Asn Asp Glu
                 35                  40                  45

Thr Asn Ser Asn Gln Asp Asn Pro Leu Gly Phe Lys Glu Ser Trp Gly
 50                  55                  60

Phe Gly Lys Val Val Phe Lys Arg Tyr Leu Arg Tyr Asp Gly Thr Glu
 65                  70                  75                  80

Ala Ser Leu His Arg Val Leu Gly Ser Trp Thr Gly Asp Ser Val Asn
                 85                  90                  95

Tyr Ala Ala Ser Arg Phe Phe Gly Ile Asn Gln Ile Gly Cys Thr Tyr
                100                 105                 110

Ser Ile Arg Phe Arg Gly Val Ser Val Thr Ile Ser Gly Gly Ser Arg
                115                 120                 125

Ala Leu Gln His Leu Cys Glu Met Ala Val Arg Ala Lys Gln Glu Leu
                130                 135                 140

Leu Gln Leu Thr Pro Val Glu Val Glu Ser Asn Val Ser Arg Arg Cys
145                 150                 155                 160

Pro Glu Gly Phe Glu Ala Phe Glu Lys Glu Ser Glu
                165                 170

<210> SEQ ID NO 71
<211> LENGTH: 172
<212> TYPE: PRT
<213> ORGANISM: Artichoke Mottled Crinkle Virus

<400> SEQUENCE: 71

Met Glu Arg Val Ile Gln Gly Asn Asp Ala Arg Glu Gln Ala Asn Gly
 1               5                  10                  15

Glu Arg Trp Asp Gly Gly Ser Gly Gly Thr Thr Ser Pro Phe Lys Leu
```

```
            20                  25                  30
Pro Asp Glu Ser Pro Ser Trp Thr Glu Trp Arg Ile His Asn Asp Glu
            35                  40                  45

Thr Asp Ser Asn Lys Asp Asn Pro Leu Gly Phe Lys Glu Ser Trp Gly
 50                  55                  60

Phe Gly Lys Val Val Phe Lys Arg Tyr Leu Arg Tyr Asp Arg Thr Glu
 65                  70                  75                  80

Thr Ser Leu His Arg Val Leu Gly Ser Trp Thr Gly Asp Ser Val Asn
                 85                  90                  95

Tyr Ala Ala Ser Arg Phe Leu Gly Val Asn Gln Ile Gly Cys Thr Tyr
                100                 105                 110

Ser Ile Arg Phe Arg Gly Val Ser Val Thr Ile Ser Gly Gly Ser Arg
                115                 120                 125

Thr Leu Gln His Leu Cys Glu Met Ala Ile Arg Ser Lys Gln Glu Leu
                130                 135                 140

Leu Gln Leu Ala Pro Val Glu Val Ser Asn Val Ser Arg Gly Arg
145                 150                 155                 160

Pro Glu Gly Ala Glu Ala Phe Lys Glu Glu Ser Glu
                165                 170

<210> SEQ ID NO 72
<211> LENGTH: 172
<212> TYPE: PRT
<213> ORGANISM: Carnation Italian ringspot virus

<400> SEQUENCE: 72

Met Glu Arg Ala Ile Gln Gly Asn Gln Ala Arg Glu Gln Ala Asn Gly
 1               5                  10                  15

Glu Arg Trp Asp Gly Gly Ser Gly Gly Thr Thr Ser Pro Phe Lys Leu
                20                  25                  30

Ser Asp Glu Ser Pro Ser Trp Thr Glu Trp Arg Leu His Asn Asp Glu
            35                  40                  45

Thr Asn Ser Asn Gln Asp Asn Pro Leu Gly Phe Lys Glu Ser Trp Gly
 50                  55                  60

Phe Gly Lys Val Val Phe Lys Arg Tyr Leu Arg Tyr Asp Arg Thr Glu
 65                  70                  75                  80

Thr Ser Leu His Arg Val Leu Gly Ser Trp Thr Gly Asn Ser Val Asn
                 85                  90                  95

Tyr Ala Ala Ser Arg Phe Phe Gly Val Asn Gln Ile Gly Cys Thr Tyr
                100                 105                 110

Ser Ile Arg Phe Arg Gly Val Ser Val Thr Ile Ser Gly Gly Ser Arg
                115                 120                 125

Thr Leu Gln His Leu Cys Glu Met Ala Ile Arg Ser Lys Gln Glu Leu
                130                 135                 140

Leu Gln Leu Thr Pro Val Glu Val Ser Asn Val Ser Arg Gly Cys
145                 150                 155                 160

Pro Glu Gly Ala Glu Ala Phe Glu Glu Glu Ser Glu
                165                 170

<210> SEQ ID NO 73
<211> LENGTH: 170
<212> TYPE: PRT
<213> ORGANISM: Maize necrotic streak virus

<400> SEQUENCE: 73

Met Glu Arg Ala Ile Gln Gly Ser Asp Ala Trp Gln Gln Thr Gly Gly
```

```
             1               5                  10                 15
        Gln Arg Arg Val Gly Gly Cys Gly Asp Ser Phe Ala Pro Phe Gln Leu
                         20                 25                 30

Pro Asp Glu Ser Pro Thr Ser Asp Glu Trp Arg Leu His His Asp Ala
                         35                 40                 45

Tyr Asp Pro Asp Thr Asp Cys Pro Leu Gly Phe Lys Glu Phe Trp Ser
                     50                 55                 60

Val Gly Lys Ala Ile Ser Lys Arg Tyr His Arg Tyr Asp Trp Lys Glu
         65                 70                 75                 80

Ala Ser Leu Asp Arg Ala Leu Gly Ser Trp Gln Gly Asp Lys Val Ile
                         85                 90                 95

Thr Glu Ala Ser Arg Phe Leu Gly Val Asp Gln Val Ser Cys Thr Tyr
                        100                105                110

Ser Ile Arg Val Arg Gly Val Ser Ile Thr Leu Ser Gly Gly Ser Arg
                        115                120                125

Ala Leu Leu Arg Leu Val Ser Met Ala Asp Arg Ile Lys Arg Ser Glu
                    130                135                140

Leu Gln Phe Ala Thr Ser Ala Val Glu Ser Val Val Ser Arg Gly Cys
        145                150                155                160

Pro Glu Glu Glu Thr Pro Lys Glu Ser Glu
                        165                170

<210> SEQ ID NO 74
<211> LENGTH: 119
<212> TYPE: PRT
<213> ORGANISM: Watermelon chlorotic stunt virus

<400> SEQUENCE: 74

Met Trp Asp Pro Leu Leu Asn Asp Phe Pro Glu Ser Val His Gly Phe
         1               5                  10                 15

Arg Cys Met Leu Ala Val Lys Tyr Leu Gln Ala Val Glu Ser Thr Tyr
                         20                 25                 30

Glu Pro Asn Thr Leu Gly His Glu Leu Ile Arg Asp Leu Ile Leu Val
                         35                 40                 45

Leu Arg Ala Arg Asp Tyr Gly Glu Ala Asn Arg Arg Tyr Ser His Phe
                     50                 55                 60

His Ser Arg Phe Glu Gly Ser Ser Lys Thr Glu Leu Arg Gln Pro Leu
         65                 70                 75                 80

His Glu Pro Cys Cys Cys Pro His Cys Pro Gly His Lys Gln Ala Ser
                         85                 90                 95

Thr Met Gly Gln Gln Ala His Val Ser Lys Ala Gln Asp Val Gln Asp
                        100                105                110

Val Ser Lys Pro Arg Cys Pro
                115

<210> SEQ ID NO 75
<211> LENGTH: 116
<212> TYPE: PRT
<213> ORGANISM: Okra yellow crinkle virus

<400> SEQUENCE: 75

Met Trp Asp Pro Leu Val Asn Glu Phe Pro Glu Ser Val His Gly Phe
         1               5                  10                 15

Arg Cys Met Leu Ala Ile Lys Tyr Leu Gln Ala Leu Glu Asp Thr Tyr
                         20                 25                 30

Glu Pro Asn Thr Leu Gly Ser Asp Leu Ile Arg Asp Leu Ile Ser Val
```

```
            35                  40                  45
Ile Arg Ala Lys Asn Tyr Val Glu Ala Thr Arg Arg Tyr Asn Phe Phe
 50                  55                  60

His Ala Arg Leu Glu Gly Ser Ser Lys Ala Glu Leu Arg Gln Pro Leu
 65                  70                  75                  80

His Glu Pro Cys Asn Cys Pro His Cys Pro Arg His Lys Gln Thr Ser
                 85                  90                  95

Val Met Asp Ser Pro Ala Asn Val Gln Lys Ala Gln Asn Val Pro Asp
            100                 105                 110

Val Gln Lys Pro
        115

<210> SEQ ID NO 76
<211> LENGTH: 116
<212> TYPE: PRT
<213> ORGANISM: Okra leaf curl virus

<400> SEQUENCE: 76

Met Trp Asp Pro Leu Val Asn Glu Phe Pro Glu Ser Val His Gly Phe
 1               5                  10                  15

Arg Cys Met Leu Ala Ile Lys Tyr Leu Gln Ala Leu Glu Asp Thr Tyr
            20                  25                  30

Glu Pro Asn Thr Leu Gly Ser Asp Leu Ile Arg Asp Leu Ile Ser Val
            35                  40                  45

Ile Arg Ala Lys Asn Tyr Val Glu Ala Thr Arg Arg Tyr Asn Tyr Phe
 50                  55                  60

His Ala Arg Leu Glu Gly Ser Ser Lys Ala Glu Leu Arg Gln Pro Leu
 65                  70                  75                  80

His Glu Pro Cys Asn Cys Pro His Cys Pro Arg His Lys Gln Thr Ser
                 85                  90                  95

Val Met Asp Leu Pro Ala Asn Val Gln Lys Ala Gln Asn Val Pro Asp
            100                 105                 110

Val Gln Lys Pro
        115

<210> SEQ ID NO 77
<211> LENGTH: 116
<212> TYPE: PRT
<213> ORGANISM: Tomato leaf curl Togo virus

<400> SEQUENCE: 77

Met Trp Asp Pro Leu Leu Asn Glu Phe Pro Asp Ser Val His Gly Phe
 1               5                  10                  15

Arg Cys Met Leu Gly Ile Lys Tyr Leu Gln Leu Leu Glu Glu Glu Tyr
            20                  25                  30

Glu Pro Asn Thr Leu Gly His Asp Leu Val Arg Asp Leu Ile Ser Val
            35                  40                  45

Val Arg Ala Lys Asn Tyr Val Glu Ala Thr Arg Arg Tyr Asn Asn Phe
 50                  55                  60

His Ala Arg Leu Glu Gly Ala Ser Thr Ala Glu Leu Arg Gln Pro Leu
 65                  70                  75                  80

Arg Gln Pro Cys Cys Cys Pro His Cys Pro Arg His Lys Gln Ala Ser
                 85                  90                  95

Phe Val Asp Val Pro Ala His Val Ser Gln Ala Lys Asn Val Gln Asp
            100                 105                 110

Val Gln Asn Ser
```

-continued

<210> SEQ ID NO 78
<211> LENGTH: 116
<212> TYPE: PRT
<213> ORGANISM: Ageratum leaf curl Cameroon virus

<400> SEQUENCE: 78

Met Trp Asp Pro Leu Leu Asn Glu Phe Pro Asp Ser Val His Gly Phe
1               5                   10                  15

Arg Cys Met Leu Gly Ile Lys Tyr Leu Gln Leu Leu Glu Glu Glu Tyr
            20                  25                  30

Glu Pro Asn Thr Leu Gly His Asp Leu Ile Arg Asp Leu Ile Ser Val
        35                  40                  45

Ile Arg Ala Lys Asn Tyr Val Glu Ala Thr Arg Tyr Asn Asn Phe
    50                  55                  60

His Ala Arg Leu Glu Gly Ala Ser Thr Ser Glu Leu Arg Gln Pro Leu
65                  70                  75                  80

His Gln Pro Cys Cys Cys Pro His Cys Pro Arg His Lys Gln Ala Ser
                85                  90                  95

Phe Met Asp Val Pro Ala His Val Pro Lys Ala Gln Asn Val Pro Asp
            100                 105                 110

Val Gln Asn Pro
        115

<210> SEQ ID NO 79
<211> LENGTH: 116
<212> TYPE: PRT
<213> ORGANISM: East African cassava mosaic Malawi virus

<400> SEQUENCE: 79

Met Trp Asp Pro Leu Leu Asn Glu Phe Pro Asp Ser Val His Gly Phe
1               5                   10                  15

Arg Cys Met Leu Ala Ile Lys Tyr Leu Gln Ala Leu Glu Glu Thr Tyr
            20                  25                  30

Glu Pro Asn Thr Leu Gly His Asp Leu Val Arg Asp Leu Ile Cys Val
        35                  40                  45

Ile Arg Ala Arg Asp Tyr Val Glu Ala Thr Arg Arg Tyr Asn His Phe
    50                  55                  60

His Ser Arg Leu Glu Gly Ala Ser Lys Ala Glu Leu Arg Gln Pro Val
65                  70                  75                  80

Gln Gln Pro Cys Cys Cys Pro His Cys Pro Arg His Lys Gln Ala Thr
                85                  90                  95

Ile Met Asp Val Pro Ala His Val Ser Lys Ala Gln Asn Val Gln Asn
            100                 105                 110

Val Gln Lys Ser
        115

<210> SEQ ID NO 80
<211> LENGTH: 116
<212> TYPE: PRT
<213> ORGANISM: South African cassava mosaic virus

<400> SEQUENCE: 80

Met Trp Asp Pro Leu Val Asn Glu Phe Pro Glu Ser Val His Gly Phe
1               5                   10                  15

Arg Cys Met Leu Ala Ile Lys Tyr Leu Gln Ala Val Glu Glu Thr Tyr
            20                  25                  30

```
Glu Pro Asn Thr Leu Gly His Asp Leu Val Arg Asp Leu Ile Cys Val
             35                  40                  45

Leu Arg Ala Arg Asp Tyr Val Glu Ala Thr Arg Arg Tyr Asn His Phe
         50                  55                  60

His Ser Arg Leu Glu Gly Ala Thr Lys Ala Glu Leu Arg Gln Pro Val
 65                  70                  75                  80

Gln Gln Pro Cys Cys Cys Pro His Cys Pro Arg His Lys Gln Ala Pro
                 85                  90                  95

Ile Met Asp Val Thr Ala His Val Ser Lys Ala Gln Asn Val Gln Asn
            100                 105                 110

Val Gln Lys Ser
        115
```

<210> SEQ ID NO 81
<211> LENGTH: 116
<212> TYPE: PRT
<213> ORGANISM: Tomato leaf curl Madagascar virus

<400> SEQUENCE: 81

```
Met Trp Asp Pro Leu Leu Asn Glu Phe Pro Asp Ser Val His Gly Phe
 1               5                  10                  15

Arg Cys Met Leu Ala Val Lys Tyr Leu Gln Ala Val Glu Glu Thr Tyr
             20                  25                  30

Glu Pro Asn Thr Leu Gly His Asp Leu Ile Arg Asp Leu Ile Ser Val
             35                  40                  45

Ile Arg Ala Arg Asp Tyr Val Glu Ala Thr Arg Arg Tyr Asn His Phe
         50                  55                  60

His Ala Arg Leu Glu Gly Ser Ser Lys Ala Glu Leu Arg Gln Pro Ile
 65                  70                  75                  80

Tyr Gln Pro Cys Cys Cys Pro His Cys Pro Arg His Lys Gln Ala Ser
                 85                  90                  95

Val Met Asp Leu Pro Ala His Val Pro Lys Ala Gln Asp Val Gln Asn
            100                 105                 110

Val Gln Lys Pro
        115
```

<210> SEQ ID NO 82
<211> LENGTH: 116
<212> TYPE: PRT
<213> ORGANISM: Tobacco leaf curl Zimbabwe virus

<400> SEQUENCE: 82

```
Met Trp Asp Pro Leu Leu Asn Glu Phe Pro Glu Ser Val His Gly Phe
 1               5                  10                  15

Arg Cys Met Leu Ala Ile Lys Tyr Leu Gln Ala Val Glu Glu Ser Tyr
             20                  25                  30

Glu Pro Asn Thr Leu Gly His Asp Leu Ile Arg Asp Leu Ile Cys Val
             35                  40                  45

Ile Arg Ala Arg Asp Tyr Val Glu Ala Thr Arg Arg Tyr Asn His Phe
         50                  55                  60

His Ala Arg Leu Glu Gly Ser Ser Lys Ala Glu Leu Arg Gln Pro Ile
 65                  70                  75                  80

Tyr Gln Pro Cys Cys Cys Pro His Cys Pro Arg His Lys Gln Thr Thr
                 85                  90                  95

Val Val Asp Leu Pro Ala Gln Leu Pro Lys Ala Gln Asn Val Pro Asp
            100                 105                 110
```

Val Gln Lys Ser
        115

<210> SEQ ID NO 83
<211> LENGTH: 116
<212> TYPE: PRT
<213> ORGANISM: Tomato begomovirus

<400> SEQUENCE: 83

Met Trp Asp Pro Leu Leu Asn Glu Phe Pro Asp Ser Val His Gly Phe
1               5                   10                  15

Arg Cys Met Leu Ala Val Lys Tyr Leu Gln Ala Val Glu Glu Thr Tyr
            20                  25                  30

Glu Pro Asn Thr Leu Gly His Asp Leu Ile Arg Asp Leu Ile Ser Val
        35                  40                  45

Ile Arg Ala Arg Asp Tyr Val Glu Ala Thr Arg Arg Tyr Asn His Phe
    50                  55                  60

His Ala Arg Leu Glu Gly Ser Ser Lys Ala Glu Leu Arg Gln Pro Ile
65                  70                  75                  80

Tyr Gln Pro Cys Cys Cys Pro His Cys Pro Arg His Lys Gln Ala Ser
                85                  90                  95

Val Met Asp Leu Pro Ala His Val Pro Lys Ala Gln Asp Val Gln Asn
            100                 105                 110

Val Gln Lys Pro
        115

<210> SEQ ID NO 84
<211> LENGTH: 116
<212> TYPE: PRT
<213> ORGANISM: Tomato leaf curl Namakely virus

<400> SEQUENCE: 84

Met Trp Asp Pro Leu Leu Asn Glu Phe Pro Asp Ser Val His Gly Phe
1               5                   10                  15

Arg Cys Met Leu Ala Ile Lys Tyr Leu Gln Ala Ile Glu Gln Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Phe Glu Gly Ala Ser Lys Val Glu Leu Arg Gln Pro Val
65                  70                  75                  80

Tyr Gln Pro Cys Cys Cys Pro His Cys Pro Arg His Lys Gln Thr Ser
                85                  90                  95

Val Met Asp Val Gln Ala His Val Ser Lys Ala Gln Asp Val Gln Asn
            100                 105                 110

Val Gln Lys Pro
        115

<210> SEQ ID NO 85
<211> LENGTH: 116
<212> TYPE: PRT
<213> ORGANISM: Pepper yellow vein Mali virus

<400> SEQUENCE: 85

Met Trp Asp Pro Leu Leu Asn Glu Phe Pro Asp Ser Val His Gly Phe
1               5                   10                  15

```
Arg Cys Met Leu Ala Ile Lys Tyr Leu Gln Ala Val Glu Asp Ser Tyr
            20                  25                  30

Glu Pro Asn Thr Leu Gly His Asp Leu Ile Arg Asp Leu Ile Cys Val
        35                  40                  45

Ile Arg Ala Arg Asp Tyr Val Glu Ala Thr Arg Arg Tyr Asn His Phe
50                  55                  60

His Ala Arg Leu Glu Gly Ser Ser Lys Ala Glu Leu Arg Gln Pro Ile
65                  70                  75                  80

Gln Gln Pro Cys Cys Cys Pro His Cys Pro Arg His Lys Gln Ala Ser
            85                  90                  95

Ile Met Asp Leu Pro Ala His Val Ser Lys Ala Gln Asp Val Gln Asn
            100                 105                 110

Val Gln Lys Pro
        115
```

```
<210> SEQ ID NO 86
<211> LENGTH: 116
<212> TYPE: PRT
<213> ORGANISM: Tomato leaf curl Sudan virus

<400> SEQUENCE: 86

Met Trp Asp Pro Leu Leu Asn Glu Phe Pro Glu Ser Val His Gly Phe
1               5                   10                  15

Arg Cys Met Leu Ala Ile Lys Tyr Leu Gln Ala Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Ser His Phe
50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
            85                  90                  95

Ile Met Asp Val Gln Ala His Val Ser Lys Ala Gln Asn Ile Gln Asn
            100                 105                 110

Val Ser Lys Ser
        115
```

```
<210> SEQ ID NO 87
<211> LENGTH: 116
<212> TYPE: PRT
<213> ORGANISM: Tomato leaf curl Oman virus

<400> SEQUENCE: 87

Met Trp Asp Pro Leu Leu Asn Glu Phe Pro Glu Ser Val His Gly Phe
1               5                   10                  15

Arg Cys Met Leu Ala Ile Lys Tyr Leu Gln Ala Val Glu Gln Thr Tyr
            20                  25                  30

Glu Pro Asn Thr Leu Gly His Asp Leu Ile Arg Asp Leu Ile Ser Val
        35                  40                  45

Ile Arg Ala Arg Asp Tyr Val Glu Ala Ser Arg Arg Tyr Asn His Phe
50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
            85                  90                  95
```

```
Val Met Asp Val Gln Ala His Val Pro Lys Ala Gln Asn Ile Gln Asn
            100                 105                 110
Val Ser Lys Pro
        115

<210> SEQ ID NO 88
<211> LENGTH: 8
<212> TYPE: PRT
<213> ORGANISM: Artificial Sequence
<220> FEATURE:
<223> OTHER INFORMATION: conserved DGAT motif
<220> FEATURE:
<221> NAME/KEY: X
<222> LOCATION: (3)..(3)
<223> OTHER INFORMATION: any amino acid other than proline
<220> FEATURE:
<221> NAME/KEY: X
<222> LOCATION: (5)..(7)
<223> OTHER INFORMATION: any amino acid other than proline
<220> FEATURE:
<221> NAME/KEY: X
<222> LOCATION: (8)..(8)
<223> OTHER INFORMATION: any nonpolar amino acid

<400> SEQUENCE: 88

Phe Leu Xaa Leu Xaa Xaa Xaa Xaa
1               5

<210> SEQ ID NO 89
<211> LENGTH: 4
<212> TYPE: PRT
<213> ORGANISM: Artificial Sequence
<220> FEATURE:
<223> OTHER INFORMATION: conserved DGAT motif

<400> SEQUENCE: 89

His Pro His Gly
1

<210> SEQ ID NO 90
<211> LENGTH: 24
<212> TYPE: PRT
<213> ORGANISM: Artificial Sequence
<220> FEATURE:
<223> OTHER INFORMATION: conserved DGAT motif
<220> FEATURE:
<221> NAME/KEY: X
<222> LOCATION: (2)..(2)
<223> OTHER INFORMATION: any amino acid
<220> FEATURE:
<221> NAME/KEY: X
<222> LOCATION: (5)..(5)
<223> OTHER INFORMATION: any amino acid
<220> FEATURE:
<221> NAME/KEY: X
<222> LOCATION: (6)..(6)
<223> OTHER INFORMATION: lysine or arginine
<220> FEATURE:
<221> NAME/KEY: X
<222> LOCATION: (7)..(7)
<223> OTHER INFORMATION: any amino acid
<220> FEATURE:
<221> NAME/KEY: X
<222> LOCATION: (9)..(11)
<223> OTHER INFORMATION: any amino acid
<220> FEATURE:
<221> NAME/KEY: X
<222> LOCATION: (13)..(15)
<223> OTHER INFORMATION: any amino acid
<220> FEATURE:
<221> NAME/KEY: X
<222> LOCATION: (16)..(16)
<223> OTHER INFORMATION: leucine or valine
```

```
<220> FEATURE:
<221> NAME/KEY: X
<222> LOCATION: (19)..(21)
<223> OTHER INFORMATION: any amino acid
<220> FEATURE:
<221> NAME/KEY: X
<222> LOCATION: (24)..(24)
<223> OTHER INFORMATION: glutamic acid or glutamine

<400> SEQUENCE: 90

Arg Xaa Gly Phe Xaa Xaa Xaa Ala Xaa Xaa Xaa Gly Xaa Xaa Xaa Xaa
1               5                   10                  15

Val Pro Xaa Xaa Xaa Phe Gly Xaa
            20

<210> SEQ ID NO 91
<211> LENGTH: 1908
<212> TYPE: DNA
<213> ORGANISM: Nicotiana benthamiana

<400> SEQUENCE: 91
atgggtgctg tttatagaag tcttttttgct aaagatggat tcctcctcc tattcctgga      60 cttgacagtt gctgggatat tttccgtttg tcagtggaaa aatatcctaa caatcggatg     120
cttggacgcc gtgagattgt agatggaaaa cctggcaagt atgtgtggat gtcttacaaa     180
gaagtatatg acattgtgat taaattagga aattccatcc ggagctgtgg tgtggacgaa     240
ggagacaaat gtggtatcta tggtgccaat tgccctgagt ggataatgag catggaggca     300
tgcaatgctc atggacttta ctgtgtgcct ctatatgaca ccttaggtgc tggtgcagtg     360
gaatttatca ttaaccatgc cgaggttaaa attgctttcg ttgaagagaa aaaacttcct     420
gagcttctga aaacttttcc aaatgcagca agtacttga agactgttgt gagttttggg     480
aatgtcactc tcaacagaa ggaagaggtt gaaaactgtg gggtgactct atactcgtgg     540
gatgagttcc tacaattggg aagtgaaaaa caatttgatc ttccagtgaa aagaaagaa     600 gatatttgta caataatgta tactagtgga acgaccggag atcccaaagg tgtgctgatt     660
tcaaataata gcattgttac tcttatagct ggagtacagc gtctgcttgg gagtgtgaat     720
gagtcgttga cagtggatga tgtatatctt tcatatcttc cactggcaca tatctttgat     780
cgggttatcg aagaatgttt cattaatcat ggtgcctcaa taggattttg gcgaggggat     840
gtcaagttac ttaccgaaga tattggagag ctgaaaccaa ctatcttctg tgctgtaccc     900
cgtgtactag acagaatata ttcaggtttg caacagaaaa tttcttctgg gggtcggctt     960
aaaagcacat tgttcaatct tgcctatgct acaaacact acaatttgaa gaagggacgt    1020
aaacactttg aagcttctcc actttctgac aaagttgtct tcagtaaggt aaaagaaggg    1080
ctaggaggca aagtacgtct tatattatct ggagcagcgc ccttgcagc tcatgtggaa    1140 gcttttctgc gagttgtggc atgttgccat gttcttcaag atatggtct gactgaaaca    1200 tgtgctggta catttgtctc actaccaaac cagtatgcta tgcttggtac agttgggccc    1260
ccggtgccca atgtggatgt gtgcttggag tcagtccctg aaatggcata tgatgctcta    1320
tcaagcaggc cacgtggaga agtatgtgtg aggggcgaca ctcttttttc aggttattac    1380
aagcgtgagg acctaacaaa agaagtcatg attgatgggg ggttccacac aggtgatatt    1440
ggtgagtggc aaccaaatgg tagcttgaaa ataattgatc gcaagaagaa catttcaag    1500 ctatcacaag gtgaatatgt tgctgtcgag aatttggaga atatatatgg caataatcct    1560
gttattgact ctatatggat atatggaaac agtttcgagt ctttccttgt tgctgttctt    1620
```

-continued

```
aacccaaacc aacgagcagt tgaacaatgg gcccaacaga atggcatatc tggggatttt    1680
gattcgctgt gtgaaaatcc aaaagttaag gagtacatac ttggagagct tacaaaagct    1740
ggaaaagaaa agaagctgaa gggctttgag ttcataaaag ctgtacacct tgatgctcag    1800
ccatttgaca tggaacgtga ccttctaact cctacattta agaagaaaag accccagttg    1860
ctcaaatact acaaggacgt gattgacagc atgtacaaga ccaaatga               1908
```

<210> SEQ ID NO 92
<211> LENGTH: 635
<212> TYPE: PRT
<213> ORGANISM: Nicotiana benthamiana

<400> SEQUENCE: 92

```
Met Gly Ala Val Tyr Arg Ser Leu Phe Ala Lys Asp Gly Phe Pro Pro
1               5                   10                  15

Pro Ile Pro Gly Leu Asp Ser Cys Trp Asp Ile Phe Arg Leu Ser Val
            20                  25                  30

Glu Lys Tyr Pro Asn Asn Arg Met Leu Gly Arg Arg Glu Ile Val Asp
        35                  40                  45

Gly Lys Pro Gly Lys Tyr Val Trp Met Ser Tyr Lys Glu Val Tyr Asp
    50                  55                  60

Ile Val Ile Lys Leu Gly Asn Ser Ile Arg Ser Cys Gly Val Asp Glu
65                  70                  75                  80

Gly Asp Lys Cys Gly Ile Tyr Gly Ala Asn Cys Pro Glu Trp Ile Met
                85                  90                  95

Ser Met Glu Ala Cys Asn Ala His Gly Leu Tyr Cys Val Pro Leu Tyr
            100                 105                 110

Asp Thr Leu Gly Ala Gly Ala Val Glu Phe Ile Ile Asn His Ala Glu
        115                 120                 125

Val Lys Ile Ala Phe Val Glu Glu Lys Lys Leu Pro Glu Leu Leu Lys
    130                 135                 140

Thr Phe Pro Asn Ala Ala Lys Tyr Leu Lys Thr Val Val Ser Phe Gly
145                 150                 155                 160

Asn Val Thr Pro Gln Gln Lys Glu Glu Val Glu Asn Cys Gly Val Thr
                165                 170                 175

Leu Tyr Ser Trp Asp Glu Phe Leu Gln Leu Gly Ser Glu Lys Gln Phe
            180                 185                 190

Asp Leu Pro Val Lys Lys Glu Asp Ile Cys Thr Ile Met Tyr Thr
        195                 200                 205

Ser Gly Thr Thr Gly Asp Pro Lys Gly Val Leu Ile Ser Asn Asn Ser
    210                 215                 220

Ile Val Thr Leu Ile Ala Gly Val Gln Arg Leu Leu Gly Ser Val Asn
225                 230                 235                 240

Glu Ser Leu Thr Val Asp Asp Val Tyr Leu Ser Tyr Leu Pro Leu Ala
                245                 250                 255

His Ile Phe Asp Arg Val Ile Glu Glu Cys Phe Ile Asn His Gly Ala
            260                 265                 270

Ser Ile Gly Phe Trp Arg Gly Asp Val Lys Leu Leu Thr Glu Asp Ile
        275                 280                 285

Gly Glu Leu Lys Pro Thr Ile Phe Cys Ala Val Pro Arg Val Leu Asp
    290                 295                 300

Arg Ile Tyr Ser Gly Leu Gln Gln Lys Ile Ser Ser Gly Gly Arg Leu
305                 310                 315                 320

Lys Ser Thr Leu Phe Asn Leu Ala Tyr Ala Tyr Lys His Tyr Asn Leu
```

```
                    325                 330                 335
Lys Lys Gly Arg Lys His Phe Glu Ala Ser Pro Leu Ser Asp Lys Val
            340                 345                 350
Val Phe Ser Lys Val Lys Glu Gly Leu Gly Gly Lys Val Arg Leu Ile
        355                 360                 365
Leu Ser Gly Ala Ala Pro Leu Ala Ala His Val Glu Ala Phe Leu Arg
    370                 375                 380
Val Val Ala Cys Cys His Val Leu Gln Gly Tyr Gly Leu Thr Glu Thr
385                 390                 395                 400
Cys Ala Gly Thr Phe Val Ser Leu Pro Asn Gln Tyr Ala Met Leu Gly
            405                 410                 415
Thr Val Gly Pro Pro Val Pro Asn Val Asp Val Cys Leu Glu Ser Val
        420                 425                 430
Pro Glu Met Ala Tyr Asp Ala Leu Ser Ser Arg Pro Arg Gly Glu Val
    435                 440                 445
Cys Val Arg Gly Asp Thr Leu Phe Ser Gly Tyr Tyr Lys Arg Glu Asp
450                 455                 460
Leu Thr Lys Glu Val Met Ile Asp Gly Trp Phe His Thr Gly Asp Ile
465                 470                 475                 480
Gly Glu Trp Gln Pro Asn Gly Ser Leu Lys Ile Ile Asp Arg Lys Lys
            485                 490                 495
Asn Ile Phe Lys Leu Ser Gln Gly Glu Tyr Val Ala Val Glu Asn Leu
        500                 505                 510
Glu Asn Ile Tyr Gly Asn Asn Pro Val Ile Asp Ser Ile Trp Ile Tyr
    515                 520                 525
Gly Asn Ser Phe Glu Ser Phe Leu Val Ala Val Leu Asn Pro Asn Gln
    530                 535                 540
Arg Ala Val Glu Gln Trp Ala Gln Gln Asn Gly Ile Ser Gly Asp Phe
545                 550                 555                 560
Asp Ser Leu Cys Glu Asn Pro Lys Val Lys Glu Tyr Ile Leu Gly Glu
            565                 570                 575
Leu Thr Lys Ala Gly Lys Glu Lys Leu Lys Gly Phe Glu Phe Ile
        580                 585                 590
Lys Ala Val His Leu Asp Ala Gln Pro Phe Asp Met Glu Arg Asp Leu
    595                 600                 605
Leu Thr Pro Thr Phe Lys Lys Lys Arg Pro Gln Leu Leu Lys Tyr Tyr
    610                 615                 620
Lys Asp Val Ile Asp Ser Met Tyr Lys Thr Lys
625                 630                 635

<210> SEQ ID NO 93
<211> LENGTH: 2091
<212> TYPE: DNA
<213> ORGANISM: Nicotiana benthamiana

<400> SEQUENCE: 93
atggaatcat cggcagaacg acgtctgaaa gctattcaaa accatcttgt tccggtcatc      60
gatgaccggt cactctcatt catccggtca aacccaaccg ccggcgaatt tgttcaaggt     120
cagggtttca gcgtagttct tcctgaaaaa ttgcagacga gaaatggaa tgtgtacaga     180 tctgcacgat ctcctctgaa gcttattact agattccctg atcatcctga aattgctaca     240
ctacatgata actttgaaca tgcagttcaa acctatcagg attacaaata cttgggtacc     300
cgtattcggg tagatggaac tattggagac tacaaatgga tgacatatgg agaggcaggg     360
```

```
actgctcgga ctgcaattgg ttctggactt cactattatg gattgcaacc gggtgctcgc    420
gtgggacttt atttcataaa taggcctgag tggctgattg tagaccatgc ctgctcagca    480
tattcatatt cttcagtccc actatatgac actcttggtc ctgatgctgt taaatatatt    540
gtcaatcatg ctgacgtaca ggccattttt tgtgtgcctg gtaccttgaa cacgttgttg    600
acctttttat cagagattcc ttctgtacgt ttgattgtgg tagtgggtgg atagatgaa     660 catctcccat ctcttccatc tacaacggga atgaagctct tatcatatac aaggctgctg    720
agtcagggtc gcagcagtat gcaacccttt tgccctccca agcctgaaga cattgctacc    780
atatgctata caagtggtac tacgggtaca ccgaagggtg tcgtactatc ccatgcgaac    840
ctgatagcaa gtgttgcggg catgacccct tccatcaagt tttatccttc tgacatatac    900
atatcctatc ttcctctcgc gcacatctat gaacgtgcca accaaattac atcggcatat    960
tatggtgttg ctgttggctt ctaccaaggg gacaatctga aattgatgga tgatttggcg   1020
acacttagac ctacaatatt tagcagtgtt cctcgtctgt acaacaggat atatgctggg   1080
atcacaaatg ctgtacaaac ttctggcatt ctgaagcaga gactgttcaa tgctgcctac   1140
aactccaaga agcaagctgt catgaatggt agaaagccat caccaatgtg gatagattg    1200 gtattcaaca aaataaagga caaactgggg gggcgagttc gtcttatgac ctcaggtgct   1260
tcaccattgt cgccagacgt gatggagttc ttgagagtat gttttggctg tctagttatg   1320
gaagggtatg gcatgactga acttcatgt gtcataagct caatgacga tagtgatctc     1380 ttaactggtc atgttggttc accaaatcct gcgtgtgaga taaaactcgt ggatgttccg   1440
gaaatgagtt acacatcaga agatcagcct catcctcgtg gagagatttg tgttagaggt   1500
cctattattt ttgaaggcta ttacaaagat gaagtgcaga cgagggaggt aattgatgaa   1560
gacgggtggc tgcatactgg tgatattgga ttatggttac ctggaggccg cttgaagatt   1620
attgacagga agaagaatat cttcaagttg gcacaaggtg aatacatagc tcctgagaaa   1680
attgagaatt tttatgccaa atgcaaattt gttgcacagt gctttgtcta tggtgatagc   1740
tttaattcct ctttagtagc agtggtttgt gtagagccag atgtctttaa ggaatgggca   1800
tcatctgagg gaatcaagta tgaaagtttg gacaactgt gtattgatcc aagagcaaag    1860
gctgcggttc ttgctgagat ggatgctgtg ggaaaggaag cgcagttgag aggtttcgaa   1920
tttgcaaaag ctgtaacatt ggtaatcgag cctttcacga tcgaaaatgg tctgctcact   1980
cccacattca aggtgaagag accgcaggca aaggcttatt ttgccaaagc aatatctgat   2040
atgtataatg agctttctac atcagatcca gtatcccaga aatcgctatg a            2091
```

<210> SEQ ID NO 94
<211> LENGTH: 696
<212> TYPE: PRT
<213> ORGANISM: Nicotiana benthamiana

<400> SEQUENCE: 94

```
Met Glu Ser Ser Ala Glu Arg Arg Leu Lys Ala Ile Gln Asn His Leu
1               5                   10                  15

Val Pro Val Ile Asp Asp Arg Ser Leu Ser Phe Ile Arg Ser Asn Pro
            20                  25                  30

Thr Ala Gly Glu Phe Val Gln Gly Gln Gly Phe Ser Val Val Leu Pro
        35                  40                  45

Glu Lys Leu Gln Thr Gly Lys Trp Asn Val Tyr Arg Ser Ala Arg Ser
    50                  55                  60

Pro Leu Lys Leu Ile Thr Arg Phe Pro Asp His Pro Glu Ile Ala Thr
```

```
                65                  70                  75                  80
Leu His Asp Asn Phe Glu His Ala Val Gln Thr Tyr Gln Asp Tyr Lys
                    85                  90                  95

Tyr Leu Gly Thr Arg Ile Arg Val Asp Gly Thr Ile Gly Asp Tyr Lys
                100                 105                 110

Trp Met Thr Tyr Gly Glu Ala Gly Thr Ala Arg Thr Ala Ile Gly Ser
                115                 120                 125

Gly Leu His Tyr Tyr Gly Leu Gln Pro Gly Ala Arg Val Gly Leu Tyr
                130                 135                 140

Phe Ile Asn Arg Pro Glu Trp Leu Ile Val Asp His Ala Cys Ser Ala
145                 150                 155                 160

Tyr Ser Tyr Ser Ser Val Pro Leu Tyr Asp Thr Leu Gly Pro Asp Ala
                165                 170                 175

Val Lys Tyr Ile Val Asn His Ala Asp Val Gln Ala Ile Phe Cys Val
                180                 185                 190

Pro Gly Thr Leu Asn Thr Leu Leu Thr Phe Leu Ser Glu Ile Pro Ser
                195                 200                 205

Val Arg Leu Ile Val Val Gly Gly Ile Asp Glu His Leu Pro Ser
210                 215                 220

Leu Pro Ser Thr Thr Gly Met Lys Leu Leu Ser Tyr Thr Arg Leu Leu
225                 230                 235                 240

Ser Gln Gly Arg Ser Ser Met Gln Pro Phe Cys Pro Pro Lys Pro Glu
                245                 250                 255

Asp Ile Ala Thr Ile Cys Tyr Thr Ser Gly Thr Thr Gly Thr Pro Lys
                260                 265                 270

Gly Val Val Leu Ser His Ala Asn Leu Ile Ala Ser Val Ala Gly Met
                275                 280                 285

Thr Leu Ser Ile Lys Phe Tyr Pro Ser Asp Ile Tyr Ile Ser Tyr Leu
                290                 295                 300

Pro Leu Ala His Ile Tyr Glu Arg Ala Asn Gln Ile Thr Ser Ala Tyr
305                 310                 315                 320

Tyr Gly Val Ala Val Gly Phe Tyr Gln Gly Asp Asn Leu Lys Leu Met
                325                 330                 335

Asp Asp Leu Ala Thr Leu Arg Pro Thr Ile Phe Ser Ser Val Pro Arg
                340                 345                 350

Leu Tyr Asn Arg Ile Tyr Ala Gly Ile Thr Asn Ala Val Gln Thr Ser
                355                 360                 365

Gly Ile Leu Lys Gln Arg Leu Phe Asn Ala Ala Tyr Asn Ser Lys Lys
                370                 375                 380

Gln Ala Val Met Asn Gly Arg Lys Pro Ser Pro Met Trp Asp Arg Leu
385                 390                 395                 400

Val Phe Asn Lys Ile Lys Asp Lys Leu Gly Gly Arg Val Arg Leu Met
                405                 410                 415

Thr Ser Gly Ala Ser Pro Leu Ser Pro Asp Val Met Glu Phe Leu Arg
                420                 425                 430

Val Cys Phe Gly Cys Leu Val Met Glu Gly Tyr Gly Met Thr Glu Thr
                435                 440                 445

Ser Cys Val Ile Ser Ser Met Asp Asp Ser Leu Leu Thr Gly His
                450                 455                 460

Val Gly Ser Pro Asn Pro Ala Cys Glu Ile Lys Leu Val Asp Val Pro
465                 470                 475                 480

Glu Met Ser Tyr Thr Ser Glu Asp Gln Pro His Pro Arg Gly Glu Ile
                485                 490                 495
```

```
Cys Val Arg Gly Pro Ile Ile Phe Glu Gly Tyr Tyr Lys Asp Glu Val
              500                 505                 510

Gln Thr Arg Glu Val Ile Asp Glu Asp Gly Trp Leu His Thr Gly Asp
          515                 520                 525

Ile Gly Leu Trp Leu Pro Gly Gly Arg Leu Lys Ile Ile Asp Arg Lys
      530                 535                 540

Lys Asn Ile Phe Lys Leu Ala Gln Gly Glu Tyr Ile Ala Pro Glu Lys
545                 550                 555                 560

Ile Glu Asn Val Tyr Ala Lys Cys Lys Phe Val Ala Gln Cys Phe Val
              565                 570                 575

Tyr Gly Asp Ser Phe Asn Ser Ser Leu Val Ala Val Val Cys Val Glu
              580                 585                 590

Pro Asp Val Phe Lys Glu Trp Ala Ser Ser Glu Gly Ile Lys Tyr Glu
          595                 600                 605

Ser Leu Gly Gln Leu Cys Ile Asp Pro Arg Ala Lys Ala Ala Val Leu
      610                 615                 620

Ala Glu Met Asp Ala Val Gly Lys Glu Ala Gln Leu Arg Gly Phe Glu
625                 630                 635                 640

Phe Ala Lys Ala Val Thr Leu Val Ile Glu Pro Phe Thr Ile Glu Asn
              645                 650                 655

Gly Leu Leu Thr Pro Thr Phe Lys Val Lys Arg Pro Gln Ala Lys Ala
              660                 665                 670

Tyr Phe Ala Lys Ala Ile Ser Asp Met Tyr Asn Glu Leu Ser Thr Ser
          675                 680                 685

Asp Pro Val Ser Gln Lys Ser Leu
      690                 695

<210> SEQ ID NO 95
<211> LENGTH: 3354
<212> TYPE: DNA
<213> ORGANISM: Nicotiana benthamiana

<400> SEQUENCE: 95
atggcgtcga tggaacagtt ggtgacgggt gacggcggag gaggaggagg accgcggtac     60
gtgcagatgc aatctgagcc ggagccatca acattatcgt cgttttactc gtttcatcag    120
gatagtagcc atgaatcaac tcgaattttc gatgaattgc cttcggctac gatcattcag    180
gtctctcgtc ctgacgccgg cgacatcagc cccatgcttc tcacttatac cattgaagtc    240
cattacaaac agttcaagtg gcaattggtg aagaaagcgt cacatgtatt ttatttacat    300
tttgcattaa agaagcgtgc attcattgag gagattcatg agaagcaaga gcaggtcaaa    360
gaatggctcc aaaacttggg gataggagat catacaactg taattcaaga cgaggatgaa    420
cctgatgatg aggctagtcc tctacgtgct gaggaaagtt ttaaatacag agatgttcca    480
tcaagtgctg ctttgccaat aattcggcca accctgggaa ggcaacactc gatgtcagat    540
cgagcaaaaa gtgctatgca gggttatttg aatcactttc ttggaaacat agatattgtc    600
aattcccagg aggtgtgcag gtttctggaa gtctctaaat tatcctttc tccagagtat    660 ggtcctaagc tgaaagaaga ctatattatg gtgaagcact accaaaaat tcaaagacac    720 gatgatagtc ggaaatgttg ttcatgtcag tggtttggct gctgtaaaga caactggcag    780
aaggtgtggg ctgtattaaa acctggattc ctggctttcc tcaaagatcc atctgacccc    840
gagccgttag atataatagt ttttgatgta ttaccagctt ccgacggaaa tggagagggc    900
cgcgtttctt tagcaaaaga aataaaggat ggaaacccctt tacgccacta ttttagggtg    960
```

```
tcttgtggta caaggtgtat taaactgagg actaagagca atgcaaaggt taaagactgg      1020
gtagtagcaa ttaacgatgc agggcttagg ccacccgagg gttggtgtca tccgcaccgt      1080
tttggttctt atgttcctcc taggggtttg acagaggatg gcagtcaggc tcagtggttt      1140
gttgatggtg aatcagcttt tgaagccata gcgttggcta ttgaagaagc aaagtcagag      1200
atctttatgt gtggctggtg gctgtgccca gaactttata tgcgacgtcc ctttcaccct      1260
aatgcactct cccggcttga tgctttactg gaagccaaag caaaacaagg agttcagatt      1320
tacatccttc tatacaaaga ggttgctatt gctttaaaaa tcaacagtgt gtatagcaag      1380
agaaagcttt taggcatcca tgagaatgtc agggtgcttc gttatccgga tcattttttca     1440 agtggtgtgt atctatggtc ccatcatgaa aaaattgtca ttgttgacaa tcagatttgc      1500
tttatcggag gactggacct gtgctttggc cgttatgatt catctgaaca caaagtgggt      1560
gattgtccac ctcttatatg gcctggaaaa gactattaca atccaaggga atctgaacca      1620
aattcctggg aagataccat gaaggatgaa ttggatcgga ataaatatcc acgcatgcca      1680
tggcatgatg tccattgcgc cctctgggga tcgccgtgcc gtgatattgc tcgacacttt      1740
gttcagcgct ggaattatgc gaagaggaac aaagctccac gtgagcaagc aattccgttg      1800
cttatgcctc agcaccacat ggttattcct cattacatgg gaatgagcaa cgagatggaa      1860
aatgaagtga atggtgttgc tcttcctcat aaaaaaatca agagacatga ttcatttcct      1920
tcagggtcat cttcccaaga cattcctttg cttatgcctc aggaagctga agggggtgaa      1980
agttttaagg aagaactaaa aataaacggc ttccatacag ggaatggttt tcatgatcag      2040
cggagcaggt ctagcagaat cccttttctct ttccggagga cccgagtaga acctctagtt     2100
ccagatttac caatgaaagg atttgtggat gatttggacc aaaatctgga gctatcttca      2160 aatgggtgc agcctggcat gaagaagtcg acaaagatt ggtgggaaac acaggagaga       2220
ggcgatcaag ttgttttccct tgaagaaagt gggcaagttg gtcctcgtgt ttcatgtcgt      2280
tgccaggtta taaggagtgt cagtcaatgg tcagctggaa caagtcaaat tgaagaaagc      2340
atacacaatg cttactgctc ccttatcgaa aaggctgaac attttgttta catagagaat      2400
caatttttca tttctggtct atctggggat gaaattataa aaaatcgtgt tttggaagca      2460
ttgtacaggc gtattatgcg agcttataat gaaaaaaagt ccttcagggt tatcattgtg      2520
ataccgcttc ttcctggatt ccagggtggt ctggatgata tggtgctgc ttcagttaga       2580 gctattatgc attggcaata tcgaacaata tgcaggggat ctaattcgat actgcataat      2640
cttaatgacc tcatgggatc tagaatgcac gactatatat cattttatgg tctcagagct      2700
tatggaagac tcttcgatgg tggccctatt gcatctagcc aggtatatgt gcatagcaag      2760
atcatgattg tcgatgacca tacagccttg attggatctg gaaatataaa tgacagaagc      2820
ttgcttggtt caagagactc tgagattggt gtaattatcg aggacaaaga gttcgttgat      2880
tcattcatgg gaggcaagcc taggaaggcg gggaaatttg cattaactct tcgccttttct    2940 ctatggtctg agcaccttgg tcttcgtact gttgaggttg gtcgaattaa ggacccggtg      3000
attgattcaa catacaagga tatttggatt gcaacggcta agacaaatac aatgatatac      3060
caggatgttt tttcttgcat acccaacgat ctgatacatt ccagggcttc actccgacaa      3120
tgcatggcat tctcgaaaga aaaacttggt cacacgacca ttgatttagg aatagctcca      3180
agcaagctag aatcttatca ggatggagat atcgagtgta tagatcccat ggagagatta      3240
aagtctgtga aaggtcatct tgtttccttc cctttggatt ttatgtgcaa agaagattta      3300
```

```
agacctgtat ttaatgaaag tgagtactat gcgtctgctc aagttttca ttga        3354
```

<210> SEQ ID NO 96
<211> LENGTH: 1117
<212> TYPE: PRT
<213> ORGANISM: Nicotiana benthamiana

<400> SEQUENCE: 96

```
Met Ala Ser Met Glu Gln Leu Val Thr Gly Asp Gly Gly Gly Gly
1               5                   10                  15

Gly Pro Arg Tyr Val Gln Met Gln Ser Glu Pro Glu Pro Ser Thr Leu
            20                  25                  30

Ser Ser Phe Tyr Ser Phe His Gln Asp Ser Ser His Glu Ser Thr Arg
        35                  40                  45

Ile Phe Asp Glu Leu Pro Ser Ala Thr Ile Ile Gln Val Ser Arg Pro
    50                  55                  60

Asp Ala Gly Asp Ile Ser Pro Met Leu Leu Thr Tyr Thr Ile Glu Val
65                  70                  75                  80

His Tyr Lys Gln Phe Lys Trp Gln Leu Val Lys Lys Ala Ser His Val
                85                  90                  95

Phe Tyr Leu His Phe Ala Leu Lys Lys Arg Ala Phe Ile Glu Glu Ile
            100                 105                 110

His Glu Lys Gln Glu Gln Val Lys Glu Trp Leu Gln Asn Leu Gly Ile
        115                 120                 125

Gly Asp His Thr Thr Val Ile Gln Asp Glu Asp Pro Asp Asp Glu
    130                 135                 140

Ala Ser Pro Leu Arg Ala Glu Glu Ser Phe Lys Tyr Arg Asp Val Pro
145                 150                 155                 160

Ser Ser Ala Ala Leu Pro Ile Ile Arg Pro Thr Leu Gly Arg Gln His
                165                 170                 175

Ser Met Ser Asp Arg Ala Lys Ser Ala Met Gln Gly Tyr Leu Asn His
            180                 185                 190

Phe Leu Gly Asn Ile Asp Ile Val Asn Ser Gln Glu Val Cys Arg Phe
        195                 200                 205

Leu Glu Val Ser Lys Leu Ser Phe Ser Pro Glu Tyr Gly Pro Lys Leu
    210                 215                 220

Lys Glu Asp Tyr Ile Met Val Lys His Leu Pro Lys Ile Gln Arg His
225                 230                 235                 240

Asp Asp Ser Arg Lys Cys Cys Ser Cys Gln Trp Phe Gly Cys Cys Lys
                245                 250                 255

Asp Asn Trp Gln Lys Val Trp Ala Val Leu Lys Pro Gly Phe Leu Ala
            260                 265                 270

Phe Leu Lys Asp Pro Ser Asp Pro Glu Pro Leu Asp Ile Ile Val Phe
        275                 280                 285

Asp Val Leu Pro Ala Ser Asp Gly Asn Gly Glu Gly Arg Val Ser Leu
    290                 295                 300

Ala Lys Glu Ile Lys Asp Gly Asn Pro Leu Arg His Tyr Phe Arg Val
305                 310                 315                 320

Ser Cys Gly Thr Arg Cys Ile Lys Leu Arg Thr Lys Ser Asn Ala Lys
                325                 330                 335

Val Lys Asp Trp Val Val Ala Ile Asn Asp Ala Gly Leu Arg Pro Pro
            340                 345                 350

Glu Gly Trp Cys His Pro His Arg Phe Gly Ser Tyr Val Pro Pro Arg
        355                 360                 365
```

```
Gly Leu Thr Glu Asp Gly Ser Gln Ala Gln Trp Phe Val Asp Gly Glu
    370                 375                 380

Ser Ala Phe Glu Ala Ile Ala Leu Ala Ile Glu Glu Ala Lys Ser Glu
385                 390                 395                 400

Ile Phe Met Cys Gly Trp Trp Leu Cys Pro Glu Leu Tyr Met Arg Arg
                405                 410                 415

Pro Phe His Pro Asn Ala Leu Ser Arg Leu Asp Ala Leu Leu Glu Ala
            420                 425                 430

Lys Ala Lys Gln Gly Val Gln Ile Tyr Ile Leu Leu Tyr Lys Glu Val
        435                 440                 445

Ala Ile Ala Leu Lys Ile Asn Ser Val Tyr Ser Lys Arg Lys Leu Leu
    450                 455                 460

Gly Ile His Glu Asn Val Arg Val Leu Arg Tyr Pro Asp His Phe Ser
465                 470                 475                 480

Ser Gly Val Tyr Leu Trp Ser His His Glu Lys Ile Val Ile Val Asp
                485                 490                 495

Asn Gln Ile Cys Phe Ile Gly Gly Leu Asp Leu Cys Phe Gly Arg Tyr
            500                 505                 510

Asp Ser Ser Glu His Lys Val Gly Asp Cys Pro Pro Leu Ile Trp Pro
        515                 520                 525

Gly Lys Asp Tyr Tyr Asn Pro Arg Glu Ser Glu Pro Asn Ser Trp Glu
    530                 535                 540

Asp Thr Met Lys Asp Glu Leu Asp Arg Asn Lys Tyr Pro Arg Met Pro
545                 550                 555                 560

Trp His Asp Val His Cys Ala Leu Trp Gly Ser Pro Cys Arg Asp Ile
                565                 570                 575

Ala Arg His Phe Val Gln Arg Trp Asn Tyr Ala Lys Arg Asn Lys Ala
            580                 585                 590

Pro Arg Glu Gln Ala Ile Pro Leu Leu Met Pro Gln His His Met Val
        595                 600                 605

Ile Pro His Tyr Met Gly Met Ser Asn Glu Met Glu Asn Gly Ser Asn
    610                 615                 620

Gly Val Ala Leu Pro His Lys Lys Ile Lys Arg His Asp Ser Phe Ser
625                 630                 635                 640

Ser Gly Ser Ser Ser Gln Asp Ile Pro Leu Leu Met Pro Gln Glu Ala
                645                 650                 655

Glu Gly Gly Glu Ser Phe Lys Glu Glu Leu Lys Ile Asn Gly Phe His
            660                 665                 670

Thr Gly Asn Gly Phe His Asp Gln Arg Ser Arg Ser Ser Arg Ile Pro
        675                 680                 685

Phe Ser Phe Arg Arg Thr Arg Val Glu Pro Leu Val Pro Asp Leu Pro
    690                 695                 700

Met Lys Gly Phe Val Asp Asp Leu Asp Gln Asn Leu Glu Leu Ser Ser
705                 710                 715                 720

Asn Gly Val Gln Pro Gly Met Lys Lys Ser Asp Lys Asp Trp Trp Glu
                725                 730                 735

Thr Gln Glu Arg Gly Asp Gln Val Val Ser Leu Glu Glu Ser Gly Gln
            740                 745                 750

Val Gly Pro Arg Val Ser Cys Arg Cys Gln Val Ile Arg Ser Val Ser
        755                 760                 765

Gln Trp Ser Ala Gly Thr Ser Gln Ile Glu Glu Ser Ile His Asn Ala
    770                 775                 780

Tyr Cys Ser Leu Ile Glu Lys Ala Glu His Phe Val Tyr Ile Glu Asn
```

Gln Phe Phe Ile Ser Gly Leu Ser Gly Asp Glu Ile Ile Lys Asn Arg
            805                 810                 815

Val Leu Glu Ala Leu Tyr Arg Arg Ile Met Arg Ala Tyr Asn Glu Lys
        820                 825                 830

Lys Ser Phe Arg Val Ile Ile Val Ile Pro Leu Leu Pro Gly Phe Gln
        835                 840                 845

Gly Gly Leu Asp Asp Ser Gly Ala Ala Ser Val Arg Ala Ile Met His
    850                 855                 860

Trp Gln Tyr Arg Thr Ile Cys Arg Gly Ser Asn Ser Ile Leu His Asn
865                 870                 875                 880

Leu Asn Asp Leu Met Gly Ser Arg Met His Asp Tyr Ile Ser Phe Tyr
                885                 890                 895

Gly Leu Arg Ala Tyr Gly Arg Leu Phe Asp Gly Gly Pro Ile Ala Ser
            900                 905                 910

Ser Gln Val Tyr Val His Ser Lys Ile Met Ile Val Asp Asp His Thr
        915                 920                 925

Ala Leu Ile Gly Ser Gly Asn Ile Asn Asp Arg Ser Leu Leu Gly Ser
    930                 935                 940

Arg Asp Ser Glu Ile Gly Val Ile Ile Glu Asp Lys Glu Phe Val Asp
945                 950                 955                 960

Ser Phe Met Gly Gly Lys Pro Arg Lys Ala Gly Lys Phe Ala Leu Thr
                965                 970                 975

Leu Arg Leu Ser Leu Trp Ser Glu His Leu Gly Leu Arg Thr Val Glu
            980                 985                 990

Val Gly Arg Ile Lys Asp Pro Val Ile Asp Ser Thr Tyr Lys Asp Ile
        995                 1000                1005

Trp Ile Ala Thr Ala Lys Thr Asn Thr Met Ile Tyr Gln Asp Val
    1010                1015                1020

Phe Ser Cys Ile Pro Asn Asp Leu Ile His Ser Arg Ala Ser Leu
    1025                1030                1035

Arg Gln Cys Met Ala Phe Ser Lys Glu Lys Leu Gly His Thr Thr
    1040                1045                1050

Ile Asp Leu Gly Ile Ala Pro Ser Lys Leu Glu Ser Tyr Gln Asp
    1055                1060                1065

Gly Asp Ile Glu Cys Ile Asp Pro Met Glu Arg Leu Lys Ser Val
    1070                1075                1080

Lys Gly His Leu Val Ser Phe Pro Leu Asp Phe Met Cys Lys Glu
    1085                1090                1095

Asp Leu Arg Pro Val Phe Asn Glu Ser Glu Tyr Tyr Ala Ser Ala
    1100                1105                1110

Gln Val Phe His
    1115

<210> SEQ ID NO 97
<211> LENGTH: 3165
<212> TYPE: DNA
<213> ORGANISM: Nicotiana benthamiana

<400> SEQUENCE: 97
atgtcgacgg agaaactgat agagaatgcg ccggcgtcgg caatgtcatc aatgcattcc      60
cttcgttgct acgtcgagcc ggcgacgatc tttgaggaat tgcccaaagc gactatcatt     120
gcggtttcaa gagcagatgc tagtgatata agcccctttg ctttgtcata cacaattgaa     180

```
gtccagtaca agcagttcaa gtggcgctta gttaagaagg cctcacaagt tgtttatttg    240
cactttgcat tgaggaaacg tgcaataatt gaggaactcc atggaaaaca agagcaggtt    300
aaagaatggc ttcaccacat tggtatagga gaacaaacag ctgtcataca tgatgatgct    360
gaacccgatg atggtgctat gcaaatttac agtgaagata gtattagaaa caggtatgtt    420
ccatcccggg ctgctttatc aatcattcgt ccagcattgg gcaggcagca aaccattaca    480
gaaaaaggga aaattgctat gcaaaagtat ctgaatcatt ttttggggaa tttggacatt    540
gtaaattctc gagaggtgtg caagtttttg gaggtatcca agttatcatt cttaccagaa    600
tatggcccaa agctcaagga aaattacgta atggttaaga atttgttgaa agttcccaaa    660
gacgaggagg atgcgggatg ttgcatatgt tattggtctg gctgctgcaa gagcaagtgg    720
caaaaggttt gggctgtttt aaaacctggt tacttggcct tactaaacaa tccttttgat    780
gcaaaattac tggacattat tgtgttcgat gtgcttccaa catctaatga aagggagag     840 aagccagtat acttagcaga ggaagtaaga gaaaaaaatc ctttgcgata tgcatttaag    900
gtttgttgtg ggaaccgcat ggtaaagttt agaaccacga gcaatgccaa agtcgatgat    960
tggatatctg caatcaatga tgctgttctt aaacctccgg agggttggtg taacccgcac   1020 cgcttttggtt cttttgctcc attgagggg acatatgatg atgccactca agctcagtgg   1080
tttatagatg gtaaagcagc atttaaggca attgcttcct caatagagag tgcaaaatct   1140
gagatctata taactggatg gtggcttttgc ccagaactgt acttgagacg tccatttcac   1200
aaccatagct catctagact tgatgcatta cttgagacta agccaaaga aggggtccag    1260 atttatattc ttctctacaa ggaggtttct attgctttaa agattaacag tttatacagt    1320
aaaagacagc ttctgaaaat tcacaaaaat gttaaagtcc tgcgatatcc gaaccatttc    1380
tctgcgggga tctacttgtg gtcgcaccat gaaaagattg tcattataga caacaagatt    1440
tgttatattg gaggtctaga tttatgtttt ggccgttatg acacaagaga acacaacgtg    1500
gctgatctgc ctccttctat ttggcctggg aaggactact ataacccaag agaatccgag    1560
ccaaattctt gggaagatgc catgaaagat gaattagatc gagagaaata tccccgaatg    1620
ccatggcatg atgtccactg tgctctattg gaccaccttg ccgagacat tgccagacac    1680 ttcgttcagc gctggaatca tgctaagaga agcaaagctc caaatgaaca gacaatacca    1740
ctgcttatgc cacagcatca catggttctt ccgcactaca tggggagaag cagacaagtt    1800
gaggctgaaa ctaagacagc tgagctgaaa cctgaagacc tgaatggaca agatccgttt    1860
ccgtctgggt caccaccgga agacctccca ctacttttac cccaggaagc tgattgtgac    1920 aacgggcct ccagtgagga tgagaagttg gctgatgatc ttcatcgcct agatctccaa    1980
agccgaatgg gaacttacca acaagataat tggtgggaga cacaagagcg agtagcagaa    2040
gtggtttcaa cagatgaatt agcagatgtt ggtcctcggg cccgttgtca ctgtcaggtc    2100 attgaagtg tcagccaatg gtctgctgga acaactcaaa ctgaagagag cattcacaaa    2160
gcttattgtt ctcttattga agaagcagaa cattttgtgt tcattgagaa tcaattttt     2220 atctcgggtc ttgctggaga tgaaactata agcaatcgcg tagctgatgc tttatacaga    2280
cgtatactgc gagcacacaa agaacataga tgtttcaggg ttataatagt gatcccacta    2340
ttacctggtt ttcagggagg tcttgatgac attggggcag caactgtgag agccttaatg    2400
cactggcaat accggacaat ttccaagagc aacaattcaa tattgcacaa tcttaatgct    2460
ctgttgggtc cagaaacccg tgattacata tcttttatg gtctaaggac gtatggccag    2520 cttttctgatg ttggccccat gttcaccagt caggtctatg tacatagtaa agtgatgata    2580
```

```
gtggatgacc gtatagcctt gattggatca tctaatataa atgacagaag tttgcttgga    2640
tctcgcgact ctgagatttg tgtagtcatt gaagataaag atttcattga ttcatccatg    2700
gacggaaagc cttggaaggc tggaaaattt gcttttagcc ttcggatttc tttgtgggca    2760
gagcaccttg gttacatgc tgaagagatt tgtcaaatca agatcccgt tgctgactct      2820 tcttacaaag atatatggat ggcaactgca gagtggaatg ccacaattta ccaagacgtg    2880
ttctcttgca tcccaaatga tcttgttcac tcaagatctg aacttcgaca atgtaggaac    2940
ctctggaaag ataagcttgg gcacactact attgatttag gtgtcgctcc tgataaacat    3000
gaatttcacg ataatgggct agtaactgta gagaatacga aagagaggtt aaagtcggtc    3060
aaaggacatc ttgtttcttt tccattggag ttcatgcgtg aagaagatct gagaccgggg    3120
tttatcgaga ctgagtttta tacttctcct caagtgttcc attaa                   3165
```

<210> SEQ ID NO 98
<211> LENGTH: 1054
<212> TYPE: PRT
<213> ORGANISM: Nicotiana benthamiana

<400> SEQUENCE: 98

```
Met Ser Thr Glu Lys Leu Ile Glu Asn Ala Pro Ala Ser Ala Met Ser
1               5                   10                  15

Ser Met His Ser Leu Arg Cys Tyr Val Glu Pro Ala Thr Ile Phe Glu
            20                  25                  30

Glu Leu Pro Lys Ala Thr Ile Ile Ala Val Ser Arg Ala Asp Ala Ser
        35                  40                  45

Asp Ile Ser Pro Leu Leu Ser Tyr Thr Ile Glu Val Gln Tyr Lys
    50                  55                  60

Gln Phe Lys Trp Arg Leu Val Lys Lys Ala Ser Gln Val Val Tyr Leu
65                  70                  75                  80

His Phe Ala Leu Arg Lys Arg Ala Ile Ile Glu Glu Leu His Gly Lys
                85                  90                  95

Gln Glu Gln Val Lys Glu Trp Leu His His Ile Gly Ile Gly Glu Gln
            100                 105                 110

Thr Ala Val Ile His Asp Asp Ala Glu Pro Asp Asp Gly Ala Met Gln
        115                 120                 125

Ile Tyr Ser Glu Asp Ser Ile Arg Asn Arg Tyr Val Pro Ser Arg Ala
    130                 135                 140

Ala Leu Ser Ile Ile Arg Pro Ala Leu Gly Arg Gln Gln Thr Ile Thr
145                 150                 155                 160

Glu Lys Gly Lys Ile Ala Met Gln Lys Tyr Leu Asn His Phe Leu Gly
                165                 170                 175

Asn Leu Asp Ile Val Asn Ser Arg Glu Val Cys Lys Phe Leu Glu Val
            180                 185                 190

Ser Lys Leu Ser Phe Leu Pro Glu Tyr Gly Lys Leu Lys Glu Asn
        195                 200                 205

Tyr Val Met Val Lys Asn Leu Leu Lys Val Pro Lys Asp Glu Glu Asp
    210                 215                 220

Ala Gly Cys Cys Ile Cys Tyr Trp Ser Gly Cys Cys Lys Ser Lys Trp
225                 230                 235                 240

Gln Lys Val Trp Ala Val Leu Lys Pro Gly Tyr Leu Ala Leu Leu Asn
                245                 250                 255

Asn Pro Phe Asp Ala Lys Leu Leu Asp Ile Ile Val Phe Asp Val Leu
            260                 265                 270
```

Pro Thr Ser Asn Glu Lys Gly Glu Lys Pro Val Tyr Leu Ala Glu
        275                 280                 285

Val Arg Glu Lys Asn Pro Leu Arg Tyr Ala Phe Lys Val Cys Cys Gly
    290                 295                 300

Asn Arg Met Val Lys Phe Arg Thr Thr Ser Asn Ala Lys Val Asp Asp
305                 310                 315                 320

Trp Ile Ser Ala Ile Asn Asp Ala Val Leu Lys Pro Pro Gly Gly Trp
                325                 330                 335

Cys Asn Pro His Arg Phe Gly Ser Phe Ala Pro Leu Arg Gly Thr Tyr
                340                 345                 350

Asp Asp Ala Thr Gln Ala Gln Trp Phe Ile Asp Gly Lys Ala Ala Phe
                355                 360                 365

Lys Ala Ile Ala Ser Ser Ile Glu Ser Ala Lys Ser Glu Ile Tyr Ile
                370                 375                 380

Thr Gly Trp Trp Leu Cys Pro Glu Leu Tyr Leu Arg Arg Pro Phe His
385                 390                 395                 400

Asn His Ser Ser Arg Leu Asp Ala Leu Leu Glu Thr Lys Ala Lys
                405                 410                 415

Glu Gly Val Gln Ile Tyr Ile Leu Leu Tyr Lys Glu Val Ser Ile Ala
                420                 425                 430

Leu Lys Ile Asn Ser Leu Tyr Ser Lys Arg Gln Leu Leu Lys Ile His
                435                 440                 445

Lys Asn Val Lys Val Leu Arg Tyr Pro Asn His Phe Ser Ala Gly Ile
                450                 455                 460

Tyr Leu Trp Ser His His Glu Lys Ile Val Ile Asp Asn Lys Ile
465                 470                 475                 480

Cys Tyr Ile Gly Gly Leu Asp Leu Cys Phe Gly Arg Tyr Asp Thr Arg
                485                 490                 495

Glu His Asn Val Ala Asp Leu Pro Pro Ser Ile Trp Pro Gly Lys Asp
                500                 505                 510

Tyr Tyr Asn Pro Arg Glu Ser Glu Pro Asn Ser Trp Glu Asp Ala Met
                515                 520                 525

Lys Asp Glu Leu Asp Arg Glu Lys Tyr Pro Arg Met Pro Trp His Asp
                530                 535                 540

Val His Cys Ala Leu Leu Gly Pro Pro Cys Arg Asp Ile Ala Arg His
545                 550                 555                 560

Phe Val Gln Arg Trp Asn His Ala Lys Arg Ser Lys Ala Pro Asn Glu
                565                 570                 575

Gln Thr Ile Pro Leu Leu Met Pro Gln His His Met Val Leu Pro His
                580                 585                 590

Tyr Met Gly Arg Ser Arg Gln Val Glu Ala Glu Thr Lys Thr Ala Glu
                595                 600                 605

Leu Lys Pro Glu Asp Leu Asn Gly Gln Asp Pro Phe Pro Ser Gly Ser
                610                 615                 620

Pro Pro Glu Asp Leu Pro Leu Leu Pro Gln Glu Ala Asp Cys Asp
625                 630                 635                 640

Asn Gly Ala Ser Ser Glu Asp Glu Lys Leu Ala Asp Asp Leu His Arg
                645                 650                 655

Leu Asp Leu Gln Ser Arg Met Gly Thr Tyr Gln Gln Asp Asn Trp Trp
                660                 665                 670

Glu Thr Gln Glu Arg Val Ala Glu Val Val Ser Thr Asp Glu Leu Ala
                675                 680                 685

```
Asp Val Gly Pro Arg Ala Arg Cys His Cys Gln Val Ile Arg Ser Val
    690                 695                 700

Ser Gln Trp Ser Ala Gly Thr Thr Gln Thr Glu Glu Ser Ile His Lys
705                 710                 715                 720

Ala Tyr Cys Ser Leu Ile Glu Glu Ala Glu His Phe Val Phe Ile Glu
                725                 730                 735

Asn Gln Phe Phe Ile Ser Gly Leu Ala Gly Asp Glu Thr Ile Ser Asn
            740                 745                 750

Arg Val Ala Asp Ala Leu Tyr Arg Arg Ile Leu Arg Ala His Lys Glu
        755                 760                 765

His Arg Cys Phe Arg Val Ile Ile Val Ile Pro Leu Leu Pro Gly Phe
770                 775                 780

Gln Gly Gly Leu Asp Asp Ile Gly Ala Ala Thr Val Arg Ala Leu Met
785                 790                 795                 800

His Trp Gln Tyr Arg Thr Ile Ser Lys Ser Asn Asn Ser Ile Leu His
                805                 810                 815

Asn Leu Asn Ala Leu Leu Gly Pro Glu Thr Arg Asp Tyr Ile Ser Phe
            820                 825                 830

Tyr Gly Leu Arg Thr Tyr Gly Gln Leu Ser Asp Val Gly Pro Met Phe
        835                 840                 845

Thr Ser Gln Val Tyr Val His Ser Lys Val Met Ile Val Asp Asp Arg
850                 855                 860

Ile Ala Leu Ile Gly Ser Ser Asn Ile Asn Asp Arg Ser Leu Leu Gly
865                 870                 875                 880

Ser Arg Asp Ser Glu Ile Cys Val Val Ile Glu Asp Lys Asp Phe Ile
                885                 890                 895

Asp Ser Ser Met Asp Gly Lys Pro Trp Lys Ala Gly Lys Phe Ala Phe
            900                 905                 910

Ser Leu Arg Ile Ser Leu Trp Ala Glu His Leu Gly Leu His Ala Glu
        915                 920                 925

Glu Ile Cys Gln Ile Lys Asp Pro Val Ala Asp Ser Ser Tyr Lys Asp
930                 935                 940

Ile Trp Met Ala Thr Ala Glu Trp Asn Ala Thr Ile Tyr Gln Asp Val
945                 950                 955                 960

Phe Ser Cys Ile Pro Asn Asp Leu Val His Ser Arg Ser Glu Leu Arg
                965                 970                 975

Gln Cys Arg Asn Leu Trp Lys Asp Lys Leu Gly His Thr Thr Ile Asp
            980                 985                 990

Leu Gly Val Ala Pro Asp Lys His  Glu Phe His Asp Asn  Gly Leu Val
        995                 1000                1005

Thr Val  Glu Asn Thr Lys Glu  Arg Leu Lys Ser Val  Lys Gly His
    1010                1015                1020

Leu Val  Ser Phe Pro Leu Glu  Phe Met Arg Glu Glu  Asp Leu Arg
    1025                1030                1035

Pro Gly  Phe Ile Glu Thr Glu  Phe Tyr Thr Ser Pro  Gln Val Phe
    1040                1045                1050

His
```

<210> SEQ ID NO 99
<211> LENGTH: 1392
<212> TYPE: DNA
<213> ORGANISM: Nicotiana benthamiana

<400> SEQUENCE: 99

```
atgggctgc cggagatgga atcaatggcg tcggcgatcg agtatcagt gccggtgctc     60
cgtttcttgc tttgttttgt cgccacaatt ccggtgagct cctccaccg ttttgtccct   120
agcgccgtcg gtagacacct ctacgccgcc gttaccggcg ctgttctctc gtacctgtca   180
tttggtttct cctcaaatct tcacttcttt gggcctatgc ttctgggtta tgtttctatg   240
gttctctctc gccgttactg cgggatcatc actttcttcg ccgcgtttgg ataccttatt   300
ggatgccatg tatactacat gagtggagac catggaagg aaggaggaat tgatgctaca    360
ggagctctaa tggtcataac gctgaaaata atttcatgtg tgattaatta ccaagatgga   420
ttgttgaagg aggaagattt gcgtgaggct cagaagaaaa atcgtctgct caaattgcca   480
tcgttacttg agtacgttgg ttgttgtctc tgttgtggaa gtcattttgc aggtccagtg   540
tatgagatga aggattacct tgactggaca gagagaaaag gaatctggaa accttcagag   600
aagggaaatc cctcaccttt agggtcaact ttaagggctc ttcttcaagc tgctatttgt   660
atggggttgt atctctacct ggtgcctctt tttccactt tccaggttca ctgatccttta    720
taccaagaat ggggtttctt caaacggtcg ggttaccaat atatggcttg ctttaccgcc   780
cggtggaaat attatttat ctggtcaatt tctgaagctg ctatcatcat atccggacta    840
gggttcagtg gttggacaaa ctcttcttca ccaaaaccac gttgggaccg tgccaaaaat   900
gttgatgtat gggtgttga gttagcaaag agctcggttc agttaccact tgtttggaat    960
attcaagtca gcacgtggct cgccactat gtatatgaga ggctcataca gaaaggaagg   1020
aagcctggtt tcttccagtt gctagctacc cagactgtca gtgctgtatg catggattg    1080
tatcctgggt acatcatttt ctttgtacag tctgctttga tgattgctgg atcaagagtc   1140
atttacagat ggcagcaagc tgctactggt actctgtttg agaagatgct tgtattgatg   1200
aactttgcat acacacttct ggttctaaac tattccgctg ttgggttcat ggtattaagc   1260
ctgcatgaaa cccttactgc atatggtagt gtatactatg ttggaacaat tgtaccagtt   1320
gtactcatcc tgcttagtaa agtagttaag cctccaaaac ctgcgacatc taaagctagg   1380
aaagtagagt ga                                                      1392
```

<210> SEQ ID NO 100
<211> LENGTH: 463
<212> TYPE: PRT
<213> ORGANISM: Nicotiana benthamiana

<400> SEQUENCE: 100

Met Gly Leu Pro Glu Met Glu Ser Met Ala Ser Ala Ile Gly Val Ser
1               5                   10                  15

Val Pro Val Leu Arg Phe Leu Leu Cys Phe Val Ala Thr Ile Pro Val
                20                  25                  30

Ser Phe Leu His Arg Phe Val Pro Ser Ala Val Gly His Leu Tyr
            35                  40                  45

Ala Ala Val Thr Gly Ala Val Leu Ser Tyr Leu Ser Phe Gly Phe Ser
        50                  55                  60

Ser Asn Leu His Phe Phe Gly Pro Met Leu Leu Gly Tyr Val Ser Met
65                  70                  75                  80

Val Leu Ser Arg Arg Tyr Cys Gly Ile Ile Thr Phe Phe Ala Ala Phe
                85                  90                  95

Gly Tyr Leu Ile Gly Cys His Val Tyr Tyr Met Ser Gly Asp Ala Trp
            100                 105                 110

Lys Glu Gly Gly Ile Asp Ala Thr Gly Ala Leu Met Val Ile Thr Leu
        115                 120                 125

```
Lys Ile Ile Ser Cys Val Ile Asn Tyr Gln Asp Gly Leu Leu Lys Glu
            130                 135                 140

Glu Asp Leu Arg Glu Ala Gln Lys Lys Asn Arg Leu Leu Lys Leu Pro
145                 150                 155                 160

Ser Leu Leu Glu Tyr Val Gly Cys Cys Leu Cys Cys Gly Ser His Phe
                165                 170                 175

Ala Gly Pro Val Tyr Glu Met Lys Asp Tyr Leu Asp Trp Thr Glu Arg
                180                 185                 190

Lys Gly Ile Trp Lys Pro Ser Glu Lys Gly Asn Pro Ser Pro Leu Gly
                195                 200                 205

Ser Thr Leu Arg Ala Leu Leu Gln Ala Ala Ile Cys Met Gly Leu Tyr
            210                 215                 220

Leu Tyr Leu Val Pro Leu Phe Pro Leu Ser Arg Phe Thr Asp Pro Leu
225                 230                 235                 240

Tyr Gln Glu Trp Gly Phe Phe Lys Arg Ser Gly Tyr Gln Tyr Met Ala
                245                 250                 255

Cys Phe Thr Ala Arg Trp Lys Tyr Tyr Phe Ile Trp Ser Ile Ser Glu
                260                 265                 270

Ala Ala Ile Ile Ile Ser Gly Leu Gly Phe Ser Gly Trp Thr Asn Ser
            275                 280                 285

Ser Ser Pro Lys Pro Arg Trp Asp Arg Ala Lys Asn Val Asp Val Leu
        290                 295                 300

Gly Val Glu Leu Ala Lys Ser Ser Val Gln Leu Pro Leu Val Trp Asn
305                 310                 315                 320

Ile Gln Val Ser Thr Trp Leu Arg His Tyr Val Tyr Glu Arg Leu Ile
                325                 330                 335

Gln Lys Gly Arg Lys Pro Gly Phe Phe Gln Leu Leu Ala Thr Gln Thr
            340                 345                 350

Val Ser Ala Val Trp His Gly Leu Tyr Pro Gly Tyr Ile Ile Phe Phe
        355                 360                 365

Val Gln Ser Ala Leu Met Ile Ala Gly Ser Arg Val Ile Tyr Arg Trp
370                 375                 380

Gln Gln Ala Ala Thr Gly Thr Leu Phe Glu Lys Met Leu Val Leu Met
385                 390                 395                 400

Asn Phe Ala Tyr Thr Leu Leu Val Leu Asn Tyr Ser Ala Val Gly Phe
                405                 410                 415

Met Val Leu Ser Leu His Glu Thr Leu Thr Ala Tyr Gly Ser Val Tyr
            420                 425                 430

Tyr Val Gly Thr Ile Val Pro Val Leu Ile Leu Leu Ser Lys Val
        435                 440                 445

Val Lys Pro Pro Lys Pro Ala Thr Ser Lys Ala Arg Lys Val Glu
    450                 455                 460

<210> SEQ ID NO 101
<211> LENGTH: 744
<212> TYPE: DNA
<213> ORGANISM: Artificial Sequence
<220> FEATURE:
<223> OTHER INFORMATION: dsRNA hairpin coding sequence

<400> SEQUENCE: 101
atgggtgctg tttatagaag tcttttttgct aaagatggat ttcctcctcc tattcctgga     60
cttgacagtt gctgggatat tttccgtttg tcagtggaaa aatatcctaa caatcggatg    120
cttggacgcc gtgagattgt agatggaaaa cctggcaagt atgtgtggat gtcttacaaa    180
```

```
gaagtatatg acattgtgat taaattagga aattccatcc ggagctgtgg tgtggacgaa      240
ggagacaaat gtggtatcta tggtgccaat tgccctgagt ggataatgag catggaggca      300
tgcaatgctc atggacttta ctgtgtgcct ctatatgaca ccttaggtgc tggtgcagtg      360
gaatttatca ttaaccatgc cgaggttaaa attgctttcg ttgaagagaa aaaacttcct      420
gagcttctga aacttttcc aaatgcagca aagtacttga agactgttgt gagttttggg       480
aatgtcactc ctcaacagaa ggaagaggtt gaaaactgtg gggtgactct atactcgtgg      540
gatgagttcc tacaattggg aagtgaaaaa caatttgatc ttccagtgaa aaagaaagaa      600
gatatttgta caataatgta tactagtgga acgaccggag atcccaaagg tgtgctgatt      660
tcaaataata gcattgttac tcttatagct ggagtacagc gtctgcttgg gagtgtgaat      720
gagtcgttga cagtggatga tgta                                            744

<210> SEQ ID NO 102
<211> LENGTH: 705
<212> TYPE: DNA
<213> ORGANISM: Artificial Sequence
<220> FEATURE:
<223> OTHER INFORMATION: dsRNA hairpin coding sequence

<400> SEQUENCE: 102
atggaatcat cggcagaacg acgtctgaaa gctattcaaa accatcttgt tccggtcatc       60
gatgaccggt cactctcatt catccggtca aacccaaccg ccggcgaatt tgttcaaggt      120
cagggtttca gcgtagttct tcctgaaaaa ttgcagacag gaaaatggaa tgtgtacaga      180
tctgcacgat ctcctctgaa gcttattact agattccctg atcatcctga aattgctaca      240
ctacatgata actttgaaca tgcagttcaa acctatcagg attacaaata cttgggtacc      300
cgtattcggg tagatggaac tattggagac tacaaatgga tgacatatgg agaggcaggg      360
actgctcgga ctgcaattgg ttctggactt cactattatg gattgcaacc gggtgctcgc      420
gtgggacttt atttcataaa taggcctgag tggctgattg tagaccatgc ctgctcagca      480
tattcatatt cttcagtccc actatatgac actcttggtc ctgatgctgt taaatatatt      540
gtcaatcatg ctgacgtaca ggccattttt tgtgtgcctg gtaccttgaa cacgttgttg      600
acctttttat cagagattcc ttctgtacgt ttgattgtgg tagtgggtgg gatagatgaa      660
catctcccat ctcttccatc tacaacggga atgaagctct atca                      705

<210> SEQ ID NO 103
<211> LENGTH: 734
<212> TYPE: DNA
<213> ORGANISM: Artificial Sequence
<220> FEATURE:
<223> OTHER INFORMATION: dsRNA hairpin coding sequence

<400> SEQUENCE: 103
atggcgtcga tggaacagtt ggtgacgggt gacggcggag gaggaggagg accgcggtac       60
gtgcagatgc aatctgagcc ggagccatca acattatcgt cgtttttactc gtttcatcag     120 gatagtagcc atgaatcaac tcgaattttc gatgaattgc cttcggctac gatcattcag      180
gtctctcgtc ctgacgccgg cgacatcagc cccatgcttc tcacttatac cattgaagtc      240
cattacaaac agttcaagtg gcaattggtg aagaaagcgt cacatgtatt ttatttacat      300
tttgcattaa agaagcgtgc attcattgag gagattcatg agaagcaaga gcaggtcaaa      360
gaatggctcc aaaacttggg gataggagat catacaactg taattcaaga cgaggatgaa      420
```

-continued

```
cctgatgatg aggctagtcc tctacgtgct gaggaaagtt ttaaatacag agatgttcca    480
tcaagtgctg ctttgccaat aattcggcca accctgggaa ggcaacactc gatgtcagat    540
cgagcaaaaa gtgctatgca gggttatttg aatcactttc ttggaaacat agatattgtc    600
aattcccagg aggtgtgcag gtttctggaa gtctctaaat tatccttttc tccagagtat    660
ggtcctaagc tgaaagaaga ctatattatg gtgaagcact taccaaaaat tcaaagacac    720
gatgatagtc ggaa                                                      734
```

<210> SEQ ID NO 104
<211> LENGTH: 543
<212> TYPE: DNA
<213> ORGANISM: Artificial Sequence
<220> FEATURE:
<223> OTHER INFORMATION: dsRNA hairpin coding sequence

<400> SEQUENCE: 104

```
atgtcgacgg agaaactgat agagaatgcg ccggcgtcgg caatgtcatc aatgcattcc     60
cttcgttgct acgtcgagcc ggcgacgatc tttgaggaat tgcccaaagc gactatcatt    120
gcggtttcaa gagcagatgc tagtgatata agcccttttgc ttttgtcata cacaattgaa    180
gtccagtaca agcagttcaa gtggcgctta gttaagaagg cctcacaagt tgtttatttg    240
cactttgcat tgaggaaacg tgcaataatt gaggaactcc atggaaaaca agagcaggtt    300
aaagaatggc ttcaccacat tggtatagga gaacaaacag ctgtcataca tgatgatgct    360
gaacccgatg atggtgctat gcaaatttac agtgaagata gtattagaaa caggtatgtt    420
ccatcccggg ctgctttatc aatcattcgt ccagcattgg gcaggcagca aaccattaca    480
gaaaagggaa aaattgctat gcaaaagtat ctgaatcatt ttttggggaa tttggacatt    540
gta                                                                  543
```

<210> SEQ ID NO 105
<211> LENGTH: 637
<212> TYPE: DNA
<213> ORGANISM: Artificial Sequence
<220> FEATURE:
<223> OTHER INFORMATION: dsRNA hairpin coding sequence

<400> SEQUENCE: 105

```
atggaatcaa tggcgtcggc gatcggagta tcagtgccgg tgctccgttt cttgctttgt     60
tttgtcgcca caattccggt gagcttcctc caccgttttg tccctagcgc cgtcggtaga    120
cacctctacg ccgccgttac cggcgctgtt ctctcgtacc tgtcatttgg tttctcctca    180
aatcttcact tctttgggcc tatgcttctg ggttatgttt ctatggttct ctctcgccgt    240
tactgcggga tcatcacttt cttcgccgcg tttggatacc ttattggatg ccatgtatac    300
tacatgagtg gagacgcatg gaaggaagga ggaattgatg ctacaggagc tctaatggtc    360
ataacgctga aaataatttc atgtgtgatt aattaccaag atggattgtt gaaggaggaa    420
gatttgcgtg aggctcagaa gaaaaatcgt ctgctcaaat tgccatcgtt acttgagtac    480
gttggttgtt gtctctgttg tggaagtcat tttgcaggtc cagtgtatga gatgaaggat    540
taccttgact ggacagagag aaaaggaatc tggaaacctt cagagaaggg aaatccctca    600
cctttagggt caactttaag ggctcttctt caagctg                             637
```

PRODUCTION OF DIHYDROSTERCULIC ACID AND DERIVATIVES THEREOF

FIELD OF THE INVENTION

The present invention relates to recombinant cells, particularly recombinant plant cells, which are capable of producing dihydrosterculic acid and/or derivatives thereof. The present invention also relates to methods of producing oil comprising dihydrosterculic acid and/or derivatives thereof.

BACKGROUND OF THE INVENTION

Dihydrosterculic acid (DHS) is a fatty acid containing a 'mid-chain' cyclopropane ring structure that can be processed into industrial oils with the rare combination of high oxidative stability and low melting points (Kinsman, 1979; Zhang et al., 2004).

Although routes for the chemical synthesis of DHS are known, these reactions generate a series of side-products requiring purification procedures (Zhang et al., 2004). In contrast, biological routes of synthesis accurately generate cyclopropanated fatty acids from membrane-bound 18:1 by cyclopropanated synthetases (CPFAS) isolated from various plants (Bao et al., 2002) and bacteria (Wang et al., 1992).

The plant CPFAS isolated from *Sterculia foetida*, and likely all plant CPFAS enzymes, are atypical lipid modifying enzymes by virtue of using 18:1 at the sn1 position of PC (Bao et al., 2003), rather than the acyl-groups attached to the sn2 position of PC, such as FAD2 (Stymne and Appelqvist, 1978). The DHS formed in transgenic tobacco cell lines was found predominantly on the PC fraction, suggesting that sn1-bound DHS is not easily moved into neutral lipid fractions, such as the glycerol backbone of triacylglycerides (TAG, (Bao et al., 2002)). Recently a cotton CPFAS (GhCP-FAS) expressed in *Arabidopsis* seed produced ~1% DHS in seed lipid analysis (Yu et al., 2011), suggesting that the transfer of DHS from the site of synthesis on PC into seed oil is problematic.

There is a need for recombinant cells with enhanced levels of DHS production.

SUMMARY OF THE INVENTION

The present inventors have developed processes and cells for producing dihydrosterculic acid (DHS) and/or a fatty acid derivative thereof.

In one aspect, the present invention provides a process for producing oil containing dihydrosterculic acid (DHS) and/or a fatty acid derivative thereof, the process comprising i) obtaining plant cells, algal cells or fungal cells comprising DHS, and/or a fatty acid derivative thereof, the DHS and/or fatty acid derivative thereof being esterified in triacylglycerols in the cells, wherein at least about 3% of the total fatty acid in extractable oil in the cells is DHS and/or a fatty acid derivative thereof, and, ii) extracting oil from the cells so as to thereby produce the oil.

In an embodiment, the plants cells of step i) are obtained as a plant or part thereof comprising said cells, such as a leaf or a stem.

In an embodiment, the part is a vegetative plant tissue. In an embodiment, the plant cells are cells other than cells in seeds.

In another aspect, the present invention provides a process for producing oil containing dihydrosterculic acid (DHS) and/or a fatty acid derivative thereof, the process comprising i) obtaining an oilseed or vegetative plant tissue comprising DHS, and/or a fatty acid derivative thereof, the DHS and/or fatty acid derivative thereof being esterified in triacylglycerols in the oilseed, wherein at least about 3% of the total fatty acid in extractable oil in the oilseed or vegetative plant tissue is DHS and/or a fatty acid derivative thereof, and ii) extracting oil from the oilseed or vegetative plant tissue so as to thereby produce the oil.

Examples of oilseeds useful for the invention include, but are not limited to, seed from a canola plant, a corn plant, a soybean plant, a lupin plant, a peanut plant, a sunflower plant, a cotton plant, a safflower plant, a *crambe* (*Crambe abyssinica*) plant, a *camelina* (*Camelina sativa*) plant, a plant of a Euphorbiaceae species such as *jatropha* (*Jatropha curcas*), a plant of a *Brassica* species other than canola such as *Brassica carinata* or *Brassica juncea*, a flax plant or an *Arabidopsis* plant.

In an embodiment, the process comprises the step of extracting the oil comprises crushing the oilseed. The process may further comprise purifying the oil, such as by degumming, decolourising, or deodorising the oil.

In a further embodiment, at least about 5%, or preferably at least about 7%, or more preferably at least about 10%, or even more preferably at least about 12%, or most preferably at least about 15%, of the total fatty acid in the extractable oil in the oilseed, vegetative plant tissue or cells is DHS and/or a fatty acid derivative thereof. In an embodiment, at least about 50%, preferably at least about 75%, more preferably at least about 90% of the DHS and/or fatty acid derivative thereof in the extractable lipid from the oilseed, vegetative plant tissue or cells is esterified in the form of triacylglycerols. Each combination of these figures is envisaged.

In another embodiment, about 3% to about 15%, about 3% to 10%, or about 3% to about 7.5% of the total fatty acid in the extractable oil in the oilseed, vegetative plant tissue or cells is DHS and/or a fatty acid derivative thereof.

In a further embodiment, the ratio of oleic acid to DHS and/or fatty acid derivative thereof in the extractable oil in the oilseed, vegetative plant tissue or cells is less than about 2:1, preferably less than about 1.5:1, more preferably less than about 1:1.

In an embodiment, step i) comprises obtaining at least about 100, or at least about 1000, or at least about 10000, seeds, or pieces of vegetative tissue from at least about 100, or at least about 1000, or at least about 10000, plants, which on average comprise at least about 3% DHS as a percentage of the total fatty acids in the extractable oil in the oilseeds or vegetative plant tissues.

In a further embodiment, there is no detectable fatty acid derivative of DHS present in the extractable oil, such as sterculic acid and/or malvalic acid.

Also provided is a recombinant plant cell, algal cell or fungal cell comprising an exogenous polynucleotide encoding a cyclopropane fatty acid synthetase (CPFAS), wherein extractable oil in the cell contains dihydrosterculic acid (DHS) and/or a fatty acid derivative thereof, and wherein the polynucleotide is operably linked to one or more promoters that are capable of directing expression of the polynucleotide in the cell, and wherein the cell has one or more of the following features, i) at least about 3%, or at least about 5%, or at least about 7%, or at least about 10%, or at least about 12%, or at least about 15%, of the total fatty acid in the extractable oil in the cell is DHS and/or a fatty acid derivative thereof, ii) the CPFAS converts oleic acid to DHS in the cell with a conversion efficiency of at least about 45%, or at least about 50%, or at least about 55%, iii) the ratio of oleic acid to DHS and/or fatty acid derivative thereof in the extractable oil in the cell is less than about 2:1, preferably less than about 1.5:1, more preferably less than about 1:1, or iv) the CPFAS comprises amino acids having a sequence as provided in any one of SEQ ID NOs: 1, or 21 to 28, a biologically active fragment thereof, or an amino acid sequence which is at least 30% identical to any one or more of SEQ ID NOs: 1, or 21 to 28, wherein the CPFAS is no longer than about 600 amino acids, more preferably no longer than 500 amino acids, in length.

Other features above relating the a process of the invention also apply to the recombinant cell of the invention.

In a preferred embodiment, the cell at least comprises features i) and/or iv). In a further embodiment, the cell comprises all four of features i), ii), iii) and iv). In another embodiment, the cell at least comprises feature iv). In a further embodiment, the cell is homozygous for the exogenous polynucleotide.

In an embodiment, a corresponding cell lacking the exogenous polynucleotide does not produce DHS.

In an embodiment, the CPFAS converts oleic acid to DHS in the cell with a conversion efficiency of about 45% to about 90%, about 45% to about 70%, about 45% to about 60%, about 55% to about 90%, or about 55% to about 70%.

In a preferred embodiment, the cell further comprises an exogenous polynucleotide encoding a silencing suppressor, wherein the polynucleotide is operably linked to one or more promoters that are capable of directing expression of the polynucleotide in the cell.

In a further preferred embodiment, the cell further comprises an exogenous polynucleotide encoding an enzyme having fatty acid acyltransferase activity such as an diacylglycerol acyltransferase (DGAT) and/or monoacylglycerol (MGAT) activity, and wherein the polynucleotide is operably linked to one or more promoters that are capable of directing expression of the polynucleotide in the cell.

In yet a further preferred embodiment, the cell further comprises an exogenous polynucleotide encoding a transcription factor polypeptide that increases the expression of one or more glycolytic or fatty acid biosynthetic genes in the cell such as a Wrinkled 1 (WRI1) transcription factor, a Leafy Cotyledon 1 (Lec1) transcription factor, a Leafy Cotyledon 2 (LEC2) transcription factor, a Fus3 transcription factor, an ABI3 transcription factor, a Dof4 transcription factor, a BABY BOOM (BBM) transcription factor, or a Dof11 transcription factor, and wherein the polynucleotide is operably linked to one or more promoters that are capable of directing expression of the polynucleotide in the cell.

In yet a further preferred embodiment, the cell further comprises an exogenous polynucleotide encoding an oleosin, and wherein the polynucleotide is operably linked to one or more promoters that are capable of directing expression of the polynucleotide in the cell.

In yet a further preferred embodiment, the cell further comprises an exogenous polynucleotide encoding a double stranded RNA (dsRNA) which comprises a nucleotide sequence which is complementary to a region of a target RNA such as a target RNA encoding an endogenous Δ12 desaturase, DHS Δ9 desaturase, palmitoyl-ACP thioesterase such as FATB, or lipid handling enzyme, preferably a fatty acid acyltransferase such as an lysophosphatidyl-choline acyltransferase (LPCAT), a lipase such as a phospholipase D, or a fatty acid synthetase such as a long-chain acyl CoA synthetase (LACS), and wherein the polynucleotide is operably linked to one or more promoters that are capable of directing expression of the polynucleotide in the cell. The cell may comprises two or more such exogenous polynucleotides encoding different dsRNAs comprising sequences complementary to different target RNAs.

In an embodiment, the cell comprises a first exogenous polynucleotide encoding CPFAS, preferably a truncated plant CPFAS or variant thereof, and one or more additional exogenous polynucleotides which encode one or more of:

i) an fatty acid acyltransferase such as an MGAT or DGAT, preferably a DGAT1, ii) a transcription factor polypeptide that increases the expression of one or more glycolytic or fatty acid biosynthetic genes in the cell such as a WRI1, LEC2 or BBM, preferably WRI1, iii) a double stranded RNA (dsRNA) which comprises a nucleotide sequence which is complementary to a region of a target RNA of an endogenous lipid handling enzyme, preferably a fatty acid acyltransferase such as an LPCAT, or a lipase such as a phospholipase D, iv) a double stranded RNA (dsRNA) which comprises a nucleotide sequence which is complementary to a region of a target RNA of an endogenous Δ12 desaturase, v) oleosin, or vi) a silencing suppressor polypeptide, wherein each exogenous polynucleotide is operably linked to a promoter which is capable of directing expression of the polynucleotide in the cell. In an embodiment, the cell comprises i) and ii), i) to iii), i) to iv), i) to v), i) to vi), i) and to vi), i) to iii) and vi), or i), and iv) to vi).

In an embodiment, the cell further comprises an exogenous polynucleotide encoding a fatty acid elongase, and wherein the polynucleotide is operably linked to one or more promoters that are capable of directing expression of the polynucleotide in the cell. In this embodiment, the fatty acid derivative may be elongated DHS (eDHS).

In an embodiment, the cell comprises two exogenous polynucleotides encoding different CPFAS enzymes, wherein each polynucleotide is operably linked to one or more promoters that are capable of directing expression of the polynucleotide in the cell. Preferably, a first exogenous polynucleotide encodes a truncated plant CPFAS or variant thereof, and a second exogenous polynucleotide encodes a bacterial or fungal CPFAS or variant thereof.

Examples of truncated plant CPFAS enzymes or variant thereofs include, but are not limited to, those comprising amino acids having a sequence as provided in any one of SEQ ID NOs: 1, or 21 to 28, a biologically active fragment thereof, or an amino acid sequence which is at least 30% identical to any one or more of SEQ ID NOs: 1, or 21 to 28, wherein the CPFAS is no longer than about 600 amino acids, more preferably no longer than 500 amino acids, in length.

Examples of bacterial or fungal CPFAS enzymes or variant thereofs include, but are not limited to, those comprising amino acids having a sequence as provided in any one of SEQ ID NOs: 51 to 58, a biologically active fragment thereof, or an amino acid sequence which is at least 30% identical to any one or more of SEQ ID NOs: 51 to 58.

In a further embodiment, the cell further comprises one or more exogenous polynucleotides encoding a glycerol-3-phosphate acyltransferase (GPAT), a 1-acyl-glycerol-3-phosphate acyltransferase (LPAAT), an acyl-CoA:lysophosphatidylcholine acyltransferase (LPCAT), a phosphatidic acid phosphatase (PAP), or a combination of two or more thereof.

In a preferred embodiment, the cell is a plant cell such as a seed or leaf cell. In an embodiment, the cell is a leaf cell.

In an embodiment, the plant cell is a cell of an oilseed plant.

As the skilled person would appreciate, the oilseed, vegetative plant tissue or cells used in a process of the invention may have one or more features as defined above for a cell of the invention.

In a further aspect, the present invention provides a method of obtaining a cell of the invention, the method comprising
  a) introducing into a cell an exogenous polynucleotide encoding a cyclopropane synthetase (CPFAS), wherein the polynucleotide is operably linked to one or more promoters that are capable of directing expression of the polynucleotide in the cell,
  b) expressing the exogenous polynucleotide in the cell, and
  c) performing one or more of the following
  i) analysing the fatty acid composition of the cell, and selecting a cell wherein at least about 3%, or at least about 5%, or at least about 7%, or at least about 10%, or at least about 12%, or at least about 15%, of the total fatty acid in extractable oil in the cell is DHS and/or a fatty acid derivative thereof,
  ii) analysing the fatty acid composition of the cell, and selecting a cell wherein the CPFAS converts oleic acid to DHS in the cell with a conversion efficiency of at least about 45%, or at least about 50%, or at least about 55%,
  iii) analysing the fatty acid composition of the cell, and selecting a cell wherein the ratio of oleic acid to DHS and/or fatty acid derivative thereof in extractable oil in the cell is less than about 2:1, preferably less than about 1.5:1, more preferably less than about 1:1, or
  iv) analysing the cell for the exogenous polynucleotide, and selecting a cell which comprises a CPFAS which comprises amino acids having a sequence as provided in any one of SEQ ID NOs: 1, or 21 to 28, a biologically active fragment thereof, or an amino acid sequence which is at least 30% identical to any one or more of SEQ ID NOs: 1, or 21 to 28, wherein the CPFAS is no longer than about 600 amino acids, more preferably no longer than 500 amino acids, in length.

In an embodiment, the selected cell is a cell as defined above.

In yet a further aspect, the present invention provides a method of selecting a nucleic acid molecule encoding a truncated cyclopropane synthetase (CPFAS), the method comprising
  i) obtaining a nucleic acid molecule operably linked to a promoter, wherein the nucleic acid encodes a truncated variant of a CPFAS,
  ii) introducing the nucleic acid molecule into a plant cell, algal cell or fungal cell in which the promoter is active;
  iii) expressing the nucleic acid molecule in the cell;
  iv) analysing the fatty acid composition of the cell; and
  v) selecting the nucleic acid molecule by selecting a cell having one or more of the following features,
  a) at least about 3%, or at least about 5%, or at least about 7%, or at least about 10%, or at least about 15%, of the total fatty acid in extractable oil in the cell is DHS and/or a fatty acid derivative thereof,
  b) converts oleic acid to DHS in the cell with a conversion efficiency of at least about 45%, or at least about 50% or at least about 55%, or
  c) comprises a ratio of oleic acid to DHS and/or fatty acid derivative thereof in extractable oil in the cell less about than 2:1, preferably less than about 1.5:1, more preferably less than about 1:1.

In an embodiment, the cell is a plant cell.

In an embodiment, the CPFAS comprises an amino acid sequence which is at least 30% identical to any one or more of SEQ ID NOs: 1, or 21 to 28. Preferably, the CPFAS is no longer than about 600 amino acids, more preferably no longer than 500 amino acids, in length.

Also provided is a transgenic plant, or part thereof, comprising a cell of the invention.

In a further aspect, the present invention provides a method of producing a transgenic plant of the invention or a part therefrom such as seed or leaf, the method comprising the steps of
  i) introducing an exogenous polynucleotide encoding the CPFAS into a cell of a plant,
  ii) regenerating a transgenic plant from the cell, and
  iii) optionally obtaining seed from the plant, a part of the plant and/or producing one or more progeny plants from the transgenic plant,
thereby producing the transgenic plant.

In another aspect, the present invention provides a method of producing a transgenic plant of the invention, the method comprising the steps of
  i) crossing two parental plants, wherein at least one is a transgenic plant of the invention,
  ii) screening one or more progeny plants from the cross for the presence or absence of the exogenous polynucleotide, and
  iii) selecting a progeny plant which comprises the exogenous polynucleotide, thereby producing the transgenic plant.

In an embodiment, step iii) comprises analysing the phenotype of the plant, or one or more progeny plants thereof, for one or more of the following features,
  a) at least about 3%, or at least about 5%, or at least about 7%, or at least about 10%, or at least about 12%, or at least about 15%, of the total fatty acid in extractable oil in the cell is DHS and/or a fatty acid derivative thereof,
  b) conversion of oleic acid to DHS in the cell with a conversion efficiency of at least about 45%, or at least about 50%, or at least about 55%, or
  c) a ratio of oleic acid to DHS and/or fatty acid derivative thereof in extractable oil in the cell of less than about 2:1, preferably less than about 1.5:1, more preferably less than about 1:1.

Also provided is a transgenic plant produced using a method of the invention. In an embodiment, the plant is homozygous for the exogenous polynucleotide which is integrated into the genome of the plant.

In a further aspect, the present invention provides a method of producing seed, the method comprising;
  i) growing a plant of the invention, and
  ii) harvesting the seed from the plant.

In another aspect, the present invention provides a method of producing DHS and/or a fatty acid derivative thereof, the method comprising culturing a cell of the invention and/or cultivating a plant, or part thereof, of the invention.

In an embodiment, the method further comprises extracting DHS and/or a fatty acid derivative thereof, from the cell and/or the plant or part thereof.

In another aspect, the present invention provides a product comprising or produced from DHS or a fatty acid derivative thereof produced from a cell of the invention and/or a plant, or part thereof, of the invention.

In yet a further aspect, the present invention provides a method of producing a fatty acid with a methyl group, the process comprising converting the cyclo-propyl group of DHS, or a fatty acid derivative thereof comprising a cyclo-propyl group, produced using the method of the invention, to a methyl group.

In an embodiment, the cyclo-propyl group is converted to a methyl group using hydrogenation.

In an embodiment, the fatty acid with a methyl group is isostearic acid having a methyl group attached at C9 or C10.

In a further aspect, the present invention provides a product comprising or produced from a fatty acid with a methyl group produced using the method of the invention.

In an embodiment, the product is a lubricant and/or used in cosmetics.

Also provided is the use of a cell of the invention and/or a plant, or part thereof, of the invention to manufacture an industrial product.

In a further aspect, the present invention provides DHS and/or a fatty acid derivative thereof produced by, or obtained from, a cell of the invention, a plant, or part thereof, of the invention or using a method of the invention.

In another aspect, the present invention provides a methylated fatty acid produced using a method of the invention.

In a further aspect, the present invention provides a composition comprising one or more of the cell of the invention, the plant or part thereof of the invention, the DHS and/or a fatty acid derivative thereof of the invention, and the methylated fatty acid of the invention.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1: V2 allows overexpression of transgenes and their efficient silencing via hairpin RNAi. A, Time course of GFP expression with either no co-infiltrated VSP or the addition of V2 or p19. Image shows one representative leaf photographed up to 7 days post infiltration (dpi), and the image at 7 dpi is used to illustrate the labelling of each infiltration zone. B, Time course of the effect of V2 or p19 on hairpin-based silencing of GFP. The image shows one representative leaf photographed at 5 dpi.

Figure 2:
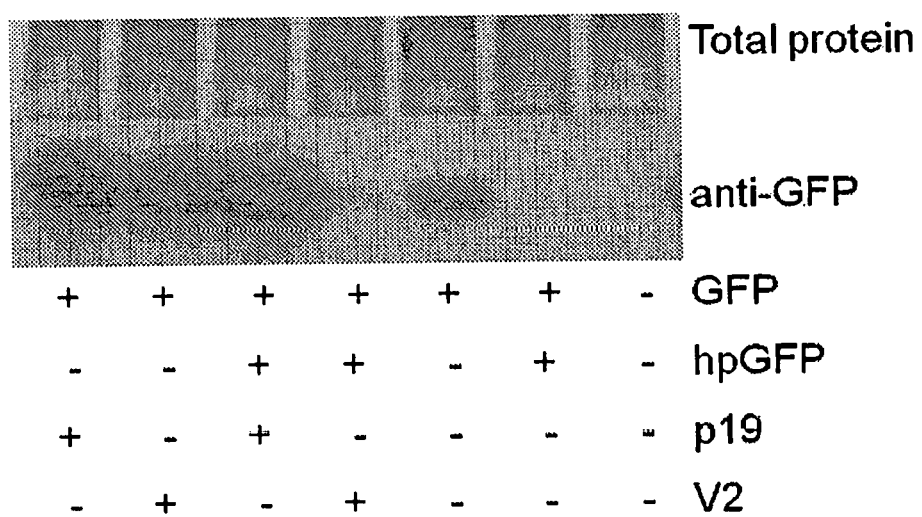

FIG. 2: Western blot analysis of GFP expression in leaves sampled at 4 dpi. Image shows one experiment from a duplicate conducted on different leaves.

Figure 3:
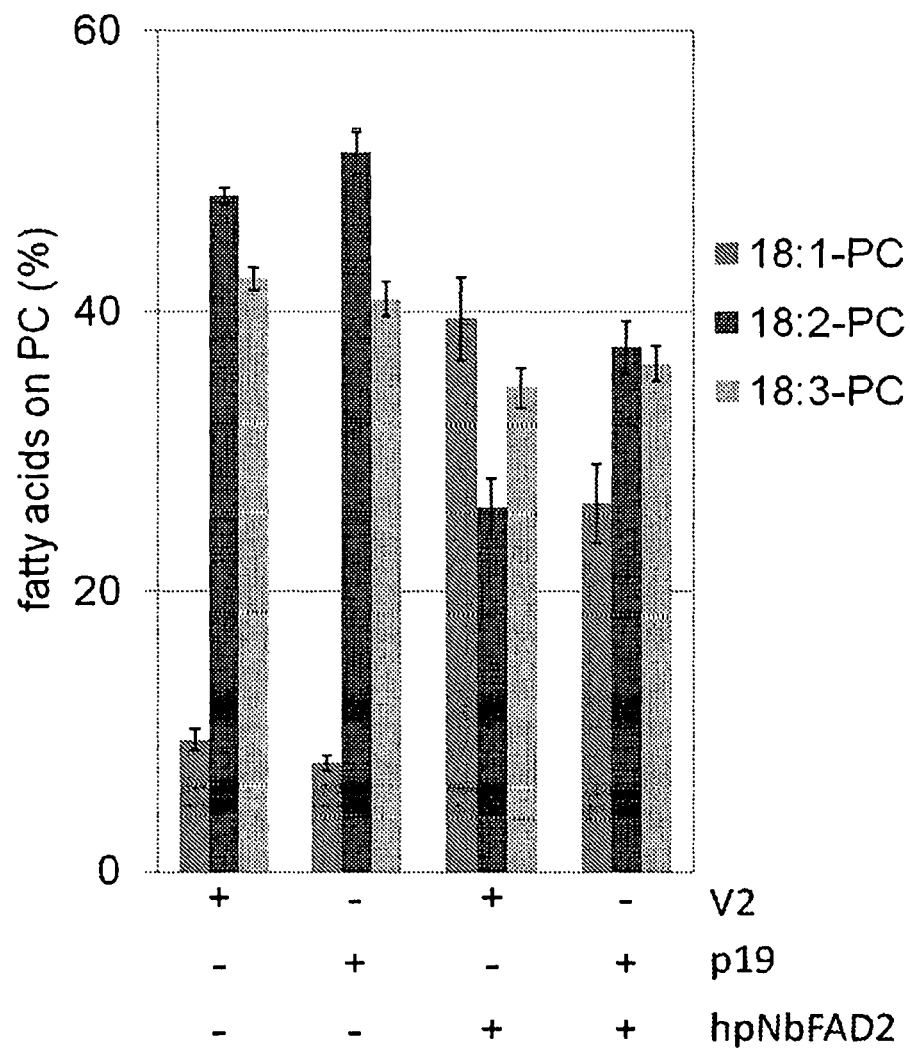

FIG. 3: Analysis of the composition of the phosphatidylcholine (PC) fraction of leaves infiltrated with various combinations of V2, p19 and hpNbFAD2. Leaves were sampled 5 dpi and the error bars represent the standard error of the mean from 5 independent leaves.

Figure 4:
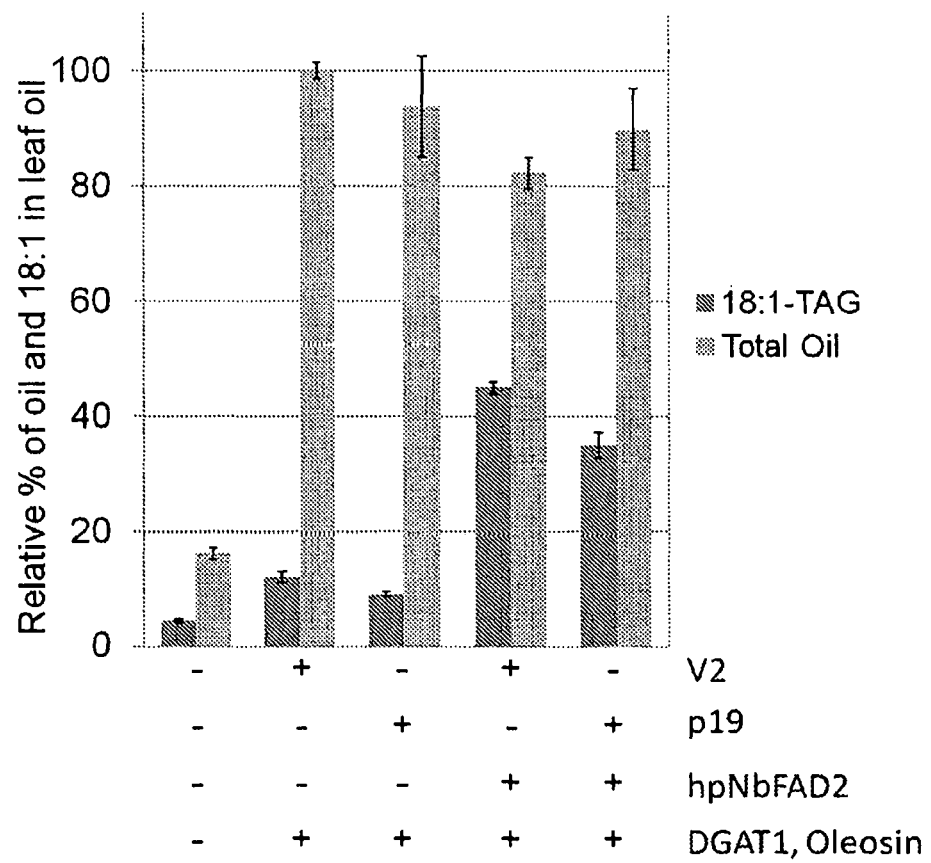

FIG. 4: Analysis of the content and composition of leaf oils when leaves were infiltrated with combinations of V2, p19, hpNbFAD2, DGAT1 and oleosin. Leaves were samples 5 dpi and error bars represent the standard error of the mean calculated from 5 independent leaves.

Figure 5:
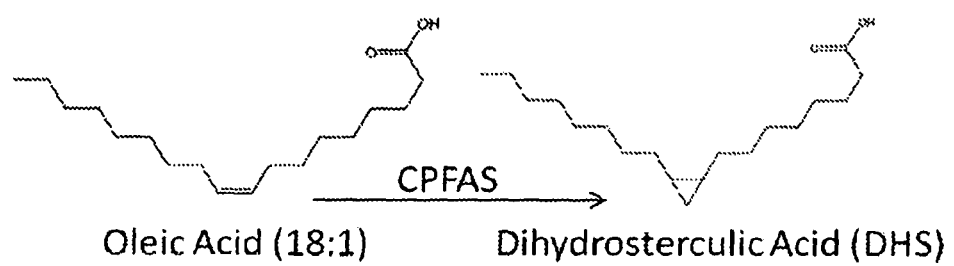

FIG. 5: The enzymatic production of DHS from oleic acid.

Figure 6:
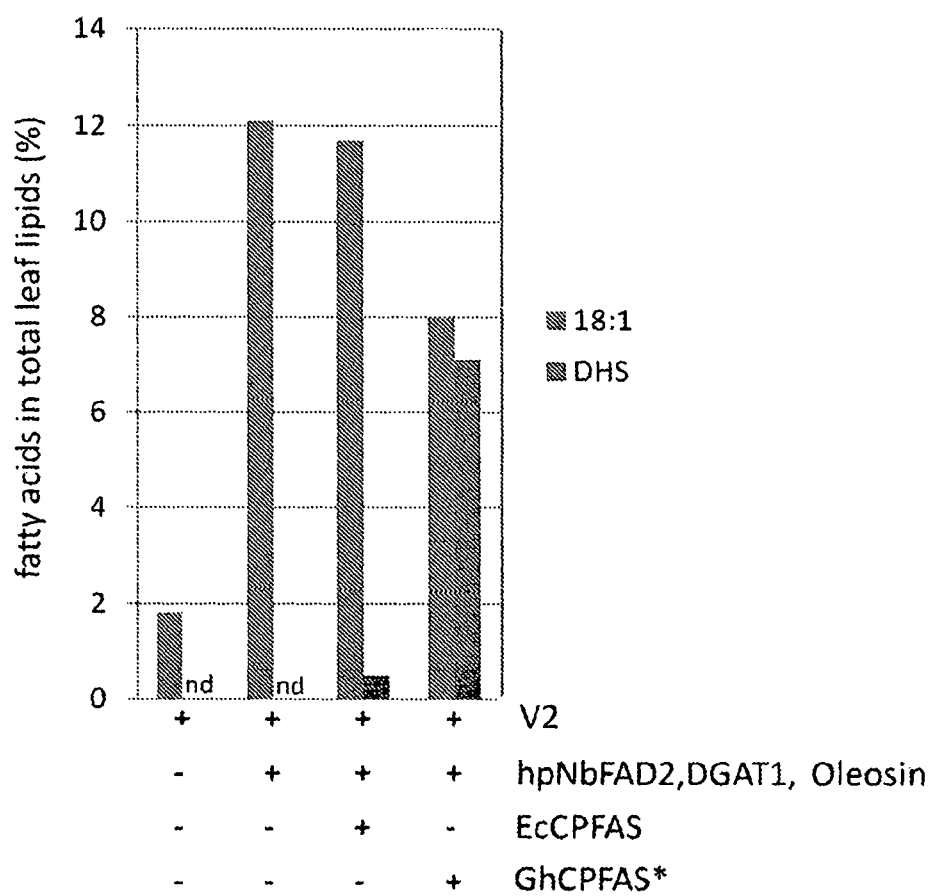

FIG. 6: Comparison of the production of DHS in leaf assays using either EcCPFAS or GhCPFAS in transient leaf assays. Leaves were harvested 4 dpi.

Figure 7:
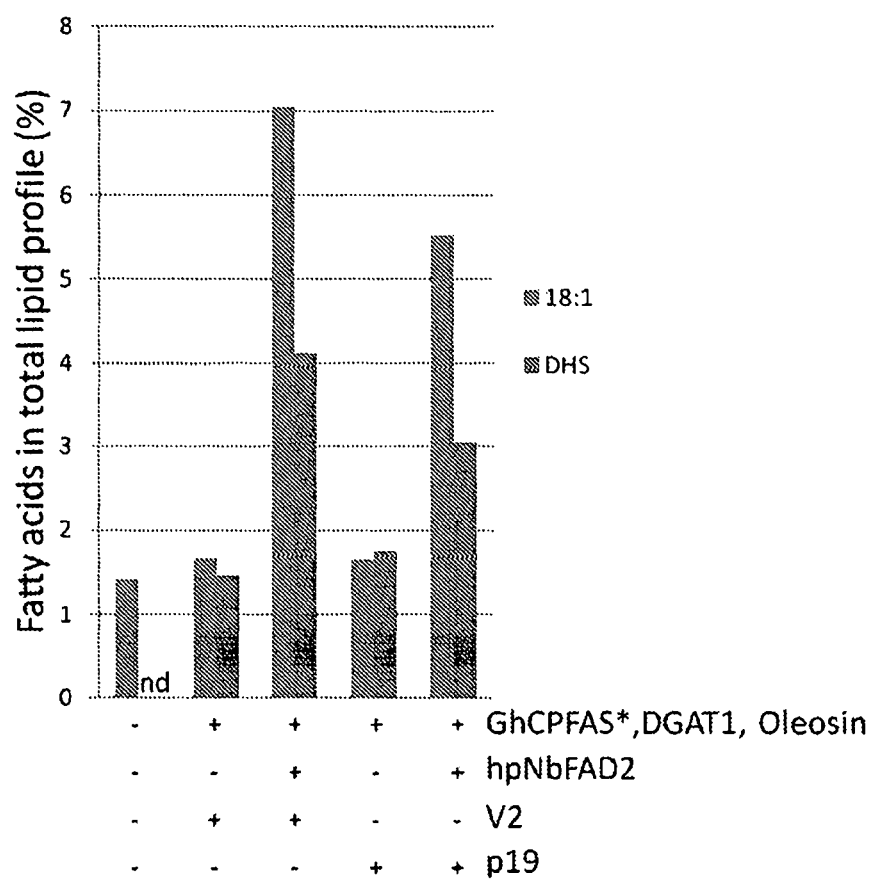

FIG. 7: Overexpression of transgenes and silencing of an endogene for improved fluxes of DHS into leaf oils. Leaves were harvested 4 dpi. These comparisons were conducted on 4 different leaves, and this figure shows results from one representative leaf.

Figure 8:
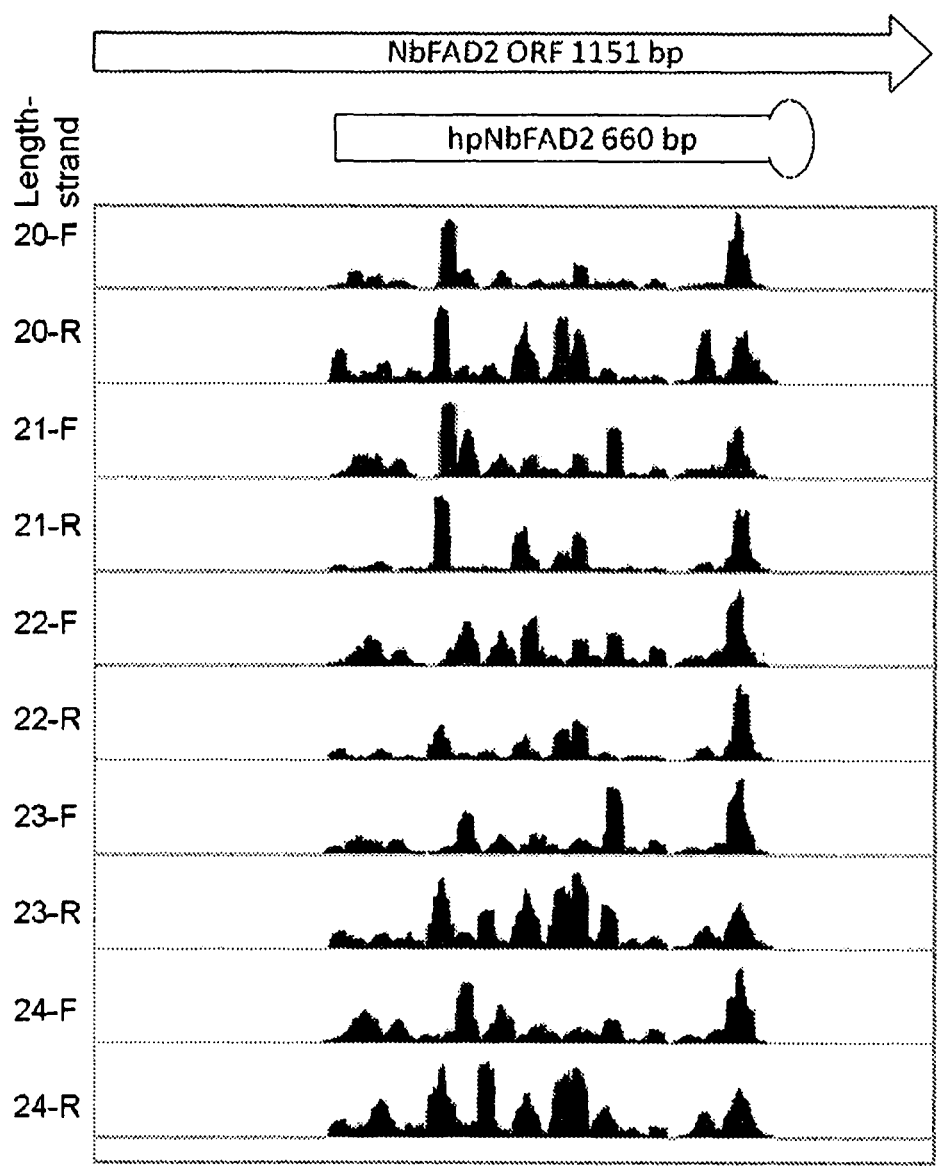

FIG. 8: 'Deep sequencing' analysis of the size and distribution of small RNA populations generated by a hairpin targeting the endogene NbFAD2. The full-length NbFAD2 is portrayed indicating the region used to generate a 660 bp hairpin, hpNbFAD2. The size and distribution of the dominate classes of small RNAs on the forward (F) and reverse (R) strand of the NbFAD2 is illustrated below. Each track is resealed to show the relatively uneven distribution of small RNAs across the target.

Figure 9:
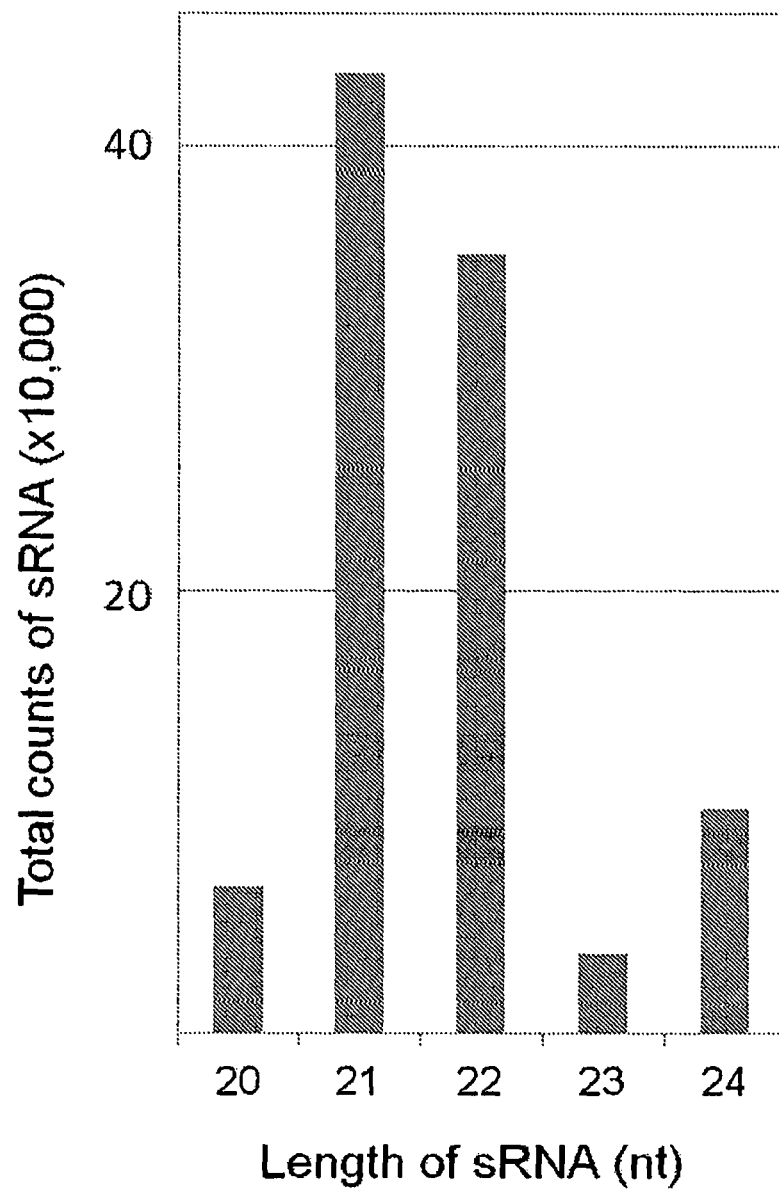

FIG. 9: Absolute numbers of the dominant small RNA size classes generated by hpNbFAD2. The relative percentage of each size class is given in the text.

Figure 10:
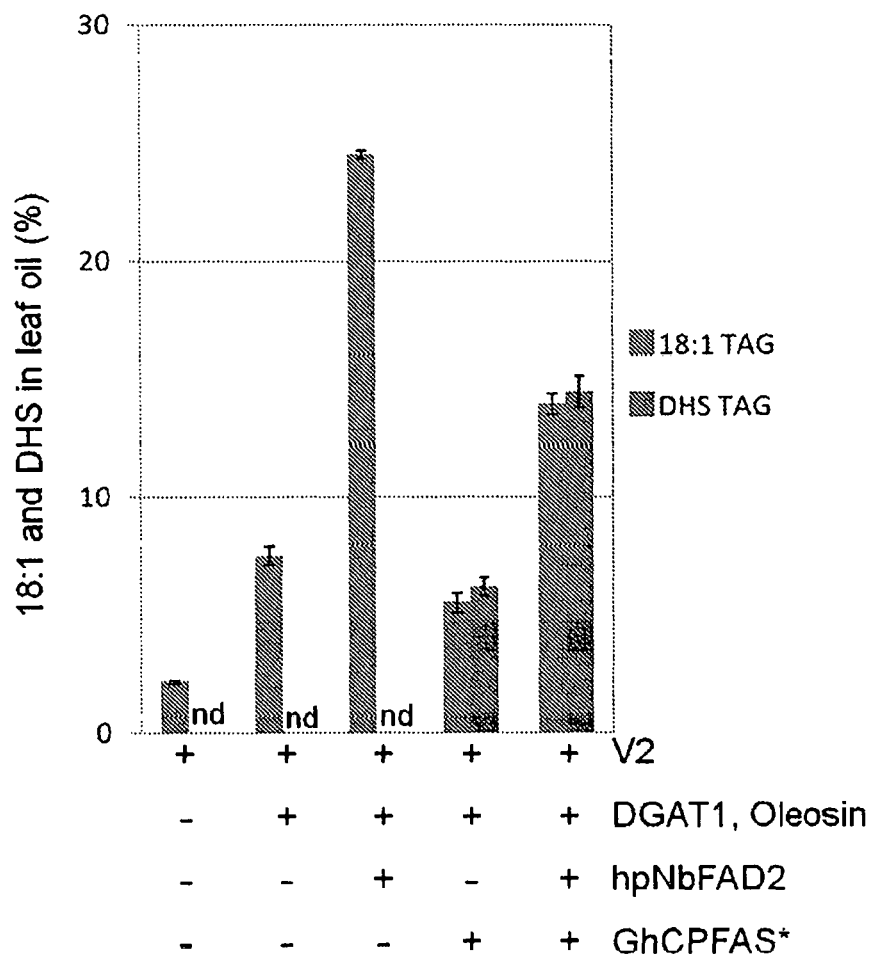

FIG. 10: DHS is accumulated in leaf oils.

Figure 11:
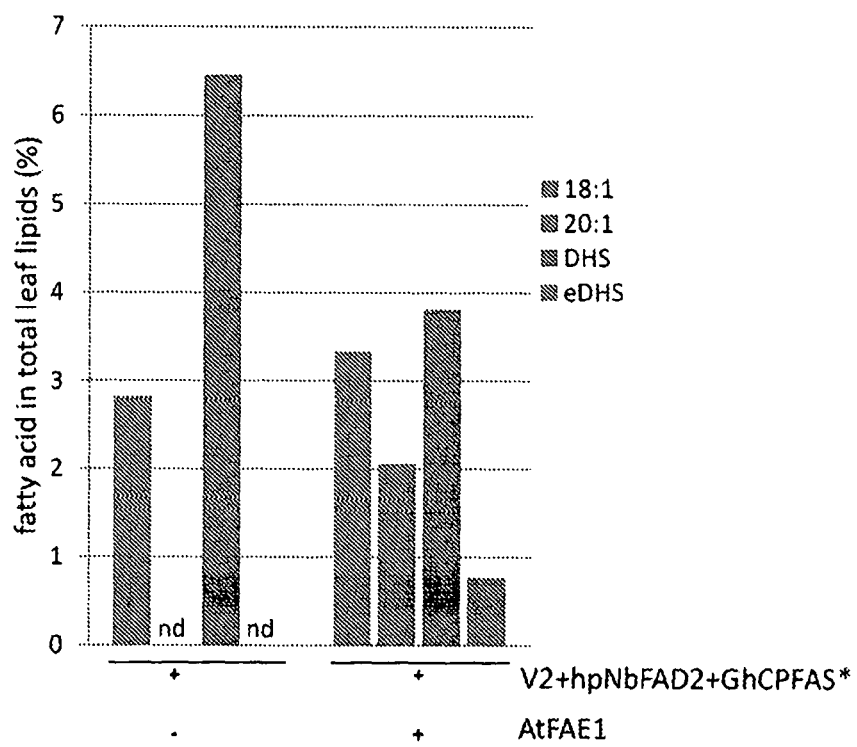

FIG. 11: Fatty acid profile of leaves producing DHS in the presence or absence of the elongase AtFAE1. Elongation experiments were conducted on 3 different leaves, and the figure shows a representative fatty acid profile from a single leaf.

Figure 12:
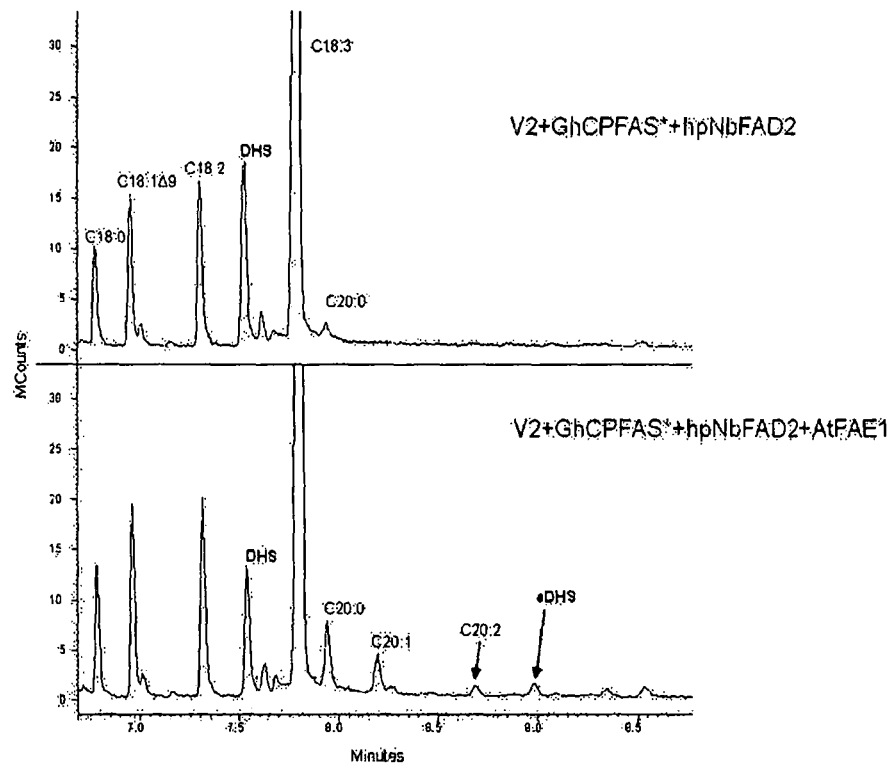
Figure 12:
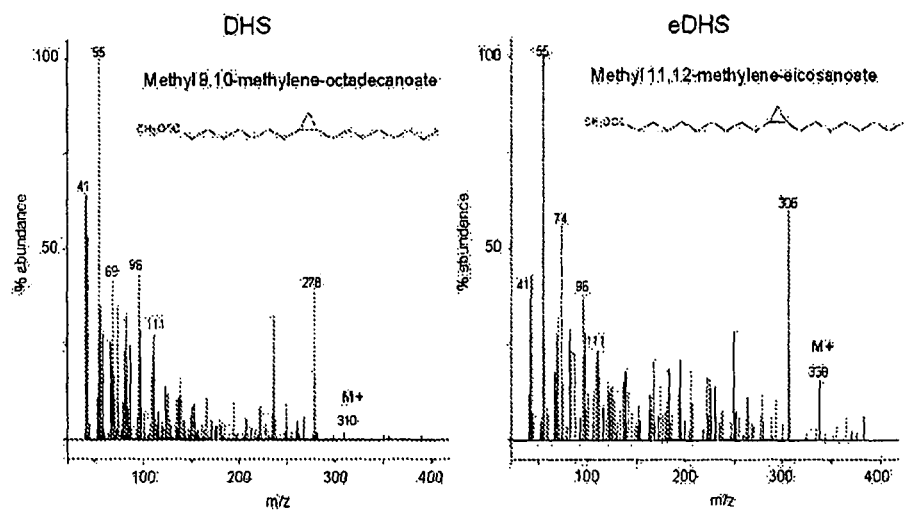

FIG. 12: The identification of eDHS using a range of GC and MS techniques. The upper panels show GC (FID) traces for lipid extracts from leaves infiltrated with the combination of genes as shown. Common and new metabolites are shown as indicated. Lower panels show the range of masses for metabolites first resolved on the GC, DHS and eDHS. The inserts for each MS indicates the structure of DHS and eDHS.

Figure 13:
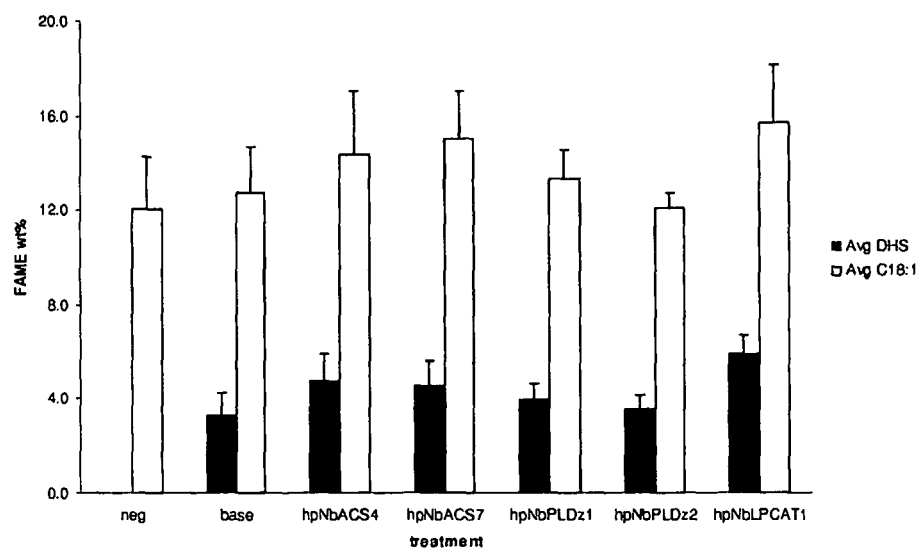

FIG. 13: Average wt % of DHS-FAME (black columns) and C18:1-FAME (white columns) from total FAME on lipid extracts from *N. benthamiana* leaf expressing GhCP-FAS*, V2, DGAT1 and WRI1 ("base"), and additional hairpin constructs against endogenous genes coding for putative lipid handling enzymes. LACS, long-chain acyl CoA synthetase; PLDz, phospholipase D zeta; LPCAT, lysophosphatidylcholine acyltransferase. Error bars are standard deviations from at least six replicates.

KEY TO THE SEQUENCE LISTING

SEQ ID NO: 1—amino acid sequence of tomato leaf yellow curl virus V2 protein

SEQ ID NO: 2—amino acid sequence of tomato bushy stunt virus P19 protein

SEQ ID NO: 3—nucleotide sequence encoding tomato leaf yellow curl virus V2 protein SEQ ID NO: 4—nucleotide sequence encoding tomato bushy stunt virus P19 protein SEQ ID NO: 5—amino acid sequence of *Sesmum indicum* oleosin protein SEQ ID NO: 6—nucleotide sequence encoding *Sesmum indicum* oleosin protein SEQ ID NO: 7—amino acid sequence of *Arabidopsis thaliana* AtFAE1 protein SEQ ID NO: 8—nucleotide acid sequence encoding *Arabidopsis thaliana* AtFAE1 protein including 5' intron sequence SEQ ID NO: 9—amino acid sequence of *Arabidopsis thaliana* AtDGAT1 protein SEQ ID NO: 10—nucleotide acid sequence encoding *Arabidopsis thaliana* AtDGAT1 protein SEQ ID NO: 11—amino acid sequence of NbFAD2 protein SEQ ID NO: 12—nucleotide sequence encoding dsRNA hairpin targeting *N. benthamiana* FAD2

SEQ ID NOs 13 to 20—oligonucleotide primers

SEQ ID NO: 21—amino acid sequence of *Gossypium hirsutum* CPFAS-1 (truncated protein)

SEQ ID NO: 22—amino acid sequence of *Gossypium hirsutum* CPFAS-2 (truncated protein)

SEQ ID NO: 23—amino acid sequence of *Gossypium hirsutum* CPFAS-3 (truncated protein)

SEQ ID NO: 24—amino acid sequence of *Oryza sativa* CPFAS (truncated protein)

SEQ ID NO: 25—amino acid sequence of *Arabidopsis thaliana* CPFAS (truncated protein)

SEQ ID NO: 26—amino acid sequence of *Sterculia foetida* CPFAS (truncated protein)

SEQ ID NO: 27—amino acid sequence of *Medicago truncatula* CPFAS (truncated protein)

SEQ ID NO: 28—amino acid sequence of *Zea mays* CPFAS (truncated protein)

SEQ ID NO: 29—amino acid sequence of *Gossypium hirsutum* CPFAS-1

SEQ ID NO: 30—amino acid sequence of *Gossypium hirsutum* CPFAS-2

SEQ ID NO: 31—amino acid sequence of *Gossypium hirsutum* CPFAS-3

SEQ ID NO: 32—amino acid sequence of *Oryza sativa* CPFAS

SEQ ID NO: 33—amino acid sequence of *Arabidopsis thaliana* CPFAS

SEQ ID NO: 34—amino acid sequence of *Sterculia foetida* CPFAS

SEQ ID NO: 35—amino acid sequence of *Medicago truncatula* CPFAS

SEQ ID NO: 36—amino acid sequence of *Zea mays* CPFAS

SEQ ID NO: 37—nucleotide sequence encoding *Gossypium hirsutum* CPFAS-1 (truncated protein)

SEQ ID NO: 38—nucleotide sequence encoding *Gossypium hirsutum* CPFAS-2 (truncated protein)

SEQ ID NO: 39—nucleotide sequence encoding *Gossypium hirsutum* CPFAS-3 (truncated protein)

SEQ ID NO: 40—nucleotide sequence encoding *Oryza sativa* CPFAS (truncated protein)

SEQ ID NO: 41—nucleotide sequence encoding *Arabidopsis thaliana* CPFAS (truncated protein)

SEQ ID NO: 42—nucleotide sequence encoding *Sterculia foetida* CPFAS (truncated protein)

SEQ ID NO: 43—nucleotide sequence encoding *Zea mays* CPFAS (truncated protein)

SEQ ID NO: 44—nucleotide sequence encoding *Gossypium hirsutum* CPFAS-1

SEQ ID NO: 45—nucleotide sequence encoding *Gossypium hirsutum* CPFAS-2

SEQ ID NO: 46—nucleotide sequence encoding *Gossypium hirsutum* CPFAS-3

SEQ ID NO: 47—nucleotide sequence encoding *Oryza sativa* CPFAS

SEQ ID NO: 48—nucleotide sequence encoding *Arabidopsis thaliana* CPFAS

SEQ ID NO: 49—nucleotide sequence encoding *Sterculia foetida* CPFAS

SEQ ID NO: 50—nucleotide sequence encoding *Zea mays* CPFAS

SEQ ID NO: 51—amino acid sequence of *Aspergillus fumigatus* CPFAS

SEQ ID NO: 52—amino acid sequence of *Escherichia coli* CPFAS

SEQ ID NO: 53—amino acid sequence of *Salmonella enterica* CPFAS

SEQ ID NO: 54—amino acid sequence of *Leishmania infantum* CPFAS

SEQ ID NO: 55—amino acid sequence of *Synechoccus* species CPFAS

SEQ ID NO: 56—amino acid sequence of *Neurospora crassa* CPFAS

SEQ ID NO: 57—amino acid sequence of *Magnaporthe grisea* CPFAS

SEQ ID NO: 58—amino acid sequence of *Coprinopsis cinerea* CPFAS

SEQ ID NO: 59—nucleotide sequence encoding *Aspergillus fumigatus* CPFAS

SEQ ID NO: 60—codon optimized E. Coll CPFAS open reading frame for plant expression SEQ ID NO: 61—nucleotide sequence encoding *Salmonella enterica* CPFAS SEQ ID NO: 62—nucleotide sequence encoding *Leishmania infantum* CPFAS SEQ ID NO: 63—Cymbiduium ringspot tombus virus p19 like silencing suppressor SEQ ID NO: 64—*Pelargonium* necrotic spot virus p19 like silencing suppressor SEQ ID NO: 65—Havel river tombus virus p19 like silencing suppressor SEQ ID NO: 66—Cucumber necrosis virus p19 like silencing suppressor SEQ ID NO: 67—Grapevine Algerian latent virus p19 like silencing suppressor SEQ ID NO: 68—Pear latent virus p19 like silencing suppressor SEQ ID NO: 69—Lisianthus necrotic virus p19 like silencing suppressor SEQ ID NO: 70—Lettuce necrotic stunt virus p19 like silencing suppressor SEQ ID NO: 71—Artichoke Mottled Crinkle virus p19 like silencing suppressor SEQ ID NO: 72—Carnation Italian ringspot virus p19 like silencing suppressor SEQ ID NO: 73—Maize necrotic steak virus virus p19 like silencing suppressor SEQ ID NO: 74—Watermelon chlorotic stunt virus V2 like silencing suppressor SEQ ID NO: 75—Okra yellow wrinkle virus V2 like silencing suppressor SEQ ID NO: 76—Okra leaf curl virus V2 like silencing suppressor SEQ ID NO: 77—Tomato leaf curl Togo virus V2 like silencing suppressor SEQ ID NO: 78—*Ageratum* leaf curl Cameroon virus V2 like silencing suppressor SEQ ID NO: 79—East African cassava mosaic Malawi virus V2 like silencing suppressor SEQ ID NO: 80—South African cassava mosaic virus V2 like silencing suppressor SEQ ID NO: 81—Tomato leaf curl Madagascar virus V2 like silencing suppressor SEQ ID NO: 82—Tomato leaf curl Zimbabwe virus V2 like silencing suppressor SEQ ID NO: 83—Tomato begomovirus V2 like silencing suppressor SEQ ID NO: 84—Tomato leaf curl Namakely virus V2 like silencing suppressor SEQ ID NO: 85—Pepper yellow vein *Mali* virus V2 like silencing suppressor SEQ ID NO: 86—Tomato leaf curl Sudan virus V2 like silencing suppressor SEQ ID NO: 87—Tomato leaf curl Oman virus V2 like silencing suppressor SEQ ID NO's 88 to 90—conserved motifs of DGATs and/or MGATs SEQ ID NO 91—open reading frame encoding *N. benthamiana* long-chain acyl CoA synthetase 4

SEQ ID NO 92—*N. benthamiana* long-chain acyl CoA synthetase 4

SEQ ID NO 93—open reading frame encoding *N. benthamiana* long-chain acyl CoA synthetase 7

SEQ ID NO 94—*N. benthamiana* long-chain acyl CoA synthetase 7

SEQ ID NO 95—open reading frame encoding *N. benthamiana* phospholipase Dz1.

SEQ ID NO 96—*N. benthamiana* phospholipase Dz1

SEQ ID NO 97—open reading frame encoding *N. benthamiana* phospholipase Dz2.

SEQ ID NO 98—*N. benthamiana* phospholipase Dz2

SEQ ID NO 99—open reading frame encoding *N. benthamiana* lysophosphatidyl-choline acyltransferase 1

SEQ ID NO 100—*N. benthamiana* lysophosphatidyl-choline acyltransferase 1

SEQ ID NO:101—nucleotide sequence encoding dsRNA hairpin targeting *N. benthamiana* long-chain acyl CoA synthetase 4

SEQ ID NO:102—nucleotide sequence encoding dsRNA hairpin targeting *N. benthamiana* long-chain acyl CoA synthetase 7

SEQ ID NO:103—nucleotide sequence encoding dsRNA hairpin targeting *N. benthamiana* phospholipase Dz1

SEQ ID NO:104—nucleotide sequence encoding dsRNA hairpin targeting *N. benthamiana* phospholipase Dz2

SEQ ID NO:105—nucleotide sequence encoding dsRNA hairpin targeting *N. benthamiana* lysophosphatidyl-choline acyltransferase 1

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, more preferably +/−5%, more preferably +/−2%, more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "exogenous" in the context of a polynucleotide or polypeptide refers to the polynucleotide or polypeptide when present in a cell in an altered amount compared to its native state. In one embodiment, the cell is a cell that does not naturally comprise the polynucleotide or polypeptide. In another embodiment, the exogenous polynucleotide or polypeptide is from a different genus. In another embodiment, the exogenous polynucleotide or polypeptide is from a different species. In one embodiment the exogenous polynucleotide or polypeptide is expressed in a host organism or cell and the exogenous polynucleotide or polypeptide is from a different species or genus.

The term "corresponding" refers to a cell, or plant or part thereof that has the same or similar genetic background as a cell, or plant or part thereof of the invention but that has not been modified as described herein (for example, the cell, or plant or part thereof lacks an exogenous polynucleotide encoding a CPFAS). A corresponding cell or, plant or part thereof can be used as a control to compare, for example, the amount of DHS and/or derivative thereof produced with a cell, or plant or part thereof modified as described herein. A person skilled in the art is able to readily determine an appropriate "corresponding" cell, plant or part thereof for such a comparison.

As used herein, the term "seedoil" refers to a composition obtained from the seed/grain of a plant which comprises at least 60% (w/w) lipid, or obtainable from the seed/grain if the seedoil is still present in the seed/grain. That is, seedoil of, or obtained using, the invention includes seedoil which is present in the seed/grain or portion thereof, as well as seedoil which has been extracted from the seed/grain. The seedoil is preferably extracted seedoil. Seedoil is typically a liquid at room temperature. Preferably, the total fatty acid (TFA) content in the seedoil predominantly (>50%) comprises fatty acids that are at least 16 carbons in length. More preferably, at least 50% of the total fatty acids in the seedoil are C18 fatty acids. The fatty acids are typically in an esterified form such as for example, TAG, DAG, acyl-CoA or phospholipid. Unless otherwise stated, the fatty acids may be free fatty acids and/or in an esterified form. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in seedoil of the invention can be found as TAG. In an embodiment, seedoil of the invention is "substantially purified" or "purified" oil that has been separated from one or more other lipids, nucleic acids, polypeptides, or other contaminating molecules with which it is associated in the seed or in a crude extract. It is preferred that the substantially purified seedoil is at least 60% free, more preferably at least 75% free, and more preferably, at least 90% free from other components with which it is associated in the seed or extract. Seedoil of the invention may further comprise non-fatty acid molecules such as, but not limited to, sterols. In an embodiment, the seedoil is canola oil (*Brassica napus, Brassica rapa* ssp.), mustard oil (*Brassica juncea*), other *Brassica* oil (e.g., *Brassica napobrassica, Brassica camelina*), sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil (*Elaeis guineensis*), cottonseed oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*), oat seed oil (*Avena sativa*), rice oil (*Oryza sativa* or *Oryza glaberrima*), or *Arabidopsis* seed oil (*Arabidopsis thaliana*). Seedoil may be extracted from seed/grain by any method known in the art. This typically involves extraction with nonpolar solvents such as diethyl ether, petroleum ether, chloroform/methanol or butanol mixtures, generally associated with first crushing of the seeds. Lipids associated with the starch in the grain may be extracted with water-saturated butanol. The seedoil may be "de-gummed" by methods known in the art to remove polysaccharides or treated in other ways to remove contaminants or improve purity, stability, or colour. The TAGs and other esters in the seedoil may be hydrolysed to release free fatty acids, or the seedoil hydrogenated, treated chemically, or enzymatically as known in the art.

As used herein, the term "fatty acid" refers to a carboxylic acid with a long aliphatic tail typically of at least 18 carbon atoms in length. Most naturally occurring fatty acids have an even number of carbon atoms because their biosynthesis involves acetate which has two carbon atoms. The fatty acids may be in a free state (non-esterified) or in an esterified form, such as part of a TAG, DAG, MAG, acyl-CoA (thio-ester) bound, or other covalently bound form. When covalently bound in an esterified form, the fatty acid is referred to herein as an "acyl" group. The fatty acid may be esterified as a phospholipid such as a phosphatidylcholine (PC), phosphatidylethanolamine, phosphatidylserine, phosphatidylglycerol, phosphatidylinositol, or diphosphatidylglycerol. Saturated fatty acids do not contain any double bonds or other functional groups along the chain. The term "saturated" refers to hydrogen, in that all carbons (apart from the carboxylic acid [—COOH] group) contain as many hydrogens as possible. In other words, the omega (w) end contains 3 hydrogens (CH3-) and each carbon within the chain contains 2 hydrogens (—CH2-). Unsaturated fatty acids are of similar form to saturated fatty acids, except that one or more alkene functional groups exist along the chain, with each alkene substituting a singly-bonded "—CH2-CH2-" part of the chain with a doubly-bonded "—CH=CH—" portion (that is, a carbon double bonded to another carbon). The two next carbon atoms in the chain that are bound to either side of the double bond can occur in a cis or trans configuration.

"Monoacylglyceride" or "MAG" is glyceride in which the glycerol is esterified with one fatty acid. As used herein, MAG comprises a hydroxyl group at an sn-1/3 (also referred to herein as sn-1 MAG or 1-MAG or 1/3-MAG) or sn-2 position (also referred to herein as 2-MAG), and therefore MAG does not include phosphorylated molecules such as PA or PC. MAG is thus a component of neutral lipids in a cell.

"Diacylglyceride" or "DAG" is glyceride in which the glycerol is esterified with two fatty acids. As used herein, DAG comprises a hydroxyl group at a sn-1,3 or sn-1,2/2,3 position, and therefore DAG does not include phosphorylated molecules such as PA or PC. DAG is thus a component of neutral lipids in a cell. In the Kennedy pathway of DAG synthesis, the precursor sn-glycerol-3-phosphate (G-3-P) is esterified to two acyl groups, each coming from a fatty acid coenzyme A ester, in a first reaction catalysed by a glycerol-3-phosphate acyltransferase (GPAT) at position sn-1 to form LysoPA, followed by a second acylation at position sn-2 catalysed by a lysophosphatidic acid acyltransferase (LPAAT) to form phosphatidic acid (PA). This intermediate is then de-phosphorylated to form DAG. In an alternative anabolic pathway, DAG may be formed by the acylation of either sn-1 MAG or preferably sn-2 MAG, catalysed by MGAT. DAG may also be formed from TAG by removal of an acyl group by a lipase, or from PC essentially by removal of a choline headgroup by any of the enzymes CPT, PDCT or PLC.

"Triacylglyceride" or "TAG" is glyceride in which the glycerol is esterified with three fatty acids. In the Kennedy pathway of TAG synthesis, DAG is formed as described above, and then a third acyl group is esterified to the glycerol backbone by the activity of DGAT. Alternative pathways for formation of TAG include one catalysed by the enzyme PDAT and the MGAT pathway (WO 2012/000026).

As used herein, the term "acyltransferase" refers to a protein which is capable of transferring an acyl group from acyl-CoA onto a substrate and includes MGATs, GPATs and DGATs.

As used herein, the term "monoacylglycerol acyltransferase" or "MGAT" refers to a protein which transfers a fatty acyl group from acyl-CoA to a MAG substrate to produce DAG. Thus, the term "monoacylglycerol acyltransferase activity" at least refers to the transfer of an acyl group from acyl-CoA to MAG to produce DAG. MGAT is best known for its role in fat absorption in the intestine of mammals, where the fatty acids and sn-2 MAG generated from the digestion of dietary fat are resynthesized into TAG in enterocytes for chylomicron synthesis and secretion. MGAT catalyzes the first step of this process, in which the acyl group from fatty acyl-CoA, formed from fatty acids and CoA, and sn-2 MAG are covalently joined. The term "MOAT" as used herein includes enzymes that act on sn-1/3 MAG and/or sn-2 MAG substrates to form sn-1,3 DAG and/or sn-1,2/2,3-DAG, respectively. In a preferred embodiment, the MGAT has a preference for sn-2 MAG substrate relative to sn-1 MAG, or substantially uses only sn-2 MAG as substrate (examples include MGATs described in Cao et al., 2003 (specificity of mouse MGAT1 for sn2-18:1-

MAG>sn1/3-18:1-MAG); Yen and Farese, 2003 (general activities of mouse MGAT1 and human MGAT2 are higher on 2-MAG than on 1-MAG acyl-acceptor substrates; and Cheng et al., 2003 (activity of human MGAT3 on 2-MAGs is much higher than on 1/3-MAG substrates).

As used herein, MGAT does not include enzymes which transfer an acyl group preferentially to LysoPA relative to MAG, such enzymes are known as LPAATs. That is, a MGAT preferentially uses non-phosphorylated monoacyl substrates, even though they may have low catalytic activity on LysoPA. A preferred MGAT does not have detectable activity in acylating LysoPA. As shown herein, a MGAT (i.e., *M. musculus* MGAT2) may also have DGAT function but predominantly functions as a MGAT, i.e., it has greater catalytic activity as a MGAT than as a DGAT when the enzyme activity is expressed in units of nmoles product/min/mg protein (also see Yen et al., 2002).

There are three known classes of MGAT, referred to as, MGAT1, MGAT2 and MGAT3, respectively. Homologs of the human MGAT1 gene (AF384163) are present (i.e. sequences are known) at least in chimpanzee, dog, cow, mouse, rat, zebrafish, *Caenorhabditis elegans, Schizosaccharomyces pombe, Saccharomyces cerevisiae, Kluyveromyces lactis, Erernothecium gossypii, Magnaporthe grisea*, and *Neurospora crassa*. Homologs of the human MGAT2 gene (AY157608) are present at least in chimpanzee, dog, cow, mouse, rat, chicken, zebrafish, fruit fly, and mosquito. Homologs of the human MGAT3 gene (AY229854) are present at least in chimpanzee, dog, cow, and zebrafish. However, homologs from other organisms can be readily identified by methods known in the art for identifying homologous sequences.

Examples of MGAT1 polypeptides include proteins encoded by MGAT1 genes from *Homo sapiens* (AF384163), *Mus musculus* (AF384162), *Pan troglodytes* (XM_001166055, XM_0526044.2), *Canis familiaris* (XM_545667.2), *Bos taurus* (NM_001001153.2), *Rattus norvegicus* (NM_001108803.1), *Danio rerio* MGAT1 (NM_001122623.1), *Caenorhabditis elegans* (NM_073012.4, NM_182380.5, NM_065258.3, NM_075068.3, NM_072248.3), *Kluyveromyces lactis* (XM_455588.1), *Ashbya gossypii* (NM_208895.1), *Magnaporthe oryzae* (XM_368741.1), *Ciona intestinalis* predicted (XM_002120843.1). Examples of MGAT2 polypeptides include proteins encoded by MGAT2 genes from *Homo sapiens* (AY157608), *Mus musculus* (AY157609), *Pan troglodytes* (XM_522112.2), *Canis familiaris* (XM_542304.1), *Bos taurus* (NM_001099136.1), *Rattus norvegicus, Gallus gallus* (XM_424082.2), *Danio rerio* (NM_001006083.1), *Drosophila melanogaster* (NM_136474.2, NM_136473.2, NM_136475.2), *Anopheles gambiae* (XM_001688709.1, XM_315985), *Tribolium castaneum* (XM_970053.1). Examples of MGAT3 polypeptides include proteins encoded by MGAT3 genes from *Homo sapiens* (AY229854), *Pan troglodytes* (XM_001154107.1, XM_001154171.1, XM_527842.2), *Canis familiaris* (XM_845212.1), *Bos taurus* (XM_870406.4), *Danio rerio* (XM_688413.4).

As used herein "MGAT pathway" refers to an anabolic pathway, different to the Kennedy pathway for the formation of TAG, in which DAG is formed by the acylation of either sn-1 MAG or preferably sn-2 MAG, catalysed by MGAT. The DAG may subsequently be used to form TAG or other lipids As used herein, the term "diacylglycerol acyltransferase" (DGAT) refers to a protein which transfers a fatty acyl group from acyl-CoA to a DAG substrate to produce TAG. Thus, the term "diacylglycerol acyltransferase activity" refers to the transfer of an acyl group from acyl-CoA to DAG to produce TAG. A DGAT may also have MGAT function but predominantly functions as a DGAT, i.e., it has greater catalytic activity as a DGAT than as a MGAT when the enzyme activity is expressed in units of nmoles product/min/mg protein (see for example, Yen et al., 2005).

There are three known types of DGAT, referred to as DGAT1, DGAT2 and DGAT3, respectively. DGAT1 polypeptides typically have 10 transmembrane domains, DGAT2 polypeptides typically have 2 transmembrane domains, whilst DGAT3 polypeptides typically have none and are thought to be soluble in the cytoplasm, not integrated into membranes. Examples of DGAT1 polypeptides include proteins encoded by DGAT1 genes from *Aspergillus fumigatus* (Accession No. XP_755172), *Arabidopsis thaliana* (CAB44774), *Ricinus communis* (AAR11479), *Vernicia fordii* (ABC94472), *Vernonia galamensis* (ABV21945, ABV21946), *Euonymus alatus* (AAV31083), *Caenorhabditis elegans* (AAF82410), *Rattus norvegicus* (NP_445889), *Homo sapiens* (NP_036211), as well as variants and/or mutants thereof. Examples of DGAT2 polypeptides include proteins encoded by DGAT2 genes from *Arabidopsis thaliana* (NP_566952.1), *Ricinus communis* (AAY16324.1), *Vernicia fordii* (ABC94474.1), *Mortierella ramanniana* (AAK84179.1), *Homo sapiens* (Q96PD7.2, Q58HT5.1), *Bos taurus* (Q70VZ8.1), *Mus musculus* (AAK84175.1), as well as variants and/or mutants thereof.

Examples of DGAT3 polypeptides include proteins encoded by DGAT3 genes from peanut (*Arachis hypogaea*, Saha, et al., 2006), as well as variants and/or mutants thereof. A DGAT has little or no detectable MGAT activity, for example, less than 300 pmol/min/mg protein, preferably less than 200 pmol/min/mg protein, more preferably 100 pmol/min/mg protein.

DGAT2 but not DGAT1 shares high sequence homology with the MGAT enzymes, suggesting that DGAT2 and MGAT genes likely share a common genetic origin. Although multiple isoforms are involved in catalysing the same step in TAG synthesis, they may play distinct functional roles, as suggested by differential tissue distribution and subcellular localization of the DGAT/MGAT family of enzymes. In mammals, MGAT1 is mainly expressed in stomach, kidney, adipose tissue, whilst MGAT2 and MGAT3 show highest expression in the small intestine. In mammals, DGAT1 is ubiquitously expressed in many tissues, with highest expression in small intestine, whilst DGAT2 is most abundant in liver. MGAT3 only exists in higher mammals and humans, but not in rodents from bioinformatic analysis. MGAT3 shares higher sequence homology to DGAT2 than MGAT1 and MGAT3. MGAT3 exhibits significantly higher DGAT activity than MGAT1 and MGAT2 enzymes (MGAT3>MGAT1>MGAT2) when either MAGs or DAGs were used as substrates, suggesting MGAT3 functions as a putative TAG synthase.

Both MGAT1 and MGAT2 belong to the same class of acyltransferases as DGAT2. Some of the motifs that have been shown to be important for DGAT2 catalytic activity in some DGAT2s are also conserved in MGAT acyltransferases. Of particular interest is a putative neutral lipid-binding domain with the concensus sequence FLXLXXXN (SEQ ID NO: 88) where each X is independently any amino acid other than proline, and N is any nonpolar amino acid, located within the N-terminal transmembrane region followed by a putative glycerol/phospholipid acyltransferase domain. The FLXLXXXN motif is found in the mouse DGAT2 (amino acids 81-88) and MGAT1/2 but not in yeast or plant DGAT2s. It is important for activity of the mouse DGAT2. Other DGAT2 and/or MGAT1/2 sequence motifs include:

1. A highly conserved YFP tripeptide in most DGAT2 polypeptides and also in MGAT1 and MGAT2, for example, present as amino acids 139-141 in mouse DGAT2. Mutating this motif within the yeast DGAT2 with non-conservative substitutions rendered the enzyme non-functional.

2. HPHG tetrapeptide (SEQ ID NO: 89), highly conserved in MGATs as well as in DGAT2 sequences from animals and fungi, for example, present as amino acids 161-164 in mouse DGAT2, and important for catalytic activity at least in yeast and mouse DGAT2. Plant DGAT2 acyltransferases have a EPHS conserved sequence instead, so conservative changes to the first and fourth amino acids can be tolerated.

3. A longer conserved motif which is part of the putative glycerol phospholipid domain. An example of this motif is RXGFX(K/R)XAXXXGXXX(L/V)VPXXXFG(E/Q) (SEQ ID NO:90), which is present as amino acids 304-327 in mouse DGAT2. This motif is less conserved in amino acid sequence than the others, as would be expected from its length, but homologs can be recognised by motif searching. The spacing may vary between the more conserved amino acids, i.e., there may be additional X amino acids within the motif, or less X amino acids compared to the sequence above.

As used herein, the term "Oleosin" refers to an amphipathic protein present in the membrane of oil bodies in the storage tissues of seeds (see, for example, Huang, 1996; Lin et al., 2005; Capuano et al., 2007; Liu et al., 2009; Shimada and Hara-Nishimura, 2010). This term encompasses caleosins which bind calcium, and steroleosins which bind sterols. However, generally a large proportion of the oleosins of oil bodies will not be caleosins and/or steroleosins. Plant seeds accumulate TAG in subcellular structures called oil bodies. These organelles consist of a TAG core surround by a phospholipid monolayer containing several embedded proteins including oleosins, caleosins and steroleosins (Jolivet et al., 2004). Oleosins represent the most abundant protein in the membrane of oil bodies.

Oleosins are of low $M_r$ (15-26,000). Within each seed species, there are usually two or more oleosins of different $M_r$. Each oleosin molecule contains a relatively hydrophilic N-terminal domain (for example, about 48 amino acid residues), a central totally hydrophobic domain (for example, of about 70-80 amino acid residues) which is particularly rich in aliphatic amino acids such as alanine, glycine, leucine, isoleucine and valine, and an amphipathic α-helical domain (for example, of about 33 amino acid residues) at or near the C-terminus. Generally, the central stretch of the hydrophobic residues is inserted into the lipid core and the amphiphatic N-terminal and/or amphiphatic C-terminal are located at the surface of the oil bodies, with positively charged residues embedded in a phospholipid monolayer and the negatively charged ones exposed to the exterior. A substantial number of oleosin protein sequences, and nucleotide sequences encoding therefor, are known from a large number of different plant species. Examples include, but are not limited to, oleosins from Arabidposis, canola, corn, rice, peanut, castor, soybean, flax, grape, cabbage, cotton, sunflower, *sorghum* and barley.

As used herein, the term "desaturase" refers to an enzyme which is capable of introducing a carbon-carbon double bond into the acyl group of a fatty acid substrate which is typically in an esterified form such as, for example, fatty acid CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, the term "Δ12 desaturase" refers to a protein which performs a desaturase reaction converting oleic acid to linoleic acid. Thus, the term "Δ12 desaturase activity" refers to the conversion of oleic acid to linoleic acid. These fatty acids may be in an esterified form, such as, for example, as part of a phospholipid.

As used herein, the term "palmitoyl-ACP thioesterase" refers to a protein which hydrolyses palmitoyl-ACP to produce free palmitic acid. Thus, the term "palmitoyl-ACP thioesterase activity" refers to the hydrolysis of palmitoyl-ACP to produce free palmitic acid. An example of a palmitoyl-ACP thioesterase is FatB.

As used herein, the term "lipid handling enzyme" refers to a protein involved in the biosynthesis or metabolism to TAG. Considering the present application relates to the production of DHS, the skilled person can readily test candidate lipid handling enzymes to ensure they are useful for the invention. Examples of lipid handling enzymes include, but are not limited to, fatty acid acyltransferase such as an lysophosphatidyl-choline acyltransferase (LPCAT), a lipase such as a phospholipase D, or a fatty acid synthetase such as a long-chain acyl CoA synthetase (LACS). Such types of enzymes are well known in the art.

As used herein, the term "acyl-CoA:lysophosphatidylcholine acyltransferase" (EC 2.3.1.23; LPCAT) refers to a protein which reversibly catalyzes the acyl-CoA-dependent acylation of lysophophatidylcholine to produce phosphatidylcholine and CoA. Thus, the term "acyl-CoA:lysophosphatidylcholine acyltransferase activity" refers to the reversible acylation of lysophophatidylcholine to produce phosphatidylcholine and CoA.

As used herein, the term "phospholipase D" (PLD) refers to a protein which hydrolyzes phosphatidylcholine to produce phosphatidic acid and a choline headgroup. Thus, the term "phospholipase D activity" refers to the hydrolysis of phosphatidylcholine to produce phosphatidic acid and a choline headgroup.

As used herein, the term "long-chain acyl CoA synthetase" (LACS) refers to a ligase family that activates the breakdown of complex fatty acids. LACS plays a crucial role in intermediary metabolism by catalyzing the formation of fatty acyl-CoA by a two-step process proceeding through an adenylated intermediate. It catalyzes the pre-step reaction for β-oxidation of fatty acids or can be incorporated in phospholipids.

As used herein, the term "Wrinkled 1" or "WRI1" or "WRL1" refers to a transcription factor of the AP2/ER-WEBP class which regulates the expression of several enzymes involved in glycolysis and de novo fatty acid biosynthesis. WRI1 has two plant-specific (AP2/EREB) DNA-binding domains. WRI1 in at least *Arabidopsis* also regulates the breakdown of sucrose via glycolysis thereby regulating the supply of precursors for fatty acid biosynthesis. In other words, it controls the carbon flow from the photosynthate to storage lipids. wri1 mutants have wrinkled seed phenotype, due to a defect in the incorporation of sucrose and glucose into TAGs.

Examples of genes which are trancribed by WRI1 include, but are not limited to, one or more, preferably all, of pyruvate kinase (At5g52920, At3g22960), pyruvate dehydrogenase (PDH) E1alpha subunit (At1g01090), acetyl-CoA carboxylase (ACCase), BCCP2 subunit (At5g15530), enoyl-ACP reductase (At2g05990; EAR), phosphoglycerate mutase (At1g22170), cytosolic fructokinase, and cytosolic phosphoglycerate mutase, sucrose synthase (SuSy) (see, for example, Liu et al., 2010b; Baud et al., 2007; Ruuska et al., 2002).

As used herein, the term "Leafy Cotyledon 2" or "LEC2" refers to a B3 domain transcription factor which participates in zygotic and in somatic embryogenesis. Its ectopic expression facilitates the embryogenesis from vegetative plant tissues (Alemanno et al., 2008). LEC2 also comprises a DNA binding region found thus far only in plant proteins. Examples of LEC2 polypeptides include proteins from *Arabidopsis thaliana* (NP_564304.1), *Medicago truncatula* (CAA42938.1) and *Brassica napus* (AD016343.1).

As used herein, the term "BABY BOOM" or "BBM" refers an AP2/ERF transcription factor that induces regeneration under culture conditions that normally do not support regeneration in wild-type plants. Ectopic expression of *Brassica napus* BBM (BnBBM) genes in *B. napus* and *Arabidopsis* induces spontaneous somatic embryogenesis and organogenesis from seedlings grown on hormone-free basal medium (Boutilier et al., 2002). In tobacco, ectopic BBM expression is sufficient to induce adventitious shoot and root regeneration on basal medium, but exogenous cytokinin is required for somatic embryo (SE) formation (Srinivasan et al., 2007). Examples of BBM polypeptides include proteins from *Arabidopsis thaliana* (NP_197245.2) and *Medicago truncatula* (AAW82334.1).

Dihydrosterculic Acid (DHS)

The production of DHS from oleic acid is shown in FIG. 5. This reaction can be achieved by the use of a cyclopropane fatty acid synthetase.

The term "cyclopropane fatty acid synthetase" (CPFAS), "cyclopropane synthase" or variants thereof refers to a polypeptide with the capacity to synthesize a fatty acid containing a cyclopropane ring. The basic reaction involves the addition of a methylene group across a double bond of a fatty acid. Thus, the polypeptide catalyzes the addition of a methylene group across the unsaturated center of an unsaturated fatty acid, and includes the addition of a methylene group across a double bond of an acyl group. The fatty acyl group may be esterified to a phospholipid; such phospholipid substrates include phosphatidylcholine, phosphatidylethanolamine, and phosphatidylglycerol. A "plant CPFAS" is an enzyme originally obtained from a plant source; the enzyme may be modified where such modifications include but are not limited to truncation, amino acid deletions, additions, substitutions, and glycosylation, and where the resulting modified enzyme possesses CPFAS activity. In a particularly preferred embodiment, a modified plant CPFAS is truncated at the N-terminal end when compared to a naturally occurring enzyme.

At least some DHS may be converted in the cell to a fatty acid derivative. Alternatively, or in addition, the DHS may be converted to a fatty acid derivative following/during extraction from the cell, oilseed or vegetative plant tissue.

Preferably, the fatty acid derivative comprises a cyclopropyl group (3-membered ring) or is a branched chain fatty acid having a methyl group as the branch.

In one embodiment, the derivative comprises 2, 4 or 6 more carbons in the acyl chain when compared to DHS, such as eDHS described in Example 6.

In another embodiment, the cyclo-propyl group or a methyl group is a mid-chain group such as isostearic acid with the methyl group attached to C9 or C10.

Some DHA fatty acid derivatives, such as sterculic acid and/or malvalic acid, have undesirable characteristics. Thus, in an embodiment, the oilseed, vegetative plant tissue or cells comprise less than about 10%, or less than about 5%, or less than about 3%, less than about 1%, or less than about 0.5% sterculic acid and/or malvalic acid, preferably the sum of the sterculic and malvalic acids is less than 0.5% of the total fatty acids in the extractable oil of the oilseed, vegetative plant tissue or cells. When using cells which naturally produce sterculic acid and/or malvalic acid, such as cotton cells, the levels of these derivatives can be reduced by downregulating the production of the enzymes directly or indirectly involved in the conversion DHS to these derivatives such as DHS Δ9 desaturase using, for example, RNA silencing.

A particularly useful DHA fatty acid derivative is isostearic acid (ISA) with a methyl group attached to C9 or C10 which has a rare combination of high oxidative stability and low melting point thus imparting valuable properties to industrial oils including increased lubricity, stability and the preferred melting properties that make it useful for cosmetic uses (WO 99/18217). DHS produced using a method of the invention can readily be converted to ISA using techniques known in the art such as hydrogenation.

Hydrogenation of an unsaturated fatty acid such as DHS refers to the addition of hydrogen atoms to the acid, causing cyclo-groups to become single ones, as carbon atoms acquire new hydrogen partners. Full hydrogenation results in a molecule containing the maximum amount of hydrogen (in other words, the conversion of an unsaturated fatty acid into a saturated one). Partial hydrogenation results in the addition of hydrogen atoms at some of the empty positions, with a corresponding reduction in the number of cyclo-groups. Examples of procedures of hydrogenation are described in Kai (1982), U.S. Pat. Nos. 4,321,210 and 3,201,431.

Polypeptides

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active fragment" is a portion of a polypeptide of the invention which maintains a defined activity of a full-length reference polypeptide for example, CPFAS activity. Biologically active fragments as used herein exclude the full-length polypeptide. Biologically active fragments can be any size portion as long as they maintain the defined activity. Preferably, the biologically active fragment maintains at least 10% of the activity of the full length polypeptide.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 40%, more preferably at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, deletions, insertions, or substitutions of residues within the amino acid sequence. A combination of deletions, insertions and substitutions can be made to arrive at the final construct, provided that the final polypeptide product possesses the desired characteristics.

Mutant (altered) polypeptides can be prepared using any technique known in the art, for example, using directed evolution or rationale design strategies (see below). Products derived from mutated/altered DNA can readily be screened using techniques described herein to determine if they possess CPFAS activity.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 1. As the skilled person would be aware, such minor changes can reasonably be predicted not to alter the activity of the polypeptide when expressed in a recombinant cell.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Directed Evolution

In directed evolution, random mutagenesis is applied to a protein, and a selection regime is used to pick out variants that have the desired qualities, for example, increased CPFAS activity. Further rounds of mutation and selection are then applied. A typical directed evolution strategy involves three steps:

1) Diversification:

The gene encoding the protein of interest is mutated and/or recombined at random to create a large library of gene variants. Variant gene libraries can be constructed through error prone PCR (see, for example, Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al., 2002, Coco, 2002) or from mixtures of both, or even from undigested parental templates (Zhao et al., 1998; Eggert et al., 2005; Jézéquek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the E. coli XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection:

The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of CPFAS activity by, for example, quantifying the level of resultant product in lipid extracted from the organism or part thereof, and determining the level of product in the extracted lipid from the organism or part thereof relative to a corresponding organism or part thereof lacking the mutated polynucleotide and optionally, expressing the parent (unmutated) polynucleotide. Alternatively, the screen may involve feeding the organism or part thereof labelled substrate and determining the level of substrate or product in the organism or part thereof relative to a corresponding organism or part thereof lacking the mutated polynucleotide and optionally, expressing the parent (unmutated) polynucleotide.

3) Amplification:

The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hallinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Also included within the scope of the invention are polypeptides defined herein which are differentially modified during or after synthesis for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides as described herein may be expressed as a fusion to at least one other polypeptide. In a preferred embodiment, the at least one other polypeptide is selected from the group consisting of: a polypeptide that enhances the stability of the fusion protein, and a polypeptide that assists in the purification of the fusion protein.

Polynucleotides

The terms "polynucleotide", and "nucleic acid" are used interchangeably. They refer to a polymeric form of nucleotides of any length, either deoxyribonucleotides or ribonucleotides, or analogs thereof. A polynucleotide of the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, chimeric DNA of any sequence, nucleic acid probes, and primers. A polynucleotide may comprise modified nucleotides such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization such as by conjugation with a labeling component.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns therefore are absent in the mRNA transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA" refers to any DNA molecule that is not naturally found in nature; also referred to herein as a "DNA construct". Typically, chimeric DNA comprises regulatory and transcribed or protein coding sequences that are not naturally found together in nature. Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The terms "genetically modified", "transgenic" and variations thereof include introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

A "recombinant polynucleotide" of the invention refers to a nucleic acid molecule which has been constructed or modified by artificial recombinant methods. The recombinant polynucleotide may be present in a cell in an altered amount or expressed at an altered rate (e.g., in the case of mRNA) compared to its native state. In one embodiment, the polynucleotide is introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, the polynucleotide is endogenous to the cell and its expression is altered by recombinant means, for example, an exogenous control sequence is introduced upstream of an endogenous gene of interest to enable the transformed cell to express the polypeptide encoded by the gene.

A recombinant polynucleotide of the invention includes polynucleotides which have not been separated from other components of the cell-based or cell-free expression system, in which it is present, and polynucleotides produced in said cell-based or cell-free systems which are subsequently purified away from at least some other components. The polynucleotide can be a contiguous stretch of nucleotides existing in nature, or comprise two or more contiguous stretches of nucleotides from different sources (naturally occurring and/or synthetic) joined to form a single polynucleotide. Typically, such chimeric polynucleotides comprise at least an open reading frame encoding a polypeptide of the invention operably linked to a promoter suitable of driving transcription of the open reading frame in a cell of interest.

In one embodiment, a cell of the invention comprises, a first exogenous polynucleotide encodes a truncated plant CPFAS or variant thereof, and a second exogenous polynucleotide encodes a bacterial or fungal CPFAS or variant thereof.

Examples of polynucleotides encoding truncated plant CPFAS enzymes or variant thereofs include, but are not limited to, those comprising i) a sequence of nucleotides selected from any one of SEQ ID NOs: 37 to 43, ii) a sequence of nucleotides which are at least 30% identical to one or more of the sequences set forth in SEQ ID NOs: 37 to 43, and/or iii) a sequence which hybridises to i) and/or ii) under stringent conditions, preferably wherein the encoded CPFAS is no longer than about 600 amino acids, more preferably no longer than 500 amino acids, in length.

Examples of polynucleotides encoding bacterial or fungal CPFAS enzymes or variant thereofs include, but are not limited to, those comprising i) a sequence of nucleotides selected from any one of SEQ ID NOs: 59 to 62, ii) a sequence of nucleotides which are at least 30% identical to one or more of the sequences set forth in SEQ ID NOs: 59 to 62, and/or iii) a sequence which hybridises to i) and/or ii) under stringent conditions.

If the cell is a plant cell, preferably the polynucleotide is optimized for plant expression using routine techniques such as those used to produce SEQ ID NO: 60.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotide for Reducing Expression Levels of Endogenous Proteins

In one embodiment, the cell comprises an introduced mutation or an exogenous polynucleotide which down-regulates the production and/or activity of an endogenous enzyme (for example, a $\Delta 12$ desaturase), typically which results in an increased production of DHS when compared to a corresponding cell lacking the introduced mutation or exogenous polynucleotide. Examples of such polynucleotides include an antisense polynucleotide, a sense polynucleotide, a catalytic polynucleotide, a microRNA, a polynucleotide which encodes a polypeptide which binds the endogenous enzyme and a double stranded RNA.

RNA Interference

RNA interference (RNAi) is particularly useful for specifically inhibiting the production of a particular protein. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with an unrelated sequence forming a loop structure, although a sequence with identity to the target RNA or its complement can form the loop structure. Typically, the dsRNA is encoded by a double-stranded DNA construct which has sense and antisense sequences in an inverted repeat structure, arranged as an interrupted palindrome, where the repeated sequences are transcribed to produce the hybridising sequences in the dsRNA molecule, and the interrupt sequence is transcribed to form the loop in the dsRNA molecule. The design and production of suitable dsRNA molecules is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology, preferably at least 19 consecutive nucleotides complementary to a region of, a target RNA, to be inactivated. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing. The double stranded region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides. The full-length sequence corresponding to the entire gene transcript may be used. The degree of identity of the sense and antisense sequences to the targeted transcript should be at least 85%, at least 90%, or at least 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

microRNA

MicroRNAs (abbreviated miRNAs) are generally 19-25 nucleotides (commonly about 20-24 nucleotides in plants) non-coding RNA molecules that are derived from larger precursors that form imperfect stem-loop structures.

miRNAs bind to complementary sequences on target messenger RNA transcripts (mRNAs), usually resulting in translational repression or target degradation and gene silencing.

In plant cells, miRNA precursor molecules are believed to be largely processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, in particular DCL-1, yielding miRNA:miRNA* duplexes. Prior to transport out of the nucleus, these duplexes are methylated. In contrast, hairpin RNA molecules having longer dsRNA regions are processed in particular by DCL-3 and DCL-4. Most mammalian cells have only a single DICER polypeptide which cleaves multiple dsRNA structures.

In the cytoplasm, the miRNA strand from the miRNA: miRNA duplex is selectively incorporated into an active RNA-induced silencing complex (RISC) for target recognition. The RISC-complexes contain a particular subset of Argonaute proteins that exert sequence-specific gene repression (see, for example, Millar and Waterhouse, 2005; Pasquinelli et al., 2005; Almeida and Allshire, 2005).

Cosuppression

Genes can suppress the expression of related endogenous genes and/or transgenes already present in the genome, a phenomenon termed homology-dependent gene silencing. Most of the instances of homology dependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

One model, the "quantitative" or "RNA threshold" model, proposes that cells can cope with the accumulation of large amounts of transgene transcripts, but only up to a point. Once that critical threshold has been crossed, the sequence-dependent degradation of both transgene and related endogenous gene transcripts is initiated. It has been proposed that this mode of cosuppression may be triggered following the synthesis of copy RNA (cRNA) molecules by reverse transcription of the excess transgene mRNA, presumably by endogenous RNA-dependent RNA polymerases. These cRNAs may hybridize with transgene and endogenous mRNAs, the unusual hybrids targeting homologous transcripts for degradation. However, this model does not account for reports suggesting that cosuppression can apparently occur in the absence of transgene transcription and/or without the detectable accumulation of transgene transcripts.

To account for these data, a second model, the "qualitative" or "aberrant RNA" model, proposes that interactions between transgene RNA and DNA and/or between endogenous and introduced DNAs lead to the methylation of transcribed regions of the genes. The methylated genes are proposed to produce RNAs that are in some way aberrant, their anomalous features triggering the specific degradation of all related transcripts. Such aberrant RNAs may be produced by complex transgene loci, particularly those that contain inverted repeats.

A third model proposes that intermolecular base pairing between transcripts, rather than cRNA-mRNA hybrids generated through the action of an RNA-dependent RNA polymerase, may trigger cosuppression. Such base pairing may become more common as transcript levels rise, the putative double-stranded regions triggering the targeted degradation of homologous transcripts. A similar model proposes intramolecular base pairing instead of intermolecular base pairing between transcripts.

Cosuppression involves introducing an extra copy of a gene or a fragment thereof into a plant in the sense orientation with respect to a promoter for its expression. A skilled person would appreciate that the size of the sense fragment, its correspondence to target gene regions, and its degree of sequence identity to the target gene can vary. In some instances, the additional copy of the gene sequence interferes with the expression of the target plant gene. Reference is made to WO 97/20936 and EP 0465572 for methods of implementing co-suppression approaches.

Expression Vector

As used herein, an "expression vector" is a DNA or RNA vector that is capable of transforming a host cell and of effecting expression of one or more specified polynucleotides. Preferably, the expression vector is also capable of replicating within the host cell. Expression vectors are typically viruses or plasmids. Expression vectors of the present invention include any vectors that function (i.e., direct gene expression) in host cells of the present invention, including in fungal, algal, and plant cells.

As used herein, "operably linked" refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence of a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers, need not be physically contiguous or located in close proximity to the coding sequences whose transcription they enhance.

Expression vectors of the present invention contain regulatory sequences such as transcription control sequences, translation control sequences, origins of replication, and other regulatory sequences that are compatible with the host cell and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or part(s) thereof.

A number of vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato; the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-$H^{30}$ symporter promoter, and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention such as the promoters for LhcB gene and PsbP gene from white mustard (*Sinapis alba*).

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

For the purpose of expression in sink tissues of the plant such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins, including the 22 kD protein complexes and proteinase inhibitors, the promoter for the granule bound starch synthase gene (GBSS), and other class I and II patatins promoters. Other promoters can also be used to express a protein in specific tissues such as seeds or fruits. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In one embodiment, the promoter directs expression in tissues and organs in which lipid biosynthesis take place. Such promoters act in seed development at a suitable time for modifying lipid composition in seeds.

In one embodiment, especially for the expression of a silencing suppressor, the promoter is a plant storage organ specific promoter. As used herein, the term "plant storage organ specific promoter" refers to a promoter that preferentially, when compared to other plant tissues, directs gene transcription in a storage organ of a plant. Preferably, the promoter only directs expression of a gene of interest in the storage organ, and/or expression of the gene of interest in other parts of the plant such as leaves is not detectable by Northern blot analysis and/or RT-PCR. Typically, the promoter drives expression of genes during growth and development of the storage organ, in particular during the phase of synthesis and accumulation of storage compounds in the storage organ. Such promoters may drive gene expression in the entire plant storage organ or only part thereof such as the seedcoat, embryo or cotyledon(s) in seeds of dicotyledonous plants or the endosperm or aleurone layer of seeds of monocotyledonous plants. In one embodiment, the plant storage organ specific promoter is a seed specific promoter. In a more preferred embodiment, the promoter preferentially directs expression in the cotyledons of a dicotyledonous plant or in the endosperm of a monocotyledonous plant, relative to expression in the embryo of the seed or relative to other organs in the plant such as leaves. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the *sorghum* kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a tuber specific promoter. Examples include, but are not limited to, the potato patatin B33, PAT21 and GBSS promoters, as well as the sweet potato sporamin promoter (for review, see Potenza et al., 2004). In a preferred embodiment, the promoter directs expression preferentially in the pith of the tuber, relative to the outer layers (skin, bark) or the embryo of the tuber.

In another embodiment, the plant storage organ specific promoter is a fruit specific promoter. Examples include, but are not limited to, the tomato polygalacturonase, E8 and Pds promoters, as well as the apple ACC oxidase promoter (for review, see Potenza et al., 2004). In a preferred embodiment, the promoter preferentially directs expression in the edible parts of the fruit, for example the pith of the fruit, relative to the skin of the fruit or the seeds within the fruit.

When there are multiple promoters present, each promoter may independently be the same or different.

The 5' non-translated leader sequence can be derived from the promoter selected to express the heterologous gene sequence of the polynucleotide, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the expression vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in, for example, plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of Agrobacterium tumor-inducing (Ti) plasmid genes are also suitable.

Recombinant DNA technologies can be used to improve expression of a transformed polynucleotide by manipulating for example, the number of copies of the polynucleotide within a host cell, the efficiency with which those polynucleotides are transcribed, the efficiency with which the resultant transcripts are translated, and the efficiency of post-translational modifications. Recombinant techniques useful for increasing the expression of polynucleotides defined herein include, but are not limited to, operatively linking the polynucleotide to a high-copy number plasmid, integration of the polynucleotide molecule into one or more host cell chromosomes, addition of vector stability sequences to the plasmid, substitutions or modifications of transcription control signals (e.g., promoters, operators, enhancers), substitutions or modifications of translational control signals (e.g., ribosome binding sites, Shine-Dalgarno sequences), modification of the polynucleotide to correspond to the codon usage of the host cell, and the deletion of sequences that destabilize transcripts.

Recombinant vectors may also contain: (a) one or more secretory signals which encode signal peptide sequences, to enable an expressed polypeptide defined herein to be secreted from the cell that produces the polypeptide, or which provide for localisation of the expressed polypeptide, for example, for retention of the polypeptide in the endoplasmic reticulum (ER) in the cell, or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Preferred signal segments include, but are not limited to, Nicotiana nectarin signal peptide (U.S. Pat. No. 5,939,288), tobacco extensin signal, or the soy oleosin oil body binding protein signal. Recombinant vectors may also include intervening and/or untranslated sequences surrounding and/or within the nucleic acid sequence of a polynucleotide defined herein.

To facilitate identification of transformants, the recombinant vector desirably comprises a selectable or screenable marker gene as, or in addition to, the nucleic acid sequence of a polynucleotide defined herein. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, that is, by "screening" (e.g., β-glucuronidase, luciferase, GFP or other enzyme activity not present in untransformed cells). The marker gene and the nucleotide sequence of interest do not have to be linked, since co-transformation of unlinked genes as for example, described in U.S. Pat. No. 4,399,216, is also an efficient process in for example, plant transformation. The actual choice of a marker is not crucial as long as it is functional (i.e., selective) in combination with the cells of choice such as a plant cell.

Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from Streptomyces viridochromogenes conferring resistance to the selective agent phosphinothricin as for example, described in EP 275957; a gene encoding a 5-enol-shikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from Klebsiella ozaenae which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985) which may be employed in calcium-sensitive bioluminescence detection; a green fluorescent protein gene (Niedz et al., 1995) or derivatives thereof; or a luciferase (luc) gene (Ow et al., 1986) which allows for bioluminescence detection. By "reporter molecule" it is meant a molecule that, by its chemical nature, provides an analytically identifiable signal that facilitates determination of promoter activity by reference to protein product.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Transfer Nucleic Acids

Transfer nucleic acids can be used to deliver an exogenous polynucleotide to a cell and comprise one, preferably two, border sequences and a polynucleotide of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell.

As used herein, the term "extrachromosomal transfer nucleic acid" refers to a nucleic acid molecule that is capable of being transferred from a bacterium such as *Agrobacterium* sp., to a eukaryotic cell such as a plant leaf cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A polynucleotide of interest is typically positioned between the left border-like sequence and the right border-like sequence of a transfer nucleic acid. The polynucleotide contained within the transfer nucleic acid may be operably linked to a variety of different promoter and terminator regulatory elements that facilitate its expression, that is, transcription and/or translation of the polynucleotide. Transfer DNAs (T-DNAs) from *Agrobacterium* sp. such as *Agrobacterium turnefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to, for example, T-DNA of an *Agrobacterium tumefaciens* Ti plasmid or from an *Agrobacterium rhizogenes* Ri plasmid, or man made variants thereof which function as T-DNA. The T-DNA may comprise an entire T-DNA including both right and left border sequences, but need only comprise the minimal sequences required in cis for transfer, that is, the right and T-DNA border sequence. The T-DNAs of the invention have inserted into them, anywhere between the right and left border sequences (if present), the polynucleotide of interest flanked by target sites for a site-specific recombinase. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art.

As used herein, "P-DNA" refers to a transfer nucleic acid isolated from a plant genome, or man made variants/mutants thereof, and comprises at each end, or at only one end, a T-DNA border-like sequence. The border-like sequence preferably shares at least 50%, at least 60%, at least 70%, at least 75%, at least 80%, at least 90% or at least 95%, but less than 100% sequence identity, with a T-DNA border sequence from an *Agrobacterium* sp. such as *Agrobacterium tumefaciens* or *Agrobacterium rhizogenes*. Thus, P-DNAs can be used instead of T-DNAs to transfer a nucleotide sequence contained within the P-DNA from, for example *Agrobacterium*, to another cell. The P-DNA, before insertion of the exogenous polynucleotide which is to be transferred, may be modified to facilitate cloning and should preferably not encode any proteins. The P-DNA is characterized in that it contains, at least a right border sequence and preferably also a left border sequence.

As used herein, a "border" sequence of a transfer nucleic acid can be isolated from a selected organism such as a plant or bacterium, or be a man made variant/mutant thereof. The border sequence promotes and facilitates the transfer of the polynucleotide to which it is linked and may facilitate its integration in the recipient cell genome. In an embodiment, a border-sequence is between 5-100 base pairs (bp) in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. Border sequences from T-DNA from *Agrobacterium* sp. are well known in the art and include those described in Lacroix et al. (2008), Tzfira and Citovsky (2006) and Glevin (2003).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mezorhizobium loti*. The bacteria are made competent for gene transfer by providing the bacteria with the machinery needed for the transformation process, that is, a set of virulence genes encoded by an *Agrobacterium* Ti-plasmid and the T-DNA segment residing on a separate, small binary plasmid. Bacteria engineered in this way are capable of transforming different plant tissues (leaf disks, calli and oval tissue), monocots or dicots, and various different plant species (e.g., tobacco, rice).

Direct transfer of eukaryotic expression plasmids from bacteria to eukaryotic hosts was first achieved several decades ago by the fusion of mammalian cells and protoplasts of plasmid-carrying *Escherichia coli* (Schaffner, 1980). Since then, the number of bacteria capable of delivering genes into mammalian cells has steadily increased (Weiss, 2003; Sizemore et al., 1995; Courvalin et al., 1995; Powell et al., 1996).

Attenuated *Shigella flexneri, Salmonella typhimurium* or *E. coli* that had been rendered invasive by the virulence plasmid (pWR100) of *S. flexneri* have been shown to be able to transfer expression plasmids after invasion of host cells and intracellular death due to metabolic attenuation. Mucosal application, either nasally or orally, of such recombinant *Shigella* or *Salmonella* induced immune responses against the antigen that was encoded by the expression plasmids. In the meantime, the list of bacteria that was shown to be able to transfer expression plasmids to mammalian host cells in vitro and in vivo has been more then doubled and has been documented for *S. typhi, S. choleraesuis, Listeria monocytogenes, Yersinia pseudotuberculosis*, and *Y. enterocolitica* (Fennelly et al., 1999; Shiau et al., 2001; Dietrich et al., 1998; Hense et al., 2001; Al-Mariri et al., 2002).

In general, it could be assumed that all bacteria that are able to enter the cytosol of the host cell (like *S. flexneri* or *L. monocytogenes*) and lyse within this cellular compartment, should be able to transfer DNA. This is known as 'abortive' or 'suicidal' invasion as the bacteria have to lyse for the DNA transfer to occur (Grillot-Courvalin et al., 1999). In addition, even many of the bacteria that remain in the phagocytic vacuole (like *S. typhimurium*) may also be able to do so. Thus, recombinant laboratory strains of *E. coli* that have been engineered to be invasive but are unable of phagosomal escape, could deliver their plasmid load to the nucleus of the infected mammalian cell nevertheless (Grillot-Courvalin et al., 1998). Furthermore, *Agrobacterium*

*tumefaciens* has recently also been shown to introduce transgenes into mammalian cells (Kunik et al., 2001).

As used herein, the terms "transfection", "transformation" and variations thereof are generally used interchangeably. "Transfected" or "transformed" cells may have been manipulated to introduce the polynucleotide(s) of interest, or may be progeny cells derived therefrom.

Recombinant Cells

The invention also provides a recombinant cell, for example, a recombinant plant cell, which is a host cell transformed with one or more polynucleotides or vectors defined herein, or combination thereof. The term "recombinant cell" is used interchangeably with the term "transgenic cell" herein. Suitable cells of the invention include any cell that can be transformed with a polynucleotide or recombinant vector of the invention, encoding for example, a polypeptide or enzyme described herein. The cell is preferably a cell which is thereby capable of being used for producing lipid. The recombinant cell may be a cell in culture, a cell in vitro, or in an organism such as for example, a plant, or in an organ such as, for example, a seed or a leaf. Preferably, the cell is in a plant, more preferably in the seed of a plant.

Host cells into which the polynucleotide(s) are introduced can be either untransformed cells or cells that are already transformed with at least one nucleic acid. Such nucleic acids may be related to lipid synthesis, or unrelated. Host cells of the present invention either can be endogenously (i.e., naturally) capable of producing polypeptide(s) defined herein, in which case the recombinant cell derived therefrom has an enhanced capability of producing the polypeptide(s), or can be capable of producing said polypeptide(s) only after being transformed with at least one polynucleotide of the invention. In an embodiment, a recombinant cell of the invention has an enhanced capacity to produce non-polar lipid.

Host cells of the present invention can be any cell capable of producing at least one protein described herein, and include fungal (including yeast), and plant cells. The cells may be prokaryotic or eukaryotic. Preferred host cells are yeast, algal and plant cells. In a preferred embodiment, the plant cell is a seed cell, in particular, a cell in a cotyledon or endosperm of a seed. Examples of algal cells useful as host cells of the present invention include, for example, *Chlamydomonas* sp. (for example, *Chlamtydomonas reinhardtii*), *Dunaliella* sp., *Haematococcus* sp., *Chlorella* sp., *Thraustochytrium* sp., *Schizoclzytrium* sp., and *Volvox* sp.

Host cells for expression of the instant nucleic acids may include microbial hosts that grow on a variety of feedstocks, including simple or complex carbohydrates, organic acids and alcohols and/or hydrocarbons over a wide range of temperature and pH values. Preferred microbial hosts are oleaginous organisms that are naturally capable of non-polar lipid synthesis.

The host cells may be of an organism suitable for a fermentation process, such as, for example, *Yarrowia lipolytica* or other yeasts.

Transgenic Plants

The invention also provides a plant comprising an exogenous polynucleotide or polypeptide of the invention, a cell of the invention, a vector of the invention, or a combination thereof. The term "plant" refers to whole plants, whilst the term "part thereof" refers to plant organs (e.g., leaves, stems, roots, flowers, fruits), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the term "plant" is used in it broadest sense. It includes, but is not limited to, any species of grass, ornamental or decorative plant, crop or cereal (e.g., oilseed, maize, soybean), fodder or forage, fruit or vegetable plant, herb plant, woody plant, flower plant, or tree. It is not meant to limit a plant to any particular structure. It also refers to a unicellular plant (e.g., microalga). The term "part thereof" in reference to a plant refers to a plant cell and progeny of same, a plurality of plant cells that are largely differentiated into a colony (e.g., volvox), a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

A "transgenic plant", "genetically modified plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof. Transgenic plant parts have a corresponding meaning.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

As used herein, the term "vegetative tissue" or "vegetative plant part" or variants thereof is any plant tissue, organ or part that does not include the organs for sexual reproduction of plants or the seed bearing organs or the closely associated tissues or organs such as flowers, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem. Vegetative parts include those parts principally involved in providing or supporting the photosynthetic capacity of the plant or related function, or anchoring the plant.

As used herein, the term "phenotypically normal" refers to a genetically modified plant or part thereof, particularly a storage organ such as a seed, tuber or fruit of the invention not having a significantly reduced ability to grow and reproduce when compared to an unmodified plant or part thereof. In an embodiment, the genetically modified plant or part thereof which is phenotypically normal comprises a recombinant polynucleotide encoding a silencing suppressor operably linked to a plant storage organ specific promoter and has an ability to grow or reproduce which is essentially the same as a corresponding plant or part thereof not comprising said polynucleotide. Preferably, the biomass, growth rate, germination rate, storage organ size, seed size and/or the number of viable seeds produced is not less than 90% of that of a plant lacking said recombinant polynucleotide when grown under identical conditions. This term docs not encompass features of the plant which may be different to the wild-type plant but which do not effect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruits. The plants may be vegetable or ornamental plants. The plants of the invention may be: corn (*Zea mays*), canola (*Brassica napus, Brassica rapa* ssp.), other Brassicas such as, for example, rutabaga (*Brassica napobrassica*), mustard (*Brassica juncea*), Ethiopian mustard (*Brassica carinata*), crambe (*Crambe abyssinica*), camelina (*Camelina sativa*), sugarbeet (*Beta vulgaris*), clover (*Trifolium* sp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), jatropha (*Jatropha curcas*), lupins, *Eucalypts*, palm, nut sage, pongamia, oats, or barley.

Other preferred plants include C4 grasses such as *Andropogon gerardi, Bouteloua curtipendula, B. gracilis, Buchloe dactyloides, Panicum virgatum, Schizachyrium scoparium, Miscanthus* species for example, *Miscanthus* x *giganteus* and *Miscanthus sinensis, Sorghastrum nutans, Sporobolus cryptandrus*, Switchgrass (*Panicum virgatum*), sugarcane (*Saccharum officinarum*), Brachyaria; C3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa*.

In a preferred embodiment, the plant is an angiosperm.

In an embodiment, the plant is an oilseed plant, preferably an oilseed crop plant. As used herein, an "oilseed plant" is a plant species used for the commercial production of lipid from the seeds of the plant. The oilseed plant may be oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Where relevant, the transgenic plants may also comprise additional transgenes encoding enzymes involved in the production of non-polar lipid such as, but not limited to LPAAT, LPCAT, PAP, or a phospholipid:diacylglycerol acyltransferase (PDAT1, PDAT2 or PDAT3; see for example, Ghosal et al., 2007), or a combination of two or more thereof. The transgenic plants of the invention may also express oleosin from an exogenous polynucleotide.

Transformation of Plants

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

As used herein, the terms "stably transforming", "stably transformed" and variations thereof refer to the integration of the polynucleotide into the genome of the cell such that they are transferred to progeny cells during cell division without the need for positively selecting for their presence. Stable transformants, or progeny thereof, can be selected by any means known in the art such as Southern blots on chromosomal DNA, or in situ hybridization of genomic DNA.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. The use of *Agrobacterium*-mediated plant integrating vectors to introduce DNA into plant cells is well known in the art (see for example, U.S. Pat. Nos. 5,177,010, 5,104,310, 5,004,863, or U.S. Pat. No. 5,159,135). The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985)).

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen such as a stainless steel or Nytex screen, onto a filter surface covered with corn cells cultured in suspension. A particle delivery system suitable for use with the present invention is the helium acceleration PDS-1000/He gun available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein, one may obtain up to 1000 or more foci of cells transiently expressing a marker gene. The number of cells in a focus that express the gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage, or cell cycle of the recipient cells, may be adjusted for optimum transformation. The execution of other routine adjustments will be known to those of skill in the art in light of the present disclosure.

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908), soybean (U.S. Pat. Nos. 5,569,834, 5,416,011), *Brassica* (U.S. Pat. No. 5,463,174), peanut (Cheng et al., 1996), and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired polynucleotide may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Enhancing Exogenous RNA Levels and Stabilized Expression

Post-transcriptional gene silencing (PTGS) is a nucleotide sequence-specific defense mechanism that can target both cellular and viral mRNAs for degradation. PTGS occurs in plants or fungi stably or transiently transformed with a recombinant polynucleotide(s) and results in the reduced accumulation of RNA molecules with sequence similarity to the introduced polynucleotide.

RNA molecule levels can be increased, and/or RNA molecule levels stabilized over numerous generations, by limiting the expression of a silencing suppressor in a storage organ of a plant or part thereof. As used herein, a "silencing suppressor" is any polynucleotide or polypeptide that can be expressed in a plant cell that enhances the level of expression product from a different transgene in the plant cell, particularly, over repeated generations from the initially transformed plant. In an embodiment, the silencing suppressor is a viral silencing suppressor or mutant thereof. A large number of viral silencing suppressors are known in the art and include, but are not limited to P19, V2, P38, Pe-Po and RPV-P0. Examples of suitable viral silencing suppressors include those described in WO 2010/057246. A silencing suppressor may be stably expressed in a plant or part thereof of the present invention.

As used herein, the term "stably expressed" or variations thereof refers to the level of the RNA molecule being essentially the same or higher in progeny plants over repeated generations, for example, at least three, at least five, or at least ten generations, when compared to corresponding plants lacking the exogenous polynucleotide encoding the silencing suppressor. However, this term(s) does not exclude the possibility that over repeated generations there is some loss of levels of the RNA molecule when compared to a previous generation, for example, not less than a 10% loss per generation.

The suppressor can be selected from any source e.g. plant, viral, mammal, etc. The suppressor may be, for example:

flock house virus B2,
pothos latent virus P14,
pothos latent virus AC2,
African cassava mosaic virus AC4,
bhendi yellow vein mosaic disease C2,
bhendi yellow vein mosaic disease C4,
bhendi yellow vein mosaic disease pcl,
tomato chlorosis virus p22,
tomato chlorosis virus CP,
tomato chlorosis virus CPm,
tomato golden mosaic virus AL2,
tomato leaf curl Java virus βC1,
tomato yellow leaf curl virus V2,
tomato yellow leaf curl virus-China C2,
tomato yellow leaf curl China virus Y10 isolate βC1,
tomato yellow leaf curl Israeli isolate V2,
mungbean yellow mosaic virus-Vigna AC2,
hibiscus chlorotic ringspot virus CP,
turnip crinkle virus P38,
turnip crinkle virus CP,
cauliflower mosaic virus P6,
beet yellows virus p21,
citrus tristeza virus p20,
citrus tristeza virus p23,
citrus tristeza virus CP,
cowpea mosaic virus SCP,
sweet potato chlorotic stunt virus p22,
cucumber mosaic virus 2b,
tomato aspermy virus HC-Pro,
beet curly top virus L2,
soil borne wheat mosaic virus 19K,
barley stripe mosaic virus Gammab,
poa semilatent virus Gammab,
peanut clump pecluvirus P15,
rice dwarf virus Pns10,
curubit aphid borne yellows virus P0,
beet western yellows virus P0,
potato virus X P25,
cucumber vein yellowing virus P1b,
plum pox virus HC-Pro,
sugarcane mosaic virus HC-Pro,
potato virus Y strain HC-Pro,
tobacco etch virus P1/HC-Pro,
turnip mosaic virus P1/HC-Pro,
cocksfoot mottle virus P1,
cocksfoot mottle virus-Norwegian isolate P1,
rice yellow mottle virus P1,
rice yellow mottle virus-Nigerian isolate P1,
rice hoja blanca virus NS3,
rice stripe virus NS3,
crucifer infecting tobacco mosaic virus 126K,
crucifer infecting tobacco mosaic virus p122,
tobacco mosaic virus p122,
tobacco mosaic virus 126,
tobacco mosaic virus 130K,
tobacco rattle virus 16K,
tomato bushy stunt virus P19,
tomato spotted wilt virus NSs,
apple chlorotic leaf spot virus P50,
grapevine virus A p10,
grapevine leafroll associated virus-2 homolog of BYV p21, as well as variants/mutants thereof. The list above provides the virus from which the suppressor can be obtained and the protein (e.g., B2, P14, etc.), or coding region designation for the suppressor from each particular virus.

Multiple copies of a suppressor may be used. Different suppressors may be used together (e.g., in tandem).

Essentially any RNA molecule which is desirable to be expressed in a plant storage organ can be co-expressed with the silencing suppressor. The RNA molecule may influence an agronomic trait, insect resistance, disease resistance, herbicide resistance, sterility, grain characteristics, and the like. The encoded polypeptides may be involved in metabolism of lipid, starch, carbohydrates, nutrients, etc., or may be responsible for the synthesis of proteins, peptides, lipids, waxes, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

In a particular example, the plants produced increased levels of enzymes for lipid production in plants such as Brassicas, for example oilseed rape or sunflower, safflower, flax, cotton, soybean or maize.

Production of Non-Polar Lipids Comprising DHS or Fatty Acid Derivatives Thereof

Techniques that are routinely practiced in the art can be used to extract, process, purify and analyze the non-polar lipids produced by cells, organisms or parts thereof of the instant invention. Such techniques are described and explained throughout the literature in sources such as, Fereidoon Shahidi, Current Protocols in Food Analytical Chemistry, John Wiley & Sons, Inc. (2001) D1.1.1-D1.1.11, and Perez-Vich et al. (1998).

Production of Seedoil

Typically, plant seeds are cooked, pressed, and/or extracted to produce crude seedoil, which is then degummed, refined, bleached, and deodorized. Generally, techniques for crushing seed are known in the art. For example, oilseeds can be tempered by spraying them with water to raise the moisture content to, for example, 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the lipid droplets, and agglomerates protein particles, all of which facilitate the extraction process.

The majority of the seedoil is released by passage through a screw press. Cakes expelled from the screw press are then solvent extracted for example, with hexane, using a heat traced column. Alternatively, crude seedoil produced by the pressing operation can be passed through a settling tank with a slotted wire drainage top to remove the solids that are expressed with the seedoil during the pressing operation. The clarified seedoil can be passed through a plate and frame filter to remove any remaining fine solid particles. If desired, the seedoil recovered from the extraction process can be combined with the clarified seedoil to produce a blended crude seedoil.

Once the solvent is stripped from the crude seedoil, the pressed and extracted portions are combined and subjected to normal lipid processing procedures (i.e., degumming, caustic refining, bleaching, and deodorization). Degumming can be performed by addition of concentrated phosphoric acid to the crude seedoil to convert non-hydratable phosphatides to a hydratable form, and to chelate minor metals that are present. Gum is separated from the seedoil by centrifugation. The seedoil can be refined by addition of a sufficient amount of a sodium hydroxide solution to titrate all of the fatty acids and removing the soaps thus formed.

Deodorization can be performed by heating the seedoil to 260° C. under vacuum, and slowly introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. if the amount of seedoil is limited, the seedoil can be placed under vacuum for example, in a Parr reactor and heated to 260° C. for the same length of time that it would have been deodorized. This treatment improves the colour of the seedoil and removes a majority of the volatile substances.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude oil to convert non-hydratable phosphatides to a hydratable form, and to chelate minor metals that are present. Gum is separated from the oil by centrifugation.

Alkali Refining

Alkali refining is one of the refining processes for treating crude oil, sometimes also referred to as neutralization. It usually follows degumming and precedes bleaching. Following degumming, the oil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. This treatment improves the colour of the oil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

Transesterification is a process that exchanges the fatty acids within and between TAGs, initially by releasing fatty acids from the TAGs either as free fatty acids or as fatty acid esters, usually fatty acid ethyl esters. When combined with a fractionation process, transesterification can be used to modify the fatty acid composition of lipids (Marangoni et al., 1995). Transesterification can use either chemical or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis or by lipases and these free fatty acids or fatty acid esters are then mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Plant Biomass for the Production of Lipid

Parts of plants involved in photosynthesis (e.g., and stems and leaves of higher plants and aquatic plants such as algae) can also be used to produce lipid. Independent of the type of plant, there are several methods for extracting lipids from green biomass. One way is physical extraction, which often does not use solvent extraction. It is a "traditional" way using several different types of mechanical extraction. Expeller pressed extraction is a common type, as are the screw press and ram press extraction methods. The amount of lipid extracted using these methods varies widely, depending upon the plant material and the mechanical process employed. Mechanical extraction is typically less efficient than solvent extraction described below.

In solvent extraction, an organic solvent (e.g., hexane) is mixed with at least the genetically modified plant green biomass, preferably after the green biomass is dried and ground. Of course, other parts of the plant besides the green biomass (e.g., lipid-containing seeds) can be ground and mixed in as well. The solvent dissolves the lipid in the biomass and the like, which solution is then separated from the biomass by mechanical action (e.g., with the pressing processes above). This separation step can also be performed by filtration (e.g., with a filter press or similar device) or centrifugation etc. The organic solvent can then be separated from the non-polar lipid (e.g., by distillation). This second separation step yields non-polar lipid from the plant and can yield a re-usable solvent if one employs conventional vapor recovery.

Production of Algae

Algaculture is a form of aquaculture involving the farming of species of algae (including microalgae, also referred to as phytoplankton, microphytes, or planktonic algae, and macroalgae, commonly known as seaweed). Species of algae useful in the present invention include, for example, *Chlamydomonas* sp. (for example, *Chlamydomonas reinhardtii*), *Dunaliella* sp., *Haematococcus* sp., *Clzlorella* sp., *Thraustochytrium* sp., *Schizochytrium* sp., and *Volvox* sp.

Mono or mixed algal cultures can be cultured in open-ponds (such as raceway-type ponds and lakes) or photo-bioreactors.

Algae can be harvested using microscreens, by centrifugation, by flocculation (using for example, chitosan, alum and ferric chloride) and by froth flotation. Interrupting the carbon dioxide supply can cause algae to flocculate on its own, which is called "autoflocculation". In froth flotation, the cultivator aerates the water into a froth, and then skims the algae from the top. Ultrasound and other harvesting methods are currently under development.

Lipid may be separated from the algae by mechanical crushing. When algae is dried it retains its lipid content, which can then be "pressed" out with an oil press. Since different strains of algae vary widely in their physical attributes, various press configurations (screw, expeller, piston, etc.) work better for specific algae types.

Osmotic shock is sometimes used to release cellular components such as lipid from algae. Osmotic shock is a sudden reduction in osmotic pressure and can cause cells in a solution to rupture.

Ultrasonic extraction can accelerate extraction processes, in particular enzymatic extraction processes employed to extract lipid from algae. Ultrasonic waves are used to create cavitation bubbles in a solvent material. When these bubbles collapse near the cell walls, the resulting shock waves and liquid jets cause those cells walls to break and release their contents into a solvent.

Chemical solvents (for example, hexane, benzene, petroleum ether) are often used in the extraction of lipids from algae. Soxhlet extraction can be used to extract lipids from algae through repeated washing, or percolation, with an organic solvent under reflux in a special glassware.

Enzymatic extraction may be used to extract lipids from algae. Enzymatic extraction uses enzymes to degrade the cell walls with water acting as the solvent. The enzymatic extraction can be supported by ultrasonication.

Supercritical $CO_2$ can also be used as a solvent. In this method, $CO_2$ is liquefied under pressure and heated to the point that it becomes supercritical (having properties of both a liquid and a gas), allowing it to act as a solvent.

Fermentation Processes for Lipid Production

As used herein, the term the "fermentation process" refers to any fermentation process or any process comprising a fermentation step. A fermentation process includes, without limitation, fermentation processes used to produce alcohols (e.g., ethanol, methanol, butanol), organic acids (e.g., citric acid, acetic acid, itaconic acid, lactic acid, gluconic acid), ketones (e.g., acetone), amino acids (e.g., glutamic acid), gases (e.g., $H_2$ and $CO_2$), antibiotics (e.g., penicillin and tetracycline), enzymes, vitamins (e.g., riboflavin, beta-carotene), and hormones. Fermentation processes also include fermentation processes used in the consumable alcohol industry (e.g., beer and wine), dairy industry (e.g., fermented dairy products), leather industry and tobacco industry. Preferred fermentation processes include alcohol fermentation processes, as are well known in the art. Preferred fermentation processes are anaerobic fermentation processes, as are well known in the art. Suitable fermenting cells, typically microorganisms that are able to ferment, that is, convert, sugars such as glucose or maltose, directly or indirectly into the desired fermentation product. Examples of fermenting microorganisms include fungal organisms such as yeast, preferably an oleaginous organism. As used herein, an "oleaginous organism" is one which accumulates at least 25% of its dry weight as triglycerides. As used herein, "yeast" includes *Saccharomyces* spp., *Saccharomyces cerevisiae, Saccharomyces carlbergensis, Candida* spp., *Kluveromyces* spp., *Pichia* spp., *Hansenula* spp., *Trichoderma* spp., *Lipomyces starkey*, and *Yarrowia lipolytica*. Preferred yeast include *Yarrowia lipolytica* or other oleaginous yeasts and strains of the *Saccharomyces* spp., and in particular, *Saccharomyces cerevisiae*.

The transgenic microorganism is preferably grown under conditions that optimize activity of CPFAS genes, fatty acid biosynthetic genes and acyltransferase genes. This leads to production of the greatest and the most economical yield of lipid. In general, media conditions that may be optimized include the type and amount of carbon source, the type and amount of nitrogen source, the carbon-to-nitrogen ratio, the oxygen level, growth temperature, pH, length of the biomass production phase, length of the lipid accumulation phase and the time of cell harvest.

Fermentation media must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon. substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host microorganism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea, glutamate). In addition to appropriate carbon and nitrogen sources, the fermentation media may also contain suitable minerals, salts, cofactors, buffers, vitamins and other components known to those skilled in the art suitable for the growth of the microorganism and promotion of the enzymatic pathways necessary for lipid production.

A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of lipid in the cells of oleaginous microorganisms requires a two-stage process, since the metabolic state must be "balanced" between growth and synthesis/storage of fats. Thus, most preferably, a two-stage fermentation process is necessary for the production of lipids in microorganisms. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of TAGs.

Although cells are typically grown at about 30° C., some studies have shown increased synthesis of unsaturated fatty acids at lower temperatures. Based on process economics, this temperature shift should likely occur after the first phase of the two-stage fermentation, when the bulk of the microorganism's growth has occurred.

It is contemplated that a variety of fermentation process designs may be applied, where commercial production of lipids using the instant nucleic acids is desired. For example, commercial production of lipid from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-batch processes are useful when catabolite repression is apt to inhibit the metabolism of the cells or where it is desirable to have limited amounts of substrate in the media at any one time Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Brock, In Biotechnology: A Textbook of Industrial Microbiology, 2nd ed., Sinauer Associates, Sunderland, Mass., (1989); or Deshpande and Mukund (1992).

Commercial production of lipid using the instant cells may also be accomplished by a continuous fermentation process, wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art.

In general, means for the purification of fatty acids, including PUFAs, may include extraction with organic solvents, sonication, supercritical fluid extraction (e.g., using carbon dioxide), saponification and physical means such as presses, or combinations thereof. Of particular interest is extraction with methanol and chloroform in the presence of water (Bligh and Dyer, 1959). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

EXAMPLES

Example 1. General Materials and Methods

Expression of Genes in Plant Cells in a Transient Expression System

Genes were expressed in plant cells using a transient expression system essentially as described by Voinnet et al. (2003) and Wood et al. (2009). Chimeric binary vectors, 35S:p19 and 35S:V2, for expression of the p19 and V2 viral silencing suppressors, respectively, were separately introduced into *Agrobacterium tumefaciens* strain GV3101:mp90. All other binary vectors containing a coding region to be expressed by a promoter, such as the strong constitutive CaMV 35S promoter, were introduced into *Agrobacterium tumefaciens* strain AGL1. The recombinant cells were grown to stationary phase at 28° C. in LB broth supplemented with 50 mg/L rifampicin and either 50 mg/L kanamycin or 80 mg/L spectinomycin according to the selectable marker gene on the binary vector. Acetosyringone (100 μM) was added to the bacterial cultures and growth continued a further 2 hours for the induction of virulence factors. The bacteria were pelleted by centrifugation at 3000 g for 5 min at room temperature before being resuspended to OD600=2.0 in infiltration buffer containing 10 mM MES pH 5.7, 10 mM $MgCl_2$ and 100 μM acetosyringone. The cells were then incubated at 28° C. with shaking for another 30 minutes and a volume of each culture required to reach a final concentration of OD600=0.3 added to a fresh tube. Mixed cultures comprising genes to be expressed included either of the 35S:p19 or 35S:V2 constructs in *Agrobacterium* unless otherwise stated. The final volume was made up with the infiltration buffer.

Leaves were then infiltrated with the culture mixture and the plants were typically grown for a further three to five days after infiltration before leaf discs were recovered for total lipid isolation. Time courses of GFP expression were conducted on the intact leaves from the first day after infiltration through to 7 days post-infiltration (dpi). *N. benthamiana* plants were grown in growth cabinets under a constant 24° C. with a 14/10 light/dark cycle with a light intensity of approximately 200 lux using Osram 'Soft White' fluorescent lighting placed directly over plants. Typically, 6 week old plants were used for experiments and true leaves that were nearly fully-expanded were infiltrated. All non-infiltrated leaves were removed by post infiltration to avoid shading.

Lipid Analysis

Total Lipid Isolation and Fractionation

Tissue samples were freeze-dried, weighed and total lipids extracted from samples of approximately 30 mg dry weight as described by Bligh and Dyer (1959). When required, TAG fractions were separated from other lipid components using a 2-phase thin-layer chromatography (TLC) system on pre-coated silica gel plates (Silica gel 60, Merck). An extracted lipid sample equivalent to 10 mg dry weight of leaf tissue was chromatographed in a first phase with hexane/diethyl ether (98/2 v/v) to remove non-polar waxes and then in a second phase using hexane/diethyl ether/acetic acid (70/30/1 v/v/v). When required, polar lipids were separated from non-polar lipids in lipid samples extracted from an equivalent of 5 mg dry weight of leaves using two-dimensional TLC (Silica gel 60, Merck), using chloroform/methanol/water (65/25/4 v/v/v) for the first direction and chloroform/methanol/$NH_4OH$/ethylpropylamine (130/70/10/1 v/v/v/v) for the second direction. The lipid spots, and appropriate standards run on the same TLC plates, were visualized by brief exposure to iodine vapour, collected into vials and transmethylated to produce FAME for GC analysis as follows.

Conversion of Fatty Acids to FAMEs

For total lipid analysis, with the exception of the analysis of DHS content, lipid extracted from an equivalent of 10 mg of dry weight leaf material was transmethylated using a solution of methanol/HCl/dichloromethane (10/1/1 v/v/v) at 80° C. for 2 hr to produce fatty acid methyl esters (FAME). For analysis of DHS in leaves, samples were transmethylated using the same reagents but with milder conditions, namely for 10 mins at 50° C., using DHS (Larodan Chemicals) as a calibration standard. The FAME were extracted into hexane, concentrated to near dryness under a stream of $N_2$ gas and quickly reconstituted in hexane prior to analysis by GC.

DHS and eDHS were determined in total lipid samples by the following method. Samples were directly treated with 0.1M sodium methoxide in methanol/chloroform (10:1) in a sealed test tube with heating at 90° C. for 60 mins to convert lipids to FAMEs. When cool, the solution was slightly acidified to pH 6-7 with acetic acid. Saline and hexane/chloroform (4:1 v/v) were added with vigorous shaking, and the hexane/chloroform layer containing FAMEs was transferred to a vial for analysis.

Capillary Gas-Liquid Chromatography (GC)

FAMEs were analysed by gas chromatography (GC) using an Agilent Technologies 6890N gas chromatograph (Palo Alto, Calif., USA) equipped with an Equity™-1 fused silica capillary column (15 m×0.1 mm i.d., 0.1 μm film thickness), an FID, a split/splitless injector and an Agilent Technologies 7683 Series auto sampler and injector. Helium was used as the carrier gas. Samples were injected in splitless mode at an oven temperature of 120° C. After injection, the oven temperature was raised to 201° C. at 10° C. $min^{-1}$ and then to 270° C. at 5° C. $min^{-1}$ and held for 20 min. Peaks were quantified with Agilent Technologies ChemStation software (Rev B.03.01 (317), Palo Alto, Calif., USA). Peak responses were similar for the fatty acids of authentic Nu-Check GLC standard-411 (Nu-Check Prep Inc, MN, USA) which contained equal proportions of 31 different fatty acid methyl esters, including 18:1, 18:0, 20:0 and 22:0. Slight variations of peak responses among peaks were balanced by multiplying the peak areas by normalization factors of each peak. The proportion of each fatty acid in total fatty acids of samples was calculated on the basis of individual and total peaks areas for the fatty acids.

Analysis of FAMEs by Gas Chromatography—Mass Spectrometry

Analysis of FAMEs by gas chromatography—mass spectrometry (GCMS) was conducted using a Varian 3800 equipped with a BPX70 capillary column (length 30 m, i.d. 0.32 mm, film thickness 0.25 μm, Phenomenex). Injections were made in the split mode using helium as the carrier gas and an initial column temperature of 60° C. raised at 20° C. $min^{-1}$ until 180° C., then raised at 2.5° C. $min^{-1}$ until 190° C., then raised at 25° C. $min^{-1}$ until 260° C. and held for 2.2 min. Mass spectra were acquired under positive electron impact in full scan mode between 40-400 amu at the rate of 2 scans per second using a Varian 1200 Single Quadrupole mass spectrometer. The mass spectra corresponding to each peak in the chromatogram was automatically compared with spectra of pure standards. Test spectra that matched standard spectra with a high degree of accuracy and eluted at the same time as an authentic standard or eluted at a plausible retention time, were identified. FAMEs were quantified by peak area integration using Varian software and assuming equivalent MS response factors on a weight basis.

Quantification of TAG Via Iatroscan

One μl of each leaf extract was loaded on one Chromarod-SII for TLC-FID Iatroscan™ (Mitsubishi Chemical Medience Corporation—Japan). The Chromarod rack was then transferred into an equilibrated developing tank containing 70 ml of a Hexane/CHCl$_3$/2-Propanol/Formic acid (85/10.716/0.567/0.0567 v/v/v/v) solvent system. After 30 min of incubation, the Chromarod rack was then dried for 3 min at 100° C. and immediately scanned on an Iatroscan MK-6s TLC-FID analyser (Mitsubishi Chemical Medience Corporation—Japan). Peak areas of DAGE internal standard and TAG were integrated using SIC-48011 integration software (Version: 7.0-E SIC System instruments Co., LTD—Japan).

TAG quantification was carried out in two steps. First, DAGE was scanned in all samples to correct the extraction yields after which concentrated TAG samples were selected and diluted. Next, TAG was quantified in diluted samples with a second scan according to the external calibration using glyceryl trilinoleate as external standard (Sigma-Aldrich).

Transformation of *Arabidopsis thaliana*

Chimeric vectors comprising genes to be used to transform *Arabidopsis* were introduced into *A. tumefaciens* strain AGL1 and cells from culture of the transformed *Agrobacterium* used to treat *A. thaliana* (ecotype Columbia) plants using the floral dip method for transformation (Clough and Bent, 1998).

Example 2. V2 Protein Acts as a Silencing Suppressor in Transient Assays

Construction of Chimeric Genes for Expression of Silencing Suppressors p19 or V2

The p19 protein from Tomato Bushy Stunt Virus (TBSV) (SEQ ID NO: 2) and the V2 protein from Tomato Yellow Leaf Roll Virus (TYLRV) (SEQ ID NO: 1) have been characterised as viral suppressor proteins (VSP), functioning as silencing suppressors (Voinnet et al., 2003; Glick et al., 2008). p19 binds to 21 nucleotide long siRNAs before they guide Argonaute-guided cleavage of homologous RNA (Ye et al., 2003). V2 is an another silencing suppressor that disrupts the function of the plant protein SGS3, a protein thought to be involved in the production of double stranded RNA intermediates from ssRNA substrates (Elmayan et al., 1998; Mourrain et al., 2000; Beclin et al., 2002) either by directly binding to SGS3 (Glick et al., 2008) or by binding dsRNA intermediates that contain a 5' overhang structure and competitively excluding SGS3 from binding these intermediates (Fukunaga and Doudna, 2009).

A DNA sequence encoding p19 (SEQ ID NO: 4), based on the genome sequence of the Tomato Bushy Stunt Virus (Hillman et al., 1989) was chemically synthesised, including an NcoI site spanning the translation start ATG codon. The DNA sequence was amplified by PCR and inserted into the pENTR/D-TOPO vector (Invitrogen), producing a plasmid designated pCW087 (pENTR-p19). Gateway LR clonase reactions were then used to introduce the p19 coding sequence into plant binary vectors under the control of either the CaMV35S promoter, generating a construct designated pCW195 (35S-p19), or the truncated napin promoter FP1, generating pCW082 (FP1-p19). In addition, the entire FP1-p19-ocs3' expression cassette from pCW082 was PCR amplified with SacI flanking sites and ligated into pCW141, a plant expression vector having a FP1-GFP gene as a screenable/selectable seed marker, thus generating a plasmid designated pCW164 (FP1-p19 and FP1-GFP). The presence of the FP1-GFP gene allowed the non-destructive identification and selection of transformed T1 seeds in mixed null/T1 populations that resulted from the dipping techniques used to transform *Arabidopsis*.

A DNA sequence encoding V2 (SEQ ID NO: 3), based on the Tomato Yellow Leaf Curl Virus genome sequence (Glick et al., 2008), was chemically synthesised, included flanking NotI and AscI restriction sites to allow direct cloning into the pENTR/D-TOPO vector (Invitrogen), generating a plasmid designated pCW192 (pENTR-V2). Gateway LR clonase reactions were used to introduce the V2 gene into plant binary vectors under the control of the 35S promoter (pCW197; 35S-V2) or for seed-specific expression under the control of the truncated napin promoter, FP1 (pCW195; FP1-V2).

The vector pUQ214 described in Brosnan et al. (2007) and comprising a 35S-GFP gene, was used as an example of a target gene, expressing GFP under the control of the 35S promoter. This binary vector included a kanamycin resistance marker gene that can be used for selection of transformed cells in plants if desired.

Function of the Suppressors in Plant Cells

In order to confirm the function of the V2 and p19 proteins as suppressors of silencing and therefore increasing transgene expression, *Agrobacterium* cells containing either of the 35S-driven VSP constructs were co-infiltrated together with *Agrobacterium* cells containing pUQ214 into *Nicotiana benthamiana* leaves as follows. Transformants of *Agrobacterium tumefaciens* strains separately harbouring each binary vector were grown overnight at 28° C. in LB broth supplemented with antibiotics (50 mg/L kanamycin or 80 mg/L spectinomycin, dependent on the selectable marker gene used) and rifampicin. Turbid cultures were supplemented with 100 µM acetosyringone and grown for a further 2 hours. Cultures were centrifuged (4000×g for 5 min at room temperature) to harvest the cells and the cell pellets gently resuspended in infiltration buffer (5 mM MES, 5 mM $MgSO_4$, pH 5.7, 100 µM acetosyringone) to an optical density of about 2.0. Cell suspensions for infiltration were prepared, combining different transformants as required, so that each *Agrobacterium* strain was present at an $OD_{600\ nm}$ of 0.3. The cell suspensions were infiltrated into the underside of fully-expanded leaves of 5-6 week old *N. benthamiana* plants using a 1 mL syringe without a needle, using gentle pressure. By these means, the cell suspensions entered primarily through the stomates and infiltrated the mesophyll cell layer of the leaves. Infiltrated areas of leaves, indicated by the water-soaked region and commonly 3 to 4 cm in diameter, were circled by a permanent marker. Plants were housed in a 24° C. plant growth room with 14:10 light:dark cycle, where the light intensity was 400-500 µEinsteins·$m^{-2}$·$s^{-1}$ at the leaf surface provided by overhead fluorescent lighting (Philips TLD 35S/865 'Cold Daylight'). Under these conditions, the *Agrobacteria* efficiently transferred the T-DNAs into the *N. benthamiana* cells.

GFP expression in the leaves was measured daily from 1-7 days after the infiltrations by measuring the fluoresence under UV light. GFP images were captured on a digital SLR (Nikon D60; 55-200 mm lens) using the NightSea fluorescent light and filter set (NightSea, Bedford, Mass., USA). Infiltrated leaves were generally left on the plant and were photographed every day from 2-7 days post infiltration, thereby a time-course of GFP expression could be determined for the same set of infiltrations. Representative fluorescence photographs are shown in FIG. 1.

The 35S:GFP construct introduced in the absence of a VSP produced a relatively low level of fluorescence, indicative of GFP expression, peaking after 2-3 days and reducing thereafter. In contrast, when the GFP construct was co-infiltrated with either the p19 or the V2 suppressor constructs, both the intensity and duration of fluorescence were greatly increased, extending to and maintained beyond more than 7 days post infiltration. These observations indicated enhanced expression of the 35S:GFP gene in the leaf assays in the presence of the VSPs, and confirmed their function as potent suppressor proteins that inhibited the endogenous co-suppression pathways in the plant cells.

Measurement of GFP Expression by Western Blot Analysis

GFP expression was also analysed by Western blot using a GFP specific antibody as follows. 1 $cm^2$ leaf samples were removed from the infiltrated zones and subjected to denaturing protein extraction, polyacrylamide gel electrophoresis (PAGE; 12% gel) and blotting to PVDF membrane essentially as described (Helliwell et al., 2006). GFP protein was detected using an anti-GFP monoclonal antibody (1:10000 dilution, Clontech) and goat anti-mouse HRP (1:5000 dilution, Promega) according to the suppliers instructions. Coomassie blue staining of high molecular proteins remaining in gels after the transfer to PVDF membranes was used to confirm equal protein loading between samples. Protein size was determined using the Pre-Stained PageRuler Protein Ladder (MBI-Fermentas P7711S).

The results of the Western blot analyses confirmed the fluorescence data, confirming the function of both p19 and V2 as silencing suppressors (FIG. 2).

Example 3. RNAi Gene Silencing can Occur Simultaneously with Silencing Suppression Hairpin RNAi Constructs Targeting GFP A binary construct pUQ218 (Brosnan et al., 2007), containing both a 35S-GFP gene and a 35S-hairpin encoding region targeted against GFP and within the same T-DNA region, was used when experiments used both GFP expression and simultaneous GFP silencing activities in the same cell. The hairpin RNA comprised the first 380 bp of the GFP coding sequence, corresponding to nucleotides 1 to 380 of Accession No. U43284. A hpGFP binary construct without the 35S-GFP gene was generated by removing the 35S-GFP component via a NheI-AvrII digestion/religation reaction, creating pCW445 (35S-hpGFP).

Co-Expression of Silencing Suppressors and Silencing Constructs with Transgene Expression The VSPs, V2 and p19, were compared in combination with GFP expression from the 35S-GFP gene and a hairpin targeting GFP (hpGFP) to silence the 35S-GFP gene, using transient assays by infiltration of the genes from *Agrobacterium* into *N. benthamiana* leaves. These were compared to control infiltrations without the hpGFP, into adjacent spots on the same leaf at the same time, to determine expression levels in the absence of the hairpin RNA. FIG. 1, panel B, shows representative photographs of the fluorescence observed from 2 to 7 days post infiltration. The combination of pCW195 (35S-p19) and pUQ218 (containing both GFP and hpGFP) resulted in high levels of GFP expression, indicating that p19 effectively suppressed silencing by the hairpin RNA of the GFP transgene. In contrast, combinations of V2, 35S-GFP and hpGFP resulted in a near-total silencing of GFP. Complete silencing of GFP was achieved with hpGFP in the absence of any VSP.

Experiments using pUQ218 generated equivalent results for GFP expression compared to the combination of separate vectors pUQ214 (35S-GFP) and pCW557 (35S-hpGFP). This indicated that the hairpin RNA construct was efficiently introduced into cells via *Agrobacterium* in the experiments described above, and that it was not necessary to link the target gene and the silencing gene on a single construct in the transient leaf assays.

Western blots of GFP protein levels (FIG. 2) using a specific antibody as in Example 2 confirmed that the co-introduction of p19 suppressed the silencing activity of hpGFP, thereby allowing strong GFP expression. In contrast, only a low level of GFP expression was detected when the combination of V2, GFP and hpGFP was introduced. This great difference between p19 and V2 with respect to suppressing the function of a hairpin RNA indicated that V2 may allow strong over-expression of transgenes simultaneously with hairpin-based RNAi strategies in the same cell.

Example 4. Silencing of an Endogenous Gene in the Presence of Silencing Suppressors In order to test whether an endogenous gene could be silenced simultaneously with expression of a silencing suppressor, a hairpin RNA construct was designed and made which would silence a FAD2 gene in N. benthamiana plants (NbFAD2) (SEQ ID NO: 11). FAD2 is a membrane-bound enzyme located on the endoplasmic reticulum (ER) which desaturates 18:1 esterified on phosphatidylcholine (18:1-PC) to form 18:2-PC. Activity of FAD2 can readily be assayed by analysing the fatty acid composition of lipid in the plant tissues and determining the ratio of 18:1 (oleic acid) to 18:2 (linoleic acid) in the total fatty acid. FAD2 is active in leaves of N. benthamiana as in other plants, resulting in low levels of 18:1-PC in the leaves. As 18:1-PC is an important metabolite for a range of alternative fatty acids metabolic pathways, a chimeric gene was made which included an inverted repeat of a 660 basepair region of NbFAD2 (SEQ ID NO: 12), corresponding to central portion of the endogenous 1151 bp transcript, to silence NbFAD2 as follows.

Construction of Hairpin Construct Targeting NbFAD2

A 660 bp fragment of NbFAD2 was generated by RT-PCR from leaf total RNA using primers designed against conserved regions of a Nicotianum tabacum FAD2 sequence in the Solgenomics database (SGN-U427167), namely forward primer NbFAD2F1 5'-TCATTGCGCACGAATGTGGC-CACCAT-3' (+451 bp co-ordinates) (SEQ ID NO: 13) and reverse primer NbFAD2R1 5'-CGAGAACA-GATGGTGCACGACG-3' (+1112 bp co-ordinates) (SEQ ID NO: 14). Total RNA was isolated from young N. benthamiana leaves using a Trizol-based method (Invitrogen and associated literature). A Platinum Taq One-Step RT-PCR reaction (Invitrogen) was performed using the cycling conditions of 50° C. (10 min), 94° C. (2 min) and 30 cycles of 50° C. (30 s)/72° C. (60 s)/92° C. (30s) and a final 72° C. (2 min). The NbFAD2 gene fragment was subsequently ligated into pENTR11 and recombined using standard Gateway procedures into the pHellsgate8 vector (Helliwell et al., 2002) to generate the plasmid designated pFN033. This construct had an inverted repeat of the 660 bp fragment under the control of the 35S promoter, thereby producing, upon transcription, a RNA hairpin directed against NbFAD2, hereafter named hpNbFAD2.

hpNbFAD2 was transformed into Agrobacterium tumefaciens strain AGL1 and infiltrated into N. benthamiana leaves in combination with Agrobacteria containing the 35S:V2 or 35S:p19 constructs. Five days post infiltration, infiltrated zones from leaves were sampled, total lipid extracted and the PC fraction analysed. The fatty acid analysis of the PC fraction of leaves infiltrated with combinations of hpNbFAD2 and V2 showed a substantial increase in the 18:1-PC content from 9% 18:1-PC to 39% 18:1-PC (FIG. 3). These percentages were based on the observed amounts of 18:1, 18:2 and 18:3 found on the PC fraction and expressed as a percentage of the sum of these three fatty acids. In comparison, the combination of p19 and hpNbFAD2 resulted in partial silencing of FAD2 activity, reflected in an increase from 8% 18:1-PC to 25% 18:1-PC, a result indicating that hpNbFAD2 could silence the endogenous FAD2 gene to a moderate extent in the presence of co-expression of p19. Previous work has shown that leaf cells infiltrated with a combination of Agrobacteria strains, each containing a separate vector, received at least one or more copies of T-DNA from each vector (Wood et al., 2009). This gave us confidence that the great majority of cells in the leaf assays described above had received and expressed both the hairpin and the suppressor encoding genes.

The increase in 18:1-PC levels was reflected in a reduction in the 18:2-PC content in the cells. In contrast, the 18:3-PC levels nearly the same, presumably due to the large amount of 18:3 generated in the FAD2-independent pathways found in the chloroplasts of leaves.

To establish that the suppressor and hairpin constructs were introduced into the same cells efficiently, constructs were also made and tested which co-located the genes within the same T-DNA constructs, thus generating single T-DNAs with 35S-p19+35S-hpNbFAD2 and 35S-V2+35S-NbFAD2 gene combinations. The entire 35S-p19-ocs3' region of pCW194 was PCR amplified using the primers including MluI flanking sites, (underlined) namely Forward primer 5' aacgcgttcgacgaattaattccaatcccaca-3' (SEQ ID NO: 15) and the OCS'3 Reverse primer 5'-ACGCGTCTGCTGAGCCTCGACATGTT-3' (SEQ ID NO: 16). The amplified fragment was ligated into the unique MluI site within pFN033 to create pCW701, containing 35S-p19+35S-hpNbFAD2. Using the same primers, the entire 35S-V2-ocs3' region of pCW197 was PCR amplified and this amplicon was ligated into the unique MluI site of pFN033 to create pCW702, containing 35S-p19+35S-hpNbFAD2. These vectors having the suppressor and hairpin encoding genes located within the same T-DNA region were transformed into Agrobacterium strain AGL1 and infiltrated into N. benthamiana leaves as before. Leaf tissues were sampled 5 dpi and the PC lipid fractions analysed for the 18:1, 18:2 and 18:3 levels. The results were indistinguishable compared to the results obtained using genes introduced on separate vectors, the inventors concluded that essentially all of the transformable leaf cells in transient leaf assays received at least one copy of each T-DNA in the infiltration mixtures.

Simultaneous Silencing of One Gene while Overexpressing a Second Gene

To test whether additional genes could be over-expressed with the aid of a silencing suppressor while silencing the endogenous FAD2 gene, additional constructs were made for over-expression of genes encoding DGAT1 and oleosin in plant cells. All plant cells possess active lipid pathways producing lipid classes such as DAG and acyl-CoA (Ohlrogge and Browse, 1995), however the esterification of these substrates via DGAT to produce TAG only occurs at significant levels in specialised organs, such oilseeds and pollen. The ectopic expression of AtDGAT1 in leaves has been shown to generate increased levels of oils (Bouvier-Nave et al., 2000). Previous studies have also shown that AtDGAT1 has some substrate specificity for 18:1 and its elongation product, 20:1 (Katavic et al., 1995). Oleosins are amphipathic proteins whose properties position these proteins on oil/hydrophilic interfaces, thereby creating a coating surrounding oil droplets and forming so called 'oil bodies' in oil-generating tissues (Tzen et al., 1992). 'Oil bodies' are considered a long term storage organelle as the oleosin layer protects the TAG from catabolic processes such as TAG lipases. Seeds of Arabidopsis mutants lacking a functional oleosin, ole1, have significantly reduced 18:1 contents and this 18:1 content was restored upon ectopic expression of an oleosin encoding gene from sesame (Scott et al., 2010).

Synthesis and Use of Constructs to Overexpress DGAT1 and Oleosin

The coding region of the AtDGAT1 gene (SEQ ID NO: 10) was cloned from Arabidopsis Col-0 mRNA collected from developing embryos using primers based on the Accession No. NG_127503. The amplicon was cloned into pENTR11 (Invitrogen) and recombined via an LR clonase reaction into a 35S binary expression vector to create 35S-AtDGAT1. The oleosin construct was used as described by Scott et al. (2010). This construct had a 35S promoter driving an oleosin coding region (SEQ ID NO: 6) isolated from sesame, encoding the protein with the amino acid sequence of Accession No AF091840 (SEQ ID NO: 5), generating the construct designated 35S-Oleosin.

Combinations of Agrobacterial strains separately containing vectors for transfer of genes encoding DGAT1, oleosin and p19 or V2 and in addition hpNbFAD2 were tested in N. benthamiana leaves and the oil content and fatty acid composition in the infiltrated tissues were analysed. Leaf samples were removed 5 dpi and freeze dried overnight. Lipids were extracted from samples of about 30 mg dry weight using the method of Bligh and Dyer (1959). TAGs in the extracted lipids were separated from polar lipids using a 2-phase TLC system on pre-coated silica gel plates (Silica gel 60, Merck). A lipid sample equivalent to 10 mg dry weight of leaf tissue was first run with hexane/diethyl ether (98/2 by vol.) to remove very non-polar waxes and a second phase was run using hexane/diethyl ether/acetic acid (70/30/1 by vol.). The lipid spots, and appropriate standards, were visualized by brief exposures to iodine vapour, collected into vials and transmethylated to produce FAME for GC analysis as described in Example 1. The data are shown in FIG. 4.

Leaves infiltrated with the genes encoding V2 and both DGAT1 and Oleosin had an approximately 5 to 6 fold increase in the TAG content. Moreover, there was a doubling of the 18:1 level calculated as a percentage of the total fatty acids in the TAG fraction, indicating that the combination of these two genes in the presence of the silencing suppressor enhanced the formation (synthesis and accumulation) of leaf oils with increased levels of oleic acid. The further addition of the silencing construct hpNbFAD2 increased the 18:1 level in the leaf oil to either 44% when using V2 or to 35% using p19 as the VSP. This assay configuration confirmed that both V2 and p19 allowed over-expression of transgenes, e.g. encoding AtDGAT1 and Oleosin. Although both silencing suppressors allowed effective simultaneous endogenous FAD2 silencing, use of V2 provided a greater extent of silencing than p19. From the efficiency of the 18:1 accumulation in TAGs, these observations were consistent with the conclusion above that over-expression of the transgenes aided by the VSPs was occurring simultaneously in the same cells as the FAD2 silencing.

In a further experiment to demonstrate that additional genes could be over-expressed with the aid of a silencing suppressor while simultaneously reducing expression of a second gene with a hairpin RNA, a construct was made to express a FAE1 enzyme (SEQ ID NO: 7). FAE1 is an enzyme that elongates saturated and monounsaturated fatty acids esterified to CoA by adding 2 carbons to the acyl chain at the carboxyl end of the fatty acid molecule (James et al., 1995). Previous studies have shown that ectopic expression of AtFAE1 resulted in production of a range of new elongated fatty acids, including a series of so-called very-long chain fatty acids (VLCFA) due to the sequential activity of AtFAE1 in cycles of elongation. The enzyme uses acyl-CoA substrates (Millar et al., 1998).

Synthesis of Construct to Express FAE1

The coding region of AtFAE1, TAIR Accession number 2139599, was chemically synthesised, subcloned into pGEMT-Easy and subcloned via the EcoRI flanking sites into the pENTR cloning vector, pCW306, to include the AttL1 and AttL2 sites, to generate pCW327. A catalase-1 intron, from the castor bean catalase-1 gene, was ligated into the unique NotI site just upstream of the AtFAE1 ORF to generate pCW465, pENTR-intron-AtFAE1. LR clonase reactions were used to recombine the intron-AtFAE1 fragment (SEQ ID NO: 8) into a 35S expression vector, generating pCW483 (35S-intron-AtFAE1). pCW483 was transformed into Agrobacterium strain AGL1 and transiently expressed in N. benthamiana leaves as above in combination with the other genes. A range of new elongation products were found in leaves expressing AtFAE1, including a significant number of VLCFA such as 20:1 (FIG. 11). Based on the known substrate specificity of AtFAE1, the inventors reasoned that 18:1-CoA would be a preferred substrate for AtFAE1, however this substrate would only be found in wild-type leaves at low levels due to the activity of NbFAD2. The inventors therefore combined the over-expression of AtFAE1 with hairpin based silencing of NbFAD2 in the presence of the silencing suppressor V2.

These experiments demonstrated that silencing suppressors such as V2 allowed over-expression of transgenes and the simultaneous silencing of endogenous genes in the same cell, and allowed an optimised substrate pool to be formed for metabolic engineering of fatty acids, e.g. 20:1 and other VLCFA.

Example 5. Small RNA Analysis of Hairpin-Based Silencing of an Endogen

Hairpin-based RNAi constructs are known to generate populations of small RNAs homologous to the hairpin, generally known as primary sRNA molecules. These primary sRNAs can trigger the production of secondary sRNAs that are homologous to regions in the target RNA outside of the hairpin-targeted region. Such sRNAs are mostly 21, 22 or 24 nucleotides in length, reflecting their biogenesis via a several pathways using different Dicer proteins. Each length may have specific functions in transcriptional gene silencing (TGS) and post-transcriptional gene silencing (PTGS). With the availability of deep sequencing technologies, the inventors investigated the small RNA populations arising from hairpin-based gene silencing of the endogenous NbFAD2 gene by the hpNbFAD2 in the transient assays, as above.

Cloning of Full-Length Open-Reading Frame of the NbFAD2 Gene

First of all, the full length open reading frame of the FAD2 gene from N. benthamiana was sequenced as follows. Genomic DNA was isolated from 20 g fresh weight of N. benthamiana leaves using a method that reduced chloroplastic and mitochondrial DNA contamination (Peterson et al., 1997). High molecular weight DNA was randomly sheared into fragments of approximately 500 bp and ligated with TruSeq library adaptors to generate a gDNA library. This library was sequenced on the HiSeq2000 platform on a complete flowcell. High quality sequences were retained to generate an alignment against the 660 bp hpNbFAD2 fragment (pFN033) using BowTie software. The full-length coding region of NbFAD2 was subsequently cloned via high fidelity PCR using primers Forward 5'-TTT ATGGGAGCTGGTGGTAATATGT-3' (SEQ ID NO: 17) and Reverse 5'-CCC TCAGAATTTGTTTTTGTACCAGAAA-3' (SEQ ID NO: 18) (start and stop codons underlined) and sequence verified using BigDye3.1 sequencing techniques.

Small RNA Analysis

Deep sequencing methods were then used to analyse the populations of sRNA generated from the hairpin RNAi silencing construct, hpNbFAD2, in leaves co-infiltrated with the construct encoding V2. Total RNA was isolated from leaves 5 dpi using Trizol reagent (Invitrogen) according to the suppliers instructions. Small RNAs (15-40 nt size range)

were purified via gel electrophoresis and analysed on an Illumina GAxII machine according to the manufacturers protocols.

Small RNAs having a sequence with identity to the NbFAD2 gene were identified and collated. The observed predominant sRNA size classes (20-24 nt) showed a non-uniform distribution across both the forward and reverse strands of the 660 bp target sequence (FIG. 8). Alignments of the small RNA reads against the full-length NbFAD2 open-reading frame sequence indicated that all of the observed sRNAs with homology to NbFAD2 had identity with the region used to generate the hairpin construct, none to the non-targeted regions. Therefore, the inventors concluded that the combination of the V2 silencing suppressor and hpNbFAD2 did not generate secondary sRNAs at an observable frequency. The absolute numbers of sRNA size classes showed that 20, 21, 22, 23 and 24 nt sRNA represented 10%, 44%, 36%, 4% and 10% of all sRNA, respectively (FIG. 9). This result confirmed that hairpins generated primary sRNAs against an endogenous gene and not secondary sRNAs, although an influence of the V2 suppressor in this result cannot be excluded.

Example 6. Engineering a Transgenic Pathway for the Synthesis of Cyclopropanated Fatty Acids in Leaf Tissue Oleic acid on the PC fraction is also the starting point for alternative metabolic pathways, and therefore an alternative metabolic pathway which uses oleic acid as a substrate was investigated as a system to compare different VSP activities in transient leaf assays. Dihydrosterculic acid (DHS) was chosen as the desired product from oleic acid. DHS is a cyclopropanated fatty acid that is produced by cyclopropane fatty acid synthetases (CPFAS) using 18:1-PC as a substrate (FIG. 5). Two different CPFAS genes were compared (FIG. 6) for their activity in leaf assays to produce DHS, namely the *Escherichia coli* CPFAS (EcCPFAS) (SEQ ID NO: 52) and the C-terminal domain of the cotton CPFAS (SEQ ID NO: 21), hereinafter termed GhCPFAS*, using leaf assays in combination with genes encoding V2, hpNbFAD2, DGAT1 and Oleosin.
Construction of Genes to Over-Express EcCPFAS and GhCPFAS* for Transient Expression in Leaves and Seeds A DNA sequence encoding an *Escherichia coli* CPFAS enzyme was chemically synthesised, based on Accession No. AE000261.1 from nucleotide 6129 for a length of 1143 bp (SEQ ID NO: 60). The encoded protein had the same amino acid sequence as the *E. coli* protein, but the nucleotide sequence was codon optimised with a codon bias more suited to eukaryotic expression. The EcCPFAS-encoding fragment was cloned into the EcoRI site of pCW391, generating pCW392, a binary T-DNA construct useful for leaf assays (35S-EcCPFAS).
GhCPFAS*

The first plant CPFAS gene to be isolated and characterised in heterologous expression systems, namely SfCPFAS from *Sterculia foetida*, was found to possess a C-terminal portion of the enzyme with excellent homology to known bacterial CPFAS enzymes and an N-terminal region with motifs with homology to FAD-binding oxidases (Bao et al., 2002). A study has found that SfCPFAS is unusual and different to other plant fatty acid modifying enzymes by acting upon the 18:1 esterified to the sn1 position of phosphatidylcholine (PC) (Bao et al., 2003).

The cotton CPFAS-1 gene shows some homology to the SfCPFAS gene and the expression of full-length GhCP-FAS-1 in tobacco BY2 cell cultures likewise resulted in about 1% DHS (Yu et al., 2011). The expression of full-length GhCPFAS-1 in seeds of fad2 fae1 mutant backgrounds of *Arabidopsis*, having elevated levels of oleic acid in seeds, also generated about 1% DHS (Yu et al., 2011). A comparison of the full-length GhCPFAS to produce DHS and a protein truncated by the first 409 amino acids, thus removing the FAD-binding oxidase domain, found that removal of the first 409 amino acids reduced DHS production in yeast by about 70% (Yu et al., 2011). Overall, these results indicated that plant CPFAS enzymes were capable of producing a low level of DHS in transgenic expression systems but that the first 409 amino acids were required for maximal activity. However, as described below the present inventors were surprised to find that in plant cells the truncated enzymes had enhanced CPFAS activity.

A DNA fragment encoding the C-terminal 469 amino acids of the full-length GhCPFAS-1 enzyme, starting at nucleotide position 1248 relative to the sequence in Accession No. AY574036 and using an internal in-frame ATG as the new start codon, was generated in RT-PCR reactions using total RNA isolated from cotton, to generate a nucleotide sequence encoding (SEQ ID NO: 37) the modified protein GhCPFAS* (SEQ ID NO: 21). The predicted length of the protein was 469 amino acids and therefore including only the region with homology to the bacterial CPFAS gene, without the N-terminal region having homology to FAD-binding oxidases. The PCR primers used to amplify this region of GhCPFAS-1 included SpeI flanking sites (underlined), and were Forward primer: 5'-TT ACTAGTATGGATGCTGCACATGGTATCT-3' (SEQ ID NO: 19) and Reverse primer: 5'-TT ACTAGTTCAATCATCCATGAAGGAATATGCAGAA-3' (SEQ ID NO: 20). The amplicon was inserted into the SpeI site of 35S-pORE4 to generate pCW618 (35S-GhCPFAS*).

The construct was introduced into *Agrobacterium* and used to infiltrate *N. benthamiana* leaves in transient assays as before, in various combinations with other genes. Analyses of the total lipid content of the infiltrated zones of these leaves indicated that GhCPFAS* efficiently produced DHS in leaves (FIG. 6). The level of DHS produced in the presence of GhCPFAS* was approximately 7% of the total fatty acids in leaf lipids, with an overall pathway conversion efficiency of 47% for conversion of oleic acid to DHS. In comparison, EcCPFAS produced less than 1% DHS in total fatty acids in leaf lipids with a conversion efficiency of 4%. GhCPFAS* was therefore used throughout the remainder of this study.

In a further experiment, the production of DHS by GhCP-FAS* was used to directly compare the efficiency of p19 or V2 to aid the simultaneous over-expression of the GhCP-FAS* transgene and silencing of the NbFAD2 gene, that is, where silencing of an endogenous gene was required to maximise flux into a novel biosynthetic pathway. Various combinations of GhCPFAS*, DGAT1, Oleosin, V2, p19, and hpNbFAD2 were infiltrated into *N. benthamiana* leaves and the production of DHS determined (FIG. 7). In the absence of hpNbFAD2, a slightly greater level of DHS production was observed in the presence of p19 compared to V2. However, in the presence of the hairpin hpNbFAD2, greater levels of DHS were observed with the use of V2. V2 allowed the greatest levels of substrate (18:1) to be produced and also the greatest levels of DHS production. Overall the use of V2 in the combined overexpression and silencing scenario generated approximately 30% more DHS in the leaf assays compared to the use of p19.

A critical step in TAG synthesis pathways involves the removal of the acyl group from the PC head group into the CoA pool. Once acyl groups enter the CoA pool, they become available for the TAG synthesis pathway termed the 'Kennedy' pathway that includes the last committed step of TAG formation catalysed by the DGAT enzyme. The movement of DHS, produced on the PC fraction of leaves, into leaf TAGs was tested by combining GhCPFAS* with DGAT1, Oleosin and hpNbFAD2 (FIG. 10). DHS produced by GhCPFAS*, DGAT1 and Oleosin was found in leaf TAGs at approximately 7% of the total fatty acid content in TAG, with a conversion efficiency of oleic acid to DHS of 55%. The inclusion of hpNbFAD2 boosted the percentage of DHS in leaf TAG from 7% to 15%, while the conversion efficiency remained unchanged at 55%. These results indicated that the combination of V2 and hpNbFAD2 doubled the flux of DHS into the metabolic pathway, using in addition CPFAS*+AtDGAT1+Oleosin, to produce plant oils having higher concentrations of cyclopropanated fatty acids.

To demonstrate whether the DHS was exchanged readily between the PC and CoA pools, a further experiment was performed which added AtFAE1 to the combination of enzymes. The present inventors reasoned that the fatty acid DHS, containing a mid-chain propane ring, was likely to form a structure similar to and intermediate between that of a saturated and a monounsaturated C18 fatty acid and that if DHS was transferred from the PC fraction into the CoA pool, it would be a suitable substrate for AtFAE1 to produce elongated DHS (eDHS). To examine if DHS, produced on PC, was transferred into the CoA pool of leaves, the chimeric 35S:AtFAE1 gene was included in combination with genes encoding V2, GhCPFAS* and hpNbFAD2, each under the control of the 35S promoter. The results of the fatty acid analysis are shown in FIG. 11. Total lipids analysed 5 dpi were enriched for DHS and a new metabolite. The new metabolite was confirmed as eDHS, an elongated product of DHS with an additional 2 carbon atoms, by using standard GC/MS techniques (FIG. 12). The conversion efficiency of DHS to eDHS averaged 15% across 6 samples compared to the conversion of 18:1 to 20:1 which averaged 28%. Collectively, these experiments provided evidence that DHS produced on PC was moved efficiently into the CoA pool and accumulated into leaf oils via expression of a combination of endogenous genes and transgenic genes.

Example 7. Transgenic Plant Studies

EcCPFAS in *Arabidopsis* Seeds

The EcCPFAS fragment (Example 6) was cloned into the EcoRI site of pCW442 generating pCW393 (FP1-EcCP-FAS) a seed-specific expression vector using the truncated FP1 promoter to drive expression of EcCPFAS. This promoter is useful for expression of transgenes in oilseeds (Ellerstrom et al., 1996). This vector was transformed into *Agrobacterium tumefaciens* strain AGL1, and used to transform *Arabidopsis* plants of the fad2/fae1 double mutant background via the floral dip method. Transgenic seeds were selected on media containing kanamycin (40 mg/L) and T2 seed of these plants analysed for DHS content as described in Example 1.

Seven independent transformed lines of *Arabidopsis* were analysed and the DHS content ranged from trace levels through to 1% DHS, consistent with the studies described above.

GhCPFAS in Seeds of *Arabidopsis* and Safflower

A plant binary expression vector was designed for the expression of transgenes using a promoter derived from the promoter of the AtOlesoin1 gene (TAIR website gene annotation At4g25140). The promoter was modified in that 6 basepairs within the 1192 bp sequence were omitted to delete common restriction enzyme sites. The AtOleosin promoter has been used for the strong seed-specific expression of transgenes in safflower and *Brassica* species (Nykiforuk et al., 2011; Van Rooijen and Moloney, 1995). This promoter is thought to be bi-directional, directing not only strong seed-specific expression of transgenes placed at the 3' end of the promoter, but also generating transcripts in the opposite direction from the 5'end of the promoter in a range of tissues. The *Arabidopsis* oleosin promoter shares features of the *Brassica napus* promoter, characterised to have a bi-functional nature (Sadanandom et al., 1996). The promoter was chemically synthesised and subcloned into pGEMT-Easy and an EcoRI fragment of this vector was blunted via the Klenow enzyme fill-in reaction and ligated into the Klenow-blunted HindIII site of pCW265 (Belide et al., 2011), generating pCW600 (AtOleosinP::empty). A SpeI-flanked fragment of pCW618 encompassing the GhCPFAS* coding region was ligated into pCW600, generating pCW619 (AtOloesin:GhCPFAS*).

This pCW619 vector was introduced into *Agrobacterium tumefaciens* strain AGL1 and used to transform *Arabidopsis* of either the fad2 or fad2fae1 mutant genotypes via the floral dip method. The same construct was also used to transform safflower of the variety S317 (high oleic background) via a method using grafting (Belide et al., 2011). 15 independent transformed lines of the fad2 mutant of *Arabidopsis* transformed with pCW619 were obtained and T2 seeds of these plants were analysed. DHS was detected in the seedoil to about 1% of total fatty acids. 20 independent transformed lines of safflower 5317 transformed with pCW619 were generated and seeds of these plants harvested at maturity. DHS contents in seeds were analysed and found to be detectable but low, being below 1% of total fatty acids in the seedoil.

Discussion

These experiments showed that the silencing suppressor protein V2 was advantageous in allowing efficient over-expression of one or more genes together with the silencing of genes, in the same cell. Although p19 allowed excellent over-expression of transgenes and was more effective than V2 as a silencing suppressor, p19 also partially blocked hairpin-based silencing of endogenous genes. It is postulated that V2 and its functional homologs block the co-suppression pathway which utilises RNA dependent RNA polymerase and SGS3 and thereby maximises expression of a desired gene, but has little effect on the hairpin-RNA or microRNA silencing pathways and thereby allows concomitant gene silencing. The use of V2 also allowed the efficient expression of numerous additional genes to the cells to form a new metabolic pathway, using either individual (separate) vectors or genes combined on single constructs, and thereby entire transgenic pathways could be assembled and tested within a few days in the transient assays. The present inventors used the V2-based leaf assays to determine that GhCPFAS* was much better than EcCPFAS in producing DHS. Finally, the optimised leaf assays demonstrated that the unusual fatty acid DHS, produced on PC, was efficiently unloaded into the CoA pool and accumulated in leaf oil. The accumulation of 15% DHS in leaf oils reported here with GhCPFAS* exceeds levels reported with any CPFAS expressed in any plant cell reported in previous studies. Such efficient movements of DHS between lipid pools in leaf cells indicated that leaves might be an ideal location for, the production of DHS rather than or alternative to oilseeds.

Example 8. Additional Genes for Increasing Cyclopropanated Fatty Acids

Preparation of Hairpin RNAi Constructs for Down-Regulation of Lipid Handling Genes In order to test whether the level of cyclopropanated fatty acids, specifically DHS, could be further increased, several candidate lipid handling genes were isolated from *N. benthamiana* and hairpin RNA constructs prepared for down-regulating these genes. These constructs were designed to be tested in the *N. benthamiana* leaf transient assay system as described in Example 6, in the presence of the 35S-V2, 35S-GhCPFAS* and 35S-AtDGAT1 constructs, but using a 35S-WRI1 gene (U.S. 61/580,574; Vanhercke et al., 2012) instead of the hpNbFAD2 construct to increase the availability of fatty acyl substrates in the assay. The assays also included a 35S-GFP marker gene to allow visual confirmation of prolonged gene expression in the transient assays after infiltration with the *Agrobacterium* mixtures. Candidate lipid handling genes that were tested included sequences encoding NbLACS4, NbLACS7, NbPLDz1, NbPLDz2, and NbLPCAT1. The nucleotide sequences of the protein coding regions and the corresponding amino acid sequences of these genes are set forth in SEQ ID NOs: 91, 93, 95, 97 and 99 respectively. The nucleotide sequences of the gene fragments used to prepare these hairpin RNA constructs are given in SEQ ID NOs: 101 to 105 respectively. The hairpin RNA constructs were made in pHellsgate12 using the gene fragments and the standard methods described in Helliwell and Waterhouse (2003).

*N. benthamiana* leaves were infiltrated with mixtures of *A. tumefaciens* strains AGL1 or VG3101 containing the following plant expression constructs—35S:GFP, 35S:V2 (in VG3101; Naim et al., 2012), 35S:AtWRI1 (U.S. 61/580, 574; Vanhercke et al., 2012), 35S:AtDGAT1 (U.S. 61/580, 574; Vanhercke et al., 2012), and 35S:GhCPFAS* in pE1776 (Bao et al. 2002). To test the effect of inhibiting the lipid handling genes, some of the mixtures additionally contained one of the following five hairpin RNA constructs for down-regulating the *N. benthamiana* genes—NbLACS4, NbLACS7, NbPLDz1, NbPLDz2, and NbLPCAT1. Infiltration mixes were prepared with each AGL1/VG3101 at 0.3 OD600 units in infiltration buffer (5 mM MES, 5 mM MgSO$_4$, 500 µM acetosyringone; 0.5× culture volume), infiltrated on the underside of 5-6 week old *N. benthamiana* leaves, and the plants left for five days at 24° C. with a 10:14 light:dark cycle in growth cabinets. On the fifth day, prolonged expression of the transgenes in the infiltrated region was confirmed by presence of the GFP signal. Leaf samples from the infiltrated zones were harvested and freeze-dried overnight. Total lipids were extracted from the dried leaf samples using chloroform:methanol:0.1 M KCl=2:1:1, followed by an additional chloroform extraction on the remaining aqueous phase. Fatty acid methyl esters (FAMEs) were prepared from the lipid extracts using 0.1 M sodium methoxide in methanol followed by hexane extraction. The FAME were analysed on a Varian CP-3800 GC-FID fitted with a BPX70 capillary column (Phenomenex 30 m×0.32 mm×0.25 µm), Average wt % s of DHS-FAME and C18:1-FAME (from total FAME) were from at least 6 replicate infiltrations.

The data are shown in FIG. 13. In comparison to expression of the 35S:GhCPFAS* with the V2, AtDGAT1 and WRI1 genes, which produced an average DHS-FAME level of 3.3% of the total extracted fatty acids, addition of the five hairpin constructs resulted in an increase in average DHS FAME levels to between 3.6% and 5.9%. The greatest increase in DHS-FAME was seen with hpNbLPCAT1 (FIG. 13). There was also a trend of higher C18:1-FAME levels with the added hairpin constructs that may have contributed to the increase in DHS-FAME, as C18:1 was the substrate for GhCPFAS*.

Discussion

The initial hypothesis behind the addition of hairpin constructs (except for hpNbLACS7) was to determine possible routes to DHS production and accumulation that could be blocked by silencing certain components of the oil accumulation pathway. However, contrary to the inventors prediction the addition of hairpin constructs to silence the five putative lipid handling enzymes all showed an increase in DHS in *N. benthamiana* leaf when co-expressed with GhCPFAS*.

The increase in DHS was possibly due to an increase in substrate availability for GhCPFAS*, as indicated by the trend of higher C18:1 seen with the addition of the hairpin constructs. In the case of NbLACS7 this enzyme is known to be located in the peroxisome and is thought to contribute to fatty acid breakdown (Fulda et al., 2002). Therefore the increase in DHS with the addition of hpNbLACS7 could be due to two possibilities—inhibition of DHS breakdown or decreased breakdown of C18:1. Based on the increase seen in C18:1 the latter explanation is more likely to be the cause of increased DHS. The combination of hairpin constructs against lipid handling enzymes as well as combining these with hpNbFAD2 may further increase DHS production and accumulation in *N. benthamiana* leaf by GhCPFAS*.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/580, 567 filed 27 Dec. 2011, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotech. 4:1087.
Al-Marini et al. (2002) Infect. Immun. 70:1915-1923.
Almeida and Allshire (2005) TRENDS Cell Biol., 15:251-258.
Alvarez et al. (2000) Theor Appl Genet 100:319-327.
Bao et al. (2002) Proc. Natl. Acad. Sci. U.S.A. 99:7172-7177.
Bao et al. (2003) Journal of Biological Chemistry 278: 12846-12853.
Baud et al. (2007) Plant J. 50:825-838.
Baumlein et al. (1991) Mol. Gen. Genet. 225:459-467.
Baumlein et al. (1992) Plant J. 2:233-239.
Beclin et al. (2002) Current Biology 12:684-688.
Belide et al. (2011) Plant Methods 7:12.
Bligh and Dyer (1959) Canadian Journal of Biochemistry and Physiology 37:911-7.

Bouvier-Nave et al. (2000) European Journal of Biochemistry/FEBS 267:85-96.
Broothaerts et al. (2005) Nature 433:629-633.
Brosnan et al. (2007) Proc. Natl. Acad. Sci. U.S.A. 104: 14741-14746.
Broun et al. (1998) Plant J. 13:201-210.
Cadwell and Joyce (1992) PCR Methods Appl. 2:28-33.
Cao et al. (2003) J Biol Chem 278:25657-25663.
Capuano et al. (2007) Biotechnol. Adv. 25: 203-206.
Cheng et al. (1996) Plant Cell Rep. 15:653-657.
Cheng et al. (2003) J Biol Chem 278:13611-13614.
Chikwamba et al. (2003) Proc. Natl. Acad. Sci. U.S.A. 100:11127-11132.
Chung et al. (2006) BMC Genomics 7:120.
Clough and Bent (1998) Plant J. 16:735-743.
Coco et al. (2001) Nature Biotechnology 19:354-359.
Coco et al. (2002) Nature Biotechnology 20:1246-1250.
Courvalin et al. (1995) Life Sci. 318:1209-1212.
Crameri et al. (1998) Nature 391:288-291.
Deshpande and Mukund (1992) Appl. Biochem. Biotechnol., 36:227.
Dietrich et al. (1998) Nature Biotech. 18:181-185.
Eggert et al. (2005) Chembiochem 6:1062-1067.
Ellerstrom et al. (1996) Plant Mol. Biol. 32:1019-1027.
Elmayan et al. (1998) Plant Cell 10: 1747-1757.
Fennelly et al. (1999) J. Immunol. 162:1603-1610.
Fujimura et al. (1985) Plant Tissue Culture Lett. 2:74.
Fukunaga and Doudna (2009) EMBO Journal 28:545-555.
Fulda et al. (2002) Plant Journal 32:93-103.
Ghosal et al. (2007) Biochimica et Biophysica Acta 1771: 1457-1463.
Glevin et al. (2003) Microbiol. Mol. Biol. Rev. 67:16-37.
Glick et al. (2008) Proc. Natl. Acad. Sci. U.S.A. 105:157-161.
Grant et al. (1995) Plant Cell Rep. 15:254-258.
Grillot-Courvalin (1999) Curr. Opin. Biotech. 10-477-481.
Grillot-Courvalin et al. (1998) Nature Biotech. 16:862-866.
Harayama (1998) Trends Biotechnol. 16: 76-82.
Hellinga (1997) Proc. Natl. Acad. Sci. 94(19):10015-10017.
Helliwell and Waterhouse (2003) Methods 30:289-295.
Helliwell et al. (2006) Plant Journal 46:183-192.
Hense et al. (2001) Cell Microbiol. 3:599-609.
Hillman et al. (1989) Virology 169:42-50.
Hinchee et al. (1988) Biotechnology 6:915-922.
Horvath et al. (2000) Proc. Natl. Acad. Sci. U.S.A. 97:1914-1919.
Huang (1996) Plant Physiol. 110: 1055-1061.
James et al. (1995) Plant Cell 7: 309-319.
Jézéquel et al. (2008) Biotechniques 45:523-532.
Jolivet et al. (2004) Plant Physiol. Biochem. 42:501-509.
Kai et al (1982) JAOCS 59:300-305.
Katavic et al. (1995) Plant Physiology 108: 399-409.
Kinsman (1979) Journal of the American Oil Chemists Society 56:A823-A827.
Koziel et al. (1996) Plant Mol. Biol. 32:393-405.
Kunik et al. (2001) Proc. Natl. Acad. Sci. U.S.A. 98:1871-1876.
Lacroix et al. (2008) Proc. Natl. Acad. Sci. U.S.A. 105: 15429-15434.
Levy et al. (2008) Proc. Natl. Acad. Sci. U.S.A. 105:10131-10136.
Lin et al (2005) Plant Physiol. Biochem. 43: 770-776.
Liu et al (2009) J. Agric. Food Chem. 57: 2308-2313.
Liu et al. (2010) Plant Physiol. Biochem. 48: 9-15.
Millar and Waterhouse (2005) Funct. Integr. Genomics 5:129-135.
Millar et al. (1998) Plant Cell 10:1889-1902.
Mourrain et al. (2000) Cell 101:533-542.
Naim et al. (in press) Advanced metabolic engineering in N. benthamiana using a draft genome and the V2 viral suppressor protein. PLOS ONE.
Needleman and Wunsch (1970) J. Mol. Biol. 48:443-453.
Ness et al. (2002) Nature Biotechnology 20:1251-1255.
Niedz et al. (1995) Plant Cell Reports 14:403.
Nykiforuk et al. (2011) Plant Biotechnology Journal 9:250-263.
Ohlrogge and Browse (1995) Plant Cell 7:957-970.
Ostermeier et al. (1999) Nature Biotechnology 17:1205-1209.
Ow et al. (1986) Science 234:856-859.
Pasquinelli et al. (2005) Curr. Opin. Genet. Develop., 15:200-205.
Perez-Vich et al. (1998) JAOCS 75:547-555
Perrin et al. (2000) Mol Breed 6:345-352.
Peterson et al. (1997) Plant Molecular Biology Reporter 15:148-153.
Potenza et al. (2004) In Vitro Cell Dev. Biol. Plant 40:1-22.
Powell et al. (1996) Vaccines 183, Abstract.
Prasher et al. (1985) Biochem. Biophys. Res. Commun. 127:31-36.
Ruuska et al. (2002) Plant Cell 14:1191-1206.
Sadanandom et al. (1996) Plant Journal 10:235-242.
Saha et al. (2006) Plant Physiol. 141:1533-1543.
Schaffner et al. (1980) Proc. Natl. Acad. Sci. U.S.A. 77:2163-2167.
Scott et al. (2010) Plant Biotechnology Journal 8:912-927.
Shiau et al. (2001) Vaccine 19:3947-3956.
Shimada and Hara-Nishimura (2010) Biol. Pharm. Bull. 33: 360-363.
Sieber et al. (2001) Nature Biotechnology 19:456-460.
Sizemore et al. (1995) Science 270:299-302.
Smith et al. (2000) Nature 407:319-320.
Stalker et al. 1988 Science 242: 419-423.
Stemmer (1994a) Proc. Natl. Acad. Sci. USA 91:10747-10751.
Stemmer (1994b) Nature 370(6488):389-391.
Stymne and Appelqvist (1978) European Journal of Biochemistry 90:223-229.
Taylor (1997) The Plant Cell 9:1245-1249.
Thillet et al. (1988) J. Biol. Chem 263:12500-12508.
Toriyama et al. (1986) Theor. Appl. Genet. 205:34.
Tzen and Huang (1992) J. Cell Biol. 117:327-335.
Tzfira and Citovsky (2006) Curr. Opin. Biotech. 17:147-154.
Vanhercke et al. (2012) Synergistic effect of WRI1 and DGAT1 coexpression on triacylglycerol biosynthesis in plants. FEBS Letters.
Vanrooijen and Moloney (1995) Bio-Technology 13:72-77.
Voinnet et al. (2003) Plant Journal 33:949-956.
Volkov et al. (1999) Nucleic acids research 27(18):e18.
Wang et al. (1992) Biochemistry 31:11020-11028.
Waterhouse et al. (1998) Proc. Natl. Acad. Sci. USA 95:13959-13964.
Weiss et al. (2003) Int. J. Med. Microbiol. 293:95:106.
Wood et al. (2009) Plant Biotechnology Journal 7:914-924.
Yang et al. (2003) Planta 216:597-603.
Ye et al. (2003) Nature 426:874-878.
Yen et al. (2002) Proc. Natl. Acad. Sci. U.S.A. 99:8512-8517.
Yen et al. (2005) J Lipid Res 46:1502-1511.
Yu et al. (2011) BMC Plant Biology 11:97.
Zhang et al. (2004) Journal of Surfactants and Detergents 7:211-215.
Zhao et al. (1998) Nature Biotechnology 16:258-261.

The invention claimed is:

1. A transgenic plant cell comprising:
   (a) a first exogenous polynucleotide encoding a cyclopropane fatty acid synthetase (CPFAS), wherein the first exogenous polynucleotide is operably linked to a promoter that is capable of directing expression of the polynucleotide in the plant cell, and
   (b) a second exogenous polynucleotide encoding a fatty acid acyltransferase, wherein the fatty acid acyltransferase is selected from the group consisting of diacylglycerol acyltransferase (DGAT), monoacylglycerol acyltransferase (MGAT), glycerol-3-phosphate acyltransferase (GPAT) and acyl-CoA:lysophosphatidylcholine acyltransferase (LPCAT), and wherein the second exogenous polynucleotide is operably linked to a promoter that is capable of directing expression of the polynucleotide in the plant cell,
   (c) a total fatty acid content which comprises dihydrosterculic acid (DHS), or DHS and one or more fatty acid derivative(s) thereof, in an amount greater than the amount in a corresponding plant cell lacking the first and second exogenous polynucleotides, wherein the DHS is, or the DHS and fatty acid derivative(s) are, esterified in triacylglycerols in the plant cell,
   wherein the fatty acid derivative(s) of DHS comprise one or more of:
   (I) a cyclo-propyl group,
   (II) a branched chain fatty acid having a methyl group as the branch, and
   (III) an elongated derivative of DHS which comprises 2 more carbons in its acyl chain than DHS, and wherein the transgenic plant cell is a leaf cell.

2. The transgenic plant cell of claim 1, wherein the fatty acid derivatives comprise isostearic acid which has a methyl group attached to C9 or C10.

3. The transgenic plant cell of claim 1, wherein the CPFAS lacks a FAD-binding oxidase domain.

4. The transgenic plant cell of claim 3, wherein the CPFAS is not more than 600 amino acids in length.

5. The transgenic plant cell of claim 1, wherein the CPFAS is a bacterial CPFAS or fungal CPFAS.

6. The transgenic plant cell of claim 1, wherein the fatty acid acyltransferase is a DGAT.

7. The transgenic plant cell of claim 1, wherein the second exogenous polynucleotide encodes a combination of two or more fatty acid acyltransferases selected from the group consisting of DGAT, MGAT, GPAT, lysophosphatidic acid acyltransferase (LPAAT) and LPCAT.

8. The transgenic plant cell of claim 1, wherein the plant cell comprises a third exogenous polynucleotide which encodes a transcription factor polypeptide that increases the expression of one or more glycolytic or fatty acid biosynthetic genes in the cell, wherein the third exogenous polynucleotide is operably linked to a promoter that is capable of directing expression of the polynucleotide in the plant cell.

9. The transgenic plant cell of claim 8, wherein the transcription factor polypeptide is a Wrinkled 1 (WRI1) transcription factor, a Leafy Cotyledon 1 (Lec1) transcription factor, a Leafy Cotyledon 2 (LEC2) transcription factor, a Fus3 transcription factor, an ABI3 transcription factor, a Dof4 transcription factor, a BABY BOOM (BBM) transcription factor or a Dof11 transcription factor.

10. The transgenic plant cell of claim 9, wherein the transcription factor polypeptide is a WRI1 transcription factor.

11. A plant comprising the transgenic plant cell of claim 1.

12. A seed obtained from the plant of claim 11, the seed comprising the first and second exogenous polynucleotides.

13. A plant part comprising the transgenic plant cell of claim 1.

14. A transgenic plant comprising:
   (a) a first exogenous polynucleotide encoding a cyclopropane fatty acid synthetase (CPFAS), wherein the first exogenous polynucleotide is operably linked to a promoter that is capable of directing expression of the polynucleotide in the leaves of the transgenic plant, and
   (b) a second exogenous polynucleotide encoding a fatty acid acyltransferase, wherein the fatty acid acyltransferase is selected from the group consisting of diacylglycerol acyltransferase (DGAT), monoacylglycerol acyltransferase (MGAT), glycerol-3-phosphate acyltransferase (GPAT) and acyl-CoA:lysophosphatidylcholine acyltransferase (LPCAT), and wherein the second exogenous polynucleotide is operably linked to a promoter that is capable of directing expression of the polynucleotide in the leaves of the transgenic plant,
   (c) a total fatty acid content in leaves of the transgenic plant which comprises dihydrosterculic acid (DHS), or DHS and one or more fatty acid derivative(s) thereof, in an amount greater than the amount in a corresponding plant leaf lacking the first and second exogenous polynucleotides, wherein the DHS is, or the DHS and fatty acid derivative(s) are, esterified in triacylglycerols in the leaves of the transgenic plant,
   wherein the fatty acid derivative(s) of DHS comprise one or more of:
   (I) a cyclo-propyl group,
   (II) a branched chain fatty acid having a methyl group as the branch, and
   (III) an elongated derivative of DHS which comprises 2 more carbons in its acyl chain than DHS.

* * * * *